(12) United States Patent
Kim et al.

(10) Patent No.: US 10,892,423 B2
(45) Date of Patent: Jan. 12, 2021

(54) CONDENSED CYCLIC COMPOUND AND ORGANIC LIGHT-EMITTING DEVICE INCLUDING THE SAME

(71) Applicant: Samsung Display Co., Ltd., Yongin-si (KR)

(72) Inventors: Youngkook Kim, Yongin-si (KR); Heechoon Ahn, Yongin-si (KR); Mieun Jun, Yongin-si (KR); Soobyung Ko, Yongin-si (KR); Seokhwan Hwang, Yongin-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 198 days.

(21) Appl. No.: 15/831,079

(22) Filed: Dec. 4, 2017

(65) Prior Publication Data

US 2018/0159050 A1    Jun. 7, 2018

(30) Foreign Application Priority Data

Dec. 7, 2016    (KR) .......................... 10-2016-0166214

(51) Int. Cl.
*H01L 51/00* (2006.01)
*H01L 51/50* (2006.01)
(Continued)

(52) U.S. Cl.
CPC ........ *H01L 51/0072* (2013.01); *C07D 401/10* (2013.01); *C07D 401/14* (2013.01);
(Continued)

(58) Field of Classification Search
CPC .. C07D 401/10; C07D 401/14; C07D 405/04; C07D 405/14; C07D 409/14;
(Continued)

(56) References Cited

U.S. PATENT DOCUMENTS 9,502,668 B2    11/2016    Adachi et al.
10,205,104 B2 *    2/2019    Lee ...................... C07D 401/10
(Continued)

FOREIGN PATENT DOCUMENTS

CN              104725369 A    *    6/2015
KR    10-2013-0075949 A          7/2013
(Continued)

OTHER PUBLICATIONS

Computer-generated English-language translation of CN-104725369-A (Year: 2015).*
(Continued)

*Primary Examiner* — Vu A Nguyen
(74) *Attorney, Agent, or Firm* — Lewis Roca Rothgerber Christie LLP

(57) ABSTRACT

An organic light-emitting device includes: a first electrode; a second electrode facing the first electrode; and an organic layer between the first electrode and the second electrode, the organic layer including an emission layer and at least one condensed cyclic compound of Formula 1. The organic light-emitting device according to an embodiment may have a low driving voltage, high efficiency, a long lifespan, and high maximum quantum efficiency:

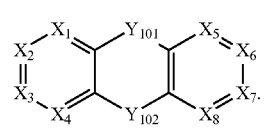

Formula 1

20 Claims, 4 Drawing Sheets

(51) Int. Cl.
    C07D 401/10    (2006.01)
    C07D 401/14    (2006.01)
    C07D 405/04    (2006.01)
    C07D 405/14    (2006.01)
    C07D 409/14    (2006.01)
    C07D 413/14    (2006.01)
    C07D 417/14    (2006.01)
    C09K 11/06     (2006.01)
    C07F 7/08      (2006.01)
(52) U.S. Cl.
    CPC ......... *C07D 405/04* (2013.01); *C07D 405/14* (2013.01); *C07D 409/14* (2013.01); *C07D 413/14* (2013.01); *C07D 417/14* (2013.01); *C07F 7/0816* (2013.01); *C09K 11/06* (2013.01); *H01L 51/0052* (2013.01); *H01L 51/0067* (2013.01); *H01L 51/0071* (2013.01); *H01L 51/0073* (2013.01); *H01L 51/0074* (2013.01); *H01L 51/0094* (2013.01); *H01L 51/506* (2013.01); *C09K 2211/1018* (2013.01); *H01L 51/504* (2013.01); *H01L 51/5012* (2013.01); *H01L 51/5072* (2013.01); *H01L 2251/301* (2013.01); *H01L 2251/552* (2013.01)
(58) Field of Classification Search
    CPC .. C07D 413/14; C07D 417/14; C07D 7/0816; C09K 2211/1018; H01L 51/0071; H01L 51/0094
    See application file for complete search history.

(56) References Cited

U.S. PATENT DOCUMENTS

| 2006/0166038 | A1* | 7/2006 | Park .................... C07D 265/38 428/690 |
| 2013/0020558 | A1 | 1/2013 | Ogiwara |
| 2014/0138669 | A1 | 5/2014 | Nakagawa et al. |
| 2014/0138670 | A1 | 5/2014 | Nakagawa et al. |
| 2014/0145151 | A1 | 5/2014 | Xia et al. |
| 2015/0141642 | A1 | 5/2015 | Adachi et al. |
| 2015/0239880 | A1 | 8/2015 | Adachi et al. |
| 2016/0020402 | A1 | 1/2016 | Kaji et al. |
| 2016/0118599 | A1 | 4/2016 | Jeong et al. |
| 2016/0141508 | A1 | 5/2016 | Jatsch et al. |
| 2016/0181548 | A1 | 6/2016 | Parham et al. |
| 2016/0218298 | A1 | 7/2016 | Lee et al. |

FOREIGN PATENT DOCUMENTS

| KR | 10-2014-0009918 A | 1/2014 | |
| KR | 10-2014-0015329 A | 2/2014 | |
| KR | 10-2014-0061365 A | 5/2014 | |
| KR | 10-2014-0067914 A | 6/2014 | |
| KR | 10-2014-0070450 A | 6/2014 | |
| KR | 10-2015-0005583 A | 1/2015 | |
| KR | 10-2015-0016242 A | 2/2015 | |
| KR | 10-2015-0050570 A | 5/2015 | |
| KR | 10-2015-0123907 A | 11/2015 | |
| KR | 10-2016-0027985 A | 3/2016 | |
| KR | 10-2016-0038006 A | 4/2016 | |
| KR | 10-2016-0047670 A | 5/2016 | |
| WO | WO 2013/011954 A1 | 1/2013 | |
| WO | WO 2013/011955 A1 | 1/2013 | |
| WO | WO 2013/100603 A1 | 7/2013 | |
| WO | WO-2016173019 A1 * | 11/2016 | ......... H01L 51/0071 |
| WO | WO-2017014951 A1 * | 1/2017 | ............ C09K 11/06 |
| WO | WO-2017114857 A1 * | 7/2017 | ............ C07F 7/0816 |

OTHER PUBLICATIONS

Tsujimoto et al., JACS 2017, 139, 4894-4900.*
STN Structure Search (Year: 2019).*

* cited by examiner

| 190 |
|-----|
| 150 |
| 110 |

| 190 |
|---|
| 150 |
| 110 |
| 210 |

| 220 |
|---|
| 190 |
| 150 |
| 110 |

| |
|---|
| 220 |
| 190 |
| 150 |
| 110 |
| 210 |

CONDENSED CYCLIC COMPOUND AND ORGANIC LIGHT-EMITTING DEVICE INCLUDING THE SAME

CROSS-REFERENCE TO RELATED APPLICATION

This application claims priority to and the benefit of Korean Patent Application No. 10-2016-0166214, filed on Dec. 7, 2016, in the Korean Intellectual Property Office, the entire content of which is incorporated herein by reference.

BACKGROUND

1. Field

One or more aspects of one or more embodiments of the present disclosure are directed toward a condensed cyclic compound for an organic light-emitting device and an organic light-emitting device including the same.

2. Description of the Related Art

Organic light-emitting devices are self-emission devices that have wide viewing angles, high contrast ratios, short response times, and excellent characteristics in terms of brightness, driving voltage, and response speed, compared to devices in the art.

An example of such organic light-emitting device may include a first electrode disposed (e.g., positioned) on a substrate, and a hole transport region, an emission layer, an electron transport region, and a second electrode, which are sequentially disposed on the first electrode. Holes provided from the first electrode, for example, may move toward the emission layer through the hole transport region, and electrons provided from the second electrode, for example, may move toward the emission layer through the electron transport region. Carriers, such as holes and electrons, may then recombine in the emission layer to produce excitons. These excitons transit from an excited state to a ground state, thereby generating light.

SUMMARY

One or more aspects of one or more embodiments of the present disclosure are directed toward a novel condensed cyclic compound and an organic light-emitting device including the same.

Additional aspects will be set forth in part in the description which follows and, in part, will be apparent from the description, or may be learned by practice of the presented embodiments.

According to an embodiment, a condensed cyclic compound is represented by Formula 1 below:

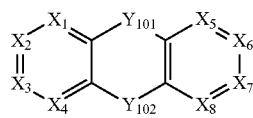

Formula 1

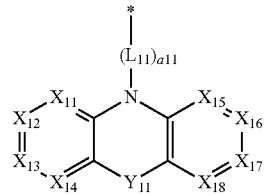

Formula 2

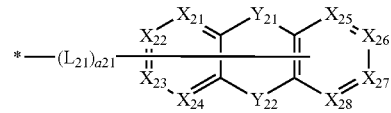

Formula 3

$*—(L_1)_{a1}—Ar_1$.

Formula 4

In Formulae 1 to 4, $X_1$ to $X_4$ may each independently be $C(R_1)$, N, or carbon linked to a group represented by Formula 2 or 3, $X_5$ to $X_8$ may each independently be $C(R_2)$, N, or carbon linked to a group represented by Formula 4, $X_{11}$ to $X_{18}$ may each independently be $C(R_3)$ or N, $X_{21}$ to $X_{28}$ may each independently be $C(R_4)$, N, or carbon linked to $(L_{21})_{a21}$, at least one of $X_1$ to $X_4$ may be carbon linked to a group represented by Formula 2 or 3, at least one of $X_5$ to $X_8$ may be carbon linked to a group represented by Formula 4, and at least one of $X_{21}$ to $X_{28}$ may be carbon linked to $(L_{21})_{a21}$, $Y_{101}$ and $Y_{102}$ may each independently be selected from $C(R_{11})(R_{12})$, $Si(R_{11})(R_{12})$, O, S, and $N(R_{11})$, $Y_{11}$, $Y_{21}$, and $Y_{22}$ may each independently be selected from $C(R_{21})(R_{22})$, $Si(R_{21})(R_{22})$, O, S, and $N(R_{21})$, $L_1$, $L_{11}$, and $L_{21}$ may each independently be a substituted or unsubstituted $C_3$-$C_{60}$ carbocyclic group or a substituted or unsubstituted $C_1$-$C_{60}$ heterocyclic group, a1, a11, and a21 may each independently be an integer from 0 to 3, wherein, when a1 is two or more, two or more $L_1(s)$ may be identical to or different from each other, when a11 is two or more, two or more $L_{11}(s)$ may be identical to or different from each other, and when a21 is two or more, two or more $L_{21}(s)$ may be identical to or different from each other, $Ar_1$ may be a substituted or unsubstituted $C_3$-$C_{60}$ carbocyclic group, a substituted or unsubstituted $C_1$-$C_{60}$ heterocyclic group, or $*—S(=O)_2(Q_{101})$, $R_1$ to $R_4$, $R_{11}$ to $R_{12}$, and $R_{21}$ to $R_{22}$ may each independently be selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted divalent non-aromatic condensed polycyclic group, a substituted or unsubstituted divalent non-aromatic condensed heteropolycyclic group, —$Si(Q_1)(Q_2)(Q_3)$, —$N(Q_1)(Q_2)$, —$B(Q_1)(Q_2)$, —$C(=O)(Q_1)$, —$S(=O)_2(Q_1)$, and —$P(=O)(Q_1)(Q_2)$, at least one substituent of the substituted $C_3$-$C_{60}$ carbocyclic group, the substituted $C_1$-$C_{60}$ heterocyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be selected from:

deuterium, —F, —Cl, —Br, —I, a hydroxyl group, a cyano group, a nitro group, an amino group, an amidino group, a hydrazino group, a hydrazono group, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —N($Q_{11}$)($Q_{12}$), —B($Q_{11}$)($Q_{12}$), —C(=O)($Q_{11}$), —S(=O)$_2$($Q_{11}$), and —P(=O)($Q_{11}$)($Q_{12}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, and a terphenyl group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, and a terphenyl group, each substituted with at least one selected from deuterium, —F, —Cl, —Br, —I, a hydroxyl group, a cyano group, a nitro group, an amino group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, a terphenyl group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), and —P(=O)($Q_{21}$)($Q_{22}$); and —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), $Q_{101}$, $Q_1$ to $Q_3$, $Q_{11}$ to $Q_{13}$, $Q_{21}$ to $Q_{23}$, and $Q_{31}$ to $Q_{33}$ may each independently be selected from hydrogen, deuterium, —F, —Cl, —Br, —I, a hydroxyl group, a cyano group, a nitro group, an amino group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, and a terphenyl group, and

* indicates a binding site to a neighboring atom.

According to another embodiment, an organic light-emitting device includes: a first electrode; a second electrode facing the first electrode; and an organic layer between the first electrode and the second electrode, the organic layer including an emission layer, wherein the organic layer includes at least one condensed cyclic compound.

BRIEF DESCRIPTION OF THE DRAWINGS

These and/or other aspects will become apparent and more readily appreciated from the following description of the embodiments, taken in conjunction with the accompanying drawings in which:

FIG. 1 is a schematic view of an organic light-emitting device according to an embodiment;

FIG. 2 is a schematic view of an organic light-emitting device according to an embodiment;

FIG. 3 is a schematic view of an organic light-emitting device according to an embodiment; and FIG. 4 is a schematic view of an organic light-emitting device according to an embodiment.

DETAILED DESCRIPTION

Reference will now be made in more detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," "one of," and "selected from," when preceding a list of elements, modify the entire list of elements and do not modify the individual elements of the list. Further, the use of "may" when describing embodiments of the present invention may refer to "one or more embodiments of the present invention."

A condensed cyclic compound according to an embodiment is represented by Formula 1 below:

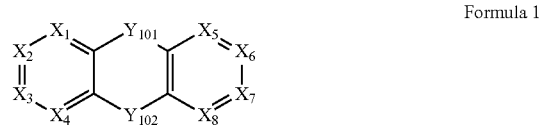

Formula 1

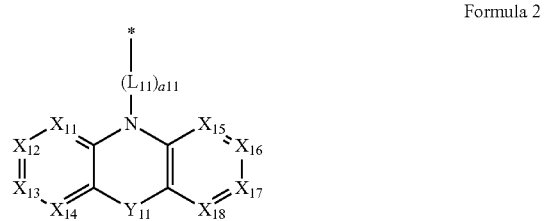

Formula 2

-continued

Formula 3

$$*\!-\!(L_{21})_{a21}\begin{array}{c}X_{22}\\X_{23}\end{array}\!\!\begin{array}{c}X_{21}\\X_{24}\end{array}\!\!\begin{array}{c}Y_{21}\\Y_{22}\end{array}\!\!\begin{array}{c}X_{25}\\X_{28}\end{array}\!\!\begin{array}{c}X_{26}\\X_{27}\end{array}$$

Formula 4

$$*\!-\!(L_1)_{a1}\!-\!Ar_1.$$

In Formula 1 to 4, $X_1$ to $X_4$ may each independently be $C(R_1)$, N, or carbon (C) linked to a group represented by Formula 2 or 3; $X_5$ to $X_8$ may each independently be $C(R_2)$, N, or carbon linked to a group represented by Formula 4; $X_{11}$ to $X_{18}$ may each independently be $C(R_3)$ or N; $X_{21}$ to $X_{28}$ may each independently be $C(R_4)$, N, or carbon linked to $(L_{21})_{a21}$, at least one of $X_1$ to $X_4$ may be carbon linked to a group represented by Formula 2 or 3; at least one of $X_5$ to $X_8$ may be carbon linked to a group represented by Formula 4; and at least one $X_{21}$ to $X_{28}$ may be carbon linked to $(L_{21})_{a21}$.

In one embodiment, $X_1$ to $X_4$ may each independently be $C(R_1)$ or carbon linked to a group represented by Formula 2 or 3; $X_5$ to $X_8$ may each independently be $C(R_2)$ or carbon linked to a group represented by Formula 4; $X_{11}$ to $X_{18}$ may each be $C(R_3)$; and $X_{21}$ to $X_{28}$ may each independently be $C(R_4)$ or carbon linked to $(L_{21})_{a21}$.

In Formulae 1 to 3, $Y_{101}$ and $Y_{102}$ may each independently be selected from $C(R_{11})(R_{12})$, $Si(R_{11})(R_{12})$, O, S, and $N(R_{11})$, and $Y_{11}$, $Y_{21}$, and $Y_{22}$ may each independently be selected from $C(R_{21})(R_{22})$, $Si(R_{21})(R_{22})$, O, S, and $N(R_{21})$.

$L_1$, $L_{11}$, and $L_{21}$ in Formulae 2 and 3 may each independently be a substituted or unsubstituted $C_3$-$C_{60}$ carbocyclic group or a substituted or unsubstituted $C_1$-$C_{60}$ heterocyclic group.

In one embodiment, $L_1$, $L_{11}$, and $L_{21}$ may each independently be selected from:

a phenylene group, a pentalenylene group, an indenylene group, a naphthylene group, an azulenylene group, a heptalenylene group, an indacenylene group, an acenaphthylene group, a fluorenylene group, a spiro-bifluorenylene group, a spiro-fluorene-benzofluorenylene group, a benzofluorenylene group, a dibenzofluorenylene group, a phenalenylene group, a phenanthrenylene group, an anlhracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a Ihiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phlhalazinylene group, a naphthyridinylene group, a quinoxalinylene group, a quinazolinylene group, a cinnolinylene group, a carbazotylene group, a phenanthridinylene group, an acridinylene group, a phenanthrolinylene group, a phenazinylene group, a benzoimidazolylene group, a benzofuranylene group, a benzothiophenylene group, an isobenzothiazolylene group, a benzoxazolylene group, an isobenzoxazolylene group, a Inazolylene group, a tetrazolylene group, an oxadiazolylene group, a ihazinylene group, a dibenzofuranylene group, a dibenzothiophenylene group, a dibenzosilolylene group, a benzocarbazolylene group, a dibenzocarbazolylene group, a thiadiazolylene group, an imidazopyridinylene group, and an imidazopyrimidinylene group; and a phenylene group, a pentalenylene group, an indenytene group, a naphthylene group, an azulenylene group, a heptalenylene group, an indacenylene group, an acenaphlhylene group, a (luorenylene group, a spiro-bifluorenylene group, a spiro-fluorene-benzofluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyrkJinylene group, a quinoxalinylene group, a quinazolinylene group, a cinnolinylene group, a carbazolylene group, a phenanthrldinylene group, an acridinylene group, a phenanthrolinylene group, a phenazinylene group, a benzoimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a dibenzosilolylene group, a benzocarbazolylene group, a dibenzocarbazolylene group, a thiadiazolylene group, an imidazopyridinylene group, and an imidazopyrimidinylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a benzocarbazolyl group, a dibenzocarbazolyl group, a thiadiazolyl group, an imidazopyridinyl group, an imidazopyrimidinyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), and $Q_{31}$ to $Q_{33}$ may each independently be selected from a $C_1$-$C_{10}$ alkyl group, a $C_1$-$C_{10}$ alkoxy group, a phenyl group, a phenyl group substituted with a $C_1$-$C_{10}$ alkyl group, a biphenyl group, a terphenyl group, a naphthyl group, and a dibenzofuranyl group.

For example, $L_1$, $L_{11}$, and $L_{21}$ may each independently be selected from groups represented by Formulae 3-1 to Formula 3-49, but embodiments of the present disclosure are not limited thereto:

Formula 3-1

Formula 3-2

Formula 3-3

Formula 3-4

Formula 3-5

Formula 3-6

Formula 3-7

Formula 3-8

Formula 3-9

Formula 3-10

Formula 3-11

Formula 3-12

Formula 3-13

Formula 3-14

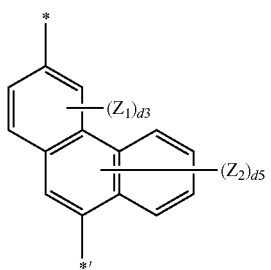
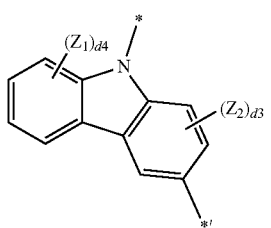
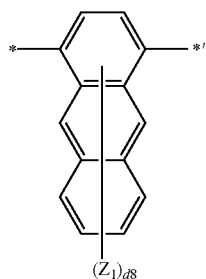
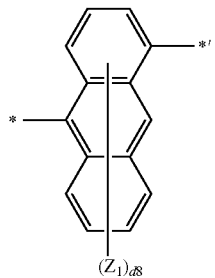
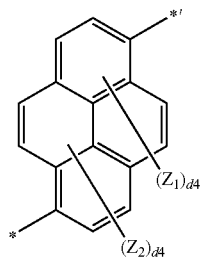
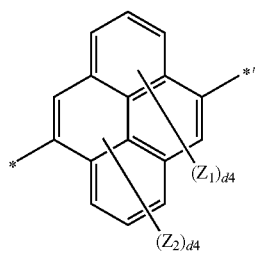
Formula 3-15
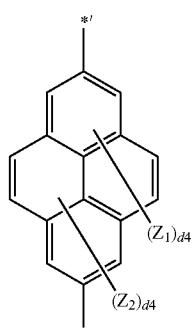
Formula 3-16
Formula 3-17
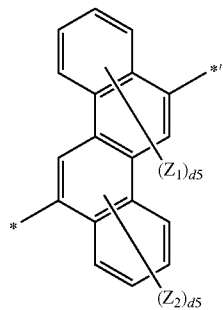
Formula 3-18
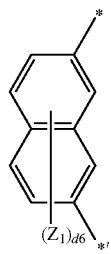
Formula 3-19
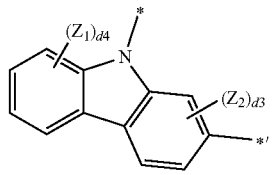
Formula 3-20
Formula 3-21
Formula 3-22
Formula 3-23
Formula 3-24
Formula 3-25
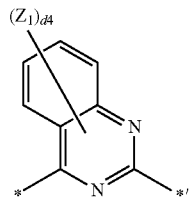
Formula 3-26
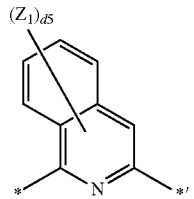

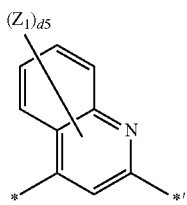
Formula 3-27
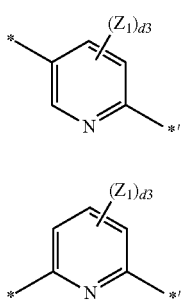
Formula 3-28
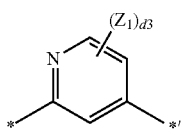
Formula 3-29
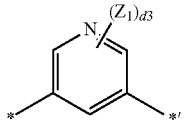
Formula 3-30
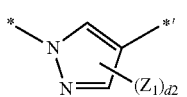
Formula 3-31

Formula 3-32

Formula 3-33

Formula 3-34

Formula 3-35
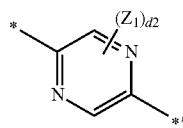
Formula 3-36
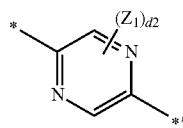
Formula 3-37
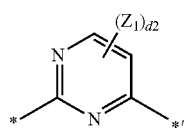
Formula 3-38
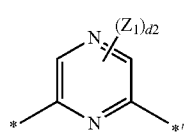
Formula 3-39
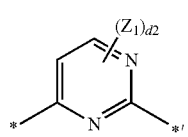
Formula 3-40
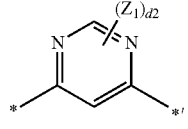
Formula 3-41
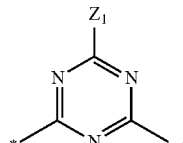
Formula 3-42
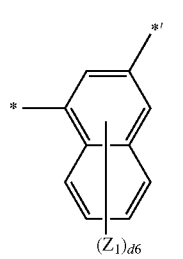
Formula 3-43
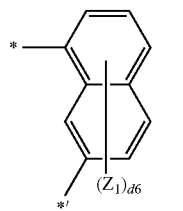
Formula 3-44
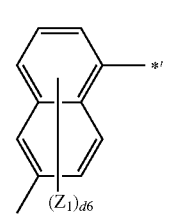
Formula 3-45

Formula 3-46
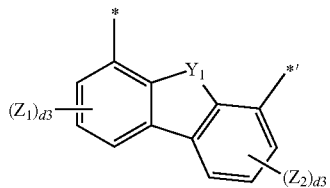

Formula 3-47
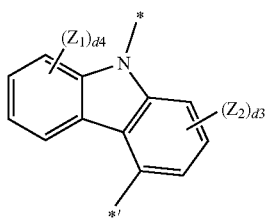

Formula 3-48
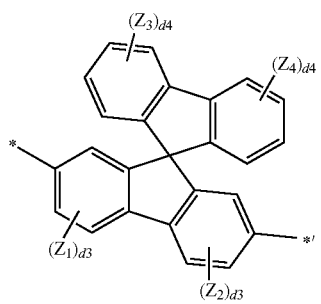

Formula 3-49
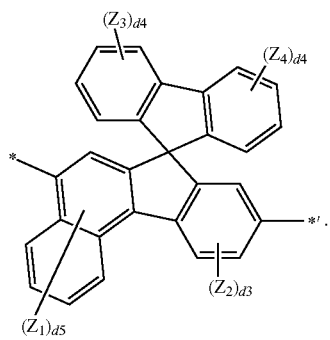

In Formulae 3-1 to 3-49, $Y_1$ may be O, S, $C(Z_5)(Z_6)$, $N(Z_5)$, or $Si(Z_5)(Z_6)$, $Z_1$ to $Z_6$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkenyl group, a $C_1$-$C_{20}$ alkynyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, —$Si(Q_{31})(Q_{32})(Q_{33})$, —$N(Q_{31})(Q_{32})$, —$B(Q_{31})(Q_{32})$, —$C(=O)(Q_{31})$, —$S(=O)_2(Q_{31})$, and —$P(=O)(Q_{31})(Q_{32})$, $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group, d2 may be 1 or 2, d3 may be an integer from 1 to 3, d4 may be an integer from 1 to 4, d5 may be an integer from 1 to 5, d6 may be an integer from 1 to 6, d8 may be an integer from 1 to 8, and

* and *' each indicate a binding site to a neighboring atom.

For example, $L_1$, $L_{11}$, and $L_{21}$ may each independently be selected from groups represented by Formulae 3-1, 3-2, 3-14, and 3-29, but embodiments of the present disclosure are not limited thereto.

a1, a11, and a21 in Formulae 2 and 3 may each independently be an integer from 0 to 3. a1, a11, and a21 respectively indicate the number of $L_1$(s), the number of $L_{11}$(s), and the number of $L_{21}$(s). When a1 is two or more, two or more $L_1$(s) may be identical to or different from each other, when a11 is two or more, two or more $L_{11}$(s) may be identical to or different from each other, and when a21 is two or more, two or more $L_{21}$(s) may be identical to or different from each other. For example, a11 may be 0 or 1, and a21 may be 0, but embodiments of the present disclosure are not limited thereto.

$Ar_1$ in Formula 4 may be a substituted or unsubstituted $C_3$-$C_{60}$ carbocyclic group, a substituted or unsubstituted $C_1$-$C_{60}$ heterocyclic group, or *—$S(=O)_2(Q_{101})$.

In one embodiment, $Ar_1$ may be selected from groups represented by Formulae 4A to 4N:

4A
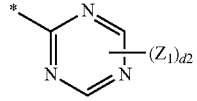

4B
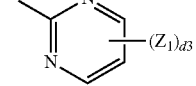

4C
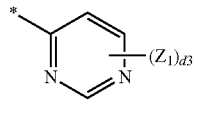

4D

4E
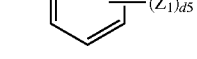

4F
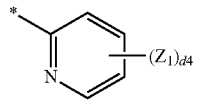

4G
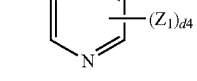

4H
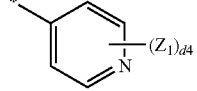

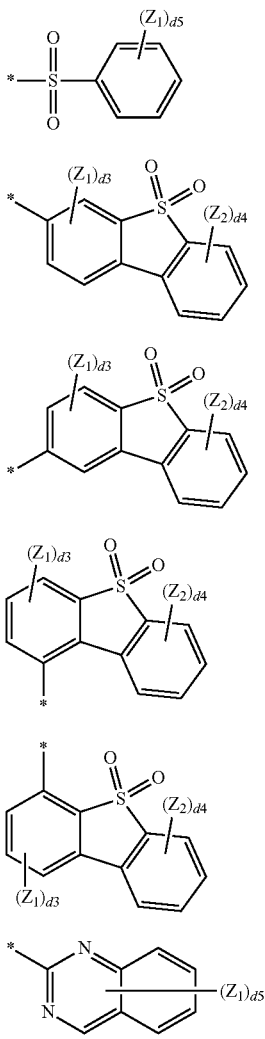

$Z_1$ and $Z_2$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkenyl group, a $C_1$-$C_{20}$ alkynyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group, d2 may be 1 or 2,
d3 may be an integer from 1 to 3,
d4 may be an integer from 1 to 4,
d5 may be an integer from 1 to 5, and
* indicates a binding site to a neighboring atom.

In one or more embodiments, $Ar_1$ may be selected from groups represented by Formulae 4-1 to 4-20, but embodiments of the present disclosure are not limited thereto:

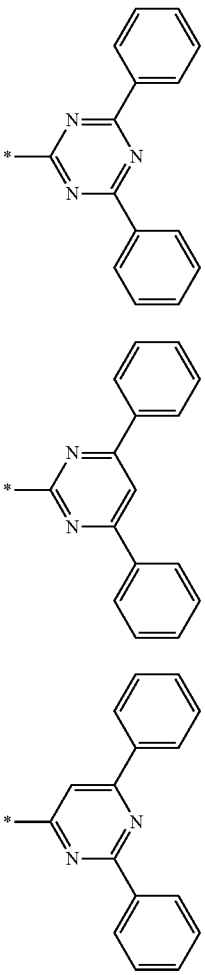

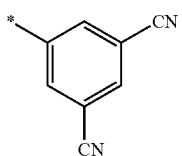 4-8

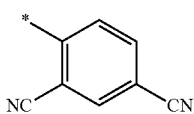 4-9

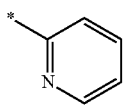 4-10

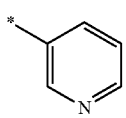 4-11

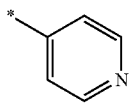 4-12

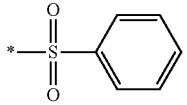 4-13

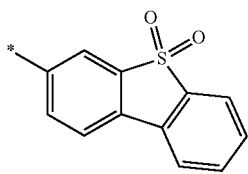 4-14

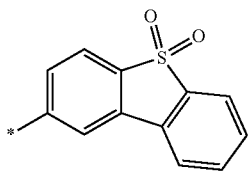 4-15

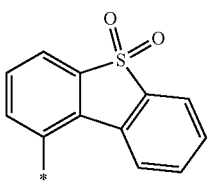 4-16

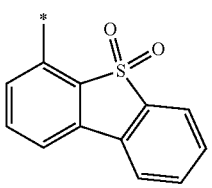 4-17

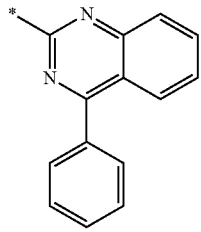 4-18

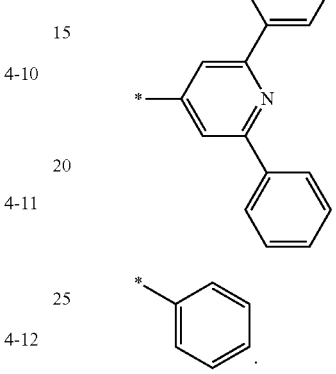 4-19

4-20

$R_1$ to $R_4$, $R_{11}$, $R_{12}$, $R_{21}$, and $R_{22}$ in Formulae 1 to 3 may each independently be selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted divalent non-aromatic condensed polycyclic group, a substituted or unsubstituted divalent non-aromatic condensed heteropolycyclic group, —Si($Q_1$)($Q_2$)($Q_3$), —N($Q_1$)($Q_2$), —B($Q_1$)($Q_2$), —C(=O)($Q_1$), —S(=O)$_2$($Q_1$), and —P(=O)($Q_1$)($Q_2$).

In one embodiment, $R_1$ to $R_4$ may each independently be selected from hydrogen, deuterium, —F, —Cl, —Br, —I, a hydroxyl group, a cyano group, a nitro group, a $C_1$-$C_{20}$ alkyl group, and a $C_1$-$C_{20}$ alkoxy group.

In one embodiment, $R_{11}$, $R_{12}$, $R_{21}$, and $R_{22}$ may each independently be selected from:

hydrogen, deuterium, —F, —Cl, —Br, —I, a hydroxyl group, a cyano group, a nitro group, a $C_1$-$C_{20}$ alkyl group, and a $C_1$-$C_{20}$ alkoxy group;

a phenyl group, a biphenyl group, a terphenyl group, a naphthyl group, a pyridinyl group, and a pyrimidinyl group; and a $C_1$-$C_{20}$ alkyl group, a $C_1$-$C_{20}$ alkoxy group, a phenyl group, a biphenyl group, a terphenyl group, a naphthyl group, a pyridinyl group, and a pyrimidinyl group, each substituted with at least one selected from deuterium, —F, —Cl, —Br, —I, a hydroxyl group, a cyano group, and a nitro group.

In one embodiment, the condensed cyclic compound represented by Formula 1 may be represented by one of Formulae 1A to 1P:
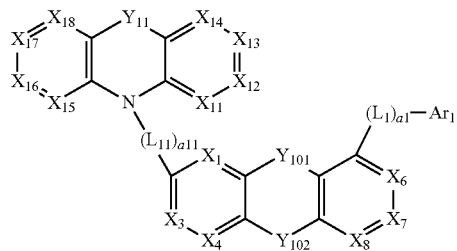
1A
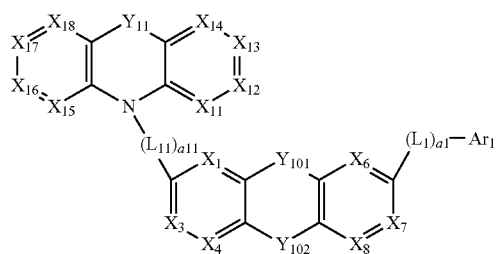
1B
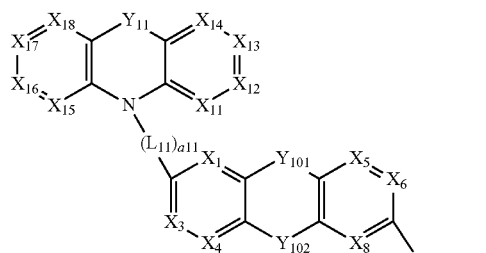
1C
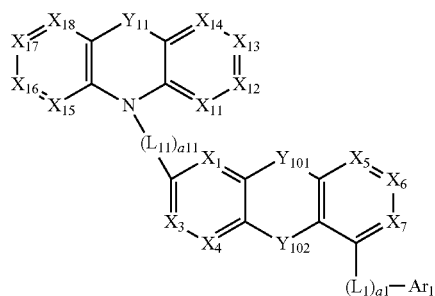
1D
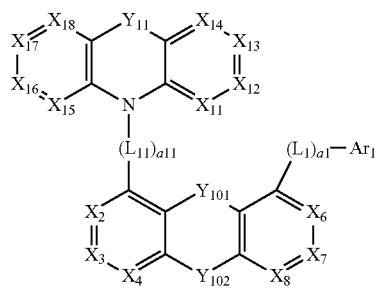
1E
-continued
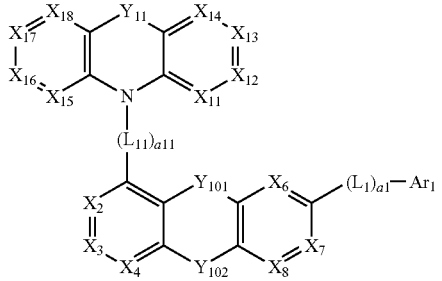
1F
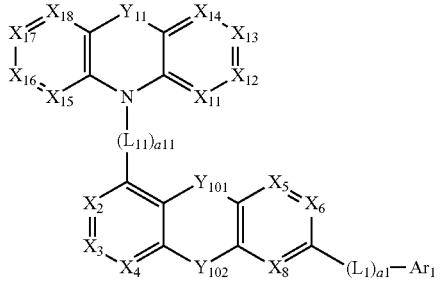
1G
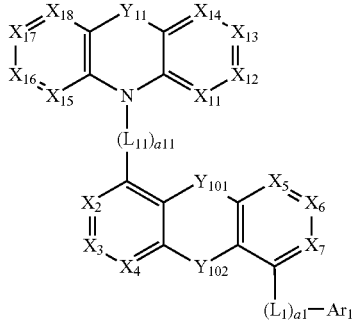
1H
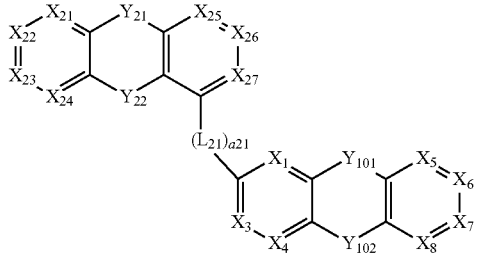
1I
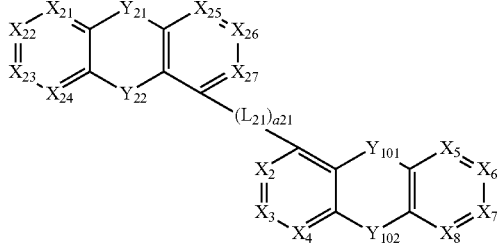
1J

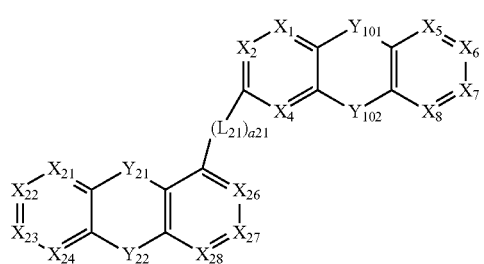
1K
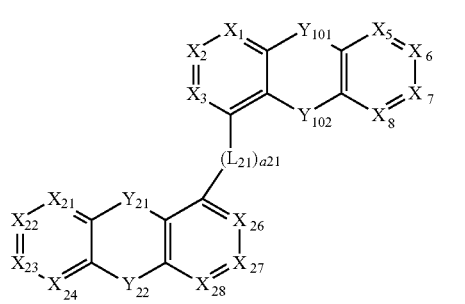
1L
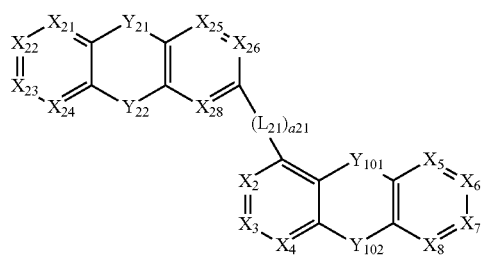
1M
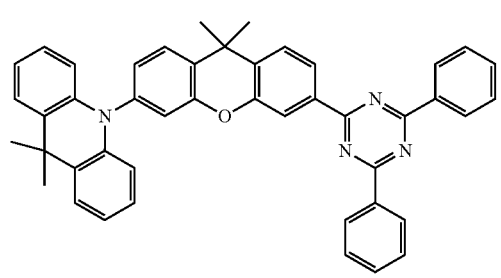
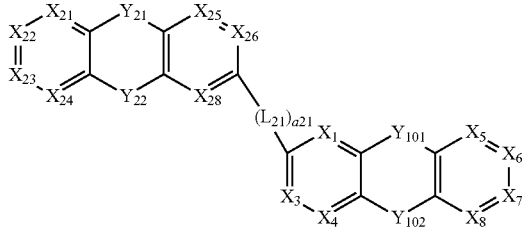
1N
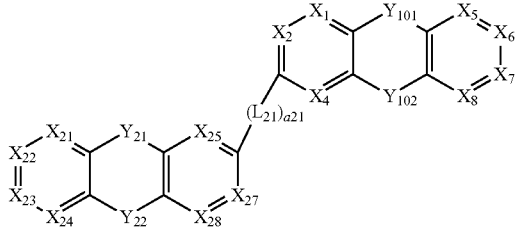
1O
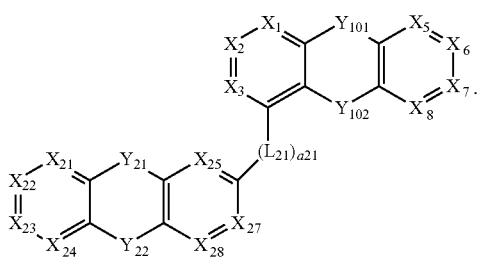
1P
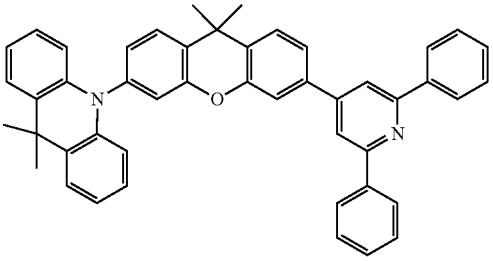
In Formulae 1A to 1P, definitions for $X_1$ to $X_8$, $X_{11}$ to $X_{18}$, $X_{21}$ to $X_{28}$, $Y_{101}$ to $Y_{102}$, $Y_{11}$, $Y_{21}$ to $Y_{22}$, $L_1$, $L_{11}$, $L_{21}$, a1, a11, and a21 are the same as those provided above.
The condensed cyclic compound represented by Formula 1 may be one of Compounds 1 to 144 below, but embodiments of the present disclosure are not limited thereto:
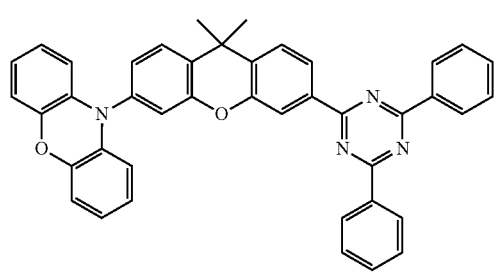
1              2
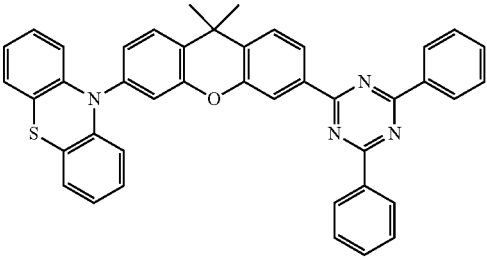
3              4

-continued
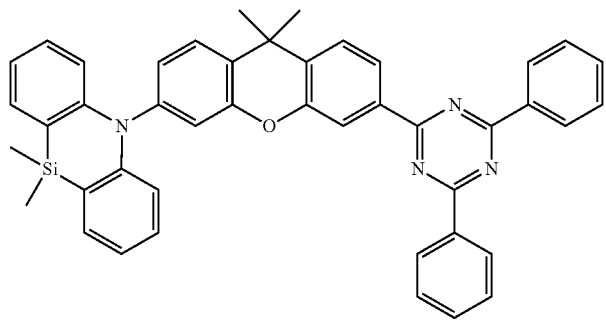
5
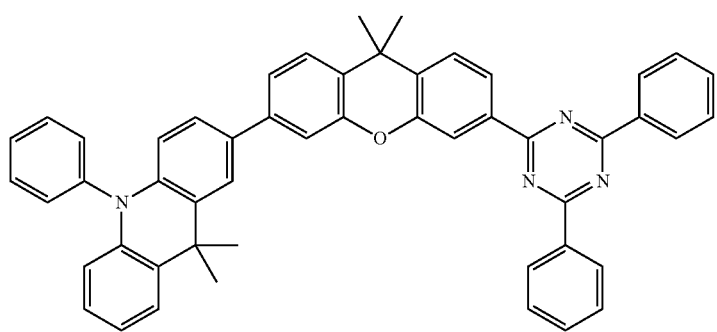
6
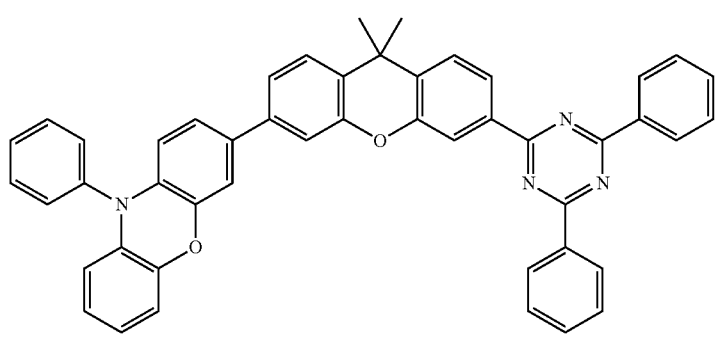
7
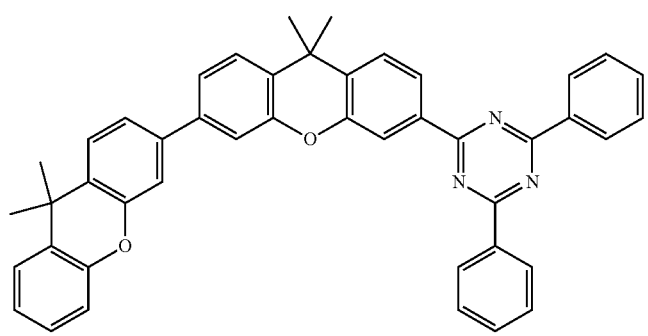
8

-continued
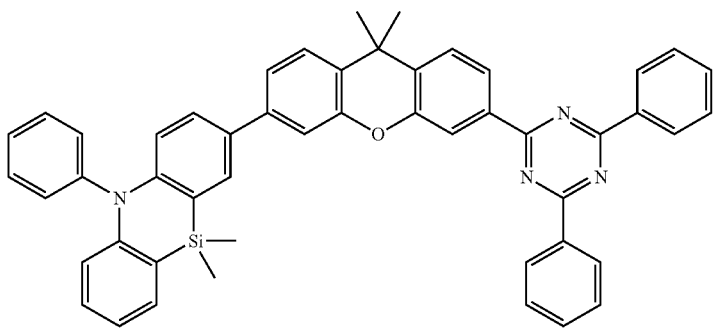
9
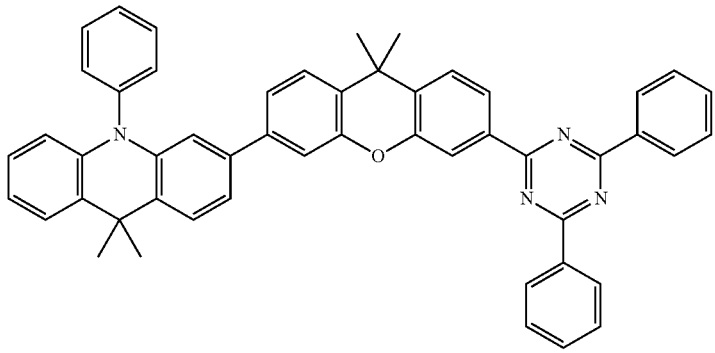
10
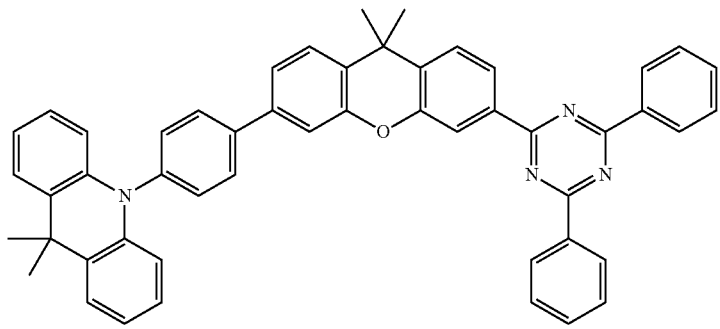
11
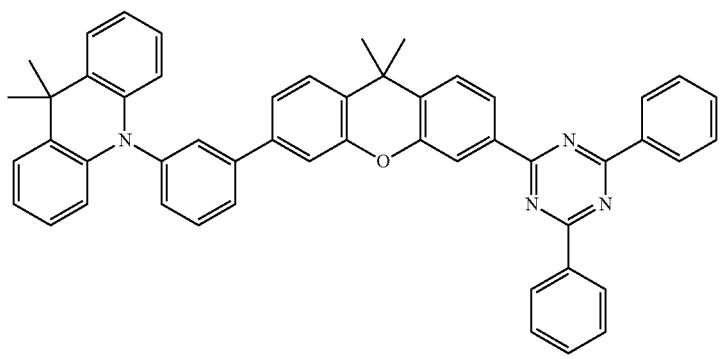
12
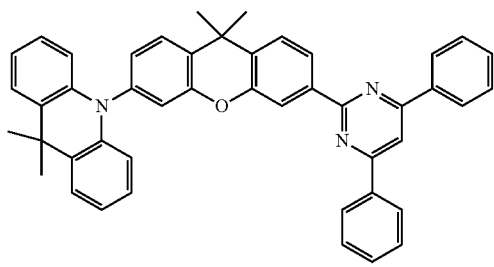
13
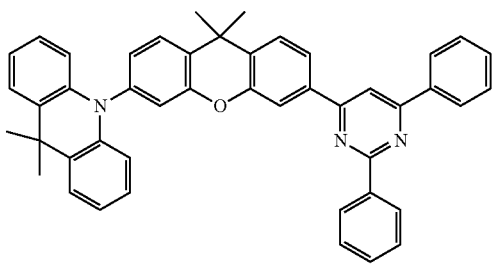
14

-continued
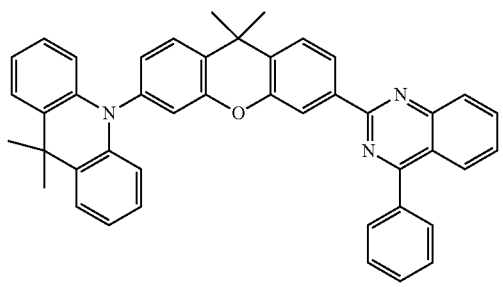
15
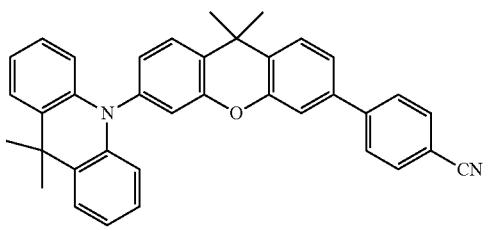
16
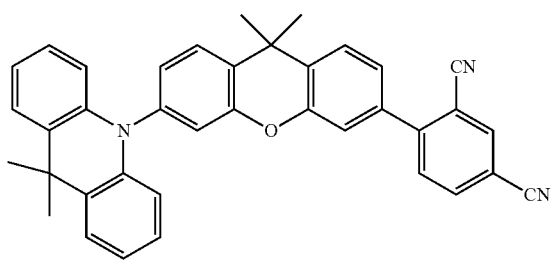
17
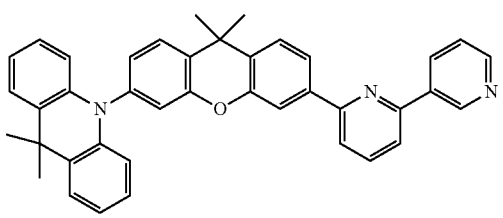
18
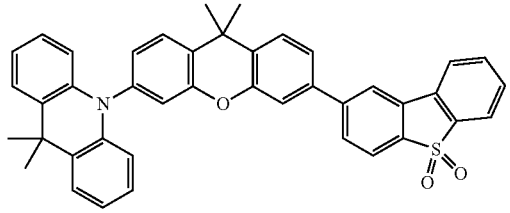
19
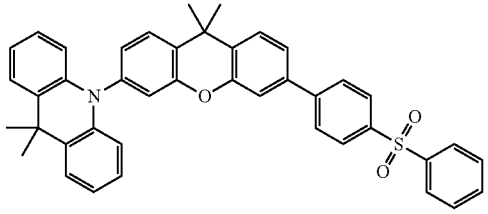
20
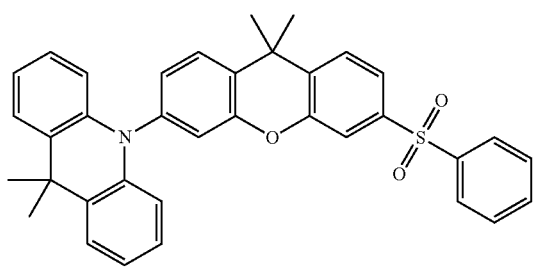
21
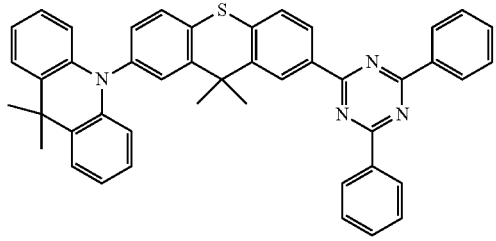
22
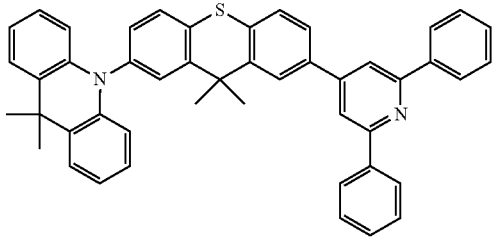
23
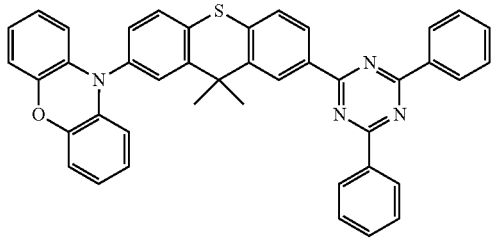
24
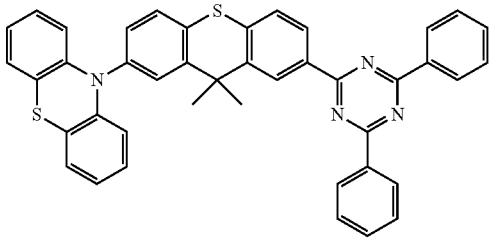
25

26
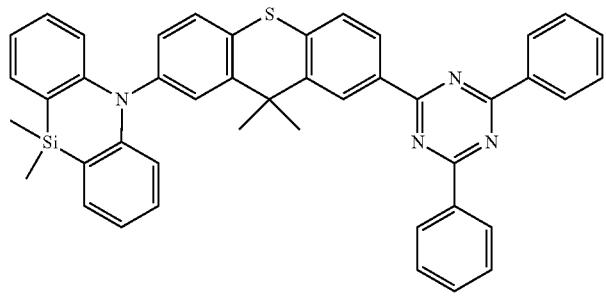
27
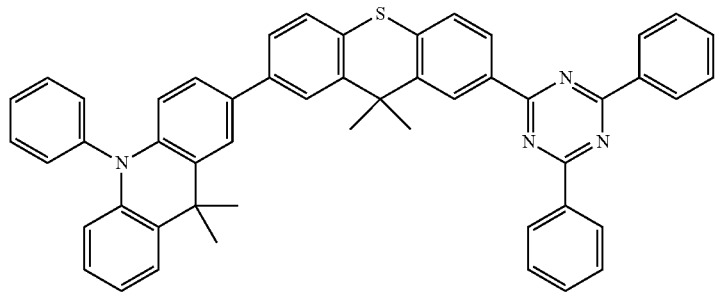
28
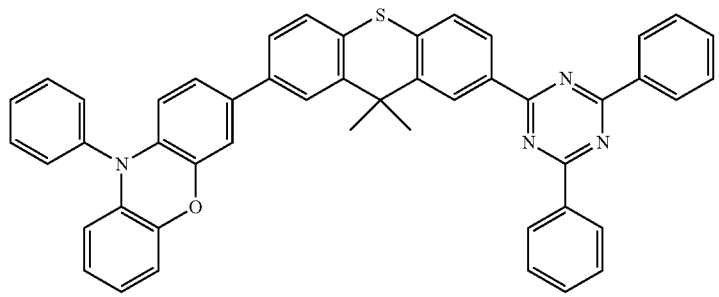
29
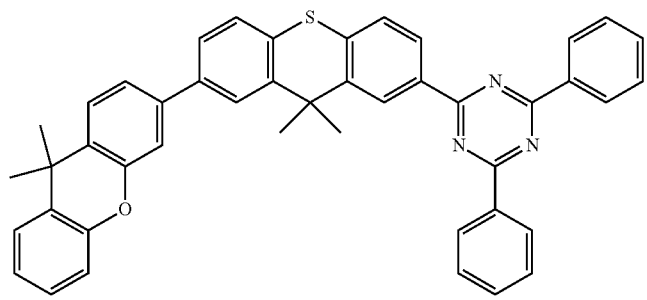
30
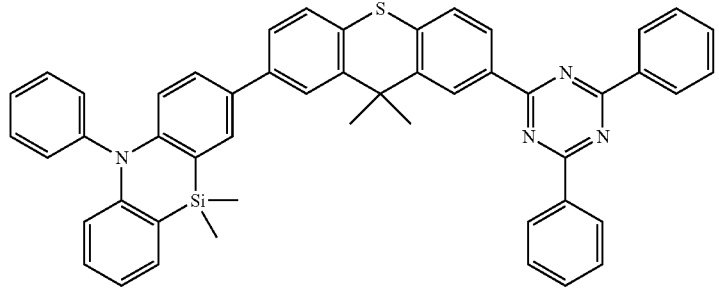

-continued
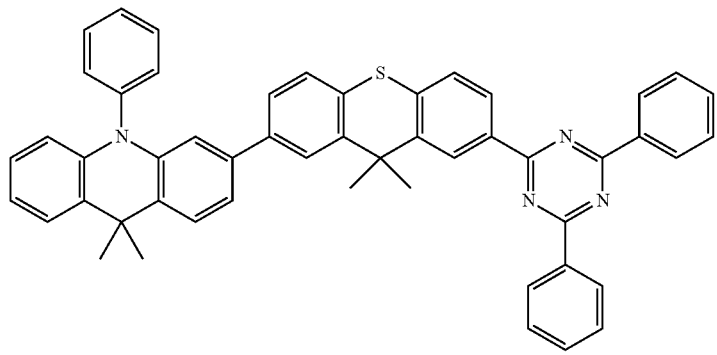
31
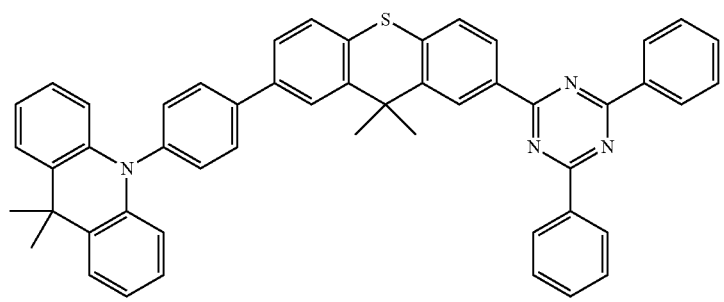
32
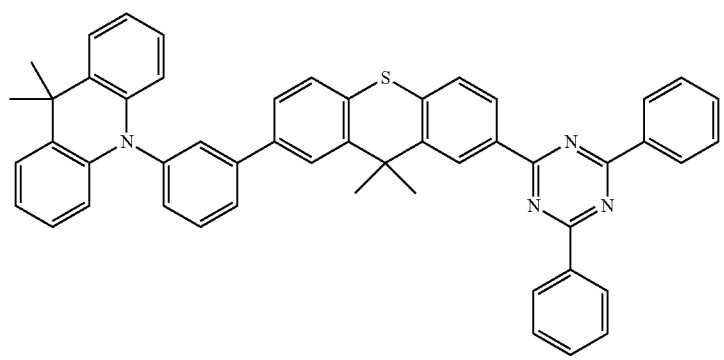
33
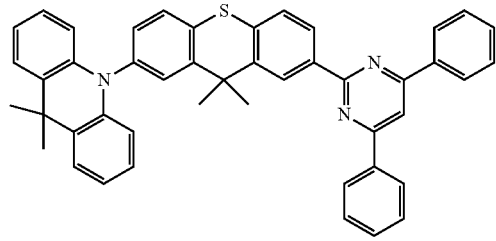
34
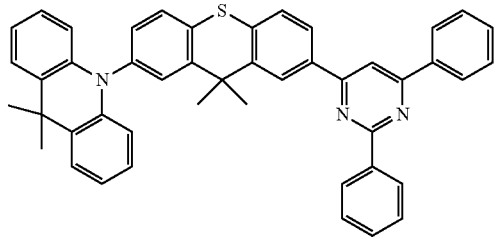
35
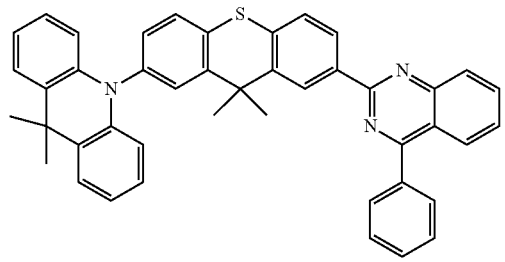
36
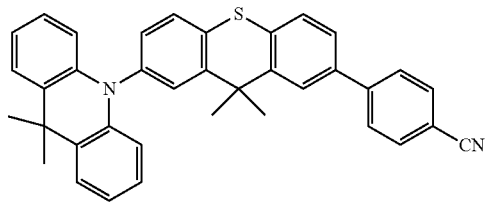
37

-continued
38
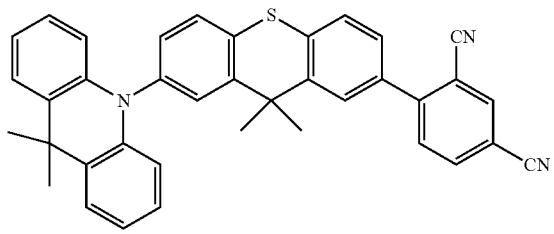
39
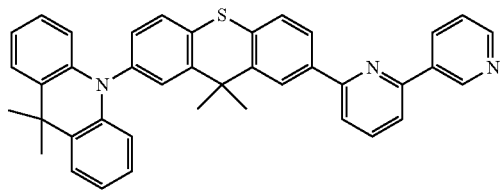
40
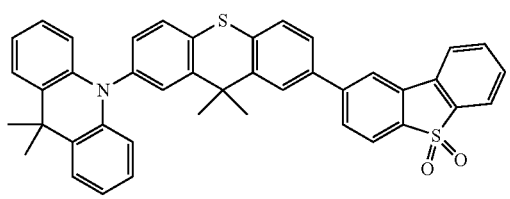
41
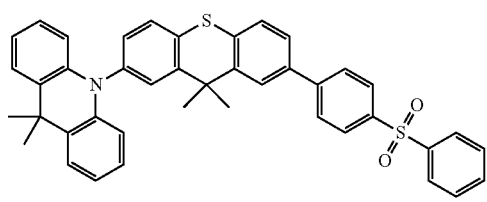
42
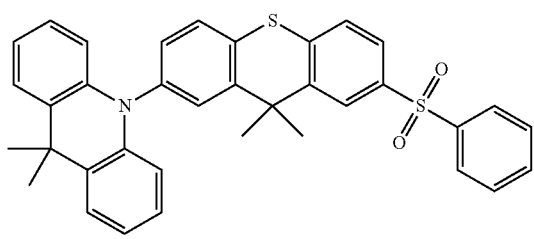
43
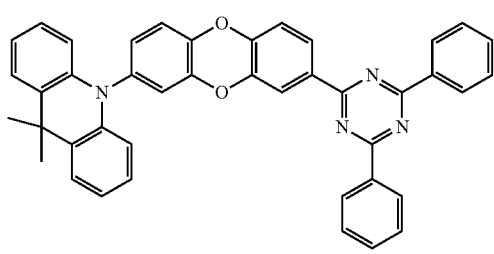
44
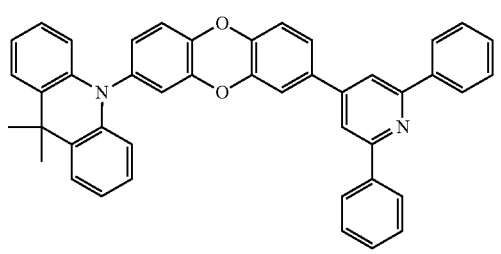
45
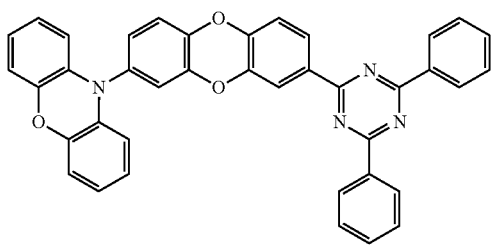
46
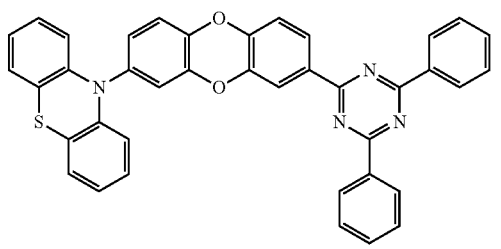
47
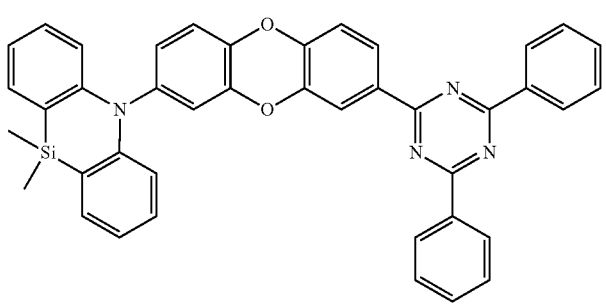

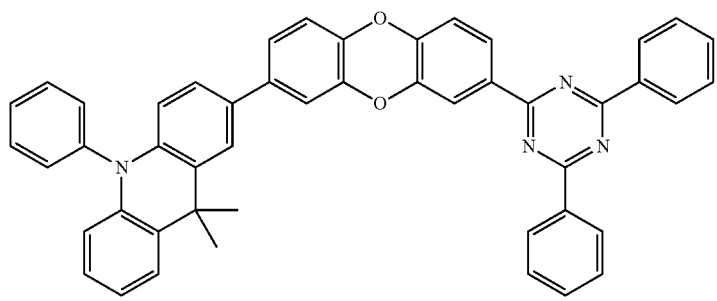
48
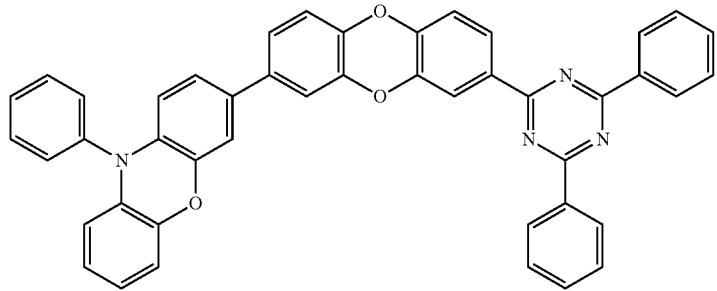
49
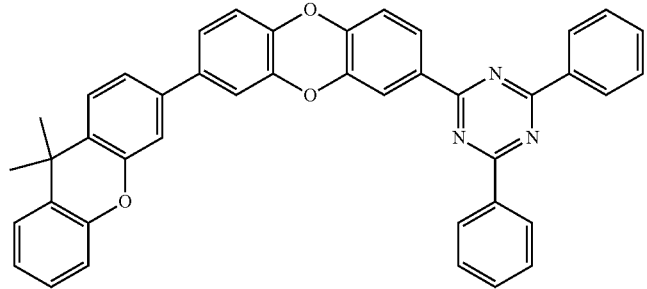
50
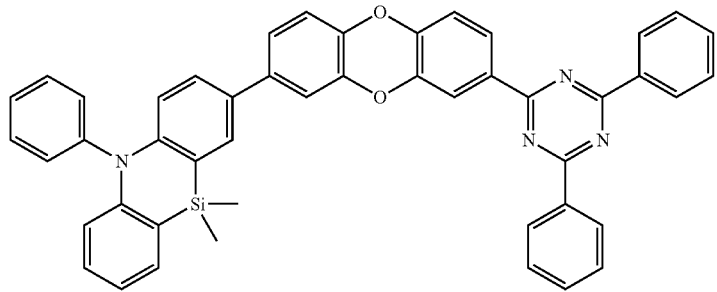
51
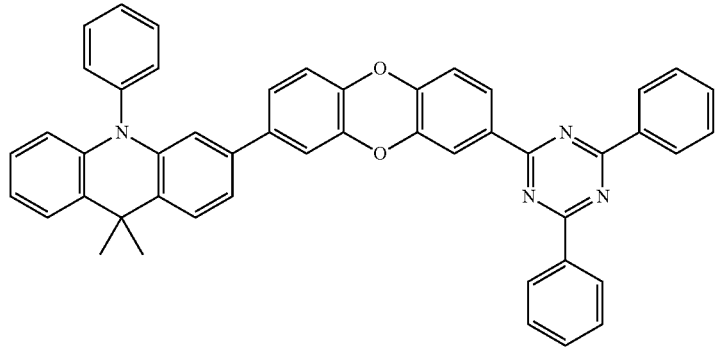
52

-continued
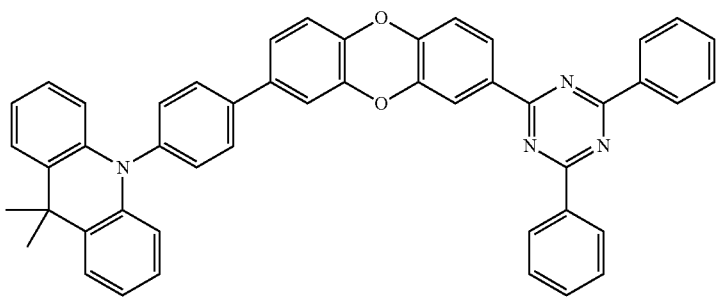
53
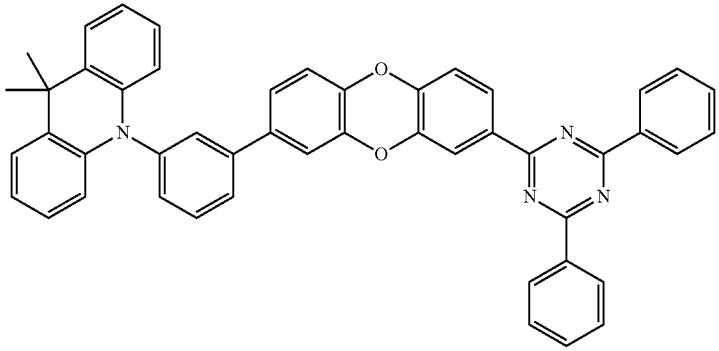
54
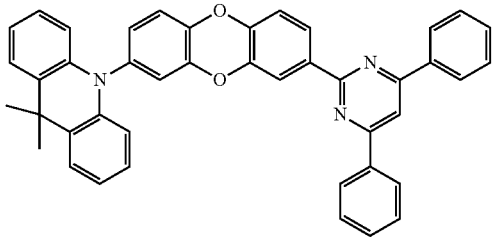
55
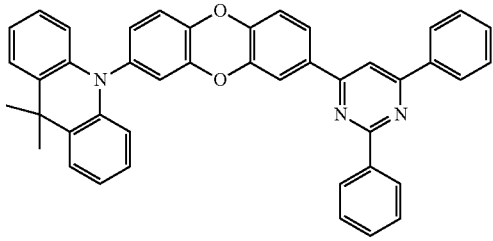
56
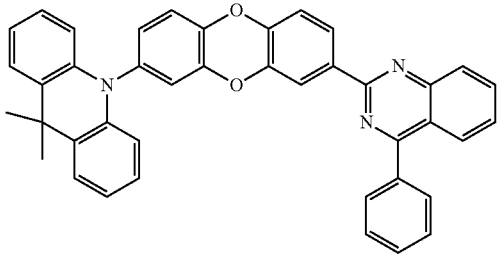
57
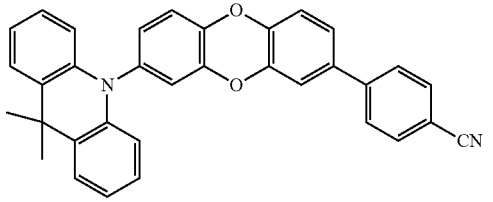
58
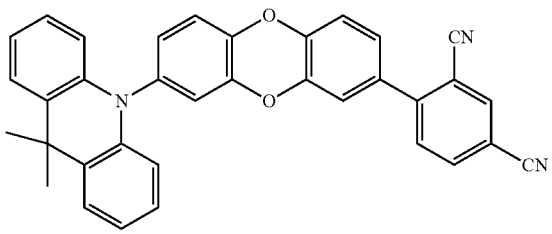
59
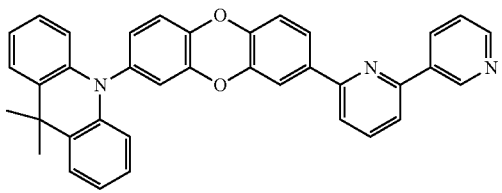
60
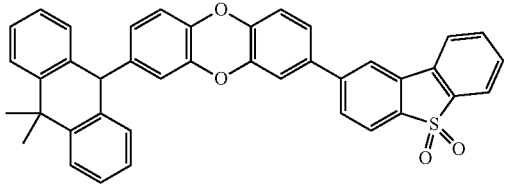
61
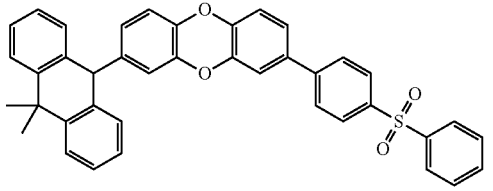
62

63
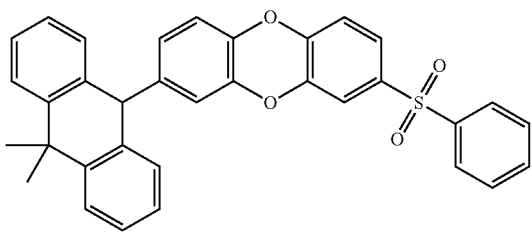
64
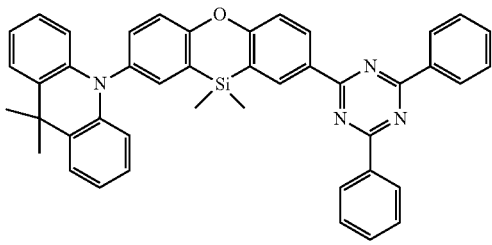
65
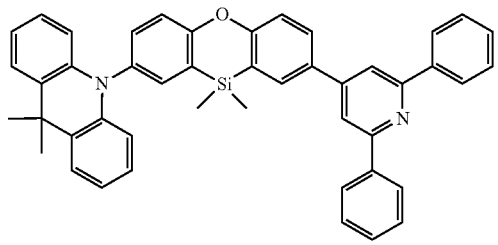
66
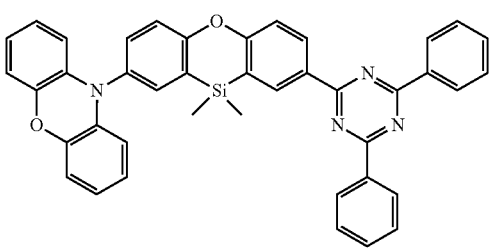
67
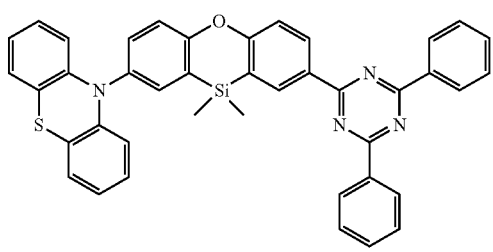
68
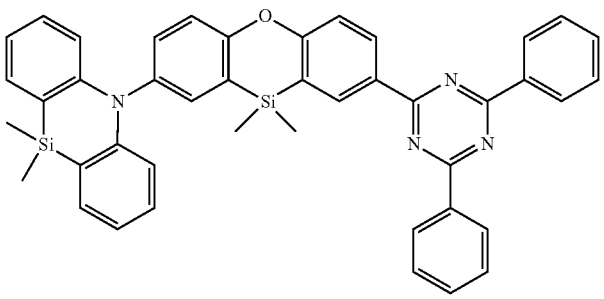
69
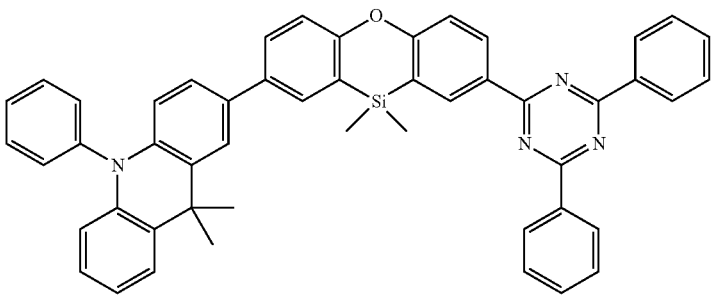
70
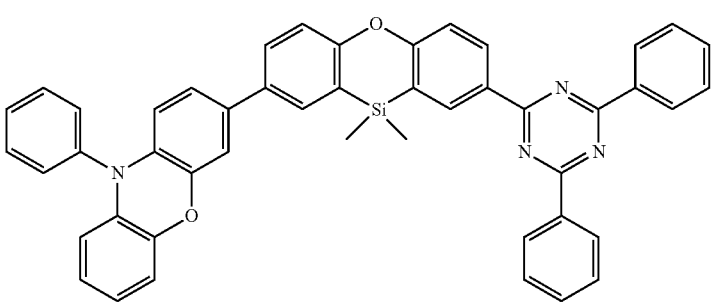

-continued
71
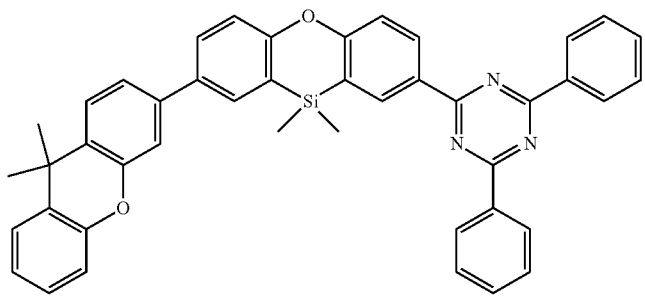
72
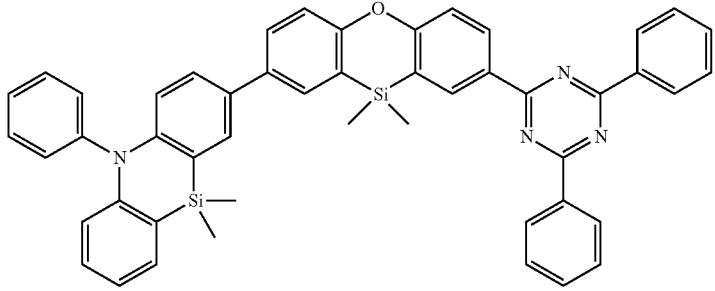
73
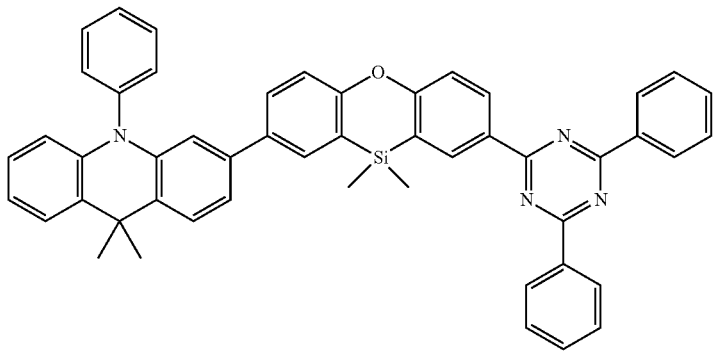
74
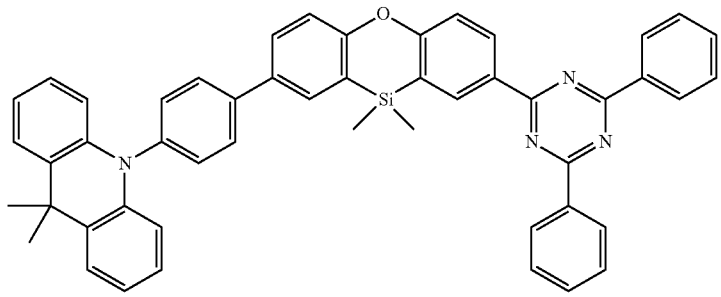
75
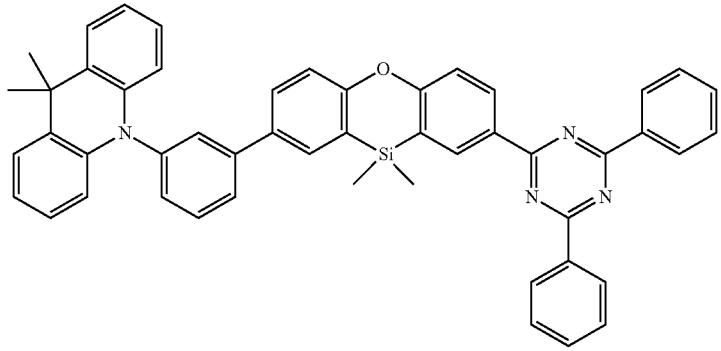

-continued
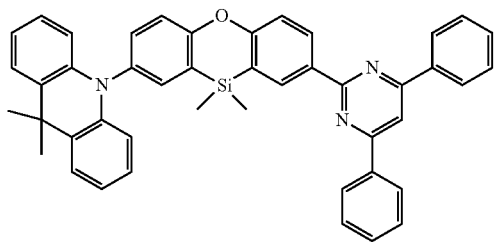
76
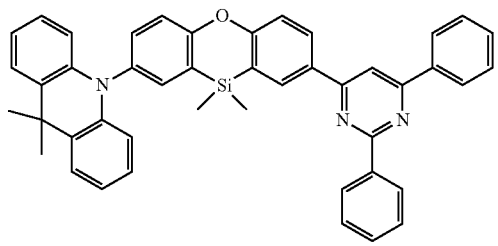
77
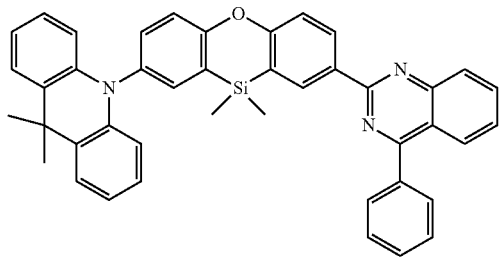
78
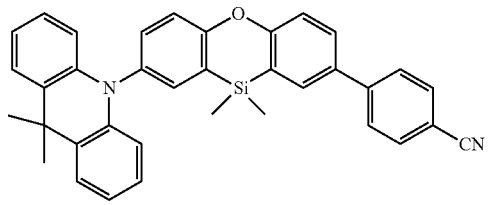
79
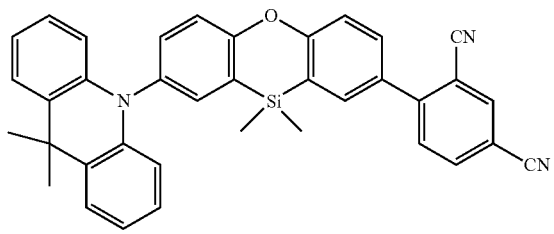
80
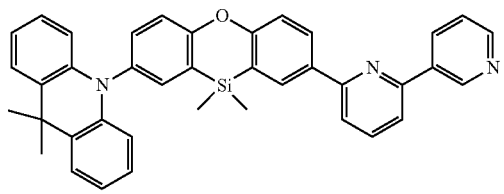
81
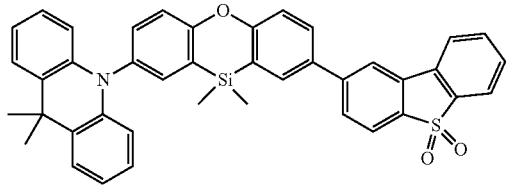
82
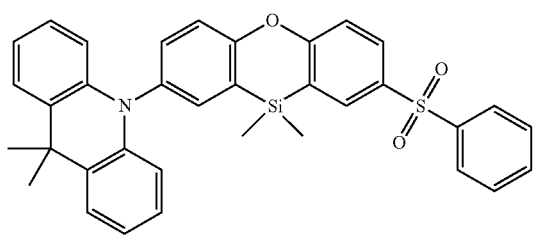
83
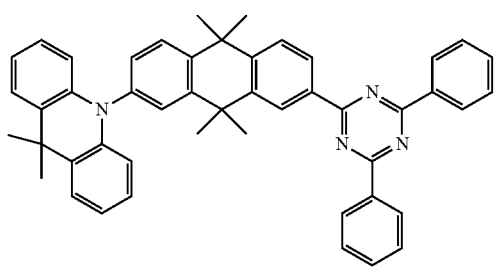
84
85
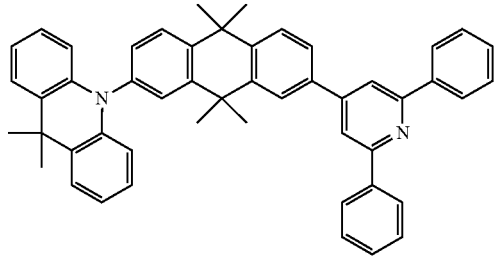
86

-continued
87
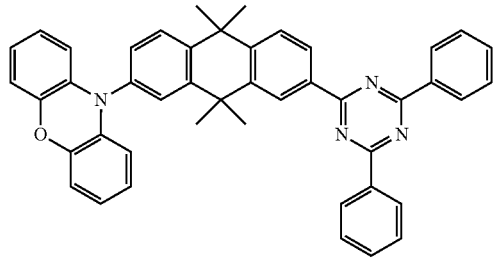
88
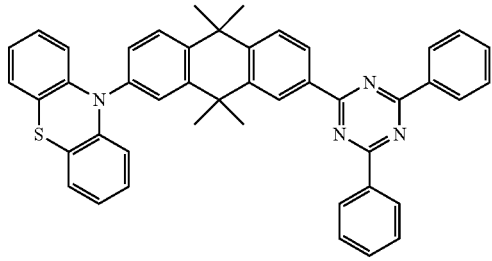
89
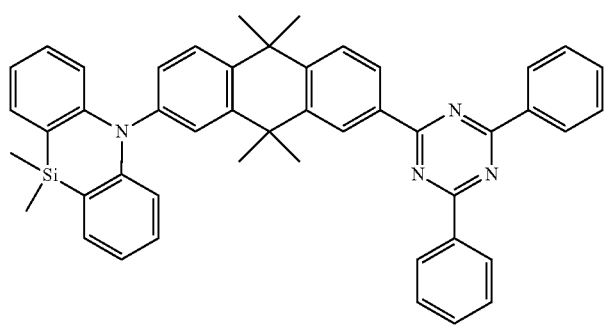
90
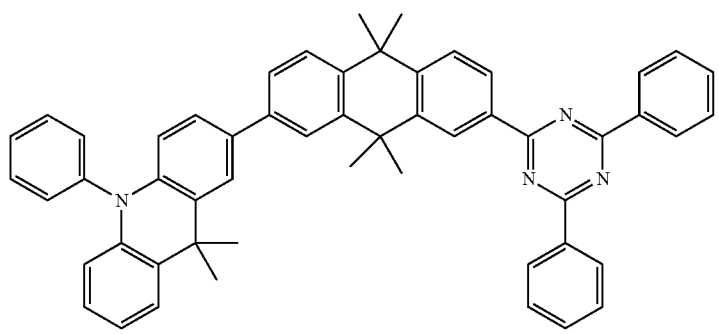
91
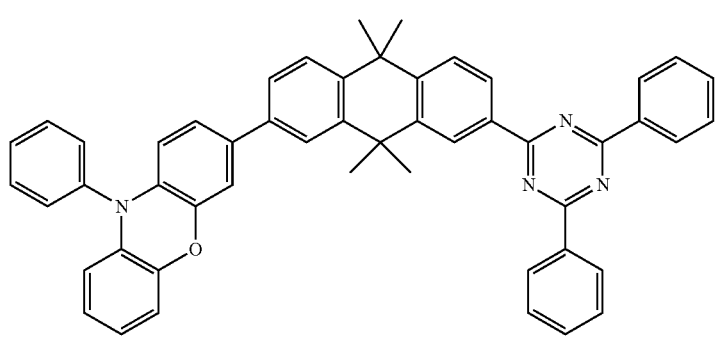
92
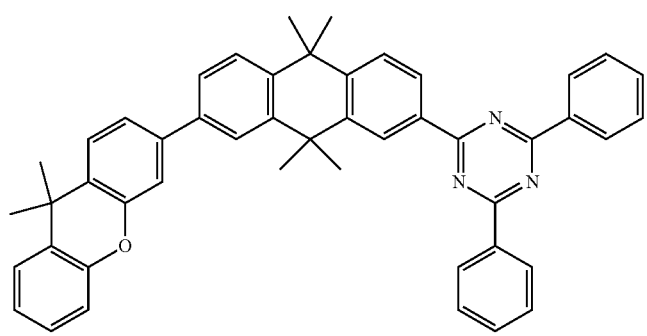

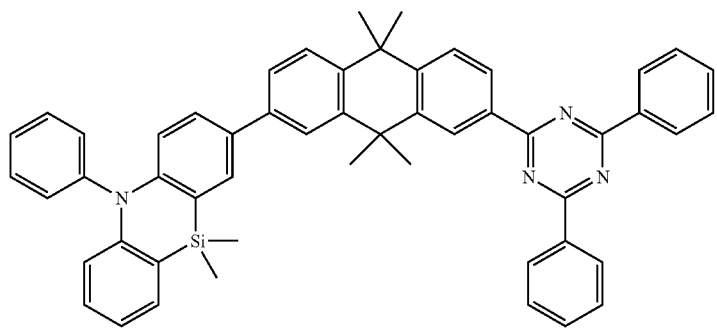
93
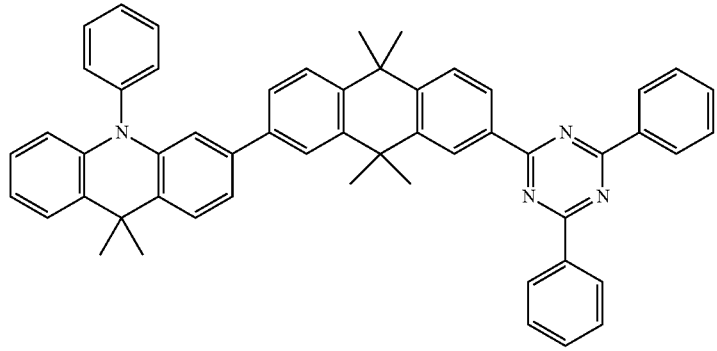
94
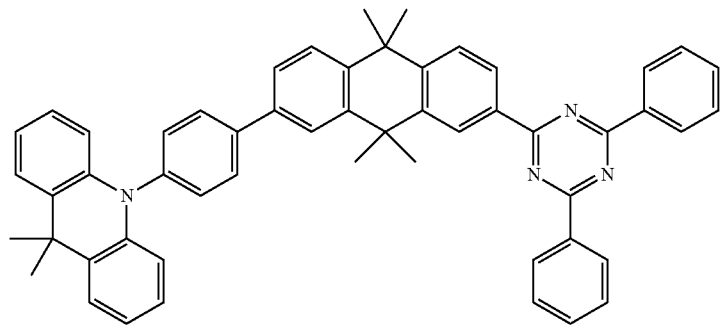
95
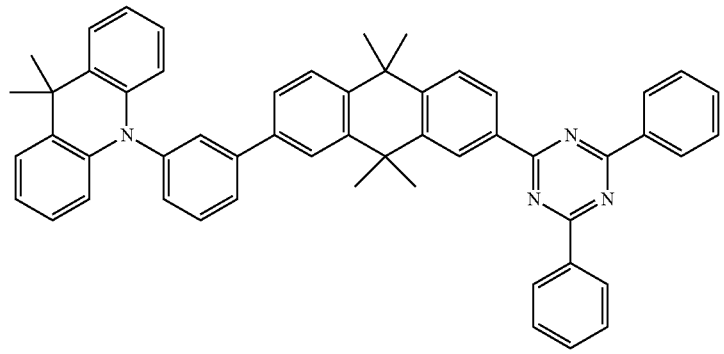
96
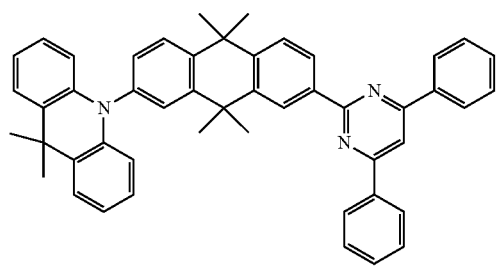
97
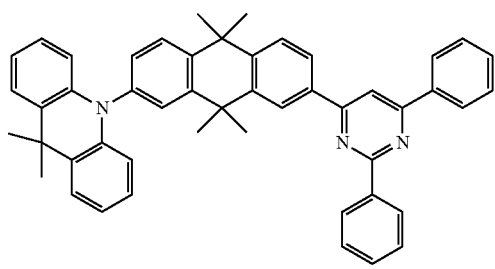
98

99
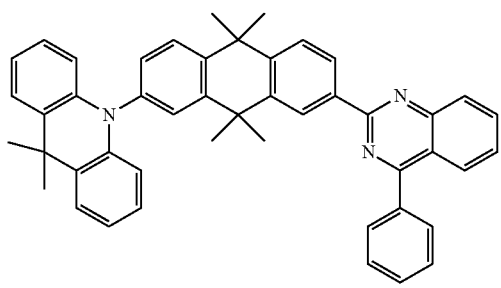
100
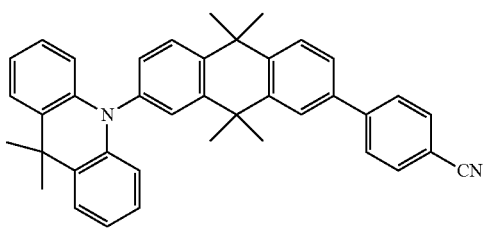
101
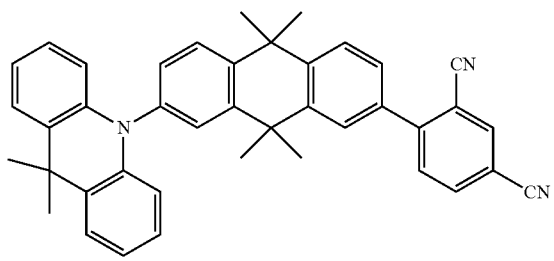
102
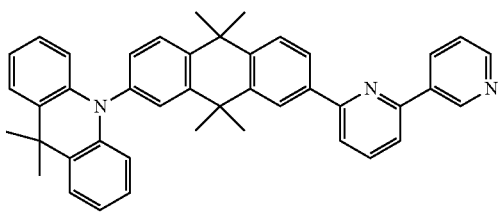
103
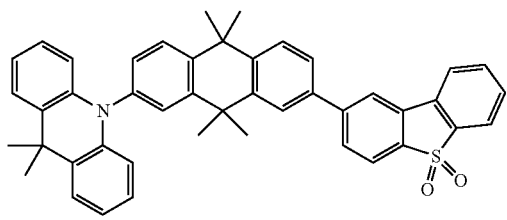
104
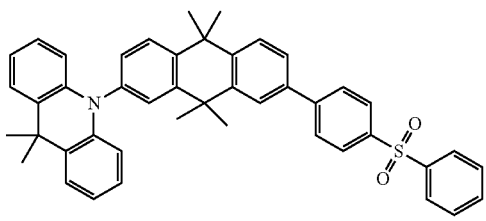
105
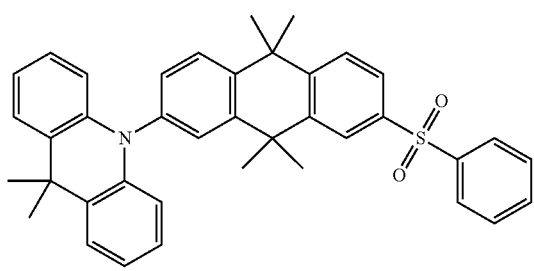
106
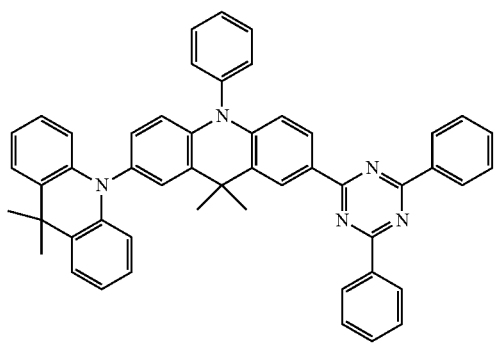
107
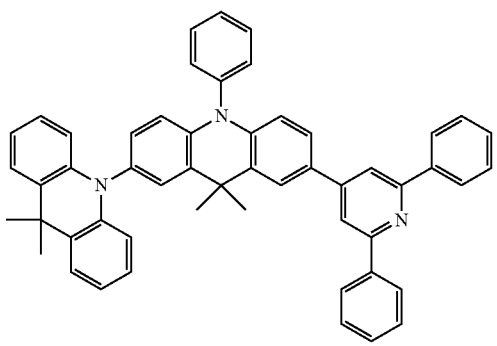

108
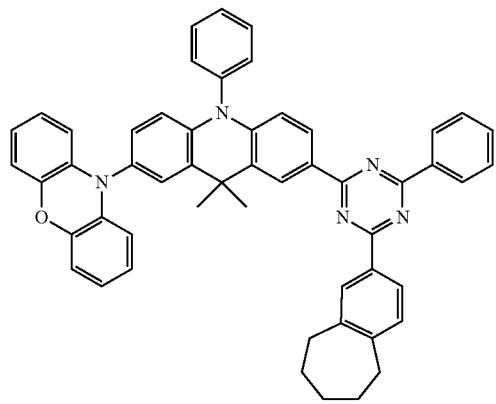
109
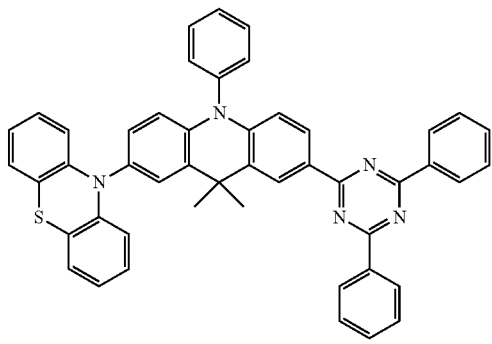
110
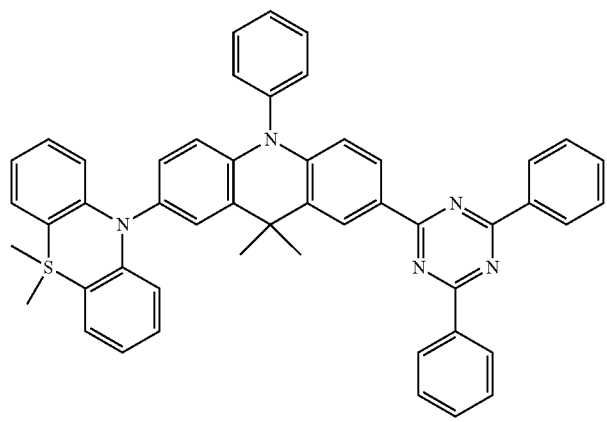
111
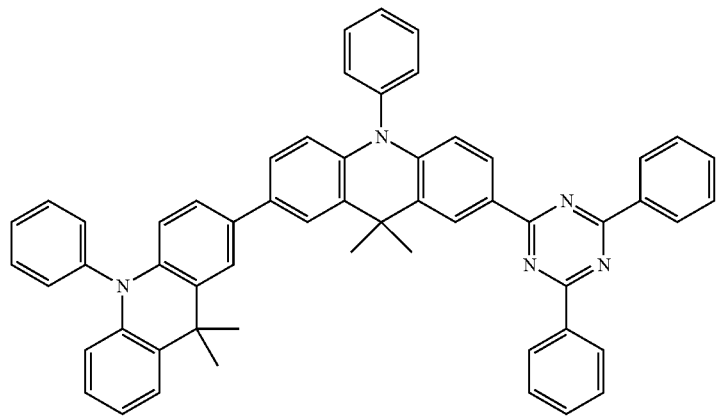

-continued
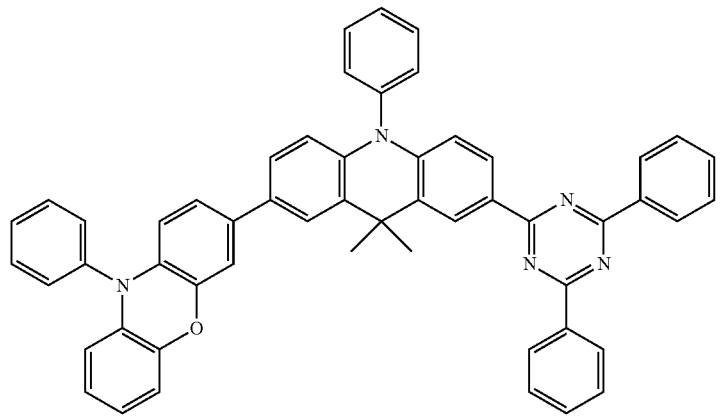
112
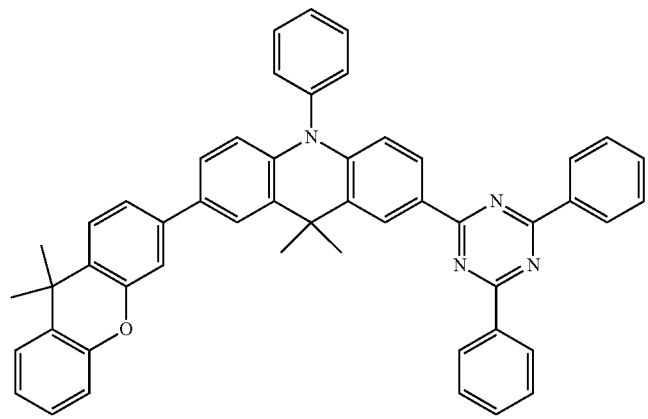
113
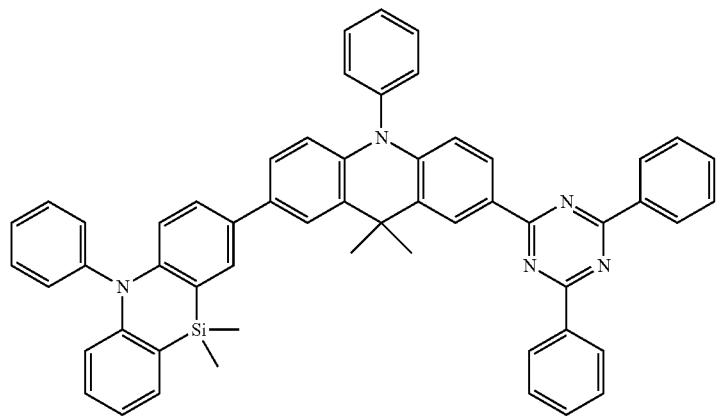
114

-continued
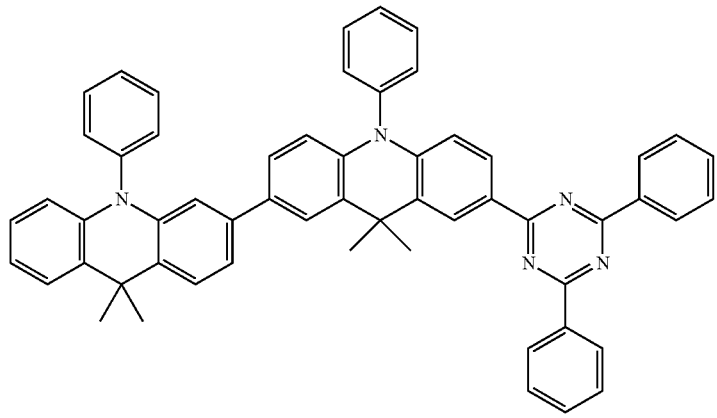
115
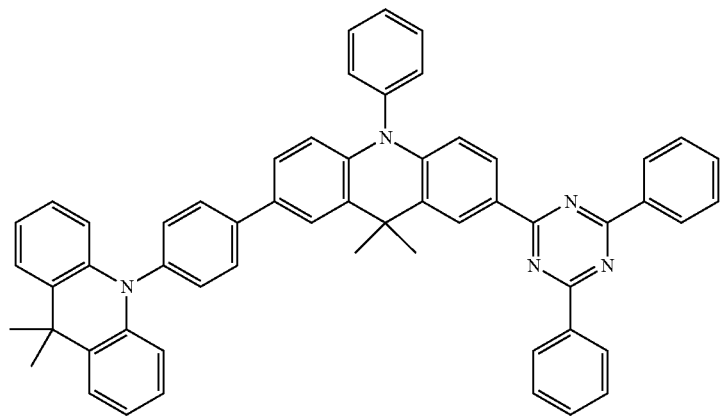
116
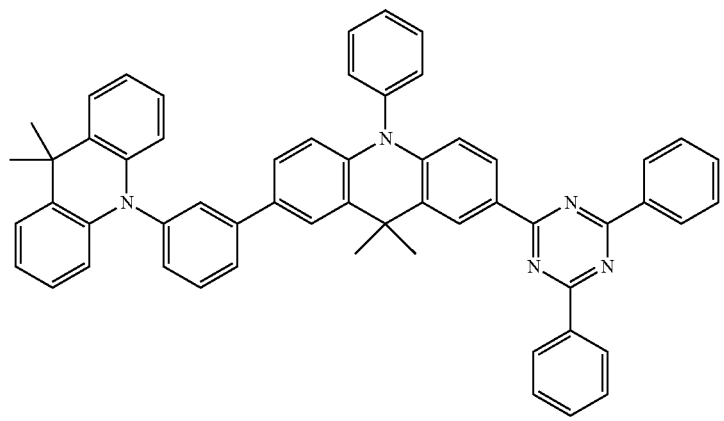
117
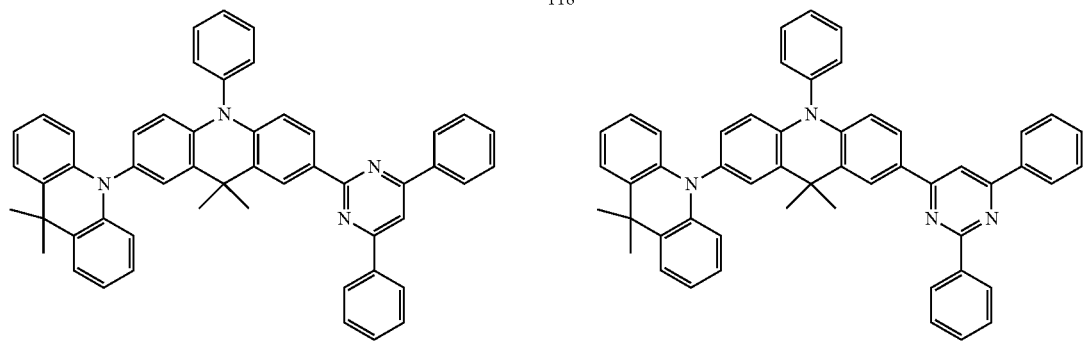
118 119

-continued
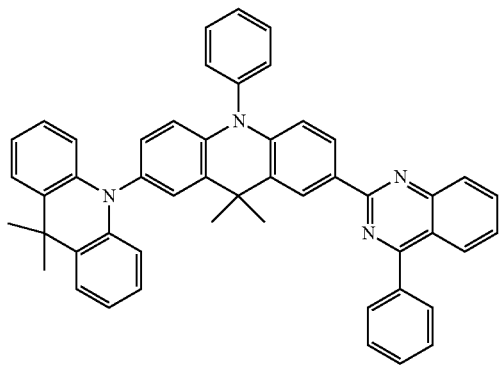
120
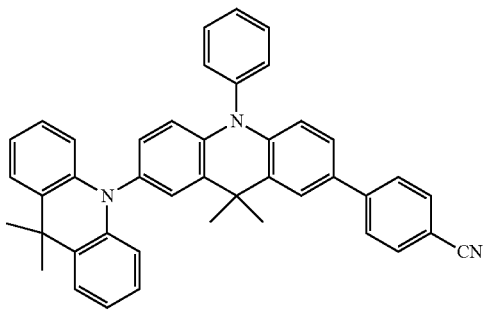
121
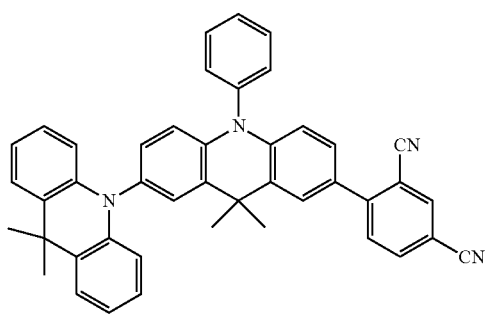
122
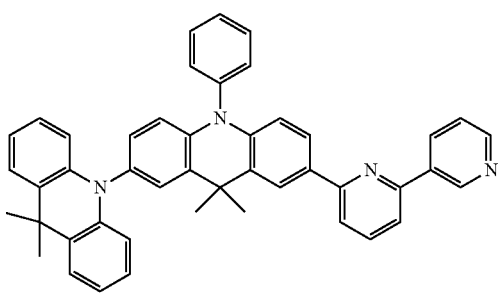
123
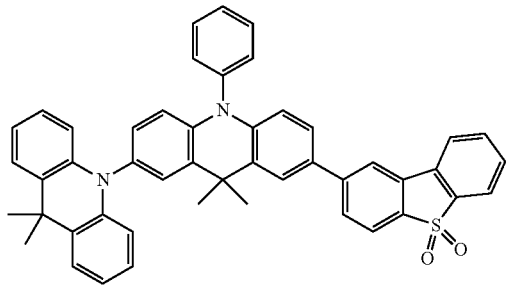
124
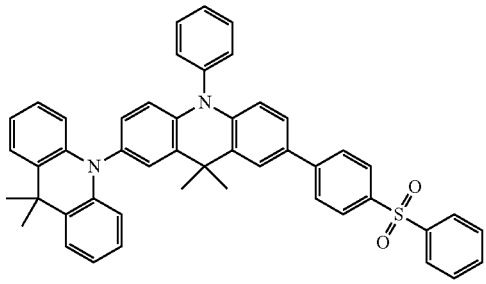
125
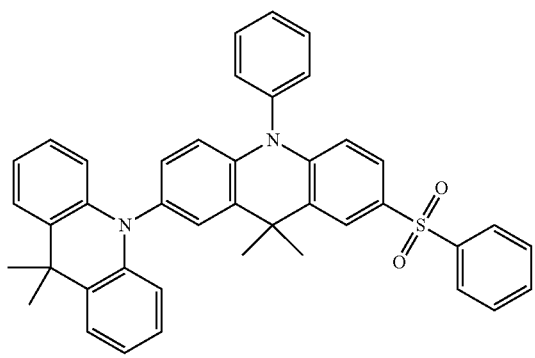
126

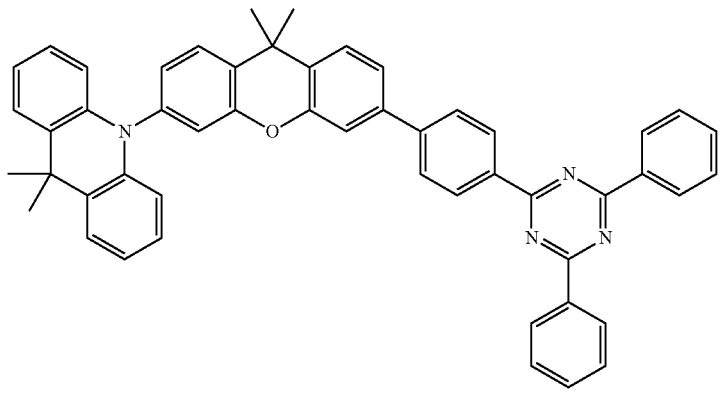
127
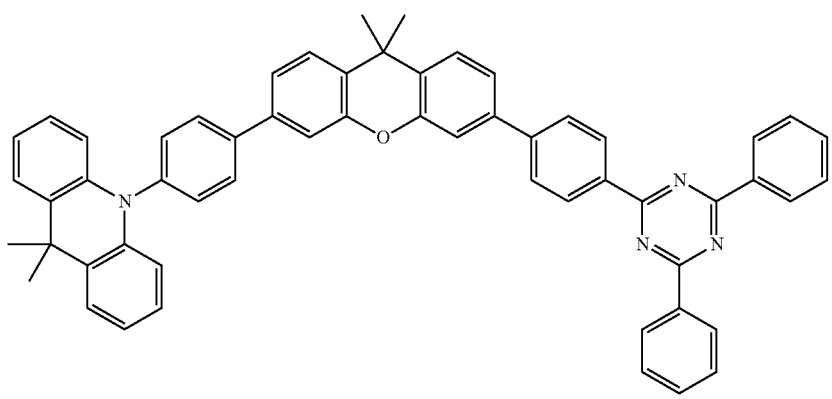
128
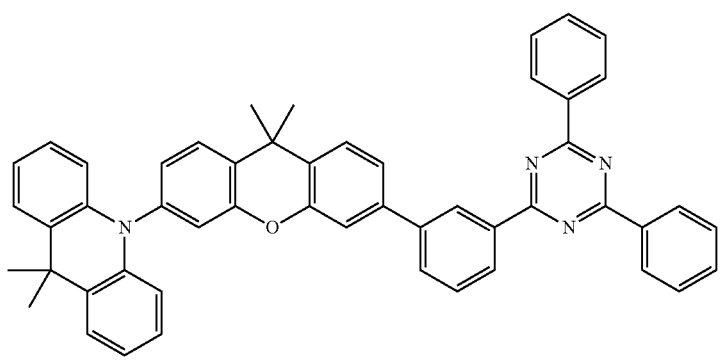
129
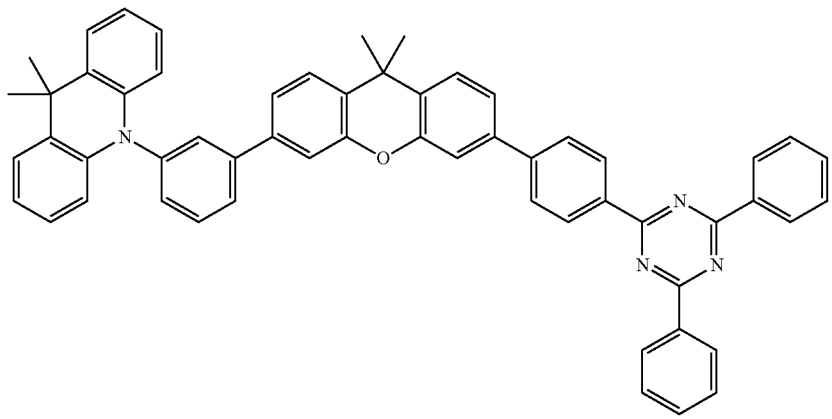
130

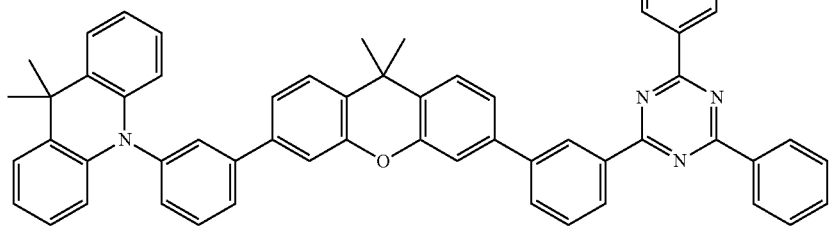
131
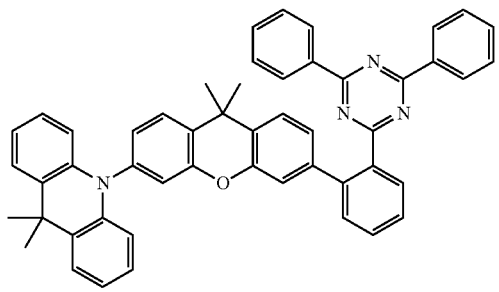
132
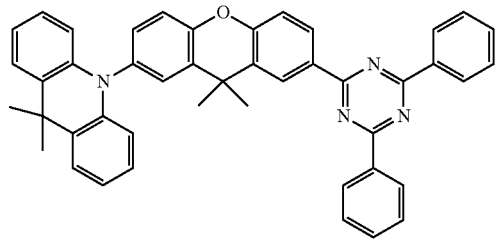
133
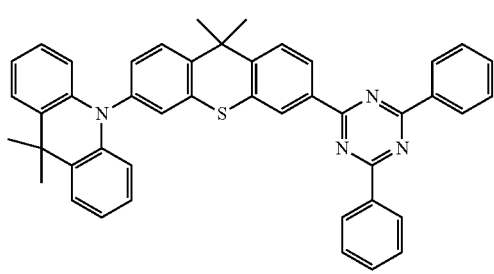
134
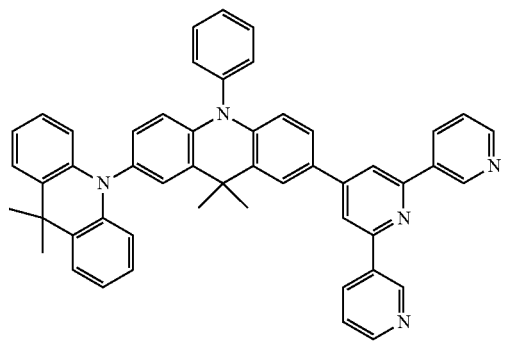
135
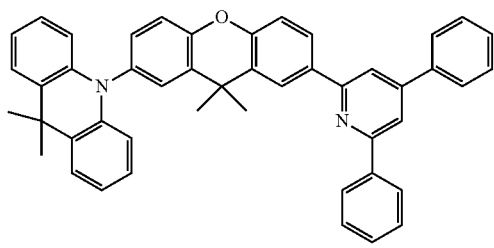
136
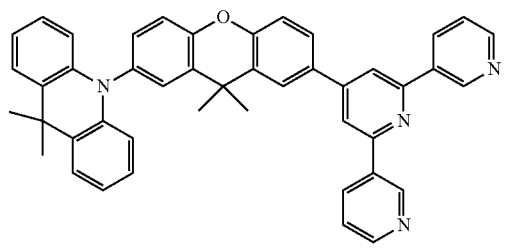
137

-continued
138 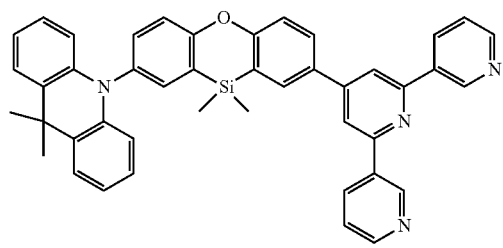
139 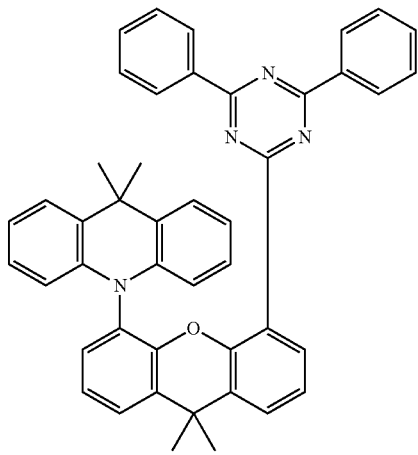
140 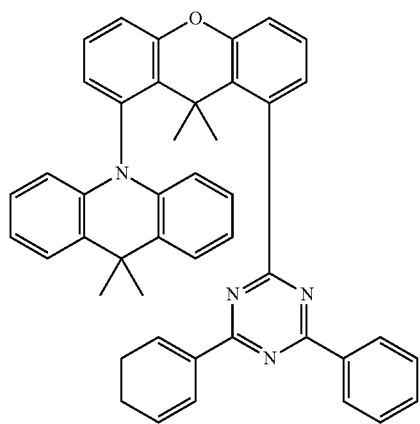
141 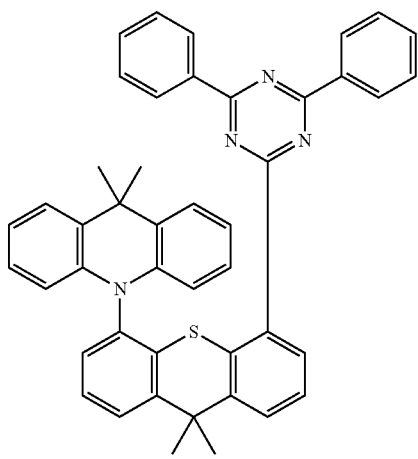
142 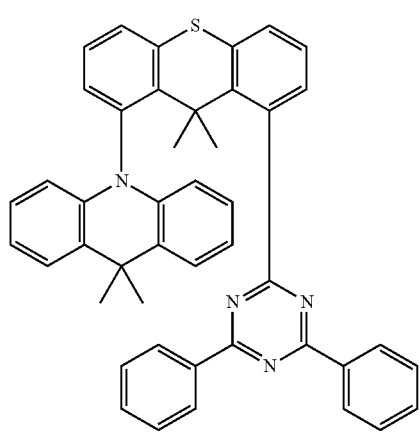
143 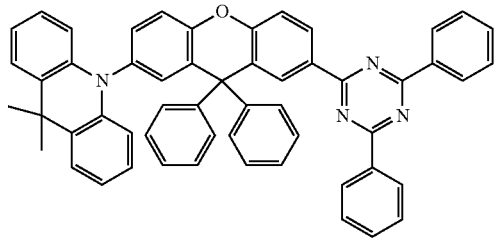

-continued

144

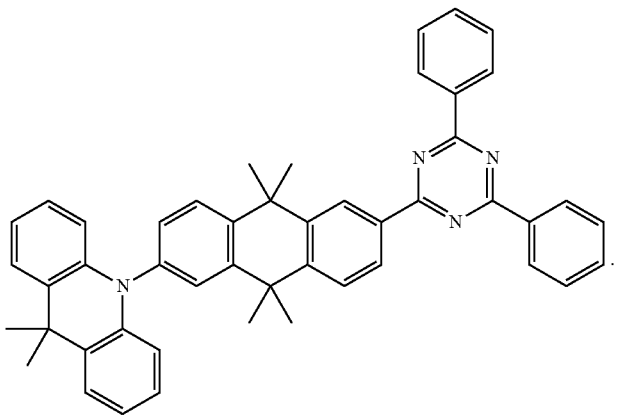

According to embodiments of the present disclosure, both a substituent exhibiting properties of an electron withdrawing group (EWG) and a substituent exhibiting properties of electron donating group (EDG) exists within the condensed cyclic compound, and a difference in energy between a singlet state and a triplet state of the entire compound may be appropriately adjusted by introducing these substituents at appropriate positions. Accordingly, the condensed cyclic compound may exhibit thermally activated delayed fluorescence (TADF).

Singlet energy and triplet energy of the condensed cyclic compound may satisfy the following equation:

$$\Delta Est = S1 - T1 < 0.3 \text{ eV}.$$

The condensed cyclic compound may include a structure comprising Formulae 1 to 4. For example, the condensed cyclic compound may have a structure in which two hexagonal rings are separated from each other by $Y_{101}$ and $Y_{102}$ in Formula 1. In this case, orbital overlap in a molecule is effectively prevented or reduced, and thus, a singlet state does not overlap (or does not substantially overlap) a triplet state. Consequently, the condensed cyclic compound may have a very small ΔEst. Accordingly, reverse intersystem crossing from a triplet excited state to a singlet excited state through thermal activation may be possible even at room temperature, thereby exhibiting delayed fluorescence.

Also, in the condensed cyclic compound, $Ar_1$, which is an electron withdrawing group (EWG) in Formula 4, is substituted with carbon in a hexagonal ring of a core of the compound, for example, a carbon hexagonal ring, so that a highest occupied molecular orbital (HOMO) and a lowest unoccupied molecular orbital (LUMO) of a molecule may be separated more effectively. Furthermore, the condensed cyclic compound may have relatively high charge (hole or electron) transport capability, and an exciton forming ratio in an emission layer of an organic light-emitting device including the condensed cyclic compound represented by Formula 1 may be improved. Accordingly, the organic light-emitting device may have a low driving voltage, high luminescence efficiency, a long lifespan, and high maximum quantum efficiency.

A synthesis method for the condensed cyclic compound represented by Formula 1 would be apparent to those of ordinary skill in the art by referring to the following examples.

At least one condensed cyclic compound represented by Formula 1 may be used between a pair of electrodes constituting an organic light-emitting device. For example, the condensed cyclic compound may be included in at least one layer selected from a hole transport region, an electron transport region, and an emission layer. In one or more embodiments, the condensed cyclic compound of Formula 1 may be used as a material for a capping layer located outside a pair of electrodes of an organic light-emitting device.

Accordingly, in an embodiment, an organic light-emitting device includes: a first electrode; a second electrode facing the first electrode; and an organic layer between the first electrode and the second electrode, the organic layer including an emission layer, wherein the organic layer includes at least one condensed cyclic compound.

The expression "(an organic layer) includes at least one condensed cyclic compound" as used herein may refer to a case in which (an organic layer) includes one or more identical condensed cyclic compounds represented by Formula 1 and a case in which (an organic layer) includes two or more different condensed cyclic compounds represented by Formula 1 (e.g., by Formulae 1A to 1J).

In one embodiment, the first electrode is an anode, and the second electrode is a cathode, and the organic layer further includes a hole transport region between the first electrode and the emission layer and an electron transport region between the emission layer and the second electrode; and the hole transport region includes a hole injection layer, a hole transport layer, an emission auxiliary layer, an electron blocking layer, or any combination thereof, and the electron transport region includes a buffer layer, a hole blocking layer, an electron control layer, an electron transport layer, an electron injection layer, or any combination thereof.

In one embodiment, the emission layer may include a dopant and a host, and the dopant may include at least one condensed cyclic compound.

The host of the emission layer may include at least one selected from an anthracene-based compound, a pyrene-based compound, and a spiro-bifluorene-based compound, but embodiments of the present disclosure are not limited thereto.

For example, the dopant of the emission layer may include, in addition to the at least one condensed cyclic compound, an amine-based compound, but embodiments of the present disclosure are not limited thereto. In this case, the at least one condensed cyclic compound and the amine-based compound may serve as dopants together.

In one or more embodiments, the emission layer may include a dopant and a host, and the host may include at least one condensed cyclic compound.

The dopant of the emission layer may include at least one selected from a styryl-based compound and an amine-based compound, but embodiments of the present disclosure are not limited thereto.

In one embodiment, the emission layer of the organic light-emitting device may be a first emission layer for emitting first color light, the organic light-emitting device may further include i) at least one second emission layer for emitting second color light, or ii) at least one second emission layer for emitting second color light and at least one third emission layer for emitting third color light, between the first electrode and the second electrode, a maximum emission wavelength of the first color light, a maximum emission wavelength of the second color light, and a maximum emission wavelength of the third color light may be identical to or different from each other, and the first color light and the second color light may be emitted in the form of mixed light, or the first color light, the second color light, and the third color light may be emitted in the form of mixed light.

The organic light-emitting device may further include at least one selected from a first capping layer (disposed (e.g., positioned) in a pathway along which light generated in an emission layer proceeds toward the outside through the first electrode) and a second capping layer (disposed in a pathway along which light generated in an emission layer proceeds toward the outside through the second electrode), and the at least one selected from the first capping layer and the second capping layer may include at least one condensed cyclic compound represented by Formula 1.

For example, the organic light-emitting device may have i) a stacked structure including a first electrode, an organic layer, a second electrode, and a second capping layer which are sequentially stacked in this stated order, ii) a stacked structure including a first capping layer, a first electrode, an organic layer, and a second electrode which are sequentially stacked in this stated order, or iii) a stacked structure including a first capping layer, a first electrode, an organic layer, a second electrode, and a second capping layer which are sequentially stacked in this stated order, and at least one selected from the first capping layer and the second capping layer may include the condensed cyclic compound.

The term "organic layer" used herein may refer to a single layer and/or a plurality of layers disposed between the first electrode and the second electrode of the organic light-emitting device. A material included in the "organic layer" is not limited to an organic material.

Description of FIG. 1

Figure 1:
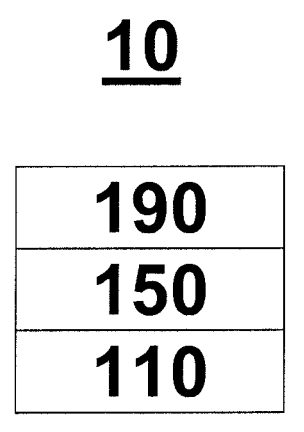

FIG. 1 is a schematic view of an organic light-emitting device 10 according to an embodiment. The organic light-emitting device 10 includes a first electrode 110, an organic layer 150, and a second electrode 190.

Hereinafter, the structure of the organic light-emitting device 10 according to an embodiment and a method of manufacturing the organic light-emitting device 10 will be described in connection with FIG. 1.

First Electrode 110

In FIG. 1, a substrate may be additionally disposed under the first electrode 110 or above the second electrode 190. The substrate may be a glass substrate or a plastic substrate, each having excellent mechanical strength, thermal stability, transparency, surface smoothness, ease of handling, and/or water resistance.

The first electrode 110 may be formed by depositing or sputtering a material for forming the first electrode 110 on the substrate. When the first electrode 110 is an anode, the material for forming the first electrode may be selected from materials with a high work function so as to facilitate hole injection.

The first electrode 110 may be a reflective electrode, a semi-transmissive electrode, or a transmissive electrode. When the first electrode 110 is a transmissive electrode, a material for forming the first electrode may be selected from indium tin oxide (ITO), indium zinc oxide (IZO), tin oxide ($SnO_2$), zinc oxide (ZnO), and any combinations thereof, but embodiments of the present disclosure are not limited thereto. In one or more embodiments, when the first electrode 110 is a semi-transmissive electrode or a reflective electrode, a material for forming the first electrode may be selected from magnesium (Mg), silver (Ag), aluminum (Al), aluminum-lithium (Al—Li), calcium (Ca), magnesium-indium (Mg—In), magnesium-silver (Mg—Ag), and any combinations thereof, but embodiments of the present disclosure are not limited thereto.

The first electrode 110 may have a single-layered structure, or a multi-layered structure including two or more layers. For example, the first electrode 110 may have a three-layered structure of ITO/Ag/ITO, but the structure of the first electrode 110 is not limited thereto.

Organic Layer 150

The organic layer 150 may be disposed on the first electrode 110. The organic layer 150 may include an emission layer.

The organic layer 150 may further include a hole transport region between the first electrode 110 and the emission layer, and an electron transport region between the emission layer and the second electrode 190.

Hole Transport Region in Organic Layer 150

The hole transport region may have i) a single-layered structure including a single layer including a single material, ii) a single-layered structure including a single layer including a plurality of different materials, or iii) a multi-layered structure having a plurality of layers including a plurality of different materials.

The hole transport region may include at least one layer selected from a hole injection layer, a hole transport layer, an emission auxiliary layer, and an electron blocking layer.

For example, the hole transport region may have a single-layered structure including a single layer including a plurality of different materials, or a multi-layered structure having a hole injection layer/hole transport layer structure, a hole injection layer/hole transport layer/emission auxiliary layer structure, a hole injection layer/emission auxiliary layer structure, a hole transport layer/emission auxiliary layer structure, or a hole injection layer/hole transport layer/electron blocking layer structure, wherein for each structure, constituting layers are sequentially stacked from the first electrode 110 in this stated order, but the structure of the hole transport region is not limited thereto.

The hole transport region may include at least one selected from m-MTDATA, TDATA, 2-TNATA, NPB (NPD), p-NPB, TPD, Spiro-TPD, Spiro-NPB, methylated NPB, TAPC, HMTPD, 4,4',4''-tris(N-carbazolyl)triphenylamine (TCTA), polyaniline/dodecylbenzenesulfonic acid (PANI/DBSA), poly(3,4-ethylenedioxythiophene)/poly (4-styrenesulfonate) (PEDOT/PSS), polyaniline/camphor sulfonic acid (PANT/CSA), polyaniline/poly(4-styrenesulfonate) (PANT/PSS), a compound represented by Formula 201, and a compound represented by Formula 202:

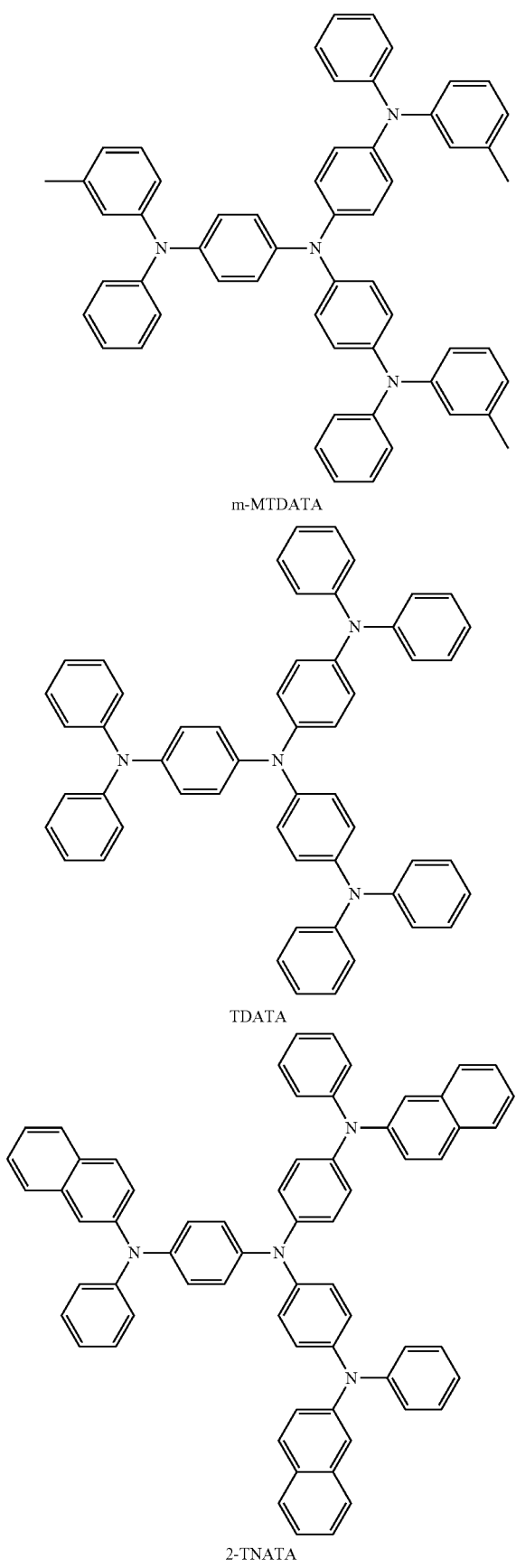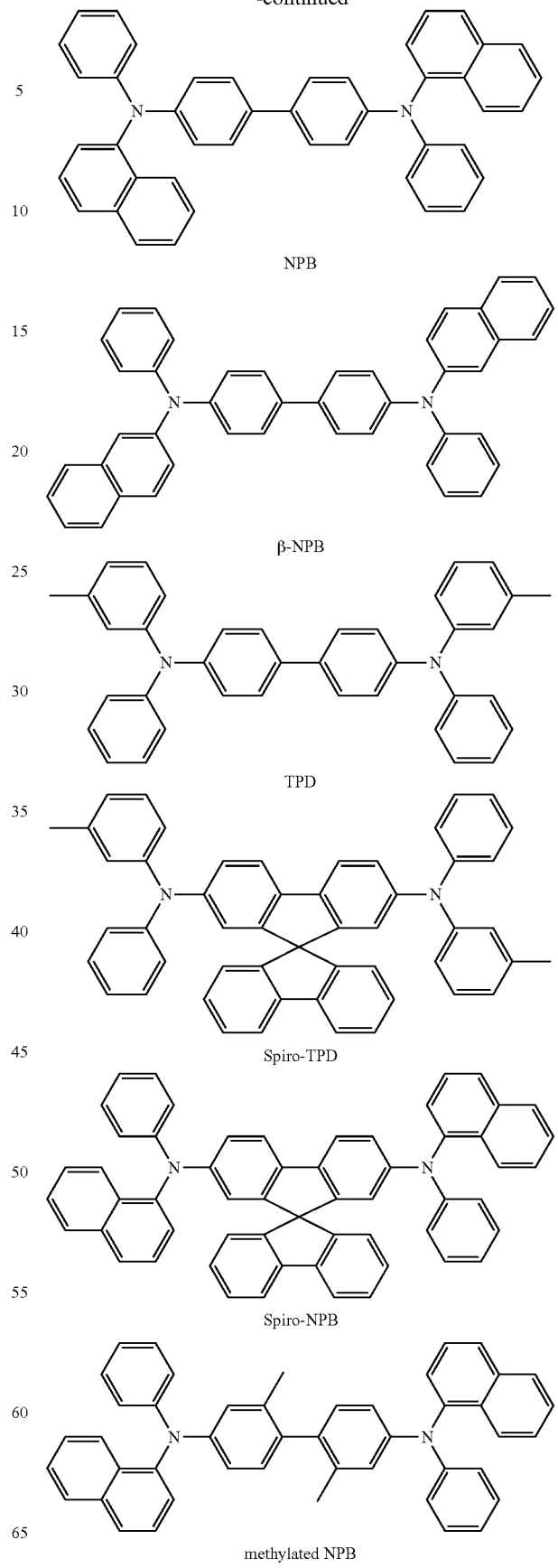

-continued

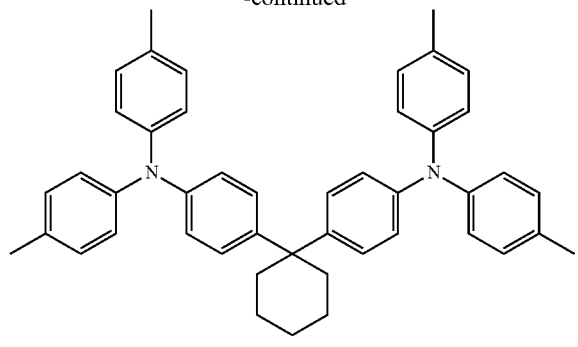

TAPC

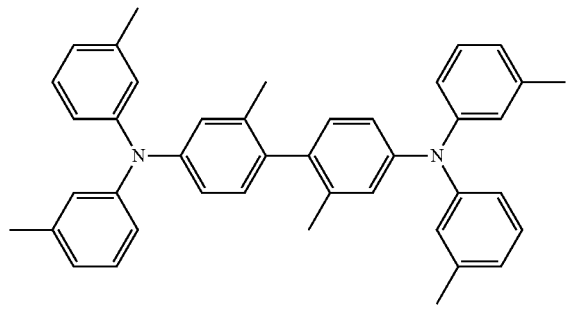

HMTPD

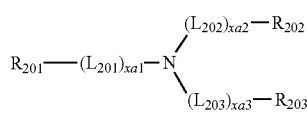

Formula 201

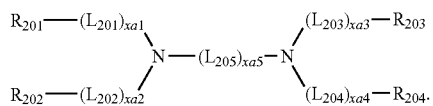

Formula 202

In Formulae 201 and 202, $L_{201}$ to $L_{204}$ may each independently be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, $L_{205}$ may be selected from *—O—*', *—S—*', *—N($Q_{201}$)- *', a substituted or unsubstituted $C_1$-$C_{20}$ alkylene group, a substituted or unsubstituted $C_2$-$C_{20}$ alkenylene group, a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, xa1 to xa4 may each independently be an integer from 0 to 3, xa5 may be an integer from 1 to 10, $R_{201}$ to $R_{204}$ and $Q_{201}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, and

* and *' each indicate a binding site to a neighboring atom.

For example, in Formula 202, $R_{201}$ and $R_{202}$ may optionally be linked via a single bond, a dimethyl-methylene group, or a diphenyl-methylene group, and $R_{203}$ and $R_{204}$ may optionally be linked via a single bond, a dimethyl-methylene group, or a diphenyl-methylene group.

In one or more embodiments, in Formulae 201 and 202, $L_{201}$ to $L_{205}$ may each independently be selected from:

a phenylene group, a pentalenylene group, an indenylene group, a naphthylene group, an azulenylene group, a heptalenylene group, an indacenylene group, an acenaphthylene group, a fluorenylene group, a spiro-bifluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group; and a phenylene group, a pentalenylene group, an indenylene group, a naphthylene group, an azulenylene group, a heptalenylene group, an indacenylene group, an acenaphthylene group, a fluorenylene group, a spiro-bifluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, —Si($Q_{31}$)($Q_{32}$)($Q_{33}$), and —N($Q_{31}$)($Q_{32}$), and $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

In one or more embodiments, xa1 to xa4 may each independently be 0, 1, or 2.

In one or more embodiments, xa5 may be 1, 2, 3, or 4.

In one or more embodiments, $R_{201}$ to $R_{204}$ and $Q_{201}$ may each independently be selected from:

a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group; and a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, —Si($Q_{31}$)($Q_{32}$)($Q_{33}$), and —N($Q_{31}$)($Q_{32}$), and $Q_{31}$ to $Q_{33}$ are the same as described above.

In one or more embodiments, at least one of $R_{201}$ to $R_{203}$ in Formula 201 may be selected from:

a fluorenyl group, a spiro-bifluorenyl group, a carbazolyl group, a dibenzofuranyl group, and a dibenzothiophenyl group; and a fluorenyl group, a spiro-bifluorenyl group, a carbazolyl group, a dibenzofuranyl group, and a dibenzothiophenyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a naphthyl group, a fluorenyl group, a spiro-bifluorenyl group, a carbazolyl group, a dibenzofuranyl group, and a dibenzothiophenyl group, but embodiments of the present disclosure are not limited thereto.

In one or more embodiments, in Formula 202, i) $R_{201}$ and $R_{202}$ may be linked via a single bond, and/or ii) $R_{203}$ and $R_{204}$ may be linked via a single bond.

In one or more embodiments, at least one of $R_{201}$ to $R_{204}$ in Formula 202 may be selected from:

a carbazolyl group; and a carbazolyl group substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a naphthyl group, a fluorenyl group, a spiro-bifluorenyl group, a carbazolyl group, a dibenzofuranyl group, and a dibenzothiophenyl group, but embodiments of the present disclosure are not limited thereto.

The compound represented by Formula 201 may be represented by Formula 201A:

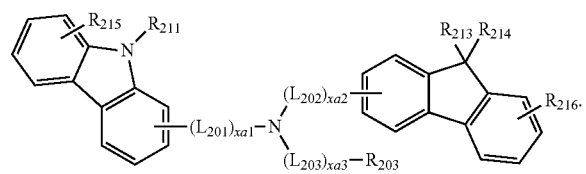

Formula 201A

In one embodiment, the compound represented by Formula 201 may be represented by Formula 201A(1) below, but embodiments of the present disclosure are not limited thereto:

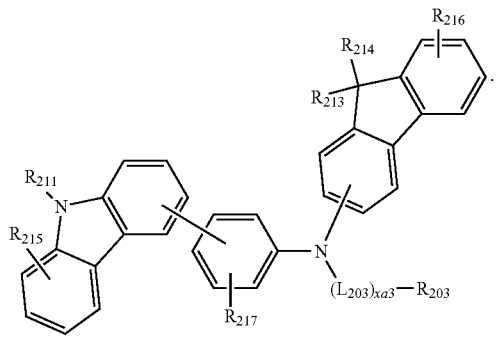

Formula 201A(1)

In one embodiment, the compound represented by Formula 201 may be represented by Formula 201A-1 below, but embodiments of the present disclosure are not limited thereto:

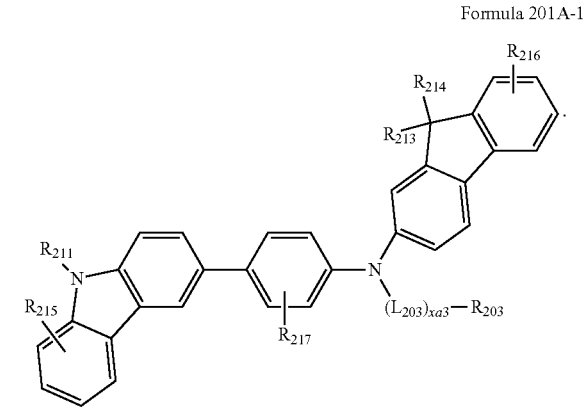

Formula 201A-1

In one embodiment, the compound represented by Formula 202 may be represented by Formula 202A:

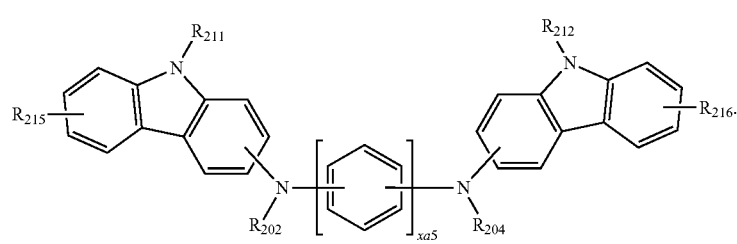

Formula 202A

In one embodiment, the compound represented by Formula 202 may be represented by Formula 202A-1:

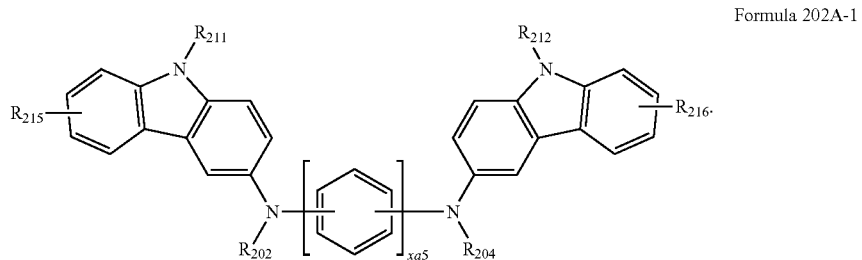

Formula 202A-1

In Formulae 201A, 201A(1), 201A-1, 202A, and 202A-1, definitions for $L_{201}$ to $L_{203}$, xa1 to xa3, xa5, and $R_{202}$ to $R_{204}$ are respectively the same as those provide above, definition for $R_{211}$ and $R_{212}$ may be understood by referring to the description provided herein in connection with $R_{203}$, and $R_{213}$ to $R_{217}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group.

The hole transport region may include at least one compound selected from Compounds HT1 to HT39, but embodiments of the present disclosure are not limited thereto:

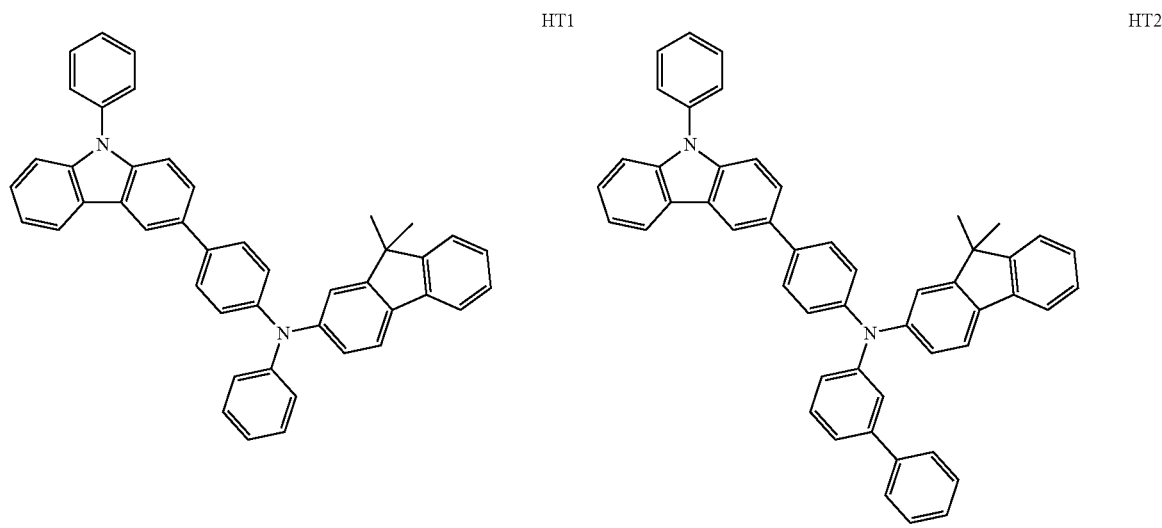

-continued
HT3
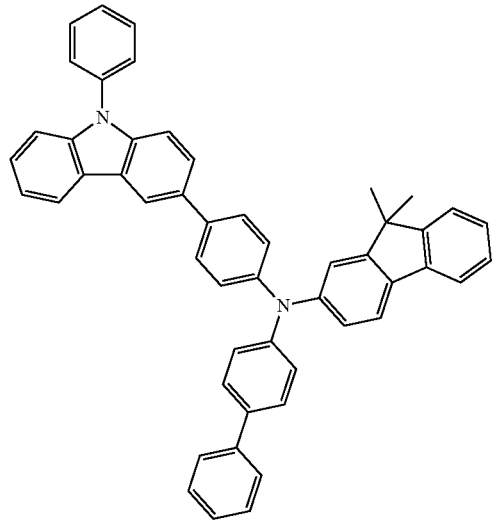
HT4
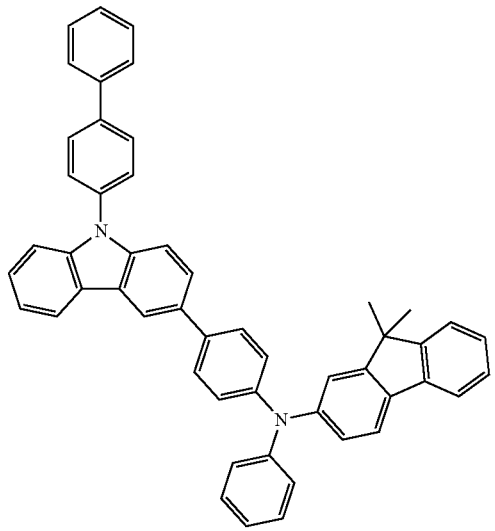
HT5
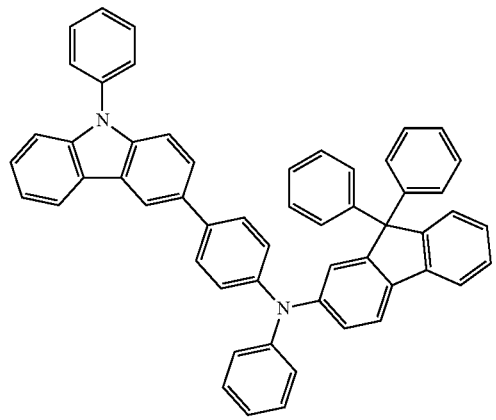
HT6
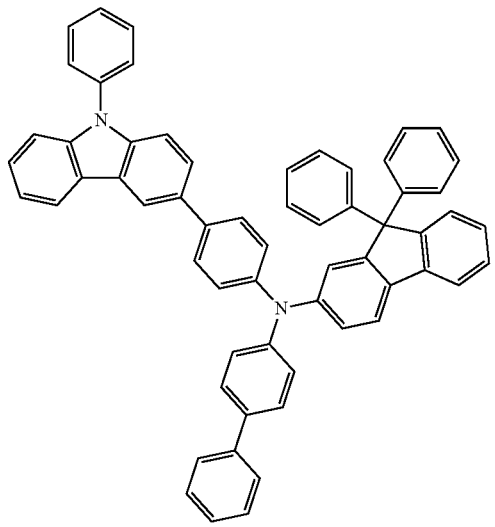

-continued
HT7
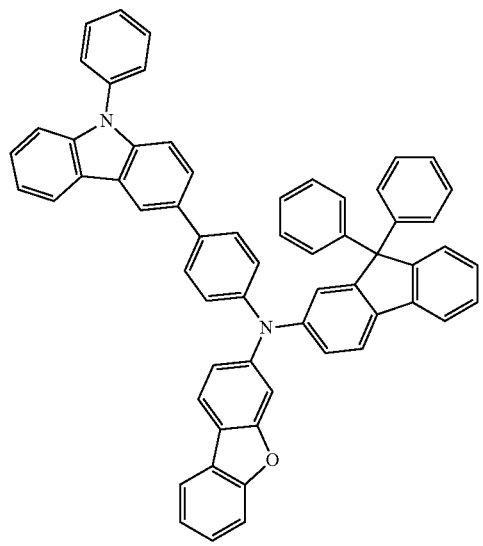
HT8
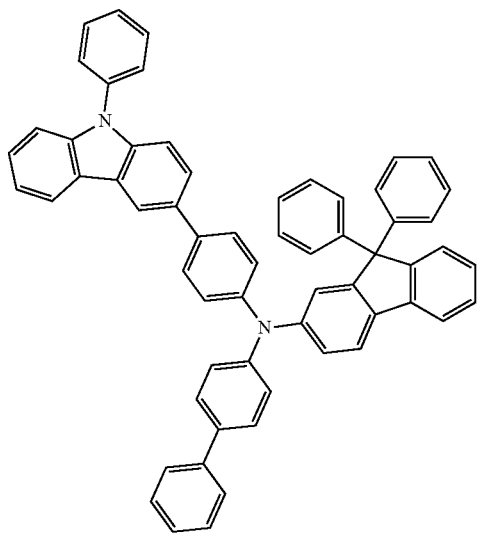
HT9
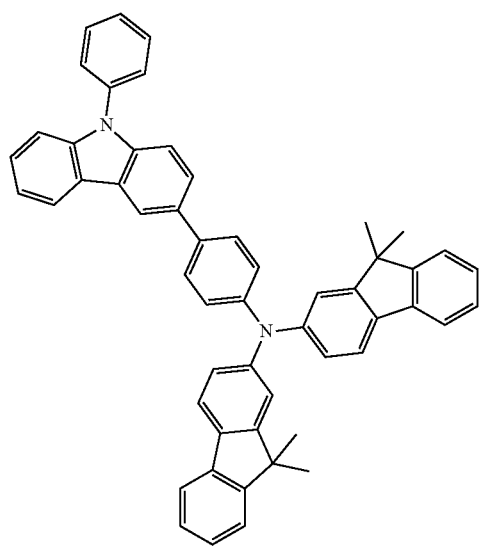
HT10
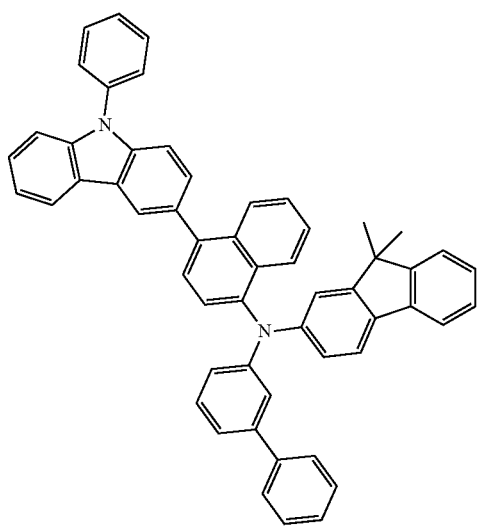
HT11
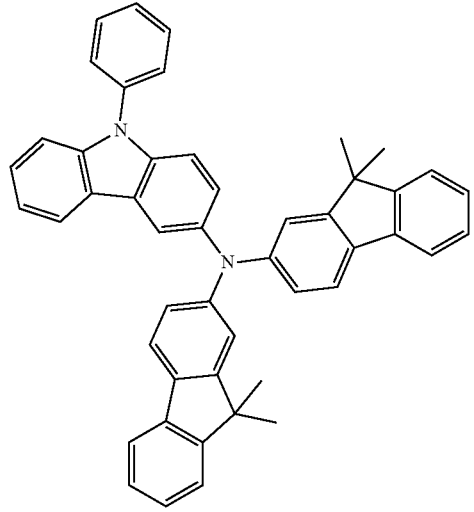
HT12
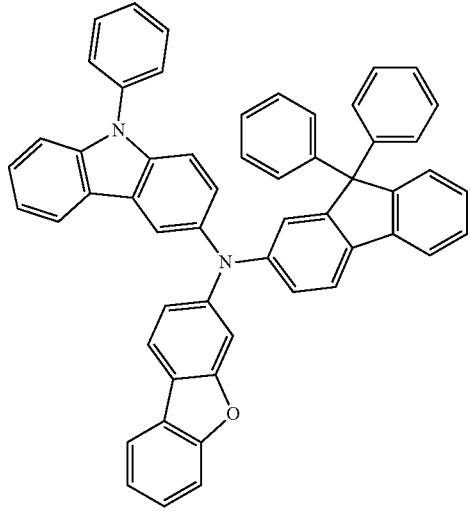

-continued
HT13
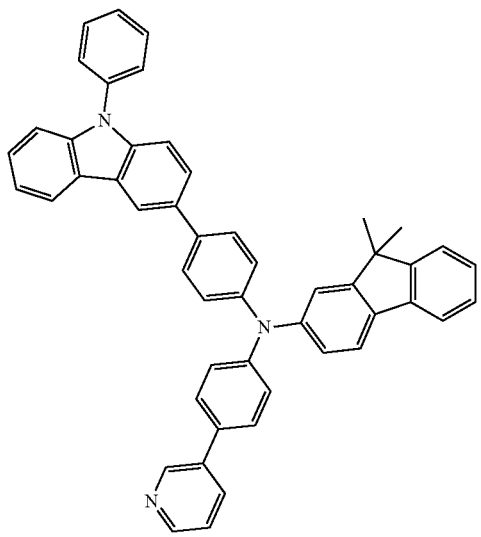
HT14
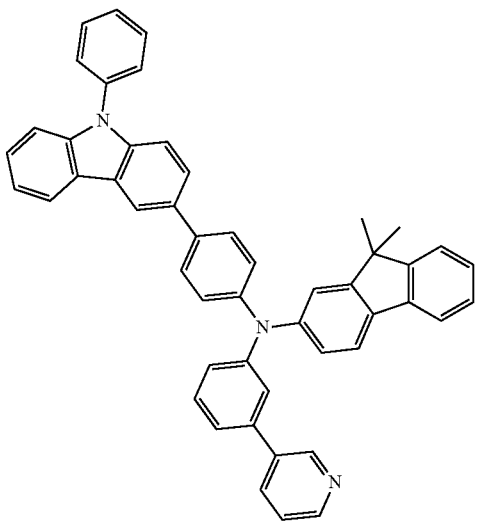
HT15
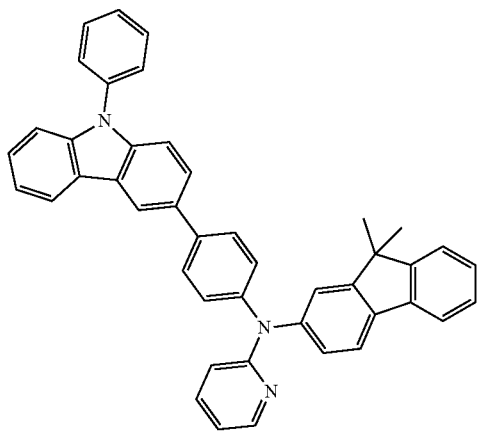
HT16
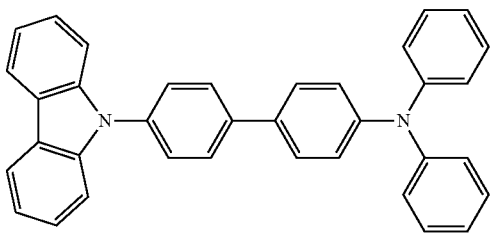
HT17
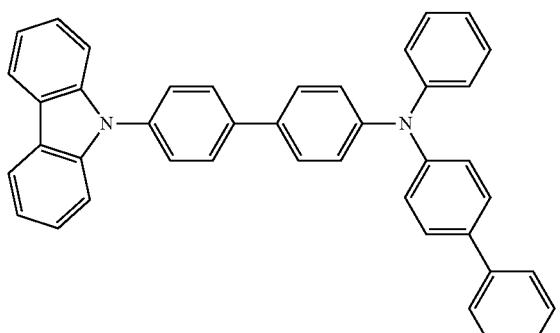
HT18
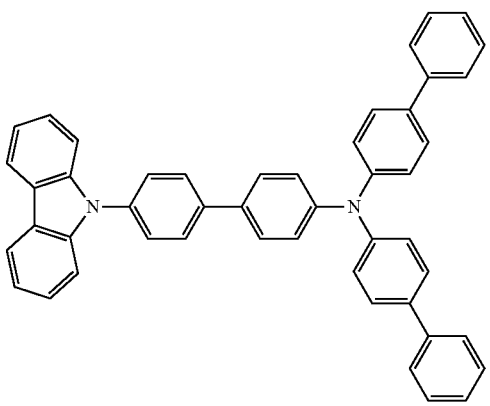

-continued
HT19
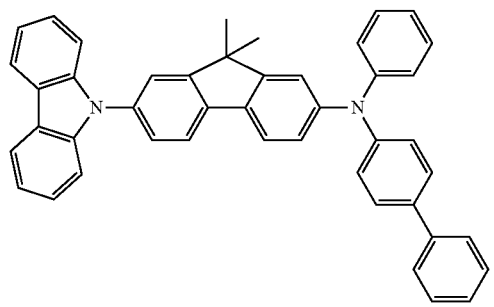
HT20
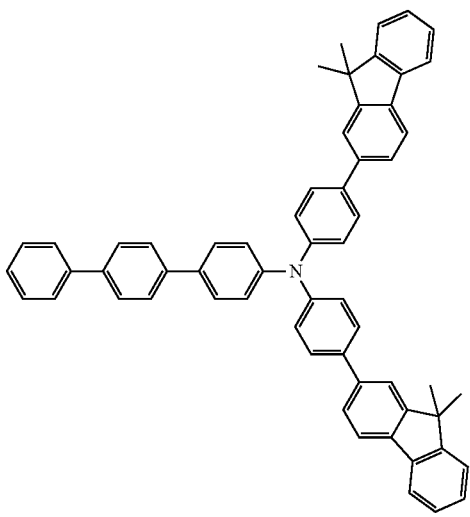
HT21
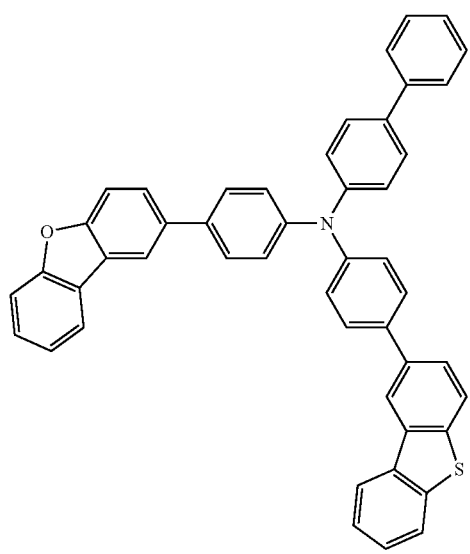
HT22
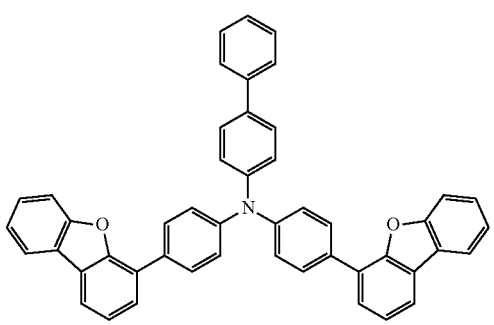
HT23
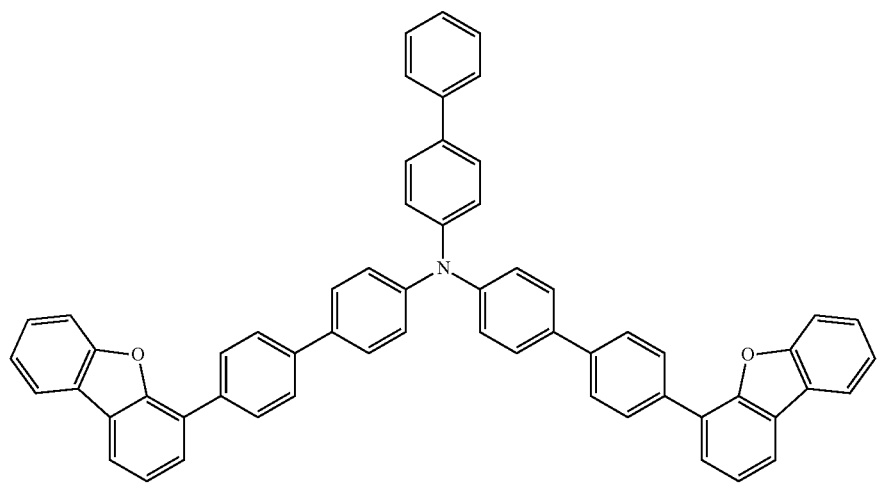

-continued
HT24
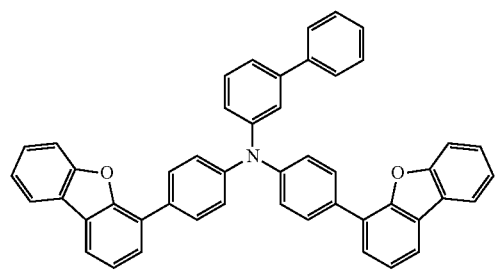
HT25
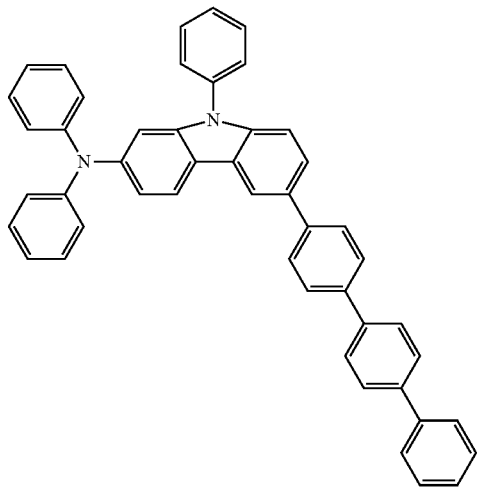
HT26
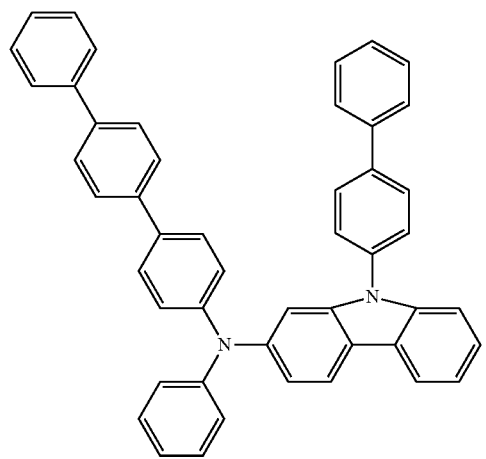
HT27
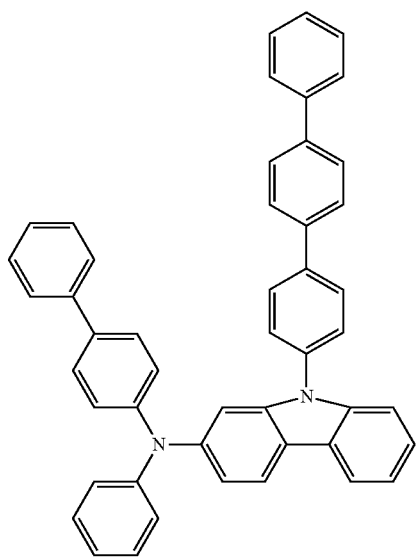
HT28
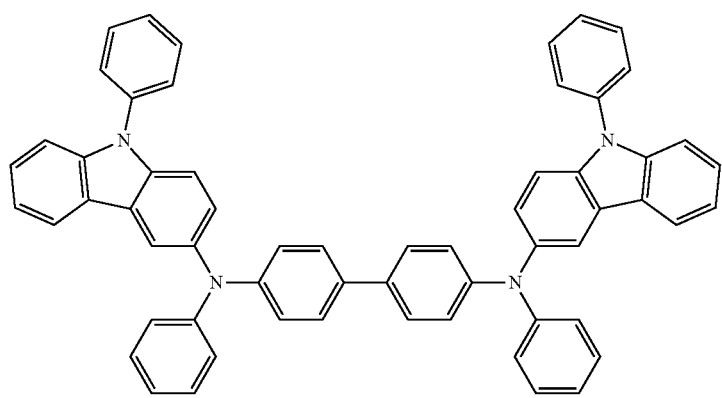

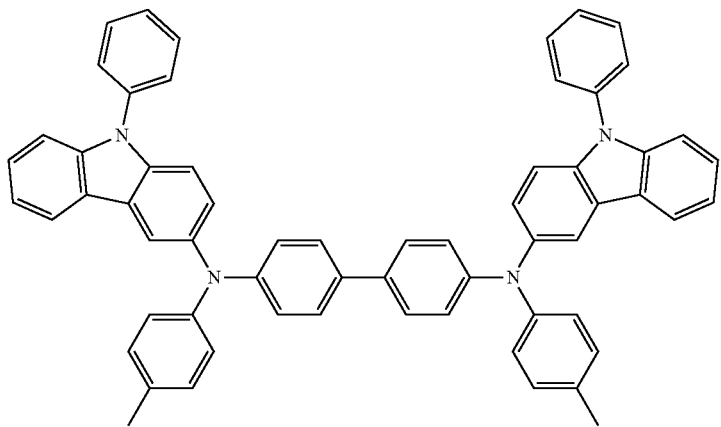
HT29
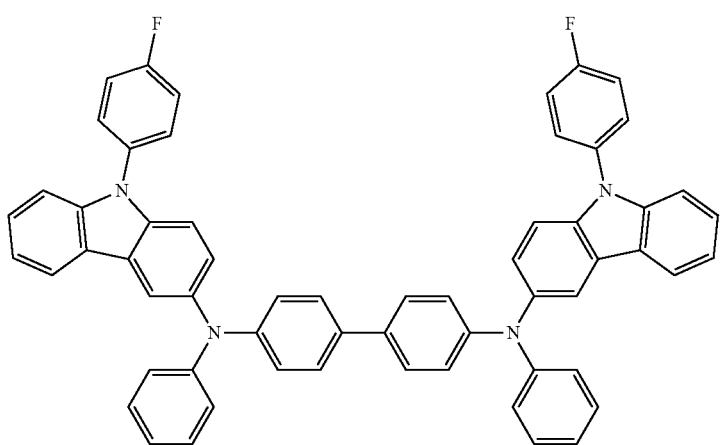
HT30
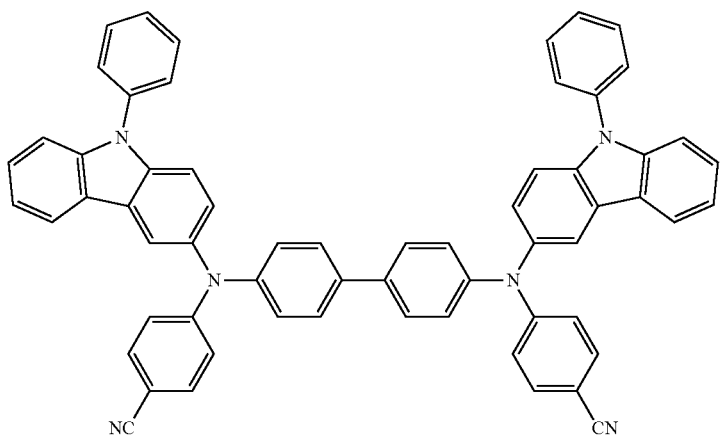
HT31

-continued
HT32
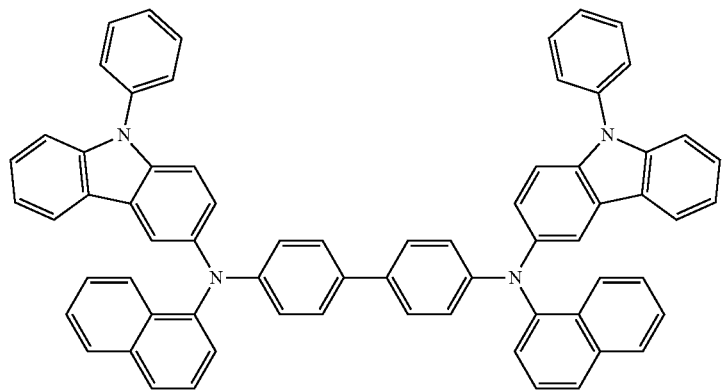
HT33
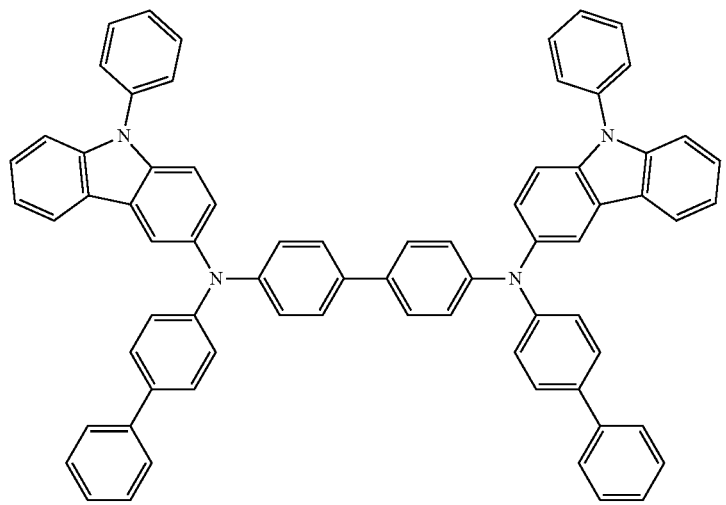
HT34
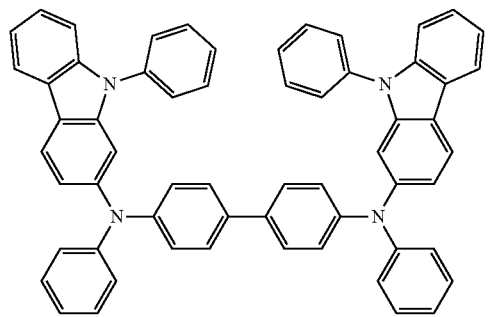
HT35
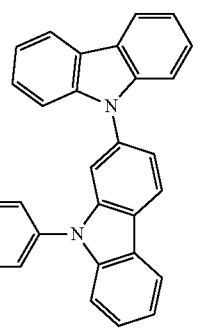
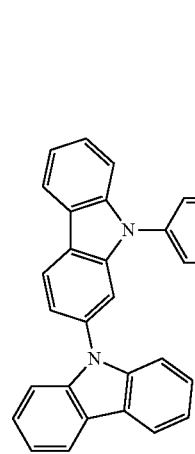

-continued

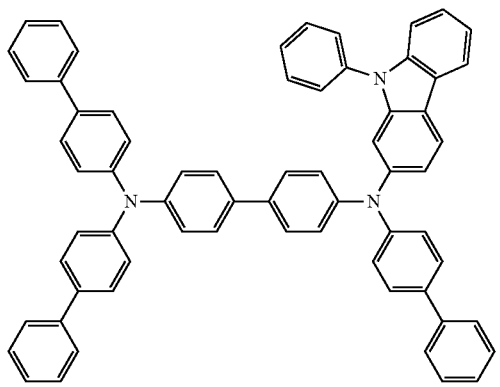
HT36

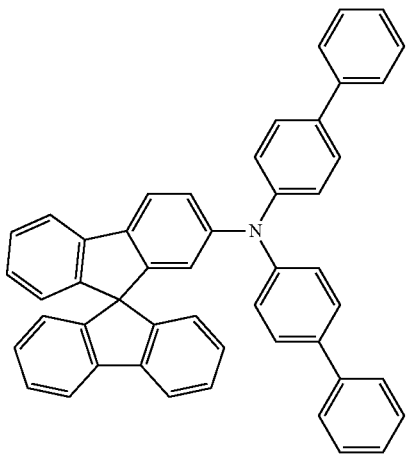
HT37

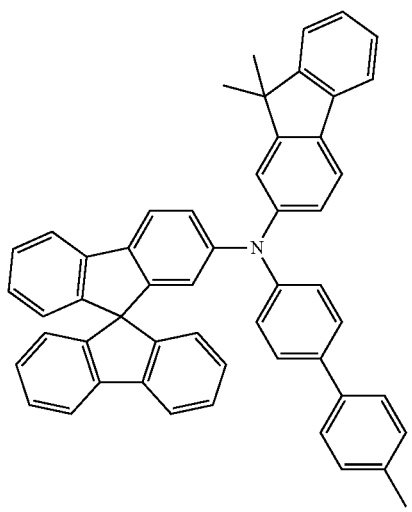
HT38

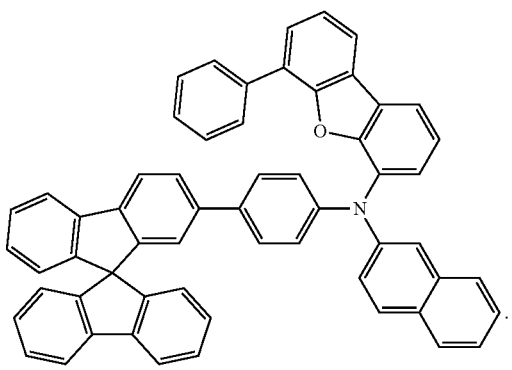
HT39

A thickness of the hole transport region may be in a range of about 100 Å to about 10,000 Å, for example, about 100 Å to about 1,000 Å. When the hole transport region includes at least one selected from a hole injection layer and a hole transport layer, the thickness of the hole injection layer may be in a range of about 100 Å to about 9,000 Å, and for example, about 100 Å to about 1,000 Å, and the thickness of the hole transport layer may be in a range of about 50 Å to about 2,000 Å, and for example, about 100 Å to about 1,500 Å. When the thicknesses of the hole transport region, the hole injection layer, and the hole transport layer are within any of these ranges, satisfactory (or suitable) hole transporting characteristics may be obtained without a substantial increase in driving voltage.

The emission auxiliary layer may increase light-emission efficiency by compensating for an optical resonance distance according to the wavelength of light emitted by an emission layer, and the electron blocking layer may block or reduce the flow of electrons from an electron transport region. The emission auxiliary layer and the electron blocking layer may each independently include any of the materials as described above.

p-Dopant

The hole transport region may further include, in addition to the materials described above, a charge-generation material for the improvement of conductive properties. The charge-generation material may be homogeneously or non-homogeneously dispersed in the hole transport region.

The charge-generation material may be, for example, a p-dopant.

In one embodiment, the p-dopant may have a lowest unoccupied molecular orbital (LUMO) energy level of about −3.5 eV or less.

The p-dopant may include at least one selected from a quinone derivative, a metal oxide, and a cyano group-containing compound, but embodiments of the present disclosure are not limited thereto.

For example, the p-dopant may include at least one selected from:

a quinone derivative, such as tetracyanoquinodimethane (TCNQ) and/or 2,3,5,6-tetrafluoro-7,7,8,8-tetracyanoquinodimethane (F4-TCNQ);

a metal oxide, such as tungsten oxide and/or molybdenum oxide;

1,4,5,8,9,12-hexaazatriphenylene-hexacarbonitrile (HAT-CN); and a compound represented by Formula 221 below, but embodiments of the present disclosure are not limited thereto:

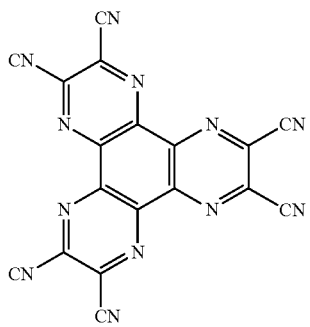

HAT-CN

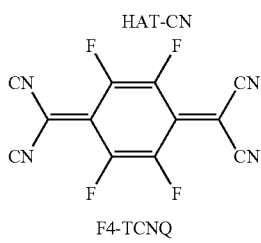

F4-TCNQ

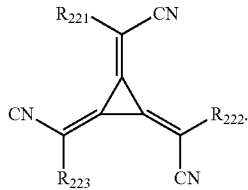

Formula 221

In Formula 221, $R_{221}$ to $R_{223}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, provided that at least one substituent selected from $R_{221}$ to $R_{223}$ has at least one substituent selected from a cyano group, —F, —Cl, —Br, —I, a $C_1$-$C_{20}$ alkyl group substituted with —F, a $C_1$-$C_{20}$ alkyl group substituted with —Cl, a $C_1$-$C_{20}$ alkyl group substituted with Br, and a $C_1$-$C_{20}$ alkyl group substituted with —I.

Emission Layer in Organic Layer 150

When the organic light-emitting device 10 is a full-color organic light-emitting device, the emission layer may be patterned into a red emission layer, a green emission layer, or a blue emission layer, according to a sub-pixel. In one or more embodiments, the emission layer may have a stacked structure of two or more layers selected from a red emission layer, a green emission layer, and a blue emission layer, in which the two or more layers contact each other or are separated from each other. In one or more embodiments, the emission layer may include two or more materials selected from a red light-emitting material, a green light-emitting material, and a blue light-emitting material, in which the two or more materials are mixed with each other in a single layer to emit white light.

The emission layer may include a host and a dopant. The dopant may include at least one selected from a phosphorescent dopant and a fluorescent dopant.

An amount of the dopant of the emission layer may be in a range of about 0.01 parts by weight to about 15 parts by weight based on 100 parts by weight of the host, but embodiments of the present disclosure are not limited thereto.

A thickness of the emission layer may be in a range of about 100 Å to about 1,000 Å, for example, about 200 Å to about 600 Å. When the thickness of the emission layer is within this range, excellent (or suitable) light-emission characteristics may be obtained without a substantial increase in driving voltage.

Host in Emission Layer

The host may include a compound represented by Formula 1.

In one or more embodiments, the host may further include a compound represented by Formula 301 below.

$$[Ar_{301}]_{xb11}\text{-}[(L_{301})_{xb1}\text{-}R_{301}]_{xb21}. \qquad \text{Formula 301}$$

In Formula 301, $Ar_{301}$ may be a substituted or unsubstituted $C_5$-$C_{60}$ carbocyclic group or a substituted or unsubstituted $C_1$-$C_{60}$ heterocyclic group, xb11 may be 1, 2, or 3, $L_{301}$ may be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group;

xb1 may be an integer from 0 to 5, $R_{301}$ may be selected from deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_{301}$)($Q_{302}$)($Q_{303}$), —N($Q_{301}$)($Q_{302}$), —B($Q_{301}$)($Q_{302}$), —C(=O)($Q_{301}$), —S(=O)$_2$($Q_{301}$), and —P(=O)($Q_{301}$)($Q_{302}$), xb21 may be an integer from 1 to 5, and $Q_{301}$ to $Q_{303}$ may each independently be selected from a $C_1$-$C_{10}$ alkyl group, a $C_1$-$C_{10}$ alkoxy group, a phenyl group, a biphenyl group, a terphenyl group, and a naphthyl group, but embodiments of the present disclosure are not limited thereto.

In one embodiment, $Ar_{301}$ in Formula 301 may be selected from:

a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, and a dibenzothiophene group; and a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, and a dibenzothiophene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), and $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group, but embodiments of the present disclosure are not limited thereto.

In Formula 301, when xb11 is two or more, two or more of $Ar_{301}$(s) may be linked via a single bond.

In one or more embodiments, the compound represented by Formula 301 may be represented by Formula 301-1 or 301-2:

group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), xb22 and xb23 may each independently be 0, 1, or 2, $L_{301}$, xb1, $R_{301}$, and $Q_{31}$ to $Q_{33}$ are the same as described above, definitions for $L_{302}$ to $L_{304}$ may each independently be the same as that provided in connection with $L_{301}$, definitions for xb2 to xb4 may each independently be the same as that provided in connection with xb1, and definitions for $R_{302}$ to $R_{304}$ may each independently be the same as that provided in connection with $R_{301}$.

For example, in Formulae 301, 301-1, and 301-2, $L_{301}$ to $L_{304}$ may each independently be selected from:

a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarba-

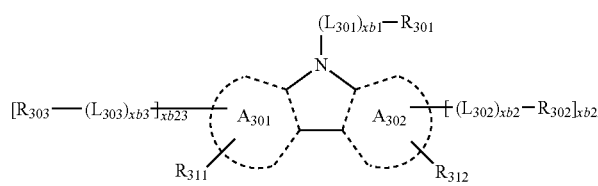

Formula 301-1

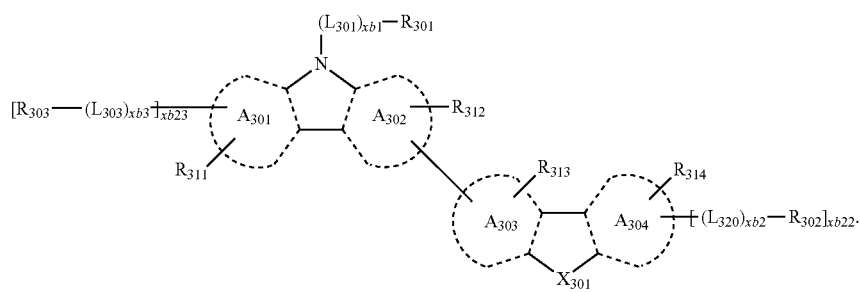

Formula 301-2

In Formulae 301-1 and 301-2, $A_{301}$ to $A_{304}$ may each independently be selected from a benzene group, a naphthalene group, a phenanthrene group, a fluoranthene group, a triphenylene group, a pyrene group, a chrysene group, a pyridine group, a pyrimidine group, an indene group, a fluorene group, a spiro-bifluorene group, a benzofluorene group, a dibenzofluorene group, an indole group, a carbazole group, a benzocarbazole group, a dibenzocarbazole group, a furan group, a benzofuran group, a dibenzofuran group, a naphthofuran group, a benzonaphthofuran group, a dinaphthofuran group, a thiophene group, a benzothiophene group, a dibenzothiophene group, a naphthothiophene group, a benzonaphthothiophene group, and a dinaphthothiophene group, $X_{301}$ may be O, S, or N-[($L_{304}$)$_{xb4}$-$R_{304}$], $R_{311}$ to $R_{314}$ may each independently be selected from hydrogen, deuterium, —F, —Cl, —Br, —I, a hydroxyl zolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzoimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group; and a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzoimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzoimidazolyl group, an isobenzothiazolyl group, a benzoxazolyl group, an isobenzoxazolyl group, a triazolyl group, a tetrazolyl group, an imidazopyridinyl group, an imidazopyrimidinyl group, an azacarbazolyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), and $Q_{31}$ and $Q_{33}$ may be the same as described above.

In one embodiment, in Formulae 301, 301-1, and 301-2, $R_{301}$ to $R_{304}$ may each independently be selected from:

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzoimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group; and a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzoimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzoimidazolyl group, an isobenzothiazolyl group, a benzoxazolyl group, an isobenzoxazolyl group, a triazolyl group, a tetrazolyl group, an imidazopyridinyl group, an imidazopyrimidinyl group, an azacarbazolyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), and $Q_{31}$ and $Q_{33}$ may be the same as described above.

In one or more embodiments, the host may include an alkaline earth metal complex. For example, the host may be selected from a Be complex (e.g. Compound H55), a Mg complex, and a Zn complex.

In an embodiment, the host may include at least one selected from 9,10-di(2-naphthyl)anthracene (ADN), 2-methyl-9,10-bis(naphthalen-2-yl)anthracene (MADN), 9,10-di-(2-naphthyl)-2-t-butyl-anthracene (TBADN), 4,4'-bis(N-carbazolyl)-1,1'-biphenyl (CBP), 1,3-di-9-carbazolylbenzene (mCP), 1,3,5-tri(carbazol-9-yl)benzene (TCP), and Compounds H1 to H55, but embodiments of the present disclosure are not limited thereto:

H1

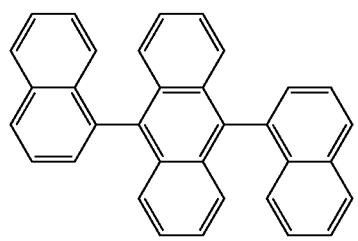

H2

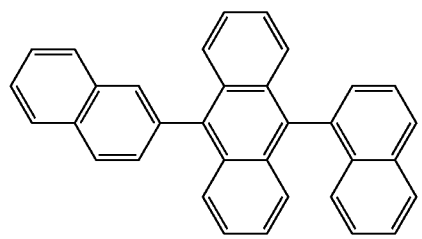

H3

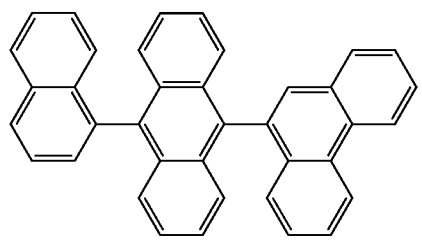

H4

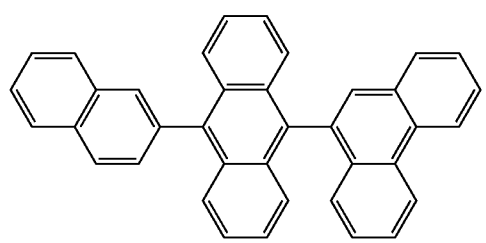

H5

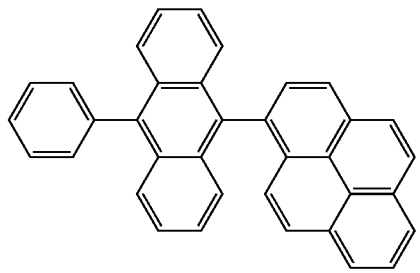

H6

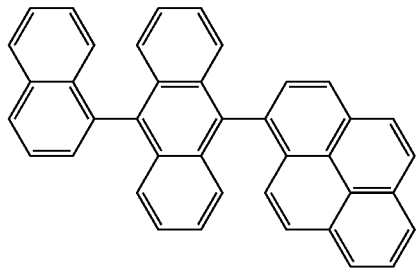

H7

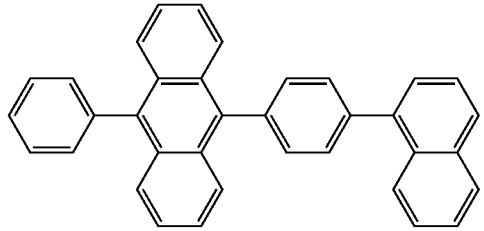

H8

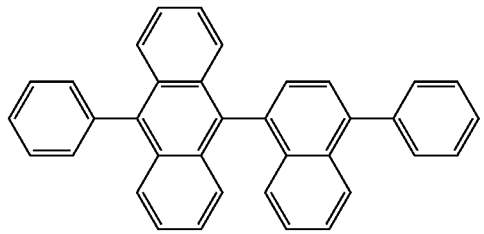

H9

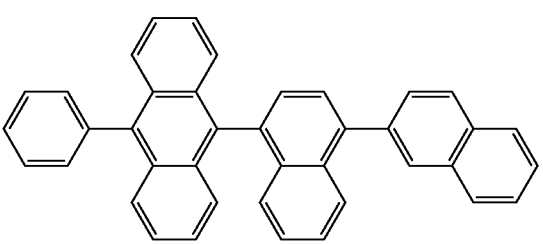

H10

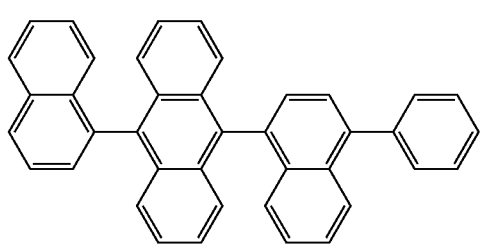

H11
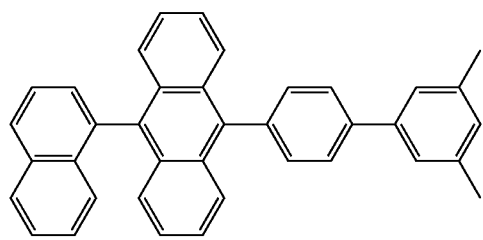
H12
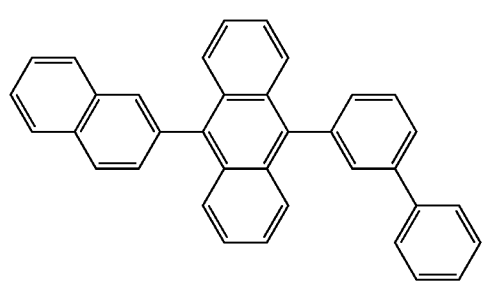
H13
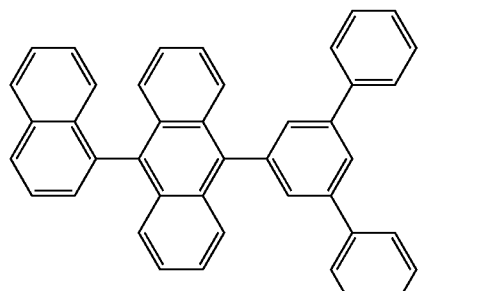
H14
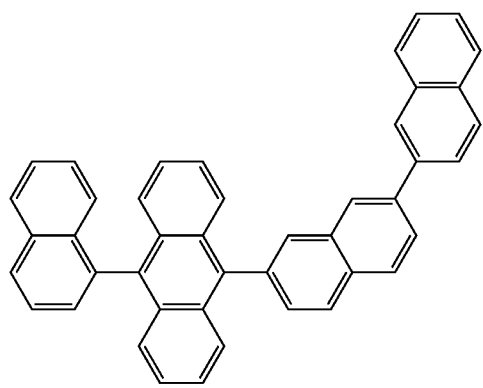
H15
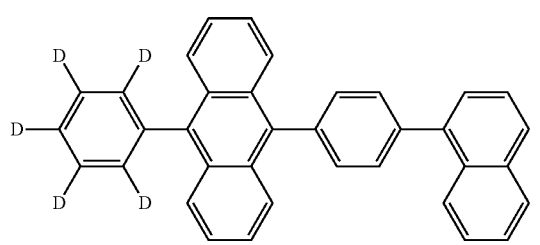
H16
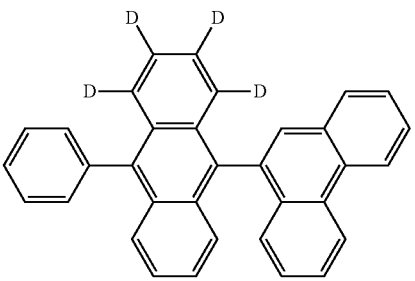
H17
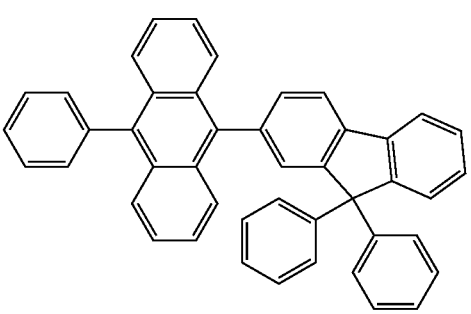
H18
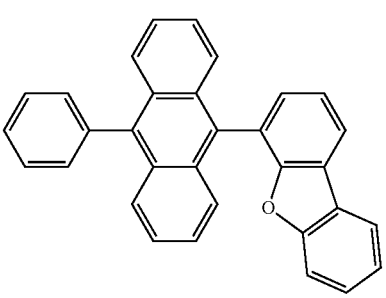
H19
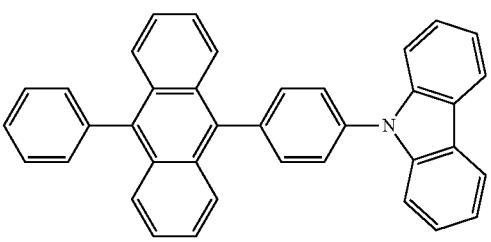
H20
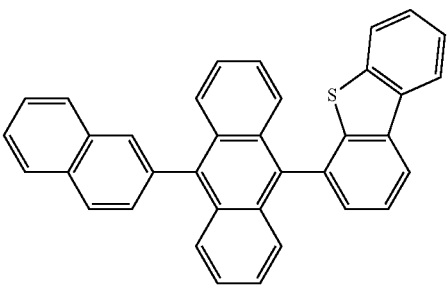

H21
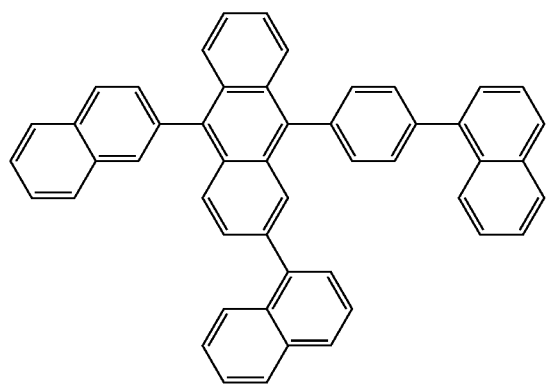
H22
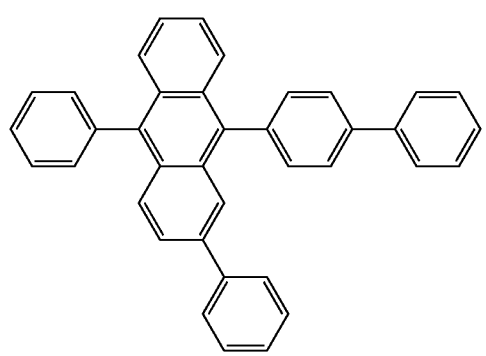
H23
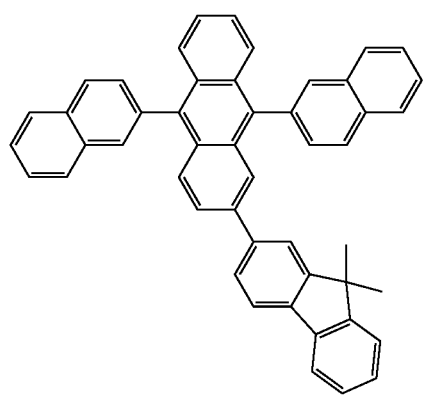
H24
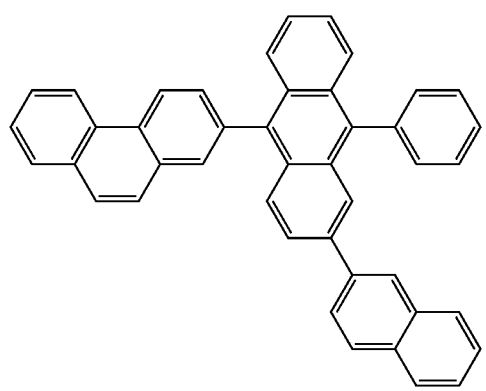
H25
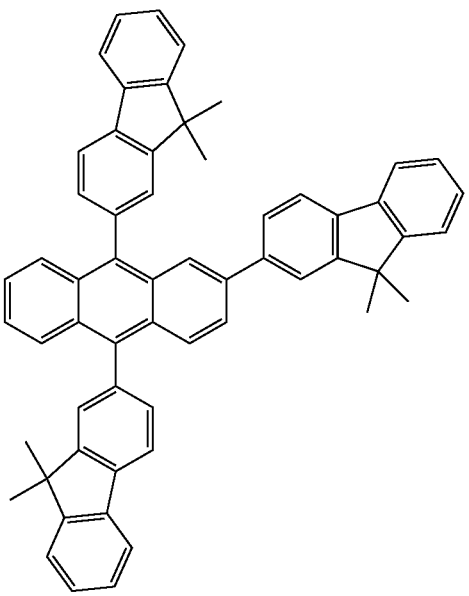
H26
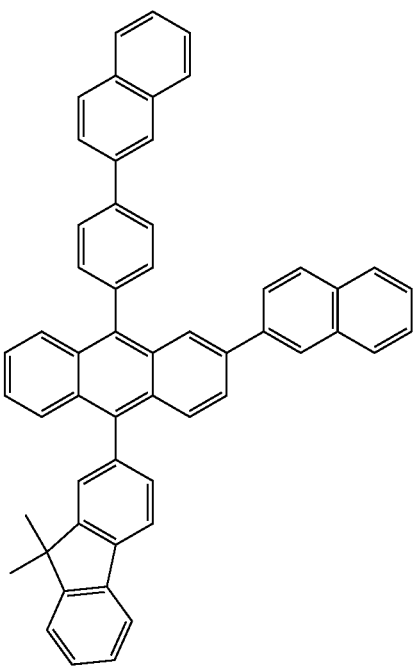

-continued
H27 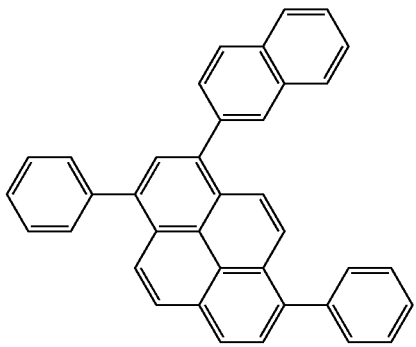
H28 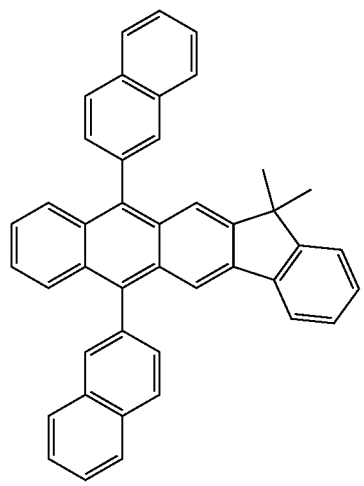
H29 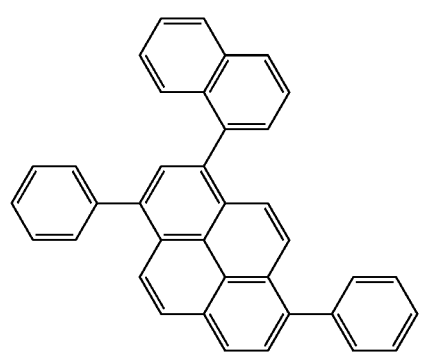
-continued
H30 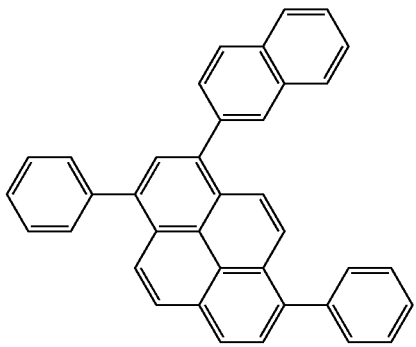
H31 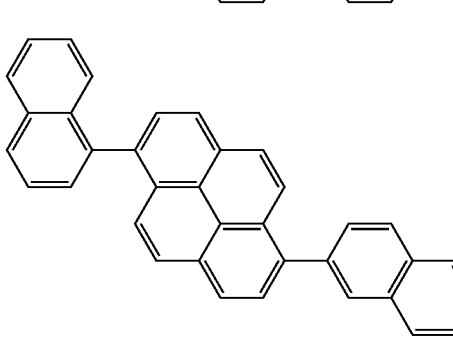
H32 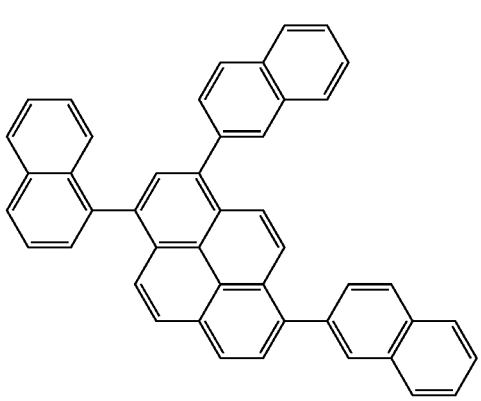
H33 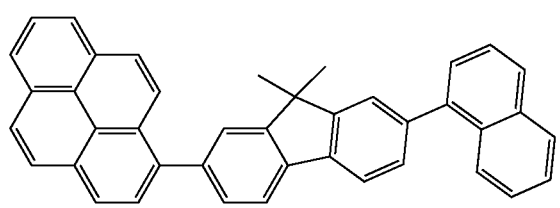
H34 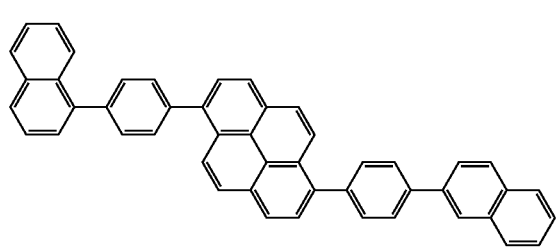

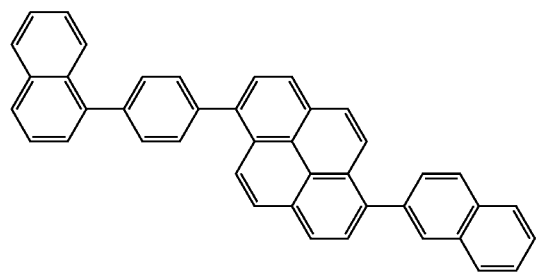
H35
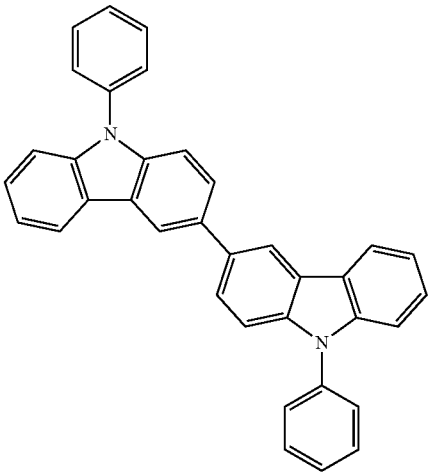
H39
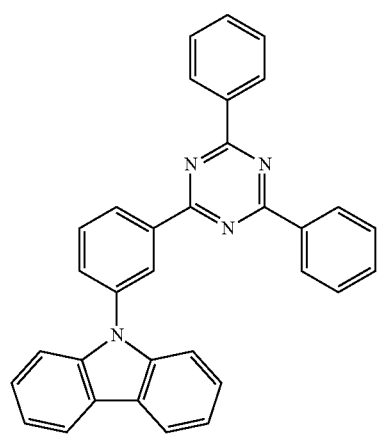
H36
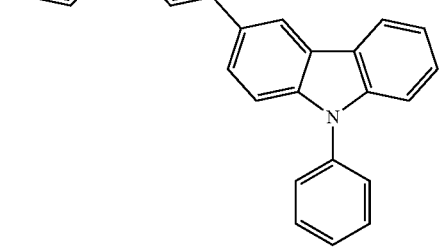
H40
H37
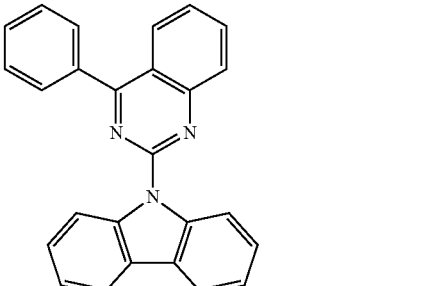
H41
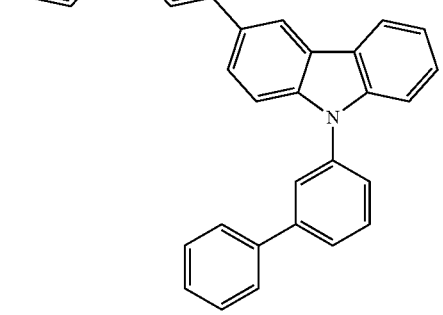
H38

111
-continued
H42
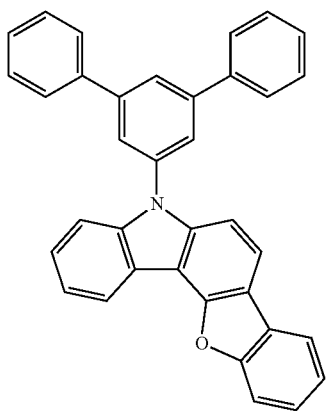
H43
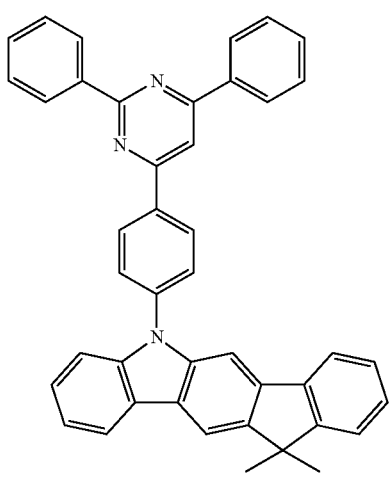
H44
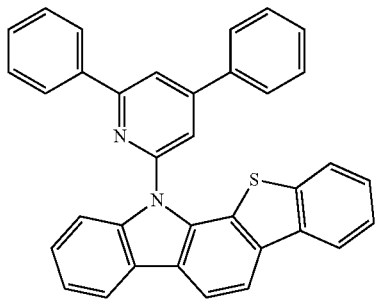
H45
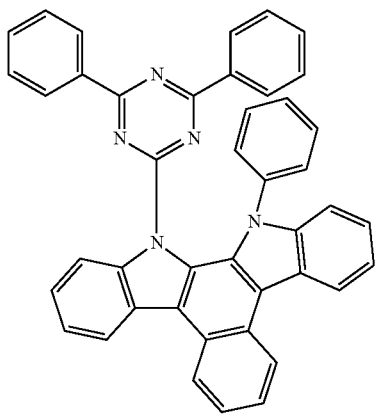
112
-continued
H46
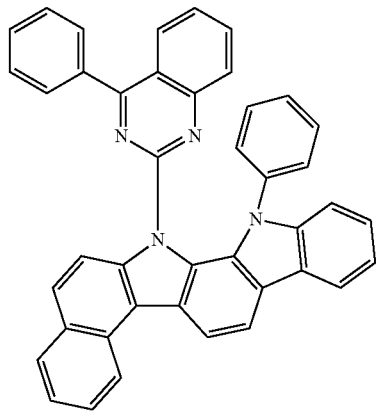
H47
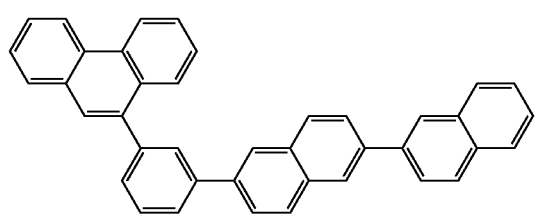
H48
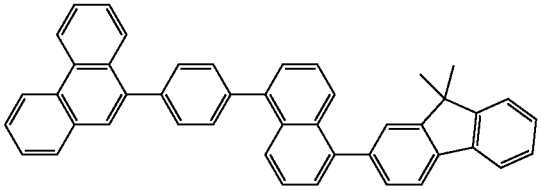
H49
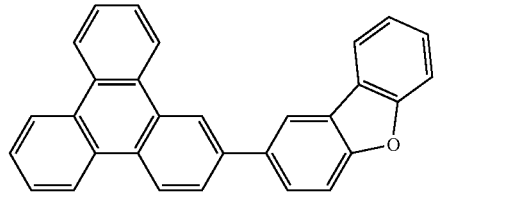
H50
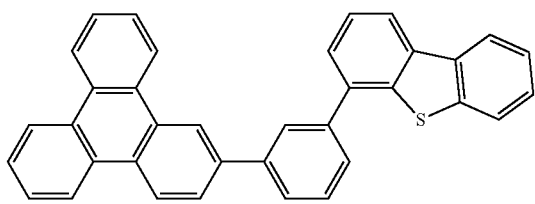
H51
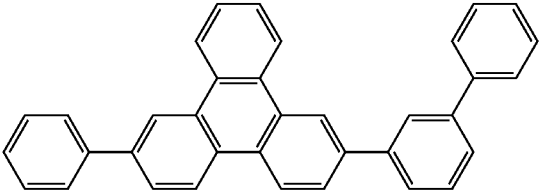

H52

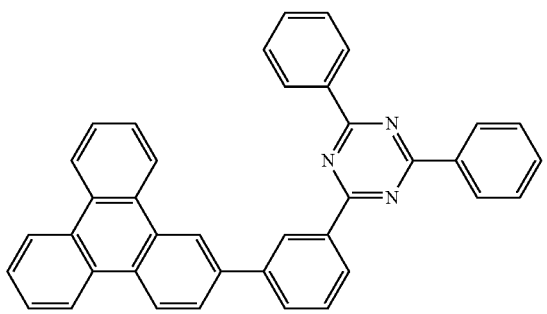

H53

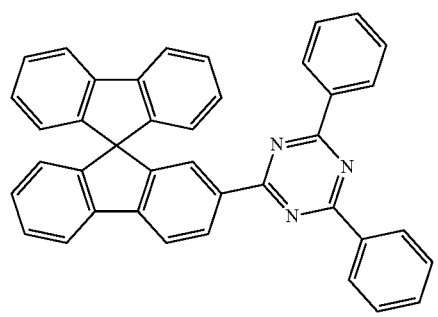

H54

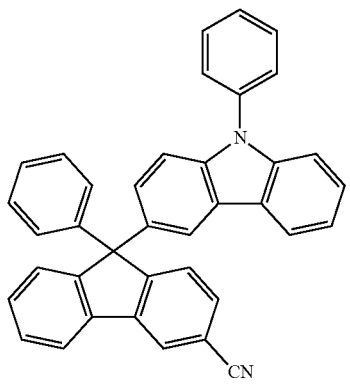

H55

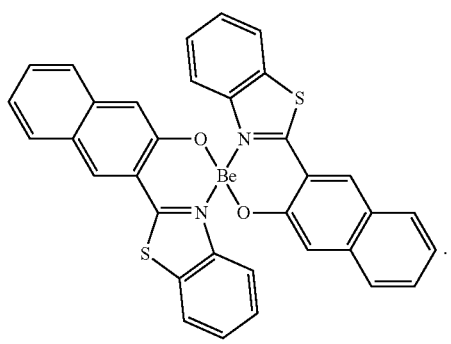

Phosphorescent Dopant Included in Emission Layer in Organic Layer 150

The phosphorescent dopant may include an organometallic complex represented by Formula 401 below:

$M(L_{401})_{xc1}(L_{402})_{xc2}$  Formula 401

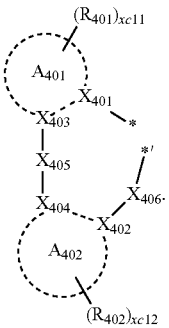

Formula 402

In Formulae 401 and 402,

M may be selected from iridium (Ir), platinum (Pt), palladium (Pd), osmium (Os), titanium (Ti), zirconium (Zr), hafnium (Hf), europium (Eu), terbium (Tb), rhodium (Rh), and thulium (Tm), $L_{401}$ may be selected from ligands represented by Formula 402, and xc1 may be 1, 2, or 3, wherein, when xc1 is two or more, two or more $L_{401}$ (s) may be identical to or different from each other, $L_{402}$ may be an organic ligand, and xc2 may be an integer from 0 to 4, wherein, when xc2 is two or more, two or more $L_{402}$(s) may be identical to or different from each other, $X_{401}$ to $X_{404}$ may each independently be nitrogen or carbon, $X_{401}$ and $X_{403}$ may be linked via a single bond or a double bond, and $X_{402}$ and $X_{404}$ may be linked via a single bond or a double bond, $A_{401}$ and $A_{402}$ may each independently be selected from a $C_5$-$C_{60}$ carbocyclic group or a $C_1$-$C_{60}$ heterocyclic group, $X_{405}$ may be a single bond, *—O—*', *—S—*', *—C(=O)—*', *—N($Q_{411}$)— ', *—C($Q_{411}$)($Q_{412}$)— *', *—C($Q_{411}$)=C($Q_{412}$)— *, *—C($Q_{411}$)=*', or *=C=*', wherein $Q_{411}$ and $Q_{412}$ may each independently be hydrogen, deuterium, a $C_1$-$C_{20}$ alkyl group, a $C_1$-$C_{20}$ alkoxy group, a phenyl group, a biphenyl group, a terphenyl group, or a naphthyl group, and * and *' each indicate a binding site to a neighboring atom, $X_{406}$ may be a single bond, O, or S, $R_{401}$ and $R_{402}$ may each independently be selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{20}$ alkyl group, a substituted or unsubstituted $C_1$-$C_{20}$ alkoxy group, a substituted or unsubstituted $C_3$-$C_{10}$ cycloalkyl group, a substituted or unsubstituted heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, —Si($Q_{401}$)($Q_{402}$)($Q_{403}$), —N($Q_{401}$)($Q_{402}$), —B($Q_{401}$)($Q_{402}$), —C(=O)($Q_{401}$), —S(=O)$_2$($Q_{401}$), and —P(=O)($Q_{401}$)($Q_{402}$), wherein $Q_{401}$ to $Q_{403}$ may each independently be selected from a $C_1$-$C_{10}$ alkyl group, a $C_1$-$C_{10}$ alkoxy group, a $C_6$-$C_{20}$ aryl group, and a $C_1$-$C_{20}$ heteroaryl group, xc11 and xc12 may each independently be an integer from 0 to 10, and

*and *' in Formula 402 each indicate a binding site to M in Formula 401.

In one embodiment, $A_{401}$ and $A_{402}$ in Formula 402 may each independently be selected from a benzene group, a naphthalene group, a fluorene group, a spiro-bifluorene group, an indene group, a pyrrole group, a thiophene group, a furan group, an imidazole group, a pyrazole group, a thiazole group, an isothiazole group, an oxazole group, an isoxazole group, a pyridine group, a pyrazine group, a pyrimidine group, a pyridazine group, a quinoline group, an isoquinoline group, a benzoquinoline group, a quinoxaline group, a quinazoline group, a carbazole group, a benzoimidazole group, a benzofuran group, a benzothiophene group, an isobenzothiophene group, a benzoxazole group, an isobenzoxazole group, a triazole group, a tetrazole group, an oxadiazole group, a triazine group, a dibenzofuran group, and a dibenzothiophene group.

In one or more embodiments, in Formula 402, i) $X_{401}$ may be nitrogen, and $X_{402}$ may be carbon, or ii) $X_{401}$ and $X_{402}$ may both be nitrogen at the same time (concurrently).

In one or more embodiments, $R_{401}$ and $R_{402}$ in Formula 402 may each independently be selected from:

hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amidino group, a hydrazino group, a hydrazono group, a phenyl group, a naphthyl group, a cyclopentyl group, a cyclohexyl group, an adamantanyl group, a norbornanyl group, and a norbornenyl group;

a cyclopentyl group, a cyclohexyl group, an adamantanyl group, a norbornanyl group, a norbornenyl group, a phenyl group, a biphenyl group, a terphenyl group, a naphthyl group, a fluorenyl group, a pyridinyl group, a pyrazinyl group, a pyrimidinyl group, a pyridazinyl group, a triazinyl group, a quinolinyl group, an isoquinolinyl group, a quinoxalinyl group, a quinazolinyl group, a carbazolyl group, a dibenzofuranyl group, and a dibenzothiophenyl group;

a cyclopentyl group, a cyclohexyl group, an adamantanyl group, a norbornanyl group, a norbornenyl group a phenyl group, a biphenyl group, a terphenyl group, a naphthyl group, a fluorenyl group, a pyridinyl group, a pyrazinyl group, a pyrimidinyl group, a pyridazinyl group, a triazinyl group, a quinolinyl group, an isoquinolinyl group, a quinoxalinyl group, a quinazolinyl group, a carbazolyl group, a dibenzofuranyl group, and a dibenzothiophenyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, an adamantanyl group, a norbornanyl group, a norbornenyl group, a phenyl group, a biphenyl group, a terphenyl group, a naphthyl group, a fluorenyl group, a pyridinyl group, a pyrazinyl group, a pyrimidinyl group, a pyridazinyl group, a triazinyl group, a quinolinyl group, an isoquinolinyl group, a quinoxalinyl group, a quinazolinyl group, a carbazolyl group, a dibenzofuranyl group, and a dibenzothiophenyl group; and —Si($Q_{401}$)($Q_{402}$)($Q_{403}$), —N($Q_{401}$)($Q_{402}$), —B($Q_{401}$)($Q_{402}$), —C(=O)($Q_{401}$), —S(=O)$_2$($Q_{401}$), and —P(=O)($Q_{401}$)($Q_{402}$), and $Q_{401}$ to $Q_{403}$ may each independently be selected from a $C_1$-$C_{10}$ alkyl group, a $C_1$-$C_{10}$ alkoxy group, a phenyl group, a biphenyl group, and a naphthyl group, but are not limited thereto.

In one or more embodiments, when xc1 in Formula 401 is two or more, two $A_{401}$(s) in two or more $L_{401}$(s) may optionally be linked via $X_{407}$, which is a linking group, or two $A_{402}$(s) in two or more $L_{401}$(s) may optionally be linked via $X_{408}$, which is a linking group (see e.g., Compounds PD1 to PD4 and PD7 below). $X_{407}$ and $X_{408}$ may each independently be a single bond, *—O—*', *—S—*', *—C(=O)—*', *—N($Q_{413}$)- *', *—C($Q_{413}$)($Q_{414}$)- *', or *—C($Q_{413}$)=C($Q_{414}$)-*' (wherein $Q_{413}$ and $Q_{414}$ may each independently be hydrogen, deuterium, a $C_1$-$C_{20}$ alkyl group, a $C_1$-$C_{20}$ alkoxy group, a phenyl group, a biphenyl group, a terphenyl group, or a naphthyl group and * and *' each indicate a binding site to a neighboring atom), but embodiments of the present disclosure are not limited thereto.

$L_{402}$ in Formula 401 may be a monovalent, divalent, or trivalent organic ligand. For example, $L_{402}$ may be selected from halogen, diketone (e.g., acetylacetonate), carboxylic acid (e.g., picolinate), —C(=O), isonitrile, —CN, and a phosphorus-containing material (e.g., phosphine and/or phosphite), but embodiments of the present disclosure are not limited thereto.

In one or more embodiments, the phosphorescent dopant may be selected from, for example, Compounds PD1 to PD25, but embodiments of the present disclosure are not limited thereto:

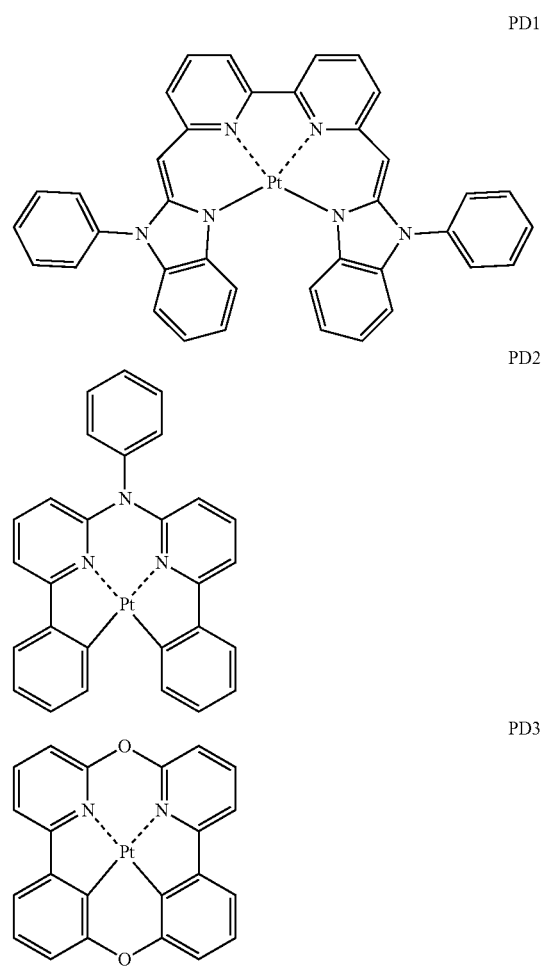

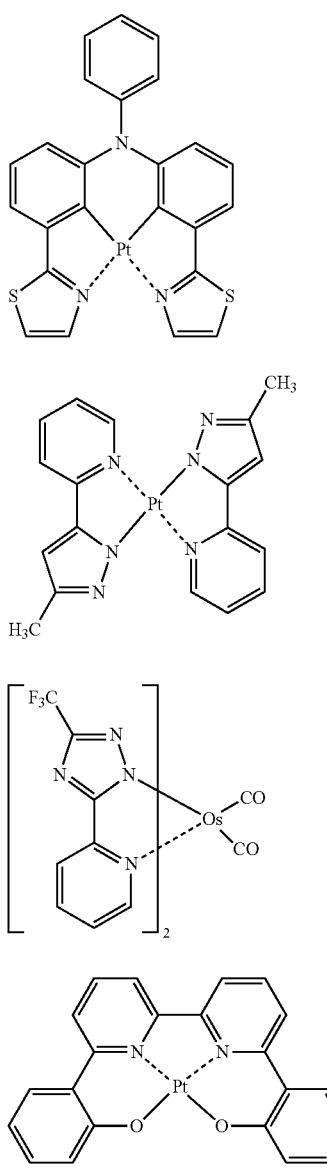
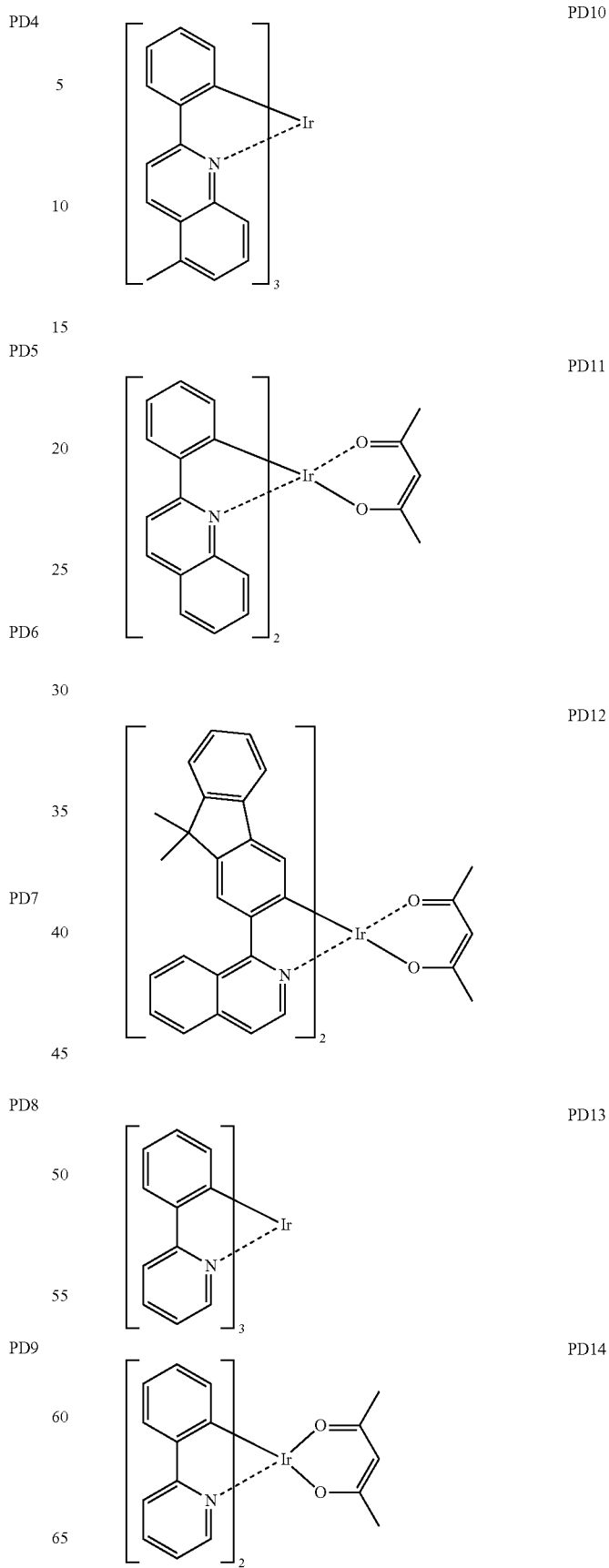

-continued
PD15
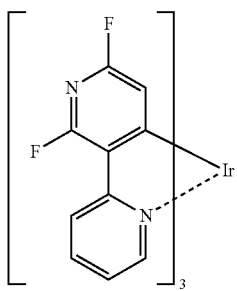
PD16
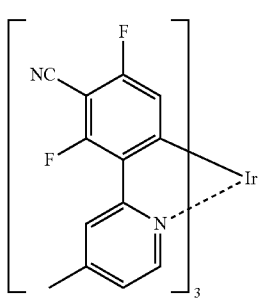
PD17
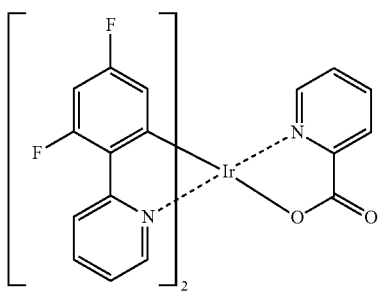
PD18
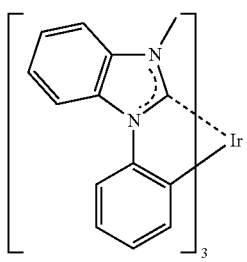
PD19
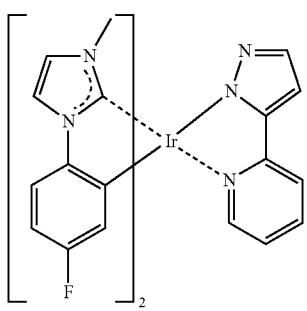
-continued
PD20
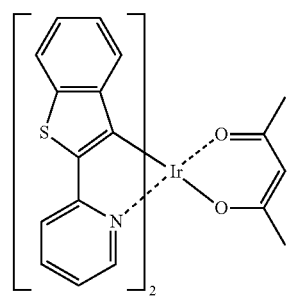
PD21
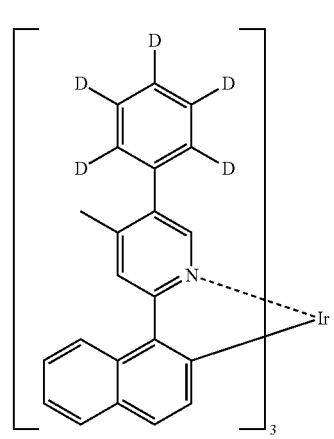
PD22
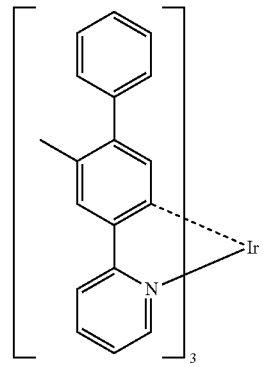
PD23
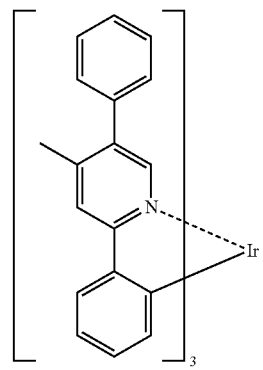

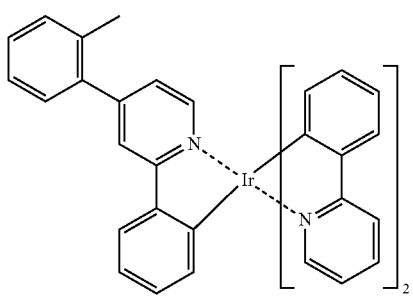

PD24

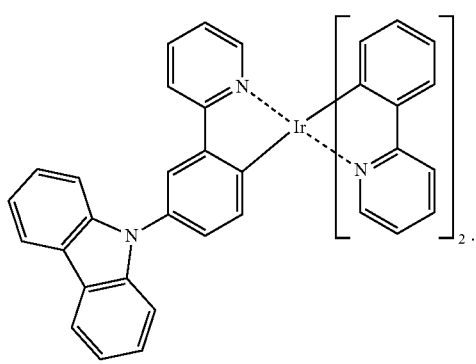

PD25

Fluorescent Dopant in Emission Layer

The fluorescent dopant may include the condensed cyclic compound represented by Formula 1.

In one embodiment, the fluorescent dopant may include an arylamine compound or a styrylamine compound.

In an embodiment, the fluorescent dopant may include a compound represented by Formula 501 below:

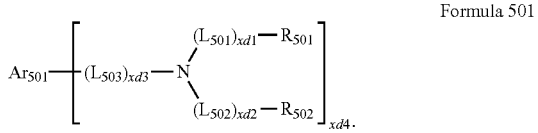

Formula 501

In Formula 501, $Ar_{501}$ may be a substituted or unsubstituted $C_5$-$C_{60}$ carbocyclic group or a substituted or unsubstituted $C_1$-$C_{60}$ heterocyclic group, $L_{501}$ to $L_{503}$ may each independently be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, xd1 to xd3 may each independently be an integer of 0 to 3, $R_{501}$ and $R_{502}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, xd4 may be an integer from 1 to 6.

In one embodiment, $Ar_{501}$ in Formula 501 may be selected from:

a naphthalene group, a heptalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, and an indenophenanthrene group; and a naphthalene group, a heptalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, and an indenophenanthrene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, and a naphthyl group.

In one or more embodiments, $L_{501}$ to $L_{503}$ in Formula 501 may each independently be selected from:

a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group; and a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group.

In one or more embodiments, $R_{501}$ and $R_{502}$ in Formula 501 may each independently be selected from:

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group; and a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, and —Si($Q_{31}$)($Q_{32}$)($Q_{33}$), and $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

In one or more embodiments, xd4 in Formula 501 may be 2, but embodiments of the present disclosure are not limited thereto.

For example, the fluorescent dopant may be selected from Compounds FD1 to FD22:

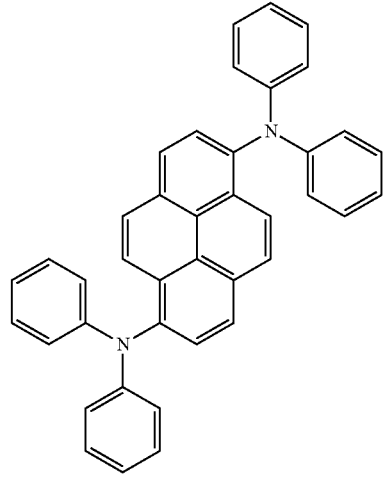

FD1

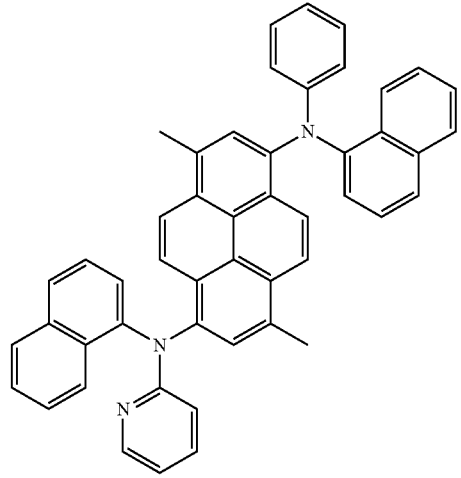

FD2

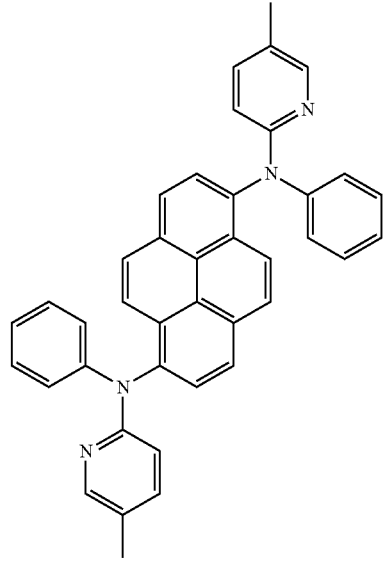

FD3

125
-continued
FD4
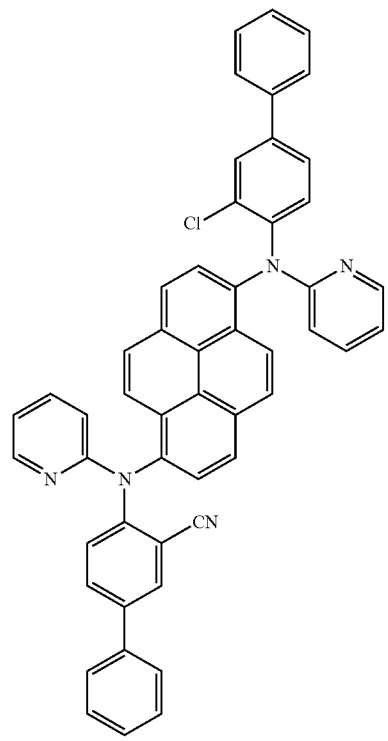
126
-continued
FD6
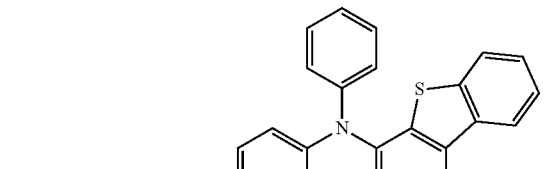
FD7
FD5
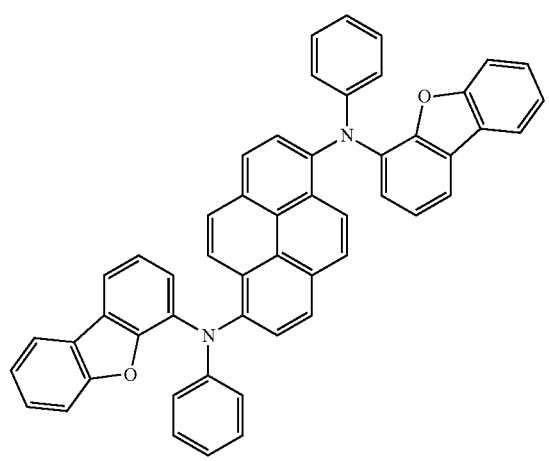
FD8
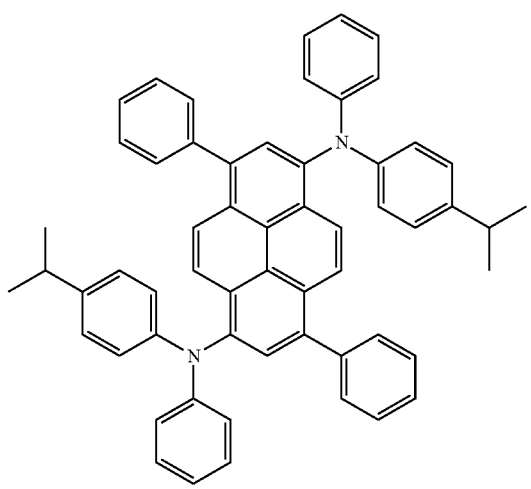

FD9
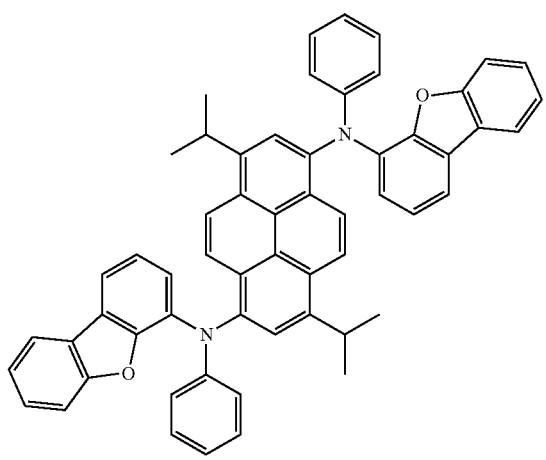
FD10
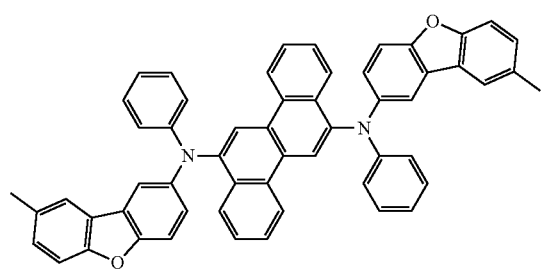
FD11
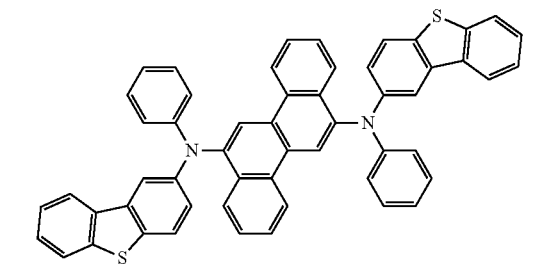
FD12
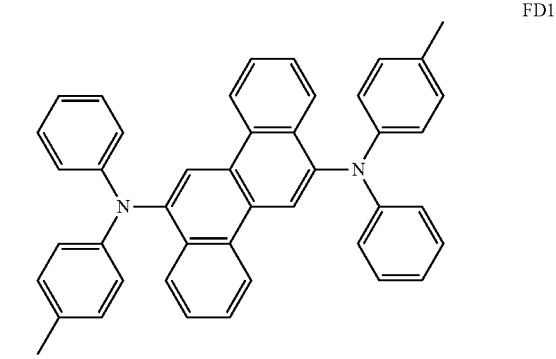
FD13
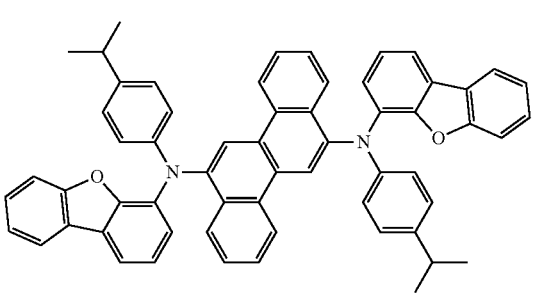
FD14
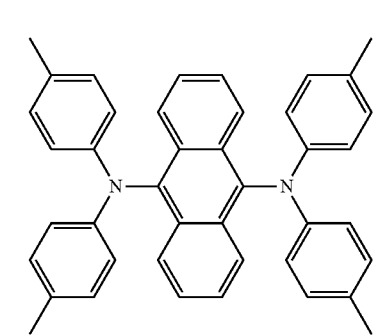
FD15
FD16
FD17
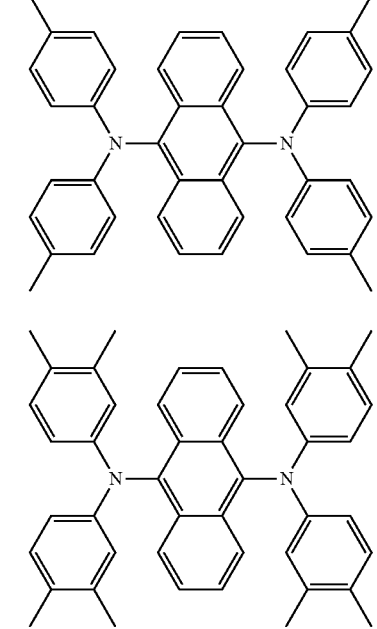

FD18
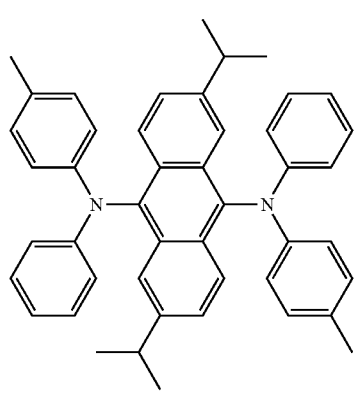
FD20
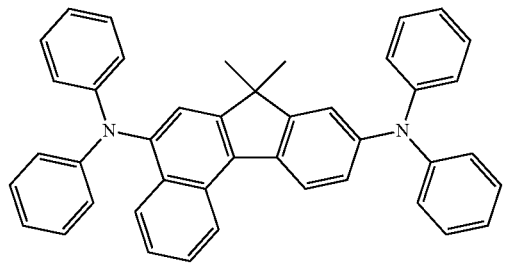
FD21
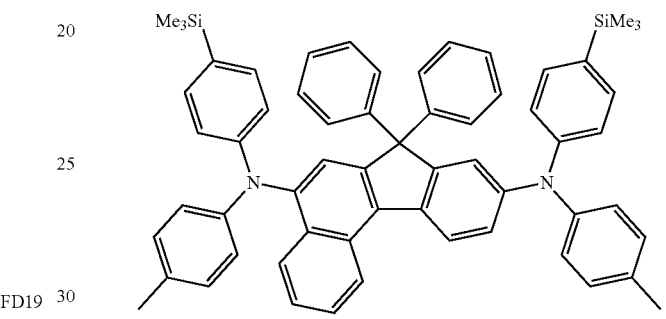
FD22
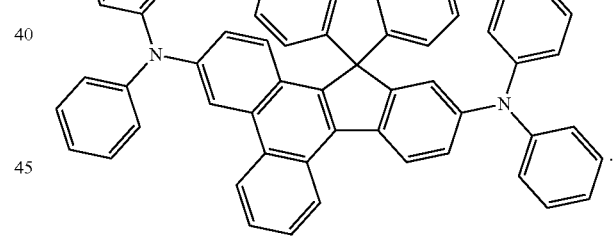
FD19
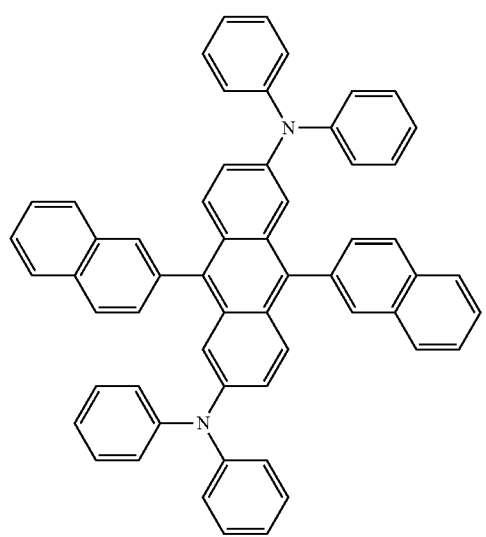
In one or more embodiments, the fluorescent dopant may be selected from the following compounds, but embodiments of the present disclosure are not limited thereto.
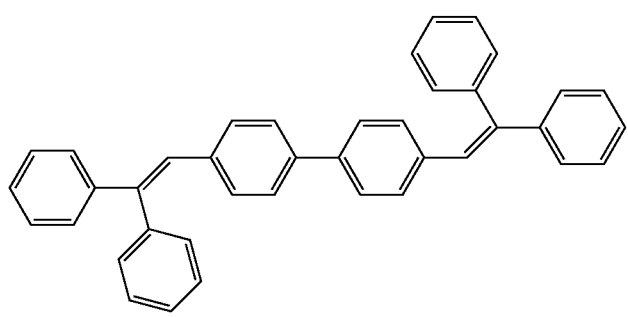
DPVBi -continued

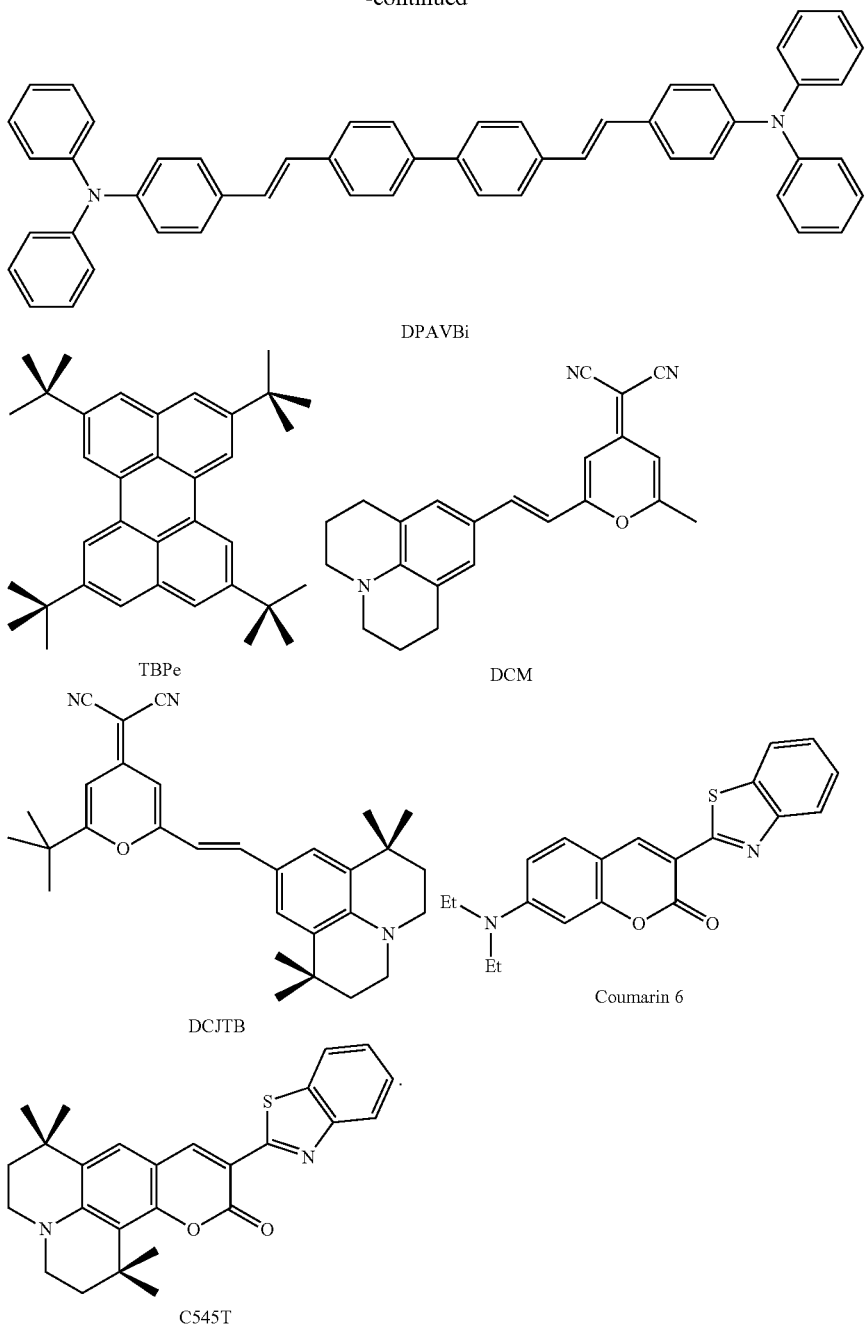

Electron Transport Region in Organic Layer 150

The electron transport region may have i) a single-layered structure including a single layer including a single material, ii) a single-layered structure including a single layer including a plurality of different materials, or iii) a multi-layered structure having a plurality of layers including a plurality of different materials.

The electron transport region may include at least one selected from a buffer layer, a hole blocking layer, an electron control layer, an electron transport layer, and an electron injection layer, but embodiments of the present disclosure are not limited thereto.

For example, the electron transport region may have an electron transport layer/electron injection layer structure, a hole blocking layer/electron transport layer/electron injection layer structure, an electron control layer/electron transport layer/electron injection layer structure, or a buffer layer/electron transport layer/electron injection layer structure, wherein for each structure, constituting layers are sequentially stacked from an emission layer. However, embodiments of the structure of the electron transport region are not limited thereto.

The electron transport region (e.g., a buffer layer, a hole blocking layer, an electron control layer, and/or an electron transport layer in the electron transport region) may include a metal-free compound containing at least one $\pi$ electron-depleted nitrogen-containing ring.

The "π electron-depleted nitrogen-containing ring" may refer to a $C_1$-$C_{60}$ heterocyclic group having at least one *—N=*' moiety as a ring-forming moiety.

For example, the "7 electron-depleted nitrogen-containing ring" may be i) a 5-membered to 7-membered heteromonocyclic group having at least one *—N=*' moiety, ii) a heteropolycyclic group in which two or more 5-membered to 7-membered heteromonocyclic groups each having at least one *—N=*' moiety are condensed with each other, or iii) a heteropolycyclic group in which at least one of 5-membered to 7-membered heteromonocyclic groups, each having at least one *—N=*' moiety, is condensed with at least one $C_5$-$C_{60}$ carbocyclic group.

Examples of the π electron-depleted nitrogen-containing ring include an imidazole, a pyrazole, a thiazole, an isothiazole, an oxazole, an isoxazole, a pyridine, a pyrazine, a pyrimidine, a pyridazine, an indazole, a purine, a quinoline, an isoquinoline, a benzoquinoline, a phthalazine, a naphthyridine, a quinoxaline, a quinazoline, a cinnoline, a phenanthridine, an acridine, a phenanthroline, a phenazine, a benzoimidazole, an isobenzothiazole, a benzoxazole, an isobenzoxazole, a triazole, a tetrazole, an oxadiazole, a triazine, thiadiazole, an imidazopyridine, an imidazopyrimidine, and an azacarbazole, but are not limited thereto.

For example, the electron transport region may include a compound represented by Formula 601:

$$[Ar_{601}]_{xe11}\text{-}[(L_{601})_{xe1}\text{-}R_{601}]_{xe21}. \quad \text{Formula 601}$$

In Formula 601, $Ar_{601}$ may be a substituted or unsubstituted $C_5$-$C_{60}$ carbocyclic group or a substituted or unsubstituted $C_1$-$C_{60}$ heterocyclic group, xe11 may be 1, 2, or 3, $L_{601}$ may each independently be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group;

xe1 may be an integer from 0 to 5, $R_{601}$ may be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_{601}$)($Q_{602}$)($Q_{603}$), —C(=O)($Q_{601}$), —S(=O)$_2$($Q_{601}$), and —P(=O)($Q_{601}$)($Q_{602}$), $Q_{601}$ to $Q_{603}$ may each independently be a $C_1$-$C_{10}$ alkyl group, a $C_1$-$C_{10}$ alkoxy group, a phenyl group, a biphenyl group, a terphenyl group, or a naphthyl group, and xe21 may be an integer from 1 to 5.

In one embodiment, at least one of xe11 number of $Ar_{601}(s)$ and xe21 number of $R_{601}(s)$ may include the π electron-depleted nitrogen-containing ring.

In one embodiment, ring $Ar_{601}$ in Formula 601 may be selected from:

a benzene group, a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, a dibenzothiophene group, a carbazole group, an imidazole group, a pyrazole group, a thiazole group, an isothiazole group, an oxazole group, an isoxazole group, a pyridine group, a pyrazine group, a pyrimidine group, a pyridazine group, an indazole group, a purine group, a quinoline group, an isoquinoline group, a benzoquinoline group, a phthalazine group, a naphthyridine group, a quinoxaline group, a quinazoline group, a cinnoline group, a phenanthridine group, an acridine group, a phenanthroline group, a phenazine group, a benzoimidazole group, an iso-benzothiazole group, a benzoxazole group, an isobenzoxazole group, a triazole group, a tetrazole group, an oxadiazole group, a triazine group, a thiadiazole group, an imidazopyridine group, an imidazopyrimidine group, and an azacarbazole group; and a benzene group, a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, a dibenzothiophene group, a carbazole group, an imidazole group, a pyrazole group, a thiazole group, an isothiazole group, an oxazole group, an isoxazole group, a pyridine group, a pyrazine group, a pyrimidine group, a pyridazine group, an indazole group, a purine group, a quinoline group, an isoquinoline group, a benzoquinoline group, a phthalazine group, a naphthyridine group, a quinoxaline group, a quinazoline group, a cinnoline group, a phenanthridine group, an acridine group, phenanthroline group, phenazine group, a benzoimidazole group, an iso-benzothiazole group, a benzoxazole group, an isobenzoxazole group, a triazole group, a tetrazole group, an oxadiazole group, a triazine group, a thiadiazole group, an imidazopyridine group, an imidazopyrimidine group, and an azacarbazole group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, —Si($Q_{31}$)($Q_{32}$)($Q_{33}$), —S(=O)$_2$($Q_{31}$), and —P(=O)($Q_{31}$)($Q_{32}$), and $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

When xe11 in Formula 601 is two or more, two or more $Ar_{601}(s)$ may be linked via a single bond.

In one or more embodiments, $Ar_{601}$ in Formula 601 may be an anthracene group.

In one or more embodiments, a compound represented by Formula 601 may be represented by Formula 601-1:

Formula 601-1

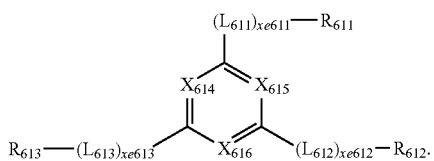

In Formula 601-1, $X_{614}$ may be N or $C(R_{614})$, $X_{615}$ may be N or $C(R_{615})$, $X_{616}$ may be N or $C(R_{616})$, and at least one selected from $X_{614}$ to $X_{616}$ may be N, definitions for $L_{611}$ to $L_{613}$ may each independently be the same as that provided in connection with $L_{601}$, definitions for xe611 to xe613 may each independently be the same as that provided in connection with xe1, definitions for $R_{611}$ to $R_{613}$ may each independently be the same as that provided in connection with $R_{601}$, $R_{614}$ to $R_{616}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, and a naphthyl group.

In one embodiment, $L_{601}$ and $L_{611}$ to $L_{613}$ in Formulae 601 and 601-1 may each independently be selected from:

a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzoimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group; and a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzoimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzoimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group, but embodiments of the present disclosure are not limited thereto.

In one or more embodiments, xe1 and xe611 to xe613 in Formulae 601 and 601-1 may each independently be 0, 1, or 2.

In one or more embodiments, in Formulae 601 and 601-1, $R_{601}$ and $R_{611}$ to $R_{613}$ may each independently be selected from:

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzoimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group;

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzoimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzoimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group; and —S($=$O)$_2$(Q$_{601}$), and —P($=$O)(Q$_{601}$)(Q$_{602}$), and Q$_{601}$ and Q$_{602}$ may be the same as described above.

The electron transport region may include at least one compound selected from Compounds ET1 to ET36, but embodiments of the present disclosure are not limited thereto:

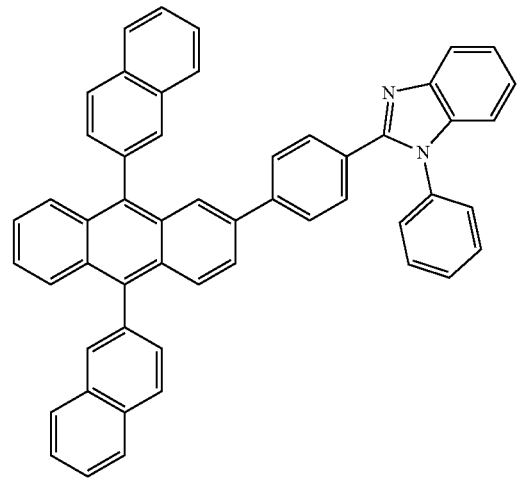

ET1

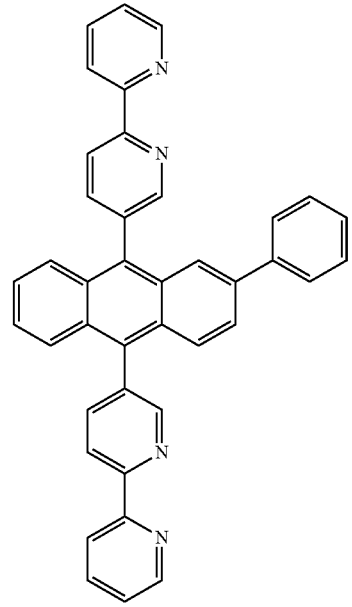

ET2

ET3
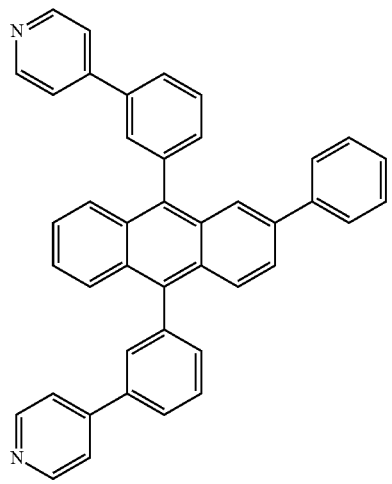
ET6
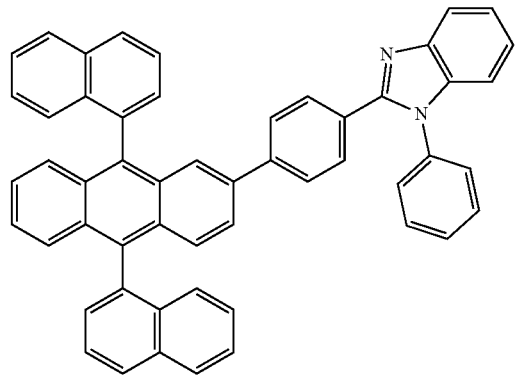
ET4
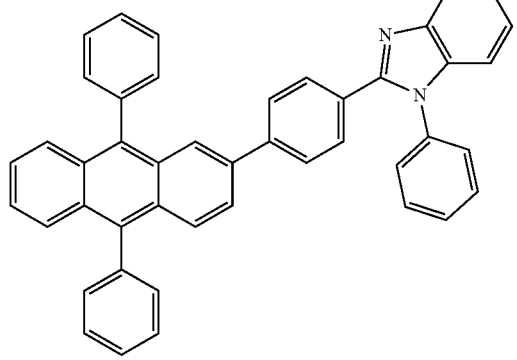
ET7
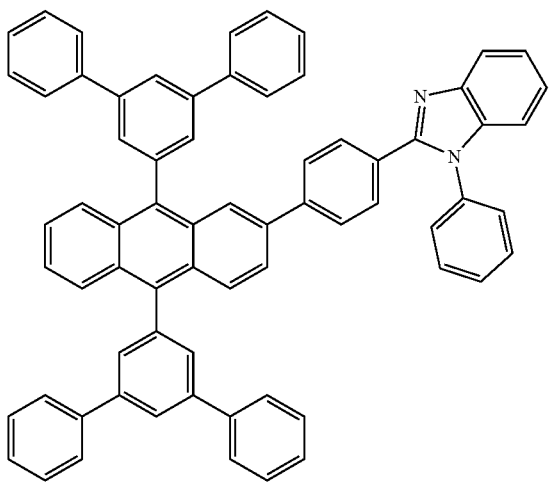
ET5
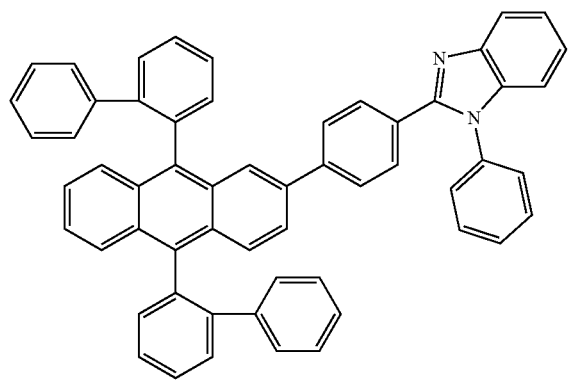
ET8
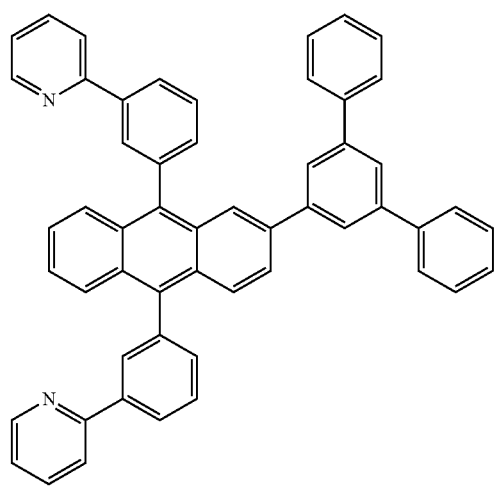

ET9
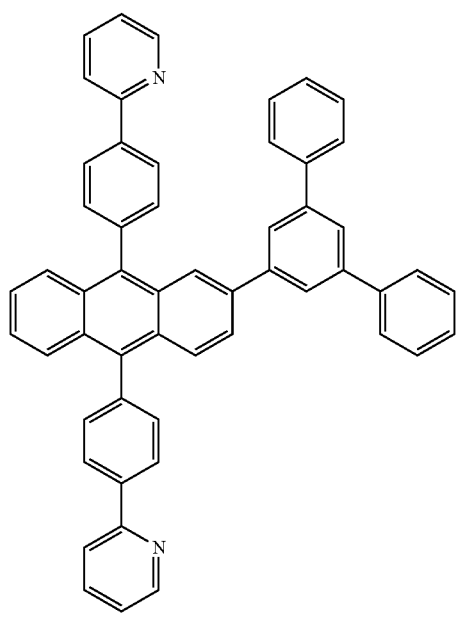
ET10
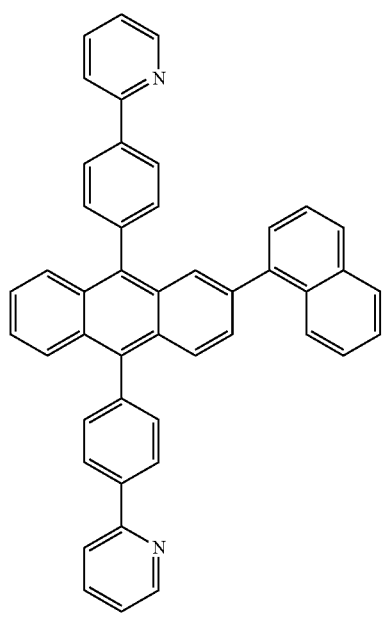
ET11
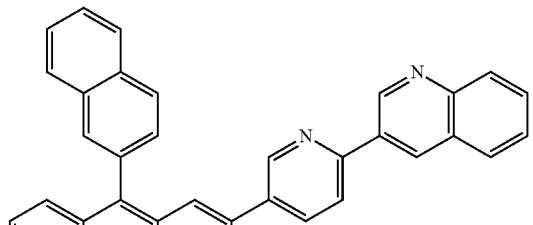
ET12
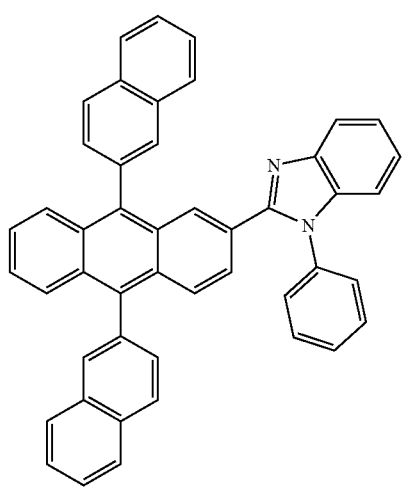
ET13
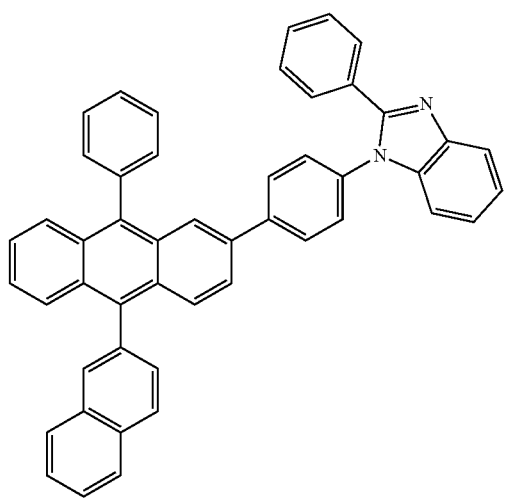

ET14
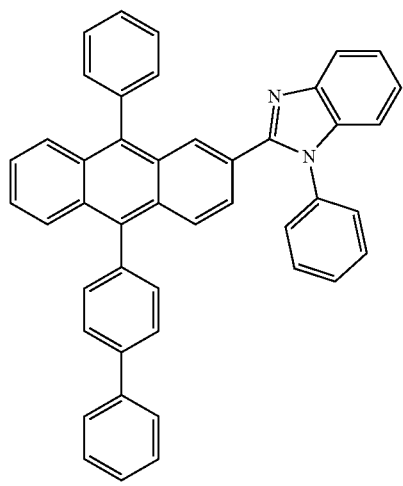
ET17
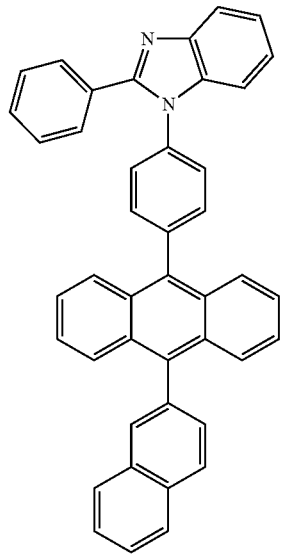
ET15
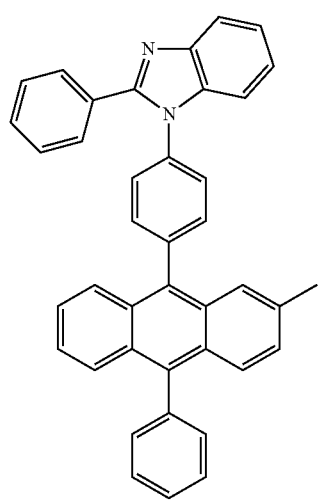
ET18
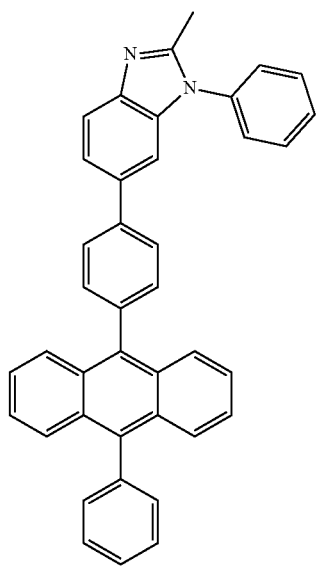
ET16
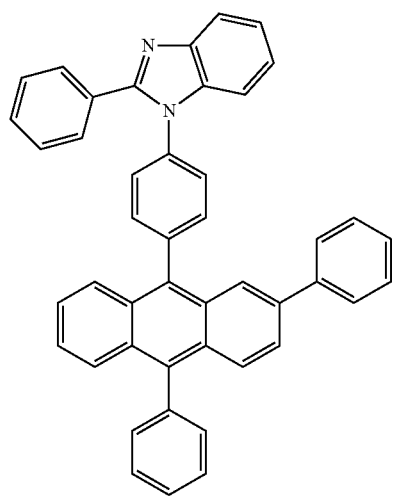
ET19
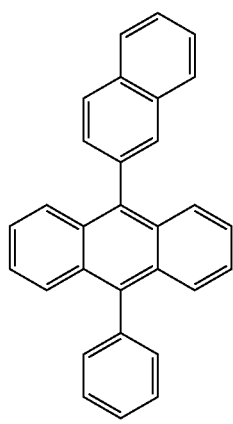

ET20
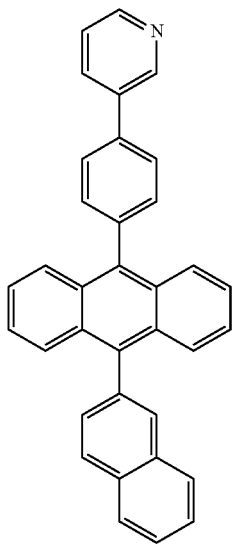
ET21
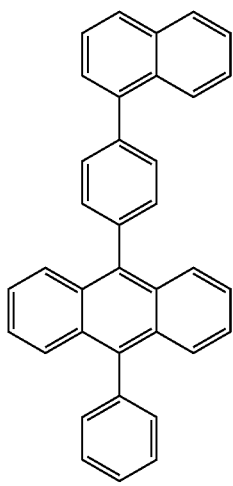
ET22
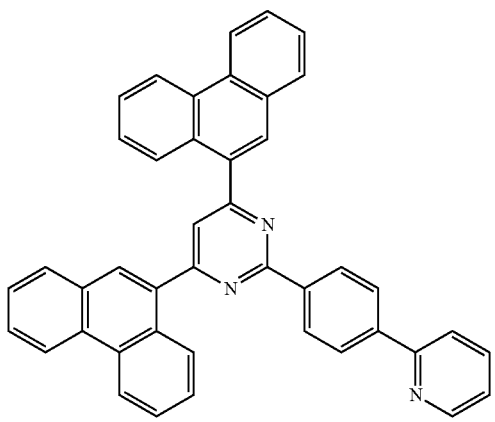
ET23
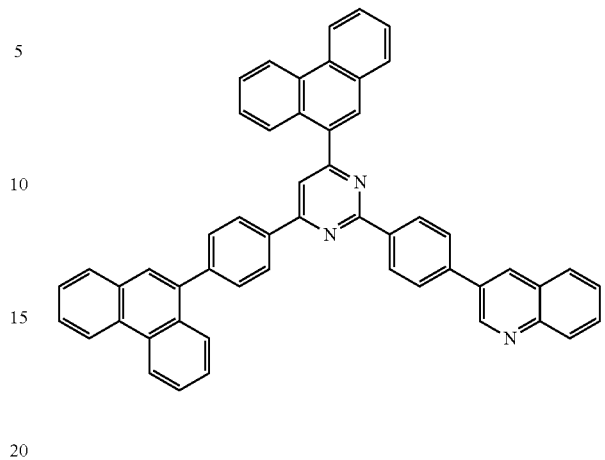
ET24
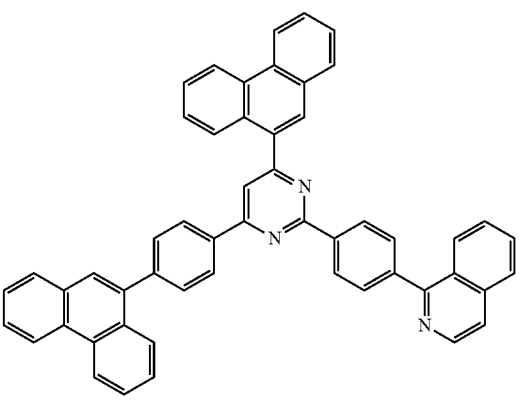
ET25
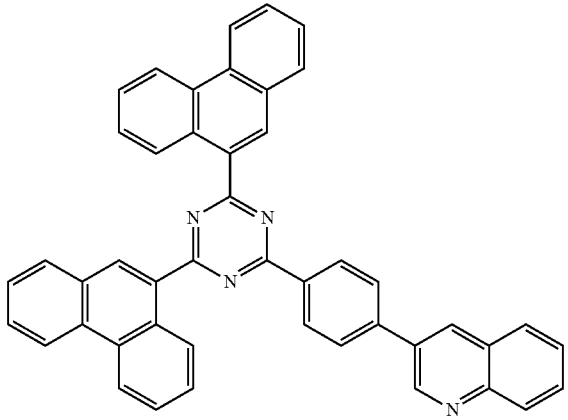

ET26
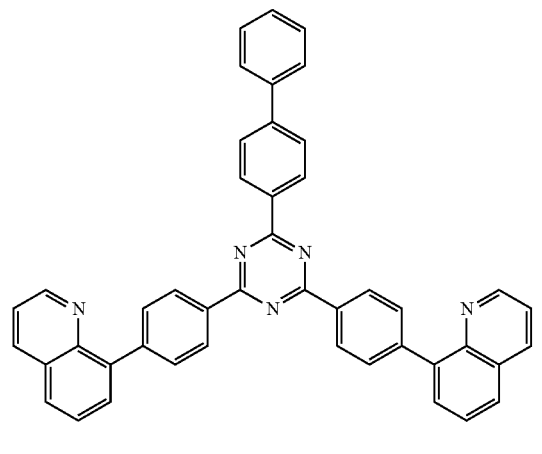
ET29
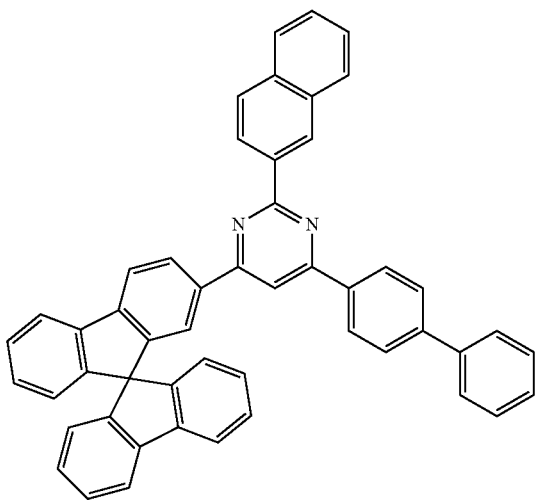
ET27
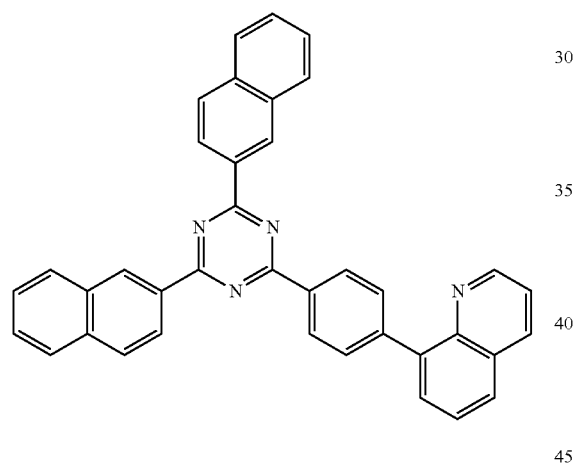
ET30
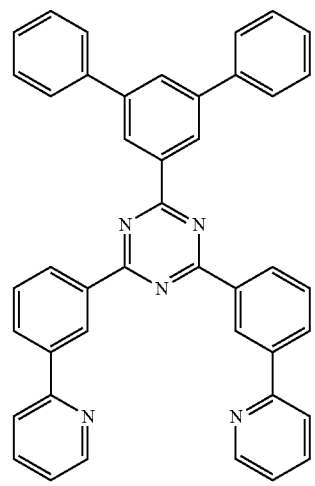
ET28
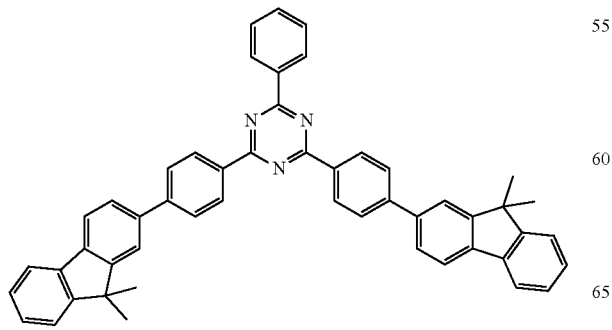
ET31
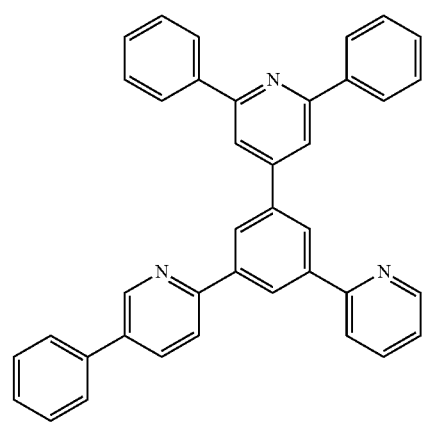

ET32
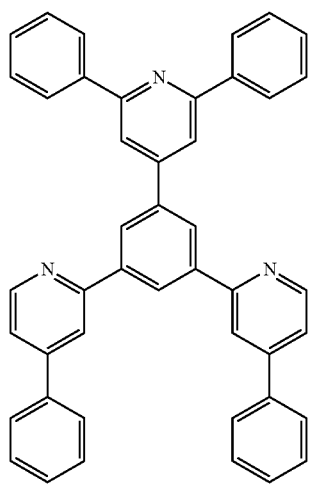
ET33
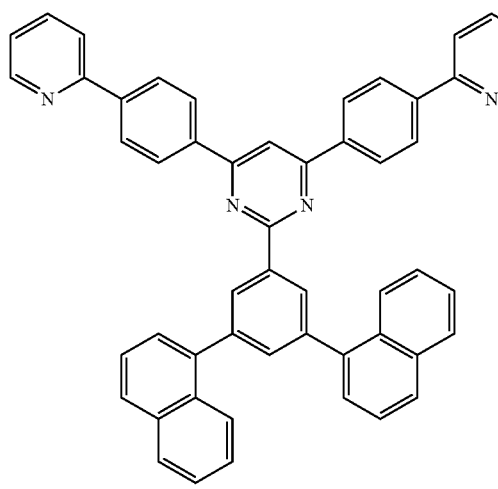
ET34
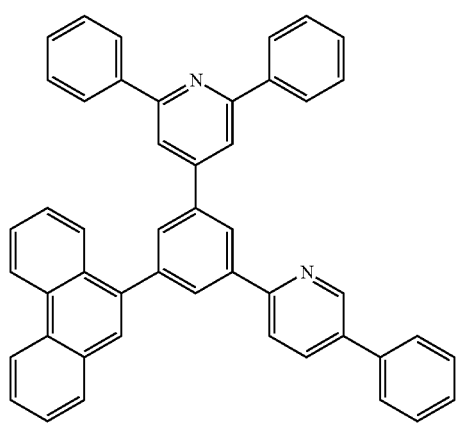
ET35
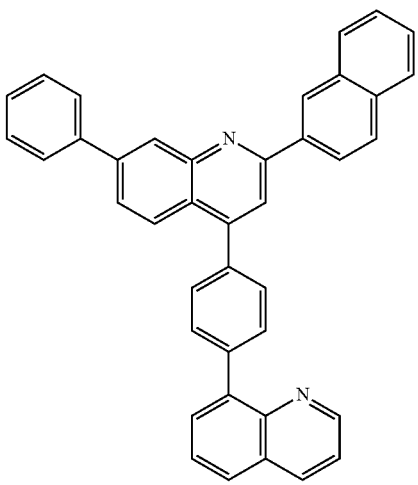
ET36
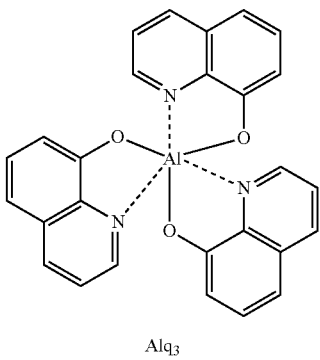
In one or more embodiments, the electron transport region may include at least one selected from 2,9-dimethyl-4,7-diphenyl-1,10-phenanthroline (BCP), 4,7-dphenyl-1,10-phenanthroline (Bphen), Alq$_3$, BAlq, 3-(biphenyl-4-yl)-5-(4-tert-butylphenyl)-4-phenyl-4H-1,2,4-triazole (TAZ), and NTAZ.

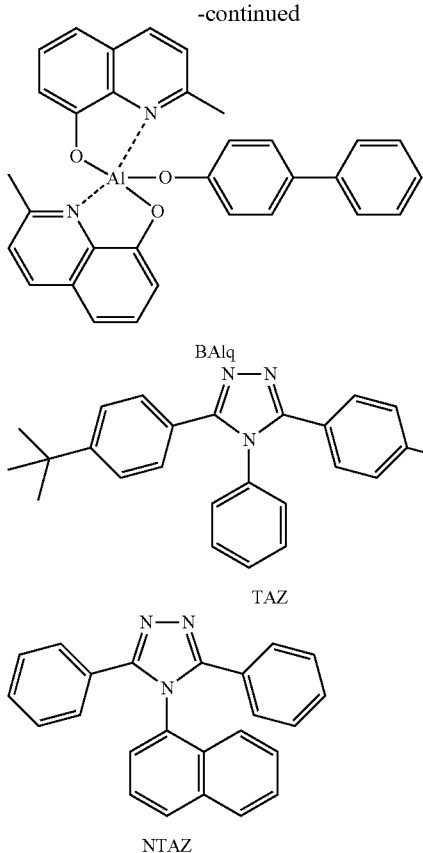

BAlq

TAZ

NTAZ

Thicknesses of the buffer layer, the hole blocking layer, and the electron control layer may each independently be in a range of about 20 Å to about 1,000 Å, for example, about 30 Å to about 300 Å. When the thicknesses of the buffer layer, the hole blocking layer, and the electron control layer are within any of these ranges, the electron transport region may have excellent (or suitable) hole blocking characteristics or electron control characteristics without a substantial increase in driving voltage.

A thickness of the electron transport layer may be in a range of about 100 Å to about 1,000 Å, for example, about 150 Å to about 500 Å. When the thickness of the electron transport layer is within the range described above, the electron transport layer may have satisfactory (or suitable) electron transport characteristics without a substantial increase in driving voltage.

The electron transport region (e.g., the electron transport layer in the electron transport region) may further include, in addition to the materials described above, a metal-containing material.

The metal-containing material may include at least one selected from alkali metal complex and alkaline earth-metal complex. The alkali metal complex may include a metal ion selected from a Li ion, a Na ion, a K ion, a Rb ion, and a Cs ion, and the alkaline earth-metal complex may include a metal ion selected from a Be ion, a Mg ion, a Ca ion, a Sr ion, and a Ba ion. A ligand coordinated with the metal ion of the alkali metal complex or the alkaline earth-metal complex may be selected from a hydroxy quinoline, a hydroxy isoquinoline, a hydroxy benzoquinoline, a hydroxy acridine, a hydroxy phenanthridine, a hydroxy phenyloxazole, a hydroxy phenylthiazole, a hydroxy diphenyloxadiazole, a hydroxy diphenylthiadiazole, a hydroxy phenylpyridine, a hydroxy phenylbenzoimidazole, a hydroxy phenylbenzothiazole, a bipyridine, a phenanthroline, and a cyclopentadiene, but embodiments of the present disclosure are not limited thereto.

For example, the metal-containing material may include a Li complex. The Li complex may include, for example, Compound ET-D1 (lithium quinolate, LiQ) or Compound ET-D2.

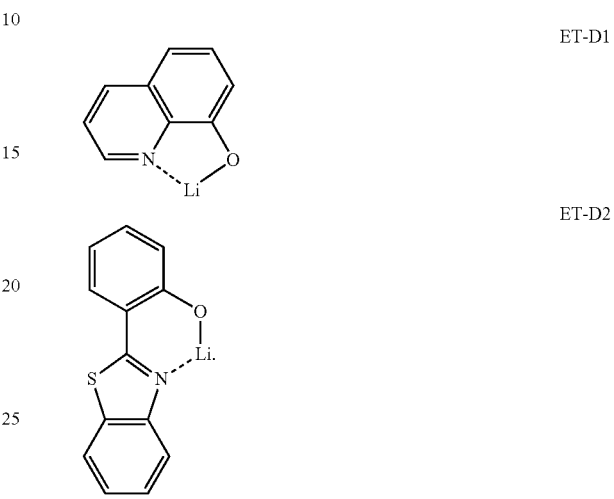

ET-D1

ET-D2

The electron transport region may include an electron injection layer that facilitates injection of electrons from the second electrode 190. The electron injection layer may directly contact the second electrode 190.

The electron injection layer may have i) a single-layered structure including a single layer including a single material, ii) a single-layered structure including a single layer including a plurality of different materials, or iii) a multi-layered structure having a plurality of layers including a plurality of different materials.

The electron injection layer may include an alkali metal, an alkaline earth metal, a rare earth metal, an alkali metal compound, an alkaline earth-metal compound, a rare earth metal compound, an alkali metal complex, an alkaline earth-metal complex, a rare earth metal complex, or any combination thereof.

The alkali metal may be selected from Li, Na, K, Rb, and Cs. In one embodiment, the alkali metal may be Li, Na, or Cs. In one or more embodiments, the alkali metal may be Li or Cs, but embodiments of the present disclosure are not limited thereto.

The alkaline earth metal may be selected from Mg, Ca, Sr, and Ba.

The rare earth metal may be selected from Sc, Y, Ce, Tb, Yb, and Gd.

The alkali metal compound, the alkaline earth-metal compound, and the rare earth metal compound may each independently be selected from oxides and halides (e.g., fluorides, chlorides, bromides, and/or iodides) of the alkali metal, the alkaline earth-metal, and the rare earth metal, respectively.

The alkali metal compound may be selected from alkali metal oxides, such as $Li_2O$, $Cs_2O$, and/or $K_2O$, and alkali metal halides, such as LiF, NaF, CsF, KF, LiI, NaI, CsI, and/or KI. In one embodiment, the alkali metal compound may be selected from LiF, $Li_2O$, NaF, LiI, NaI, CsI, and KI, but embodiments of the present disclosure are not limited thereto.

The alkaline earth metal compound may be selected from BaO, SrO, CaO, $Ba_xSr_{1-x}O$ (0<x<1), and $Ba_xCa_{1-x}O$ (0<x<1). In one embodiment, the alkaline earth-metal compound may be selected from BaO, SrO, and CaO, but embodiments of the present disclosure are not limited thereto.

The rare earth metal compound may be selected from $YbF_3$, $ScF_3$, $ScO_3$, $Y_2O_3$, $Ce_2O_3$, $Gd\ F_3$, and $TbF_3$. In one embodiment, the rare earth metal compound may be selected from $YbF_3$, $ScF_3$, $TbF_3$, $YbI_3$, $ScI_3$, and $TbI_3$, but embodiments of the present disclosure are not limited thereto.

The alkali metal complex, the alkaline earth-metal complex, and the rare earth metal complex may respectively include an ion of alkali metal, alkaline earth-metal, and rare earth metal as described above; and a ligand coordinated with a metal ion of the alkali metal complex, the alkaline earth-metal complex, or the rare earth metal complex may be selected from hydroxy quinoline, hydroxy isoquinoline, hydroxy benzoquinoline, hydroxy acridine, hydroxy phenanthridine, hydroxy phenyl oxazole, hydroxy phenylthiazole, hydroxy diphenyl oxadiazole, hydroxy diphenylthiadiazole, hydroxy phenylpyridine, hydroxy phenylbenzoimidazole, hydroxy phenylbenzothiazole, bipyridine, phenanthroline, and cyclopentadiene, but embodiments of the present disclosure are not limited thereto.

The electron injection layer may include an alkali metal, an alkaline earth metal, a rare earth metal, an alkali metal compound, an alkaline earth-metal compound, a rare earth metal compound, an alkali metal complex, an alkaline earth-metal complex, a rare earth metal complex, or any combination thereof, as described above. In one or more embodiments, the electron injection layer may further include an organic material. When the electron injection layer further includes an organic material, an alkali metal, an alkaline earth metal, a rare earth metal, an alkali metal compound, an alkaline earth-metal compound, a rare earth metal compound, an alkali metal complex, an alkaline earth-metal complex, a rare earth metal complex, or any combination thereof may be homogeneously or non-homogeneously dispersed in a matrix including the organic material.

A thickness of the electron injection layer may be in a range of about 1 Å to about 100 Å, for example, about 3 Å to about 90 Å. When the thickness of the electron injection layer is within the range described above, the electron injection layer may have satisfactory (or suitable) electron injection characteristics without a substantial increase in driving voltage.

Second Electrode 190

The second electrode 190 may be disposed on the organic layer 150 having the structure according to one or more embodiments of the present disclosure. The second electrode 190 may be a cathode, which is an electron injection electrode, and in this regard, a material for forming the second electrode 190 may be selected from metal, an alloy, an electrically conductive compound, and combinations thereof, which have a relatively low work function.

The second electrode 190 may include at least one selected from lithium (Li), silver (Ag), magnesium (Mg), aluminum (Al), aluminum-lithium (Al—Li), calcium (Ca), magnesium-indium (Mg—In), magnesium-silver (Mg—Ag), ITO, and IZO, but embodiments of the present disclosure are not limited thereto. The second electrode 190 may be a transmissive electrode, a semi-transmissive electrode, or a reflective electrode.

The second electrode 190 may have a single-layered structure, or a multi-layered structure including two or more layers.

Figure 3:
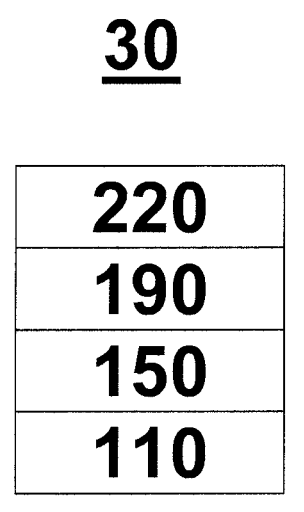
Figure 4:
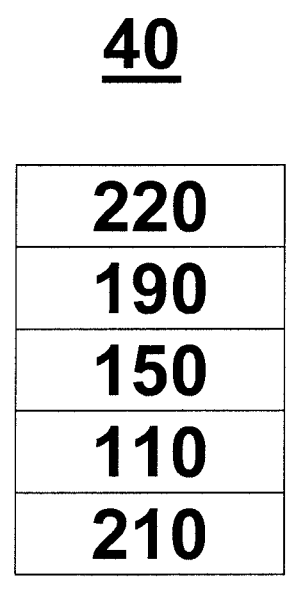

Description of FIGS. 2 to 4

Figure 2:
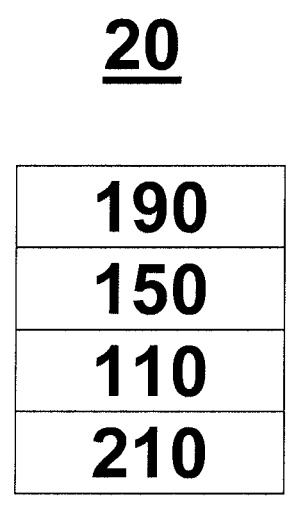

An organic light-emitting device 20 of FIG. 2 includes a first capping layer 210, a first electrode 110, an organic layer 150, and a second electrode 190 which are sequentially stacked in this stated order; an organic light-emitting device 30 of FIG. 3 includes a first electrode 110, an organic layer 150, a second electrode 190, and a second capping layer 220 which are sequentially stacked in this stated order; and an organic light-emitting device 40 of FIG. 4 includes a first capping layer 210, a first electrode 110, an organic layer 150, a second electrode 190, and a second capping layer 220 which are sequentially stacked in this stated order.

Regarding FIGS. 2 to 4, descriptions of the first electrode 110, the organic layer 150, and the second electrode 190 may be understood by referring to the respective descriptions thereof presented in connection with FIG. 1.

In the organic layer 150 of each of the organic light-emitting devices 20 and 40, light generated in the emission layer may pass through the first electrode 110, which may be a semi-transmissive electrode or a transmissive electrode, and the first capping layer 210 toward the outside; and in the organic layer 150 of each of the organic light-emitting devices 30 and 40, light generated in the emission layer may pass through the second electrode 190, which may be a semi-transmissive electrode or a transmissive electrode, and the second capping layer 220 toward the outside.

The first capping layer 210 and the second capping layer 220 may increase external luminescent efficiency according to the principle of constructive interference.

The first capping layer 210 and the second capping layer 220 may each independently be an organic capping layer including an organic material, an inorganic capping layer including an inorganic material, or a composite capping layer including an organic material and an inorganic material.

At least one selected from the first capping layer 210 and the second capping layer 220 may each independently include at least one material selected from carbocyclic compounds, heterocyclic compounds, amine-based compounds, porphyrin derivatives, phthalocyanine derivatives, a naphthalocyanine derivatives, alkali metal complexes, and alkaline earth-based complexes. The carbocyclic compound, the heterocyclic compound, and the amine-based compound may be optionally substituted with a substituent containing at least one element selected from O, N, S, Se, Si, F, Cl, Br, and I. In one embodiment, at least one selected from the first capping layer 210 and the second capping layer 220 may each independently include an amine-based compound.

In one embodiment, at least one selected from the first capping layer 210 and the second capping layer 220 may each independently include the compound represented by Formula 201 or the compound represented by Formula 202.

In one or more embodiments, at least one selected from the first capping layer 210 and the second capping layer 220 may each independently include a compound selected from Compounds HT28 to HT33 (above) and Compounds CP1 to CP5 (below), but embodiments of the present disclosure are not limited thereto.

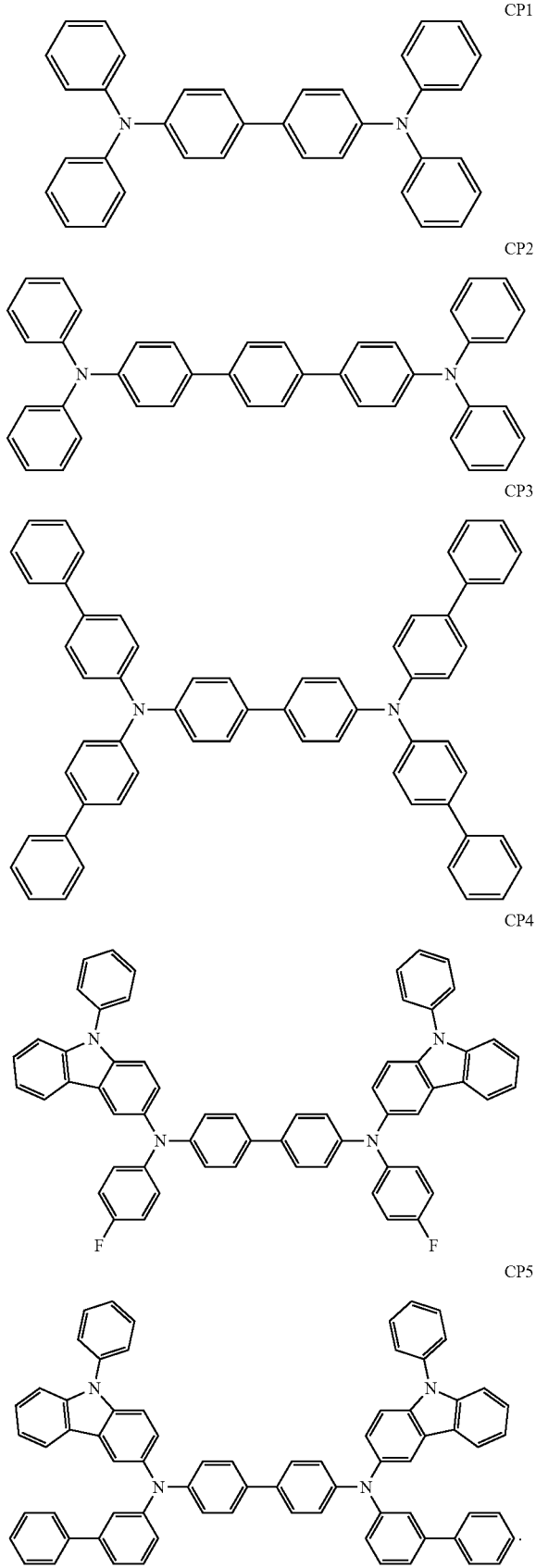 [SMILES: c1ccc(N(c2ccccc2)c2ccc(-c3ccc(N(c4ccccc4)c4ccccc4)cc3)cc2)cc1 ; c1ccc(N(c2ccccc2)c2ccc(-c3ccc(-c4ccc(N(c5ccccc5)c5ccccc5)cc4)cc3)cc2)cc1 ; c1ccc(-c2ccc(N(c3ccc(-c4ccccc4)cc3)c3ccc(-c4ccc(N(c5ccc(-c6ccccc6)cc5)c5ccc(-c6ccccc6)cc5)cc4)cc3)cc2)cc1 ; Fc1ccc(N(c2ccc(-c3ccc(N(c4ccc(F)cc4)c4ccc5c(c4)c4ccccc4n5-c4ccccc4)cc3)cc2)c2ccc3c(c2)c2ccccc2n3-c2ccccc2)cc1 ; c1ccc(-c2cccc(N(c3ccc(-c4ccc(N(c5cccc(-c6ccccc6)c5)c5ccc6c(c5)c5ccccc5n6-c5ccccc5)cc4)cc3)c3ccc4c(c3)c3ccccc3n4-c3ccccc3)c2)cc1]

Hereinbefore, the organic light-emitting device according to an embodiment has been described in connection with FIGS. 1-4. However, embodiments of the present disclosure are not limited thereto.

Layers constituting the hole transport region, the emission layer, and layers constituting the electron transport region may each independently be formed in a certain region by using one or more suitable methods selected from vacuum deposition, spin coating, casting, Langmuir-Blodgett (LB) deposition, ink-jet printing, laser-printing, and laser-induced thermal imaging.

When layers constituting the hole transport region, the emission layer, and layers constituting the electron transport region are formed by vacuum deposition, for example, the vacuum deposition may be performed at a deposition temperature of about 100° C. to about 500° C., at a vacuum degree of about $10^{-8}$ torr to about $10^{-3}$ torr, and at a deposition rate of about 0 Å/sec to about 100 Å/sec, by taking into account a material to be included in a layer to be formed, and the structure of a layer to be formed.

When layers constituting the hole transport region, the emission layer, and layers constituting the electron transport region are formed by spin coating, for example, the spin coating may be performed at a coating speed of about 2,000 rpm to about 5,000 rpm and at a heat treatment temperature of about 80° C. to about 200° C., by taking into account a material to be included in a layer to be formed, and the structure of a layer to be formed.

General Definition of Substituents

The term "$C_1$-$C_{60}$ alkyl group" as used herein may refer to a linear or branched aliphatic saturated hydrocarbon monovalent group having 1 to 60 carbon atoms, and non-limiting examples thereof include a methyl group, an ethyl group, a propyl group, an isobutyl group, a sec-butyl group, a tert-butyl group, a pentyl group, an iso-amyl group, and a hexyl group. The term "$C_1$-$C_{60}$ alkylene group" as used herein may refer to a divalent group having the same structure as the $C_1$-$C_{60}$ alkyl group.

The term "$C_2$-$C_{60}$ alkenyl group" as used herein may refer to a hydrocarbon group having at least one carbon-carbon double bond in the middle or at either terminus of the $C_2$-$C_{60}$ alkyl group, and non-limiting examples thereof include an ethenyl group, a propenyl group, and a butenyl group. The term "$C_2$-$C_{60}$ alkenylene group" as used herein may refer to a divalent group having the same structure as the $C_2$-$C_{60}$ alkenyl group.

The term "$C_2$-$C_{60}$ alkynyl group" as used herein may refer to a hydrocarbon group having at least one carbon-carbon triple bond in the middle or at either terminus of the $C_2$-$C_{60}$ alkyl group, and non-limiting examples thereof include an ethynyl group, and a propynyl group. The term "$C_2$-$C_{60}$ alkynylene group" as used herein may refer to a divalent group having the same structure as the $C_2$-$C_{60}$ alkynyl group.

The term "$C_1$-$C_{60}$ alkoxy group" as used herein may refer to a monovalent group represented by —$OA_{101}$ (wherein $A_{101}$ is the $C_1$-$C_{60}$ alkyl group), and non-limiting examples thereof include a methoxy group, an ethoxy group, and an isopropoxy group.

The term "$C_3$-$C_{10}$ cycloalkyl group" as used herein may refer to a monovalent saturated hydrocarbon monocyclic group having 3 to 10 carbon atoms, and non-limiting examples thereof include a cyclopropyl group, a cyclobutyl group, a cyclopentyl group, a cyclohexyl group, and a cycloheptyl group. The term "$C_3$-$C_{10}$ cycloalkylene group" as used herein may refer to a divalent group having the same structure as the $C_3$-$C_{10}$ cycloalkyl group.

The term "$C_1$-$C_{10}$ heterocycloalkyl group" used herein may refer to a monovalent monocyclic group having at least one heteroatom selected from N, O, Si, P, and S as a ring-forming atom and 1 to 10 carbon atoms, and non-limiting examples thereof include a 1,2,3,4-oxatriazolidinyl group, a tetrahydrofuranyl group, and a tetrahydrothiophenyl group. The term "$C_1$-$C_{10}$ heterocycloalkylene group" as used herein may refer to a divalent group having the same structure as the $C_1$-$C_{10}$ heterocycloalkyl group.

The term $C_3$-$C_{10}$ cycloalkenyl group used herein may refer to a monovalent monocyclic group that has 3 to 10 carbon atoms and at least one carbon-carbon double bond in the ring thereof and no aromaticity, and non-limiting examples thereof include a cyclopentenyl group, a cyclohexenyl group, and a cycloheptenyl group. The term "$C_3$-$C_{10}$ cycloalkenylene group" as used herein may refer to a divalent group having the same structure as the $C_3$-$C_{10}$ cycloalkenyl group.

The term "$C_1$-$C_{10}$ heterocycloalkenyl group" as used herein may refer to a monovalent monocyclic group that has at least one heteroatom selected from N, O, Si, P, and S as a ring-forming atom, 1 to 10 carbon atoms, and at least one double bond in its ring. Non-limiting examples of the $C_1$-$C_{10}$ heterocycloalkenyl group include a 4,5-dihydro-1,2,3,4-oxatriazolyl group, a 2,3-dihydrofuranyl group, and a 2,3-dihydrothiophenyl group. The term "$C_1$-$C_{10}$ heterocycloalkenylene group" as used herein may refer to a divalent group having the same structure as the $C_1$-$C_{10}$ heterocycloalkenyl group.

The term "$C_6$-$C_{60}$ aryl group" as used herein may refer to a monovalent group having a carbocyclic aromatic system having 6 to 60 carbon atoms, and the term "$C_6$-$C_{60}$ arylene group" as used herein may refer to a divalent group having a carbocyclic aromatic system having 6 to 60 carbon atoms. Non-limiting examples of the $C_6$-$C_{60}$ aryl group include a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each independently include two or more rings, the respective rings may be fused (condensed) to each other.

The term "$C_1$-$C_{60}$ heteroaryl group" as used herein may refer to a monovalent group having a carbocyclic aromatic system that has at least one heteroatom selected from N, O, Si, P, and S as a ring-forming atom, in addition to 1 to 60 carbon atoms. The term "$C_1$-$C_{60}$ heteroarylene group" as used herein may refer to a divalent group having a carbocyclic aromatic system that has at least one heteroatom selected from N, O, Si, P, and S as a ring-forming atom, in addition to 1 to 60 carbon atoms. Non-limiting examples of the $C_1$-$C_{60}$ heteroaryl group include a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group each independently include two or more rings, the respective rings may be condensed (fused) with each other.

The term "$C_6$-$C_{60}$ aryloxy group" as used herein may refer to a group represented by —$OA_{102}$ (wherein $A_{102}$ is the $C_6$-$C_{60}$ aryl group), and a $C_6$-$C_{60}$ arylthio group used herein may refer to a group represented by —$SA_{103}$ (wherein $A_{103}$ is the $C_6$-$C_{60}$ aryl group).

The term "monovalent non-aromatic condensed polycyclic group" as used herein may refer to a monovalent group having two or more rings condensed (fused) with each other, only carbon atoms as ring-forming atoms (e.g., having 8 to 60 carbon atoms), and no aromaticity in its entire molecular structure. A non-limiting example of the monovalent non-aromatic condensed polycyclic group is a fluorenyl group. The term "divalent non-aromatic condensed polycyclic group," used herein, may refer to a divalent group having the same structure as the monovalent non-aromatic condensed polycyclic group.

The term "monovalent non-aromatic condensed heteropolycyclic group" as used herein may refer to a monovalent group having two or more rings condensed (fused) to each other, at least one heteroatom selected from N, O, Si, P, and S, other than carbon atoms (e.g., 1 to 60 carbon atoms), as a ring-forming atom, and no aromaticity in its entire molecular structure. A non-limiting example of the monovalent non-aromatic condensed heteropolycyclic group is a carbazolyl group. The term "divalent non-aromatic condensed heteropolycyclic group" as used herein may refer to a divalent group having the same structure as the monovalent non-aromatic condensed heteropolycyclic group.

The term "$C_3$-$C_{60}$ carbocyclic group" as used herein may refer to a monocyclic or polycyclic group having 3 to 60 carbon atoms, in which ring-forming atoms are carbon atoms only. The $C_3$-$C_{60}$ carbocyclic group may be an aromatic carbocyclic group or a non-aromatic carbocyclic group. The $C_3$-$C_{60}$ carbocyclic group may be a ring (such as benzene), a monovalent group (such as a phenyl group), or a divalent group (such as a phenylene group). In one or more embodiments, depending on the number of substituents connected to the $C_3$-$C_{60}$ carbocyclic group, the $C_3$-$C_{60}$ carbocyclic group may be a trivalent group or a quadrivalent group.

The term "$C_1$-$C_{60}$ heterocyclic group" as used herein may refer to a group having the same structure as the $C_1$-$C_{60}$ carbocyclic group, except that as a ring-forming atom, at least one heteroatom selected from N, O, Si, P, and S is used, in addition to carbon (the number of carbon atoms may be in a range of 1 to 60).

At least one substituent of the substituted $C_5$-$C_{60}$ carbocyclic group, the substituted $C_1$-$C_{60}$ heterocyclic group, the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_1$-$C_{10}$ heterocycloalkenylene group, the substituted $C_6$-$C_{60}$ arylene group, the substituted $C_1$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be selected from:

deuterium (-D), —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —N($Q_{11}$)($Q_{12}$), —B($Q_{11}$)($Q_{12}$), —C(=O)($Q_{11}$), —S(=O)$_2$($Q_{11}$), and —P(=O)($Q_{11}$)($O_{12}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), and —P(=O)($Q_{21}$)($Q_{22}$); and —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), and $Q_{11}$ to $Q_{13}$, $Q_{21}$ to $Q_{23}$, and $Q_{31}$ to $Q_{33}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, and a terphenyl group.

The term "Ph" used herein may refer to a phenyl group, the term "Me" used herein may refer to a methyl group, the term "Et" used herein may refer to an ethyl group, the term "ter-Bu" or "Bu$^t$" used herein may refer to a tert-butyl group, the term "OMe" used herein may refer to a methoxy group, and "D" may refer to deuterium.

The term "biphenyl group" as used herein may refer to a phenyl group substituted with a phenyl group. For example, the "biphenyl group" may be described as a substituted phenyl group having a $C_6$-$C_{60}$ aryl group as a substituent.

The term "terphenyl group" as used herein may refer to a phenyl group substituted with a biphenyl group. For example, the "terphenyl group" may be described as a phenyl group having, as a substituent, a $C_6$-$C_{60}$ aryl group substituted with a $C_6$-$C_{60}$ aryl group.

* and *' used herein, unless defined otherwise, each refer to a binding site to a neighboring atom in a corresponding formula.

Hereinafter, a compound according to embodiments of the present disclosure and an organic light-emitting device according to embodiments of the present disclosure will be described in more detail with reference to Synthesis Examples and Examples. The expression "B was used instead of A" used in describing Synthesis Examples may refer to an identical molar equivalent of B being used in place of A.

EXAMPLES

Synthesis Example 1: Synthesis of Compound 1

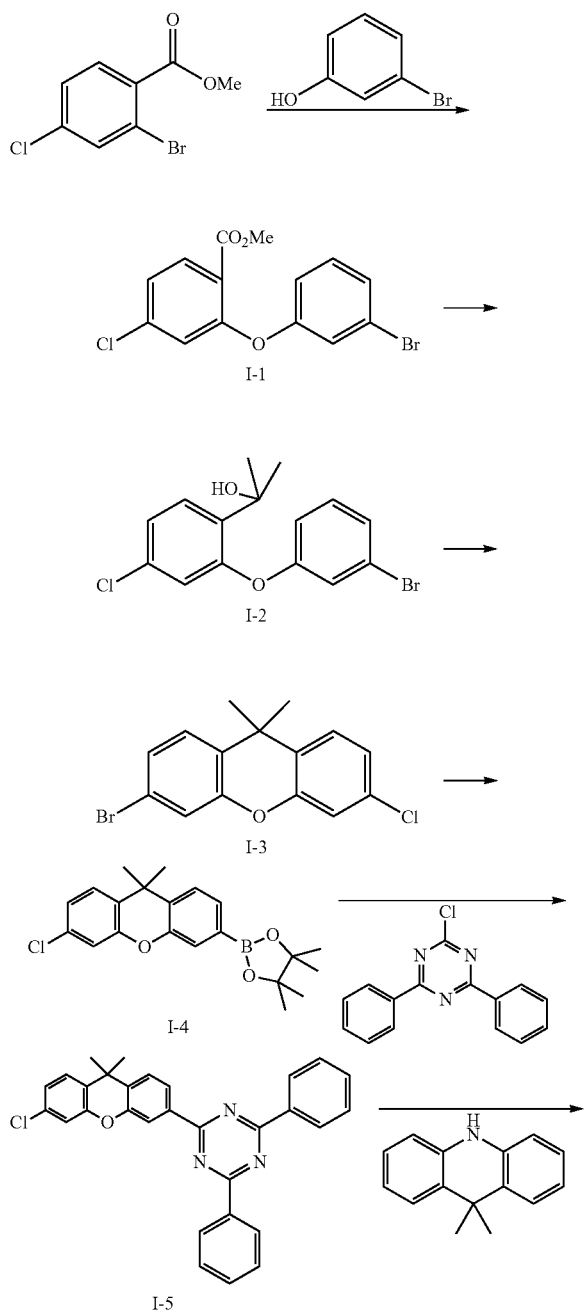

-continued

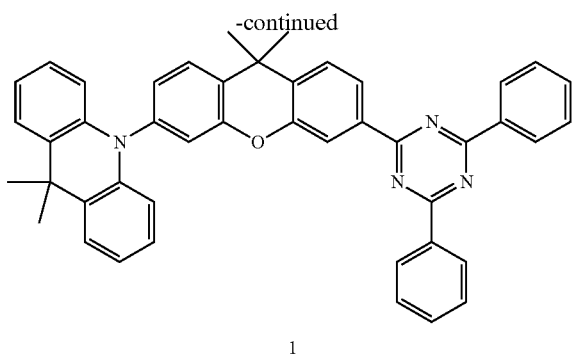

1

Synthesis of Intermediate I-1

20 g (80.0 mmol) of methyl 2-bromo-4-chlorobenzoate and 14 g (80.0 mmol) of 3-bromophenol were diluted in 100 mL of pyridine, and then, 16.6 g (126.0 mmol) of $K_2CO_3$ and 7.6 g (95.5 mmol) of CuO were sequentially added dropwise thereto. The reaction mixture was stirred at a temperature of 130° C. for 5 hours. Then, the reaction mixture was slowly cooled to room temperature and filtered under reduced pressure. A filtrate obtained therefrom was neutralized with conc. HCl at a temperature of 0° C. Then, an organic layer was extracted therefrom by using 100 mL of ethyl acetate. The extracted organic layer was dried by using anhydrous magnesium sulfate, and a distillation process was performed thereon under reduced pressure. Then, the residue obtained therefrom was separated and purified by silica gel column chromatography to obtain 25.7 g (yield: 94%) of Intermediate I-1. The obtained compound was identified by Liquid Chromatography-Mass Spectrometry (LC-MS): ($C_{14}H_{10}BrClO_3$ M+ cal.: 340.0 found: 341.0).

Synthesis of Intermediate I-2

25 g (73.1 mmol) of Intermediate I-1 was diluted in 150 mL of tetrahydrofuran (THF), and 153.5 mL of methyl magnesium chloride (1 M, 153.5 mmol) was slowly added dropwise thereto at a temperature of −78° C. After the same temperature was kept for 30 minutes, the reaction mixture was slowly heated to room temperature and additionally stirred for 7 hours. After the reaction was terminated by using 1N HCl, an organic layer was extracted therefrom by using 150 mL of ethyl acetate. The extracted organic layer was dried by using anhydrous magnesium sulfate and filtered under reduced pressure. Then, the residue obtained therefrom was separated and purified by silica gel column chromatography to obtain 22.7 g (yield: 91%) of Intermediate I-2. The obtained compound was identified by LC-MS: ($C_{15}H_{14}BrClO_2$ M+ cal.: 340.0 found: 341.0).

Synthesis of Intermediate I-3

22 g (64.4 mmol) of Intermediate I-2 was dissolved in 140 mL of dichloromethane, and 0.1 mL of methanesulfonic acid was added thereto. By using 1 mL of triethylamine, the reaction was terminated after 10 minutes, and a distillation process was performed thereon under reduced pressure. Then, the residue obtained therefrom was separated and purified by silica gel column chromatography to obtain 16.2 g (yield: 78%) of Intermediate I-3. The obtained compound was identified by LC-MS: ($C_{15}H_{12}BrClO$ M+ cal.: 322.0 found: 323.0).

Synthesis of Intermediate I-4

16 g (49.4 mmol) of Intermediate I-3 was dissolved in 150 mL of THF, and 20 mL of n-BuLi (2.5 M, 50.0 mmol) was slowly added thereto at a temperature of −78° C. Then, the reaction solution was stirred at the same temperature for 1 hour. 10.5 mL (51.0 mmol) of 2-isopropoxy-4,4,5,5-tetramethyl-1,3,2-dioxaborolane was slowly added dropwise to the reaction solution at a temperature of −78° C. The resultant reaction solution was heated to room temperature and stirred for 3 hours. The reaction was terminated by adding 100 mL of 10% HCl (aq) to the reaction solution, and an organic layer was extracted therefrom by using 150 mL of diethylether. The extracted organic layer was dried by using anhydrous magnesium sulfate, and a distillation process was performed thereon under reduced pressure. Then, the residue obtained therefrom was separated and purified by silica gel column chromatography to obtain 15.6 g (yield: 85%) of Intermediate I-4. The obtained compound was identified by LC-MS: ($C_{21}H_{24}BrClO_3$ M+ cal.: 370.2 found: 371.2).

Synthesis of Intermediate I-5

15 g (40.0 mmol) of Intermediate I-4, 11.8 g (44.0 mmol) of 2-chloro-4,6-diphenyl-1,3,5-triazine, 2.3 g (2.0 mmol) of Pd(PPh$_3$)$_4$, and 11.5 g (120.0 mmol) of $K_2CO_3$ were dissolved in 150 mL of a mixed solution of THF/H$_2$O (1:1), and then, the reaction mixture was stirred at a temperature of 80° C. for 5 hours. The reaction mixture was cooled to room temperature, and an organic layer was extracted therefrom by using 100 mL of diethylether. The extracted organic layer was dried by using anhydrous magnesium sulfate, and a distillation process was performed thereon under reduced pressure. Then, the residue obtained therefrom was separated and purified by silica gel column chromatography to obtain 15.6 g (yield: 85%) of Intermediate I-5. The obtained compound was identified by LC-MS: ($C_{30}H_{22}ClN_3O$ M+ cal.: 475.1 found: 476.1).

Synthesis of Compound 1

2.4 g (5.0 mmol) of Intermediate I-5, 1.2 g (5.5 mmol) of 9,9-dimethyl-9,10-dihydroacridine, 0.23 g (0.25 mmol) of Pd$_2$(dba)$_3$, 0.05 g (0.25 mmol) of P(tBu)$_3$, and 0.72 g (7.5 mmol) of NaOtBu were dissolved in 20 mL of toluene, and the reaction solution was heated under reflux for 5 hours. Then, the reaction solution was cooled to room temperature, and an organic layer was extracted therefrom by using 30 mL of diethylether. The extracted organic layer was dried by using anhydrous magnesium sulfate, and a distillation process was performed thereon under reduced pressure. Then, the residue obtained therefrom was separated and purified by silica gel column chromatography to obtain 2.6 g (yield: 79%) of Compound 1. The obtained compound was identified by LC-MS and NMR: ($C_{45}H_{36}N_4O$ M+ cal.: 648.3 found: 649.3).

Synthesis Example 2: Synthesis of Compound 3

2.4 g (yield: 76%) of Compound 3 was obtained in the same (or substantially the same) manner as in Synthesis of Compound 1, except that Intermediate I-5 and 10H-phenoxazine were used instead of Intermediate I-5 and 9,9- dimethyl-9,10-dihydroacridine. The obtained compound was identified by LC-MS and NMR.

($C_{42}H_{30}N_4O_2$ M+ cal.: 622.2 found: 623.2).

Synthesis Example 3: Synthesis of Compound 4

2.3 g (yield: 73%) of Compound 4 was obtained in the same (or substantially the same) manner as in Synthesis of Compound 1, except that Intermediate I-5 and 10H-phenothiazine were used instead of Intermediate I-5 and 9,9-dimethyl-9,10-dihydroacridine. The obtained compound was identified by LC-MS and NMR. ($C_{42}H_{30}N_4OS$ M+ cal.: 638.2 found: 639.2).

Synthesis Example 4: Synthesis of Compound 5

2.1 g (yield: 64%) of Compound 5 was obtained in the same (or substantially the same) manner as in Synthesis of Compound 1 except that Intermediate I-5 and 10,10-dimethyl-5,10-dihydrodibenzo[b,e][1,4]azasiline were used instead of Intermediate I-5 and 9,9-dimethyl-9,10-dihydroacridine. The obtained compound was identified by LC-MS and NMR. ($C_{44}H_{36}N_4OSi$ M+ cal.: 664.3 found: 665.3).

Synthesis Example 5: Synthesis of Compound 6 by using 30 mL of diethylether. The extracted organic layer was dried by using anhydrous magnesium sulfate, and a distillation process was performed thereon under reduced pressure. Then, the residue obtained therefrom was separated and purified by silica gel column chromatography to obtain 2.6 g (yield: 72%) of Compound 6. The obtained compound was identified by LC-MS and NMR: ($C_{51}H_{40}N_4O$ M+ cal.: 724.3 found: 725.3).

Synthesis Example 6: Synthesis of Compound 10

2.6 g (yield: 73%) of Compound 10 was obtained in the same (or substantially the same) manner as in Synthesis of Compound 6 except that Intermediate I-5 and (9,9-dimethyl-10-phenyl-9,10-dihydroacridin-3-yl)boronic acid were used instead of Intermediate I-5 and (9,9-dimethyl-10-phenyl-9,10-dihydroacridin-2-yl)boronic acid. The obtained compound was identified by LC-MS and NMR: ($C_{51}H_{40}N_4O$ M+ cal.: 724.3 found: 725.3).

Synthesis Example 7: Synthesis of Compound 12

2.8 g (yield: 77%) of Compound 12 was obtained in the same (or substantially the same) manner as in Synthesis of

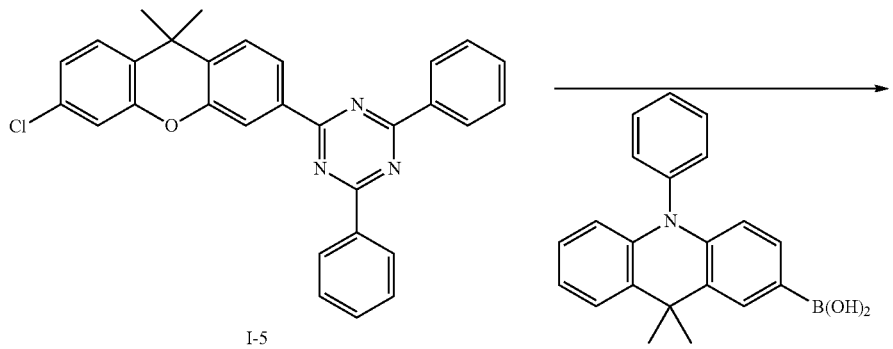

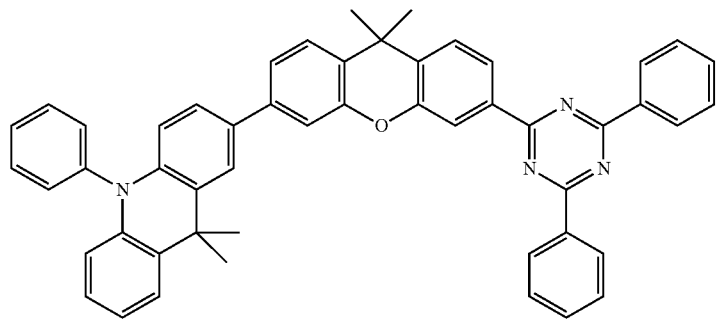

2.4 g (5.0 mmol) of Intermediate I-5, 1.8 g (44.0 mmol) of (9,9-dimethyl-10-phenyl-9,10-dihydroacridin-2-yl)boronic acid, 0.29 g (0.25 mmol) of Pd(PPh$_3$)$_4$, and 2.1 g (15.0 mmol) of K$_2$CO$_3$ were dissolved in 30 mL of 1,4-dioxane, and the reaction mixture was stirred at a temperature of 90° C. for 5 hours. The reaction mixture was cooled to room temperature, and an organic layer was extracted therefrom Compound 6 except that Intermediate I-5 and (3-(9,9-dimethylacridin-10(9H)-yl)phenyl)boronic acid were used instead of Intermediate I-5 and (9,9-dimethyl-10-phenyl-9,10-dihydroacridin-2-yl)boronic acid. The obtained compound was identified by LC-MS and NMR: ($C_{51}H_{40}N_4O$ M+ cal.: 724.3 found: 725.3).

Synthesis Example 8: Synthesis of Compound 13

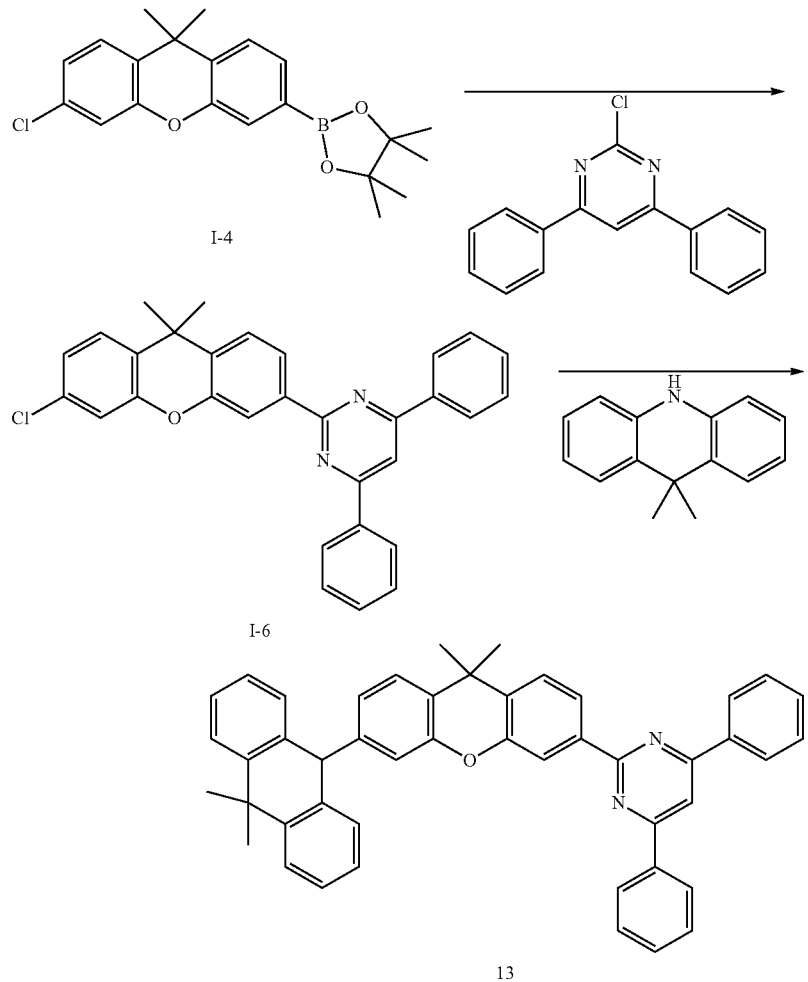

Synthesis of Intermediate I-6

3.0 g (8.0 mmol) of Intermediate I-4, 2.4 g (8.8 mmol) of 2-chloro-4,6-diphenylpyrimidine, 0.46 g (0.4 mmol) of Pd(PPh$_3$)$_4$, and 3.3 g (24.0 mmol) of K$_2$CO$_3$ were dissolved in 30 mL of a mixed solution of THF/H$_2$O (1:1), and the reaction mixture was stirred at a temperature of 80° C. for 5 hours. Then, the reaction mixture was cooled to room temperature, and an organic layer was extracted therefrom by using 30 mL of diethylether. The extracted organic layer was dried by using anhydrous magnesium sulfate, and a distillation process was performed thereon under reduced pressure. Then, the residue obtained therefrom was separated and purified by silica gel column chromatography to obtain 3.1 g (yield: 81%) of Intermediate I-6. The obtained compound was identified by LC-MS: (C$_{31}$H$_{23}$ClN$_2$O M+ cal.: 474.1 found: 475.1).

Synthesis of Compound 13

2.4 g (yield: 75%) of Compound 13 was obtained in the same (or substantially the same) manner as in Synthesis of Compound 1 except that Intermediate I-6 and 9,9-dimethyl-9,10-dihydroacridine were used instead of Intermediate I-5 and 9,9-dimethyl-9,10-dihydroacridine. The obtained compound was identified by LC-MS and NMR: (C$_{46}$H$_{37}$N$_3$O M+ cal.: 647.3 found: 648.3).

Synthesis Example 9: Synthesis of Intermediates I-7 to I-15

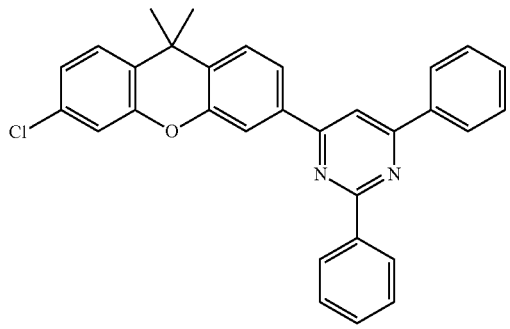

I-8

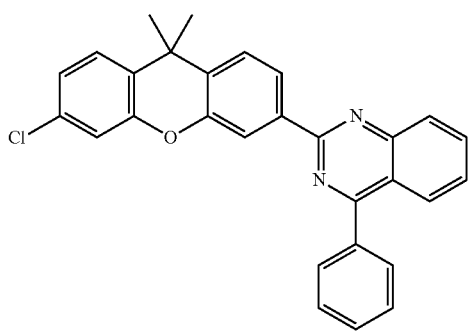

I-9

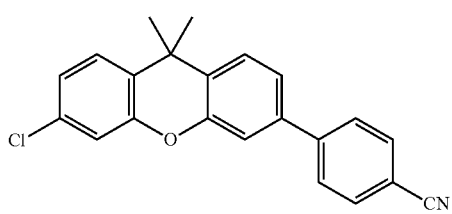

I-10

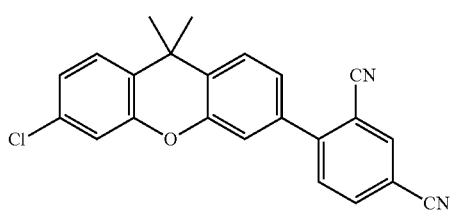

I-11

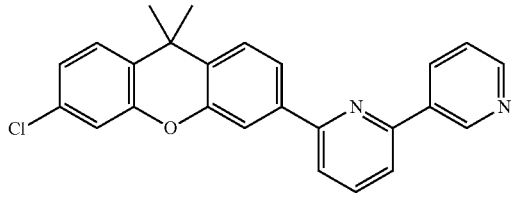

I-12

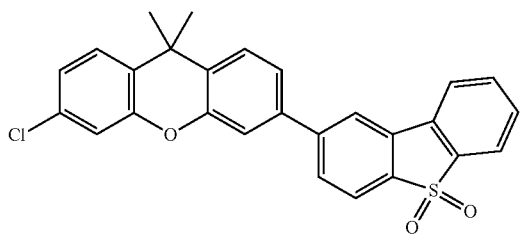

I-13

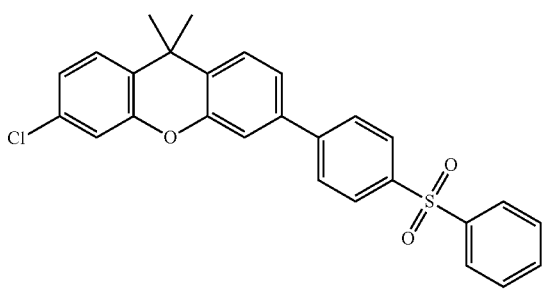

I-15

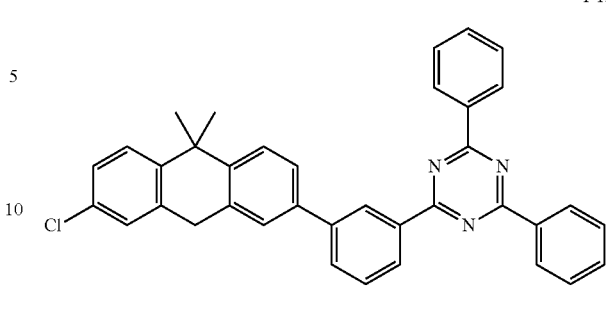

Synthesis of Intermediate I-7

2.96 g (yield: 78%) of Intermediate I-7 was obtained in the same (or substantially the same) manner as in Synthesis of Intermediate I-6 except that Intermediate I-4 and 4-chloro-2,6-diphenylpyrimidine were used instead of Intermediate 1-4 and 2-chloro-4,6-diphenylpyrimidine. The obtained compound was identified by LC-MS: ($O_{31}H_{23}ClN_2O$ M+ cal.: 474.1 found 475.1).

Synthesis of Intermediate I-8

2.59 g (yield: 72%) of Intermediate I-8 was obtained in the same (or substantially the same) manner as in Synthesis of Intermediate I-6 except that Intermediate I-4 and 2-chloro-4-phenylquinazoline were used instead of Intermediate I-4 and 2-chloro-4,6-diphenylpyrimidine. The obtained compound was identified by LC-MS: ($C_{29}H_{21}ClN_2O$ M+ cal.: 448.1 found 449.1).

Synthesis of Intermediate I-9

2.38 g (yield: 86%) of Intermediate I-9 was obtained in the same (or substantially the same) manner as in Synthesis of Intermediate I-6 except that Intermediate I-4 and 4-bromobenzonitrile were used instead of Intermediate I-4 and 2-chloro-4,6-diphenylpyrimidine. The obtained compound was identified by LC-MS: ($C_{22}H_{16}ClNO$ M+ cal.: 345.1 found: 346.1).

Synthesis of Intermediate I-10

2.46 g (yield: 83%) of Intermediate I-10 was obtained in the same (or substantially the same) manner as in Synthesis of Intermediate I-6 except that Intermediate I-4 and 4-bromoisophthalonitrile were used instead of Intermediate I-4 and 2-chloro-4,6-diphenylpyrimidine. The obtained compound was identified by LC-MS: ($O_{23}H_{15}ClN_2O$ M+ cal.: 370.1 found: 371.1).

Synthesis of Intermediate I-11

2.2 g (yield: 69%) of Intermediate I-11 was obtained in the same (or substantially the same) manner as in Synthesis of Intermediate I-6 except that Intermediate I-4 and 6-bromo-2,3'-bipyridine were used instead of Intermediate I-4 and 2-chloro-4,6-diphenylpyrimidine. The obtained compound was identified by LC-MS: ($C_{25}H_{19}ClN_2O$ M+ cal.: 398.1 found: 399.1).

Synthesis of Intermediate I-12

2.6 g (yield: 71%) of Intermediate I-12 was obtained in the same (or substantially the same) manner as in Synthesis of Intermediate I-6 except that Intermediate I-4 and 2-bromodibenzo[b,d]thiophene 5,5-dioxide were used instead of Intermediate I-4 and 2-chloro-4,6-diphenylpyrimidine. The obtained compound was identified by LC-MS: ($C_{27}H_{19}ClO_3S$ M+ cal.: 398.1 found: 399.1).

Synthesis of Intermediate I-13

2.53 g (yield: 69%) of Intermediate I-13 was obtained in the same (or substantially the same) manner as in Synthesis of Intermediate I-6 except that Intermediate I-4 and 1-bromo-4-(phenylsulfonyl)benzene were used instead of Intermediate I-4 and 2-chloro-4,6-diphenylpyrimidine. The obtained compound was identified by LC-MS: ($C_{27}H_{21}ClO_3S$ M+ cal.: 460.1 found: 461.1).

Synthesis of Intermediate I-15

3.62 g (yield: 82%) of Intermediate I-15 was obtained in the same (or substantially the same) manner as in Synthesis of Intermediate I-6 except that Intermediate I-4 and 2-(3-bromophenyl)-4,6-diphenyl-1,3,5-triazine were used instead of Intermediate I-4 and 2-chloro-4,6-diphenylpyrimidine. The obtained compound was identified by LC-MS: ($C_{36}H_{26}ClN_3O$ M+ cal.: 551.2 found: 552.2).

Synthesis Example 10: Synthesis of Compound 14

2.4 g (yield: 74%) of Compound 14 was obtained in the same (or substantially the same) manner as in Synthesis of Compound 1 except that Intermediate I-7 and 9,9-dimethyl-9,10-dihydroacridine were used instead of Intermediate I-5 and 9,9-dimethyl-9,10-dihydroacridine. The obtained compound was identified by LC-MS and NMR: ($C_{46}H_{37}N_3O$ M+ cal.: 647.3 found: 648.3).

Synthesis Example 11: Synthesis of Compound 15

2.21 g (yield: 71%) of Compound 15 was obtained in the same (or substantially the same) manner as in Synthesis of Compound 1 except that Intermediate I-8 and 9,9-dimethyl-9,10-dihydroacridine were used instead of Intermediate I-5 and 9,9-dimethyl-9,10-dihydroacridine. The obtained compound was identified by LC-MS and NMR: ($C_{44}H_{38}N_3O$ M+ cal.: 621.3 found: 622.3).

Synthesis Example 12: Synthesis of Compound 16

2.02 g (yield: 78%) of Compound 16 was obtained in the same (or substantially the same) manner as in Synthesis of Compound 1 except that Intermediate I-9 and 9,9-dimethyl-9,10-dihydroacridine were used instead of Intermediate I-5 and 9,9-dimethyl-9,10-dihydroacridine. The obtained compound was identified by LC-MS and NMR: ($C_{37}H_{30}N_2O$ M+ cal.: 518.2 found: 519.2).

Synthesis Example 13: Synthesis of Compound 17

2.07 g (yield: 76%) of Compound 17 was obtained in the same (or substantially the same) manner as in Synthesis of Compound 1 except that Intermediate I-10 and 9,9-dimethyl-9,10-dihydroacridine were used instead of Intermediate I-5 and 9,9-dimethyl-9,10-dihydroacridine. The obtained compound was identified by LC-MS and NMR: ($C_{38}H_{29}N_3O$ M+ cal.: 543.2 found: 544.2).

Synthesis Example 14: Synthesis of Compound 18

1.91 g (yield: 67%) of Compound 18 was obtained in the same (or substantially the same) manner as in Synthesis of Compound 1 except that Intermediate I-11 and 9,9-dimethyl-9,10-dihydroacridine were used instead of Intermediate I-5 and 9,9-dimethyl-9,10-dihydroacridine. The obtained compound was identified by LC-MS and NMR: ($C_{40}H_{33}N_3O$ M+ cal.: 571.3 found: 572.3).

Synthesis Example 15: Synthesis of Compound 19

2.34 g (yield: 74%) of Compound 19 was obtained in the same (or substantially the same) manner as in Synthesis of Compound 1 except that Intermediate I-12 and 9,9-dimethyl-9,10-dihydroacridine were used instead of Intermediate I-5 and 9,9-dimethyl-9,10-dihydroacridine. The obtained compound was identified by LC-MS and NMR: ($C_{42}H_{33}NO_3S$ M+ cal.: 631.2 found: 632.2).

Synthesis Example 16: Synthesis of Compound 20

2.25 g (yield: 71%) of Compound 20 was obtained in the same (or substantially the same) manner as in Synthesis of Compound 1 except that Intermediate I-13 and 9,9-dimethyl-9,10-dihydroacridine were used instead of Intermediate I-5 and 9,9-dimethyl-9,10-dihydroacridine. The obtained compound was identified by LC-MS and NMR: ($C_{42}H_{35}NO_3S$ M+ cal.: 633.2 found: 634.2).

Synthesis Example 17: Synthesis of Compound 21

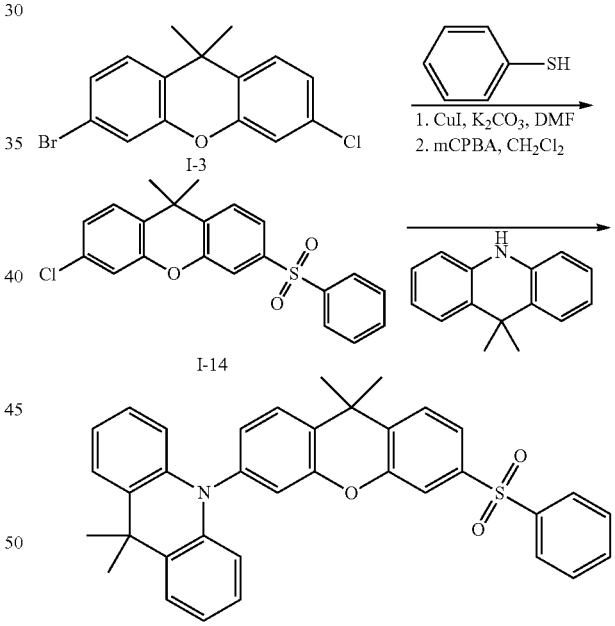

Synthesis of Intermediate I-14

3.88 g (12.0 mmol) of Intermediate I-3, 1.10 g (10.0 mmol) of benzenethiol, 0.19 g (1.0 mmol) of CuI, and 2.76 g (20.0 mmol) of $K_2CO_3$ were dissolved in 50 mL of DMF, and the reaction solution was stirred at a temperature of 100° C. for 16 hours. Then, the reaction solution was cooled to room temperature, and an organic layer was extracted therefrom by using 40 mL of diethylether. The extracted organic layer was dried by using anhydrous magnesium sulfate, and a distillation process was performed thereon under reduced pressure. Then, the residue obtained therefrom was separated and purified by silica gel column chromatography to obtain an intermediate product. Then, the obtained compound was dissolved in 30 mL of dichloromethane, and a solution in which 6.9 g (40 mmol) of m-CPBA was dissolved in 30 mL of dichloromethane was slowly added dropwise thereto at a temperature of 0° C. The resultant mixture was slowly heated to room temperature and stirred for 24 hours. Then, 60 mL of a saturated NaHCO$_3$ aqueous solution was added thereto and additionally stirred for 30 minutes, and an organic layer was extracted therefrom by using 30 mL of dichloromethane. The extracted organic layer was dried by using anhydrous magnesium sulfate, and a distillation process was performed thereon under reduced pressure. Then, the residue obtained therefrom was separated and purified by silica gel column chromatography to obtain 2.49 g (yield: 54%) of Intermediate I-14. The obtained compound was identified by LC-MS: (C$_{21}$H$_{17}$ClO$_3$S M+ cal.: 384.1 found: 385.1).

Synthesis of Compound 21

1.84 g (yield: 66%) of Compound 21 was obtained in the same (or substantially the same) manner as in Synthesis of Compound 1 except that Intermediate I-14 and 9,9-dimethyl-9,10-dihydroacridine were used instead of Intermediate I-5 and 9,9-dimethyl-9,10-dihydroacridine. The obtained compound was identified by LC-MS and NMR: (C$_{36}$H$_{31}$NO$_3$S M+ cal.: 557.2 found: 558.2).

Synthesis Example 18: Synthesis of Compound 129

2.83 g (yield: 78%) of Compound 129 was obtained in the same (or substantially the same) manner as in Synthesis of Compound 1 except that Intermediate I-15 and 9,9-dimethyl-9,10-dihydroacridine were used instead of Intermediate I-5 and 9,9-dimethyl-9,10-dihydroacridine. The obtained compound was identified by LC-MS and NMR: (C$_{51}$H$_{40}$N$_4$O M+ cal.: 724.3 found: 725.3).

Synthesis Example 19: Synthesis of Compound 22

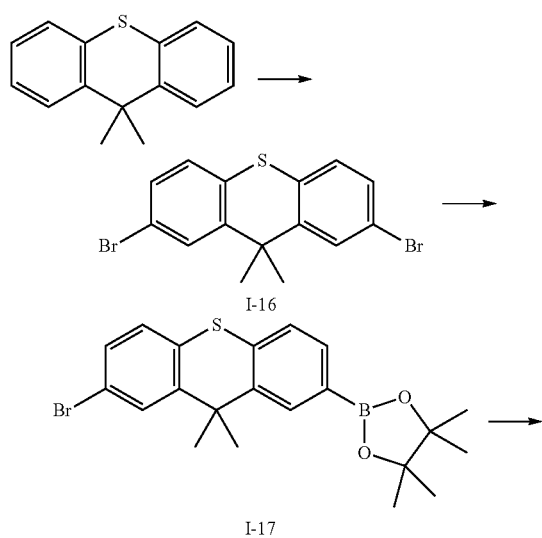

I-16

I-17

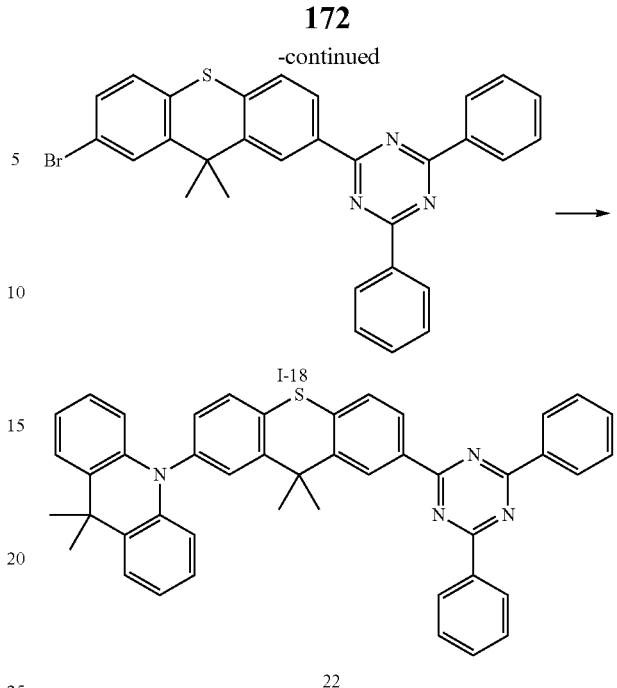

I-18

22

Synthesis of Intermediate I-16

4.5 g (20.0 mmol) of 9,9-dimethyl-9H-thioxanthene was dissolved in 30 mL of acetic acid, and then, a solution of 2.25 mL (44.0 mmol) of Br$_2$ dissolved in 30 mL of acetic acid was slowly added dropwise thereto at a temperature of 0° C. Then, the reaction solution was stirred at room temperature for 5 hours. 50 mL of a saturated Na$_2$S$_2$O$_3$ aqueous solution was added thereto and stirred, and an organic layer was extracted therefrom by using 100 mL of diethylether. The extracted organic layer was dried by using anhydrous magnesium sulfate, and a distillation process was performed thereon under reduced pressure. Then, the residue obtained therefrom was separated and purified by silica gel column chromatography to obtain 5.53 g (yield: 72%) of Intermediate I-16. The obtained compound was identified by LC-MS: (C$_{15}$H$_{12}$Br$_2$S M+ cal.: 381.9 found: 382.9).

Synthesis of Intermediate I-17

5.53 g (14.4 mmol) of Intermediate I-16 was dissolved in 50 mL of THF, and 5.8 mL of n-BuLi (2.5M, 14.5 mmol) was slowly added thereto at a temperature of −78° C. Then, the reaction solution was stirred at the same temperature for 1 hour. 3.5 mL (17.3 mmol) of 2-isopropoxy-4,4,5,5-tetramethyl-1,3,2-dioxaborolane was slowly added dropwise to the reaction solution at a temperature of −78° C., and the resultant reaction solution was slowly heated to room temperature and stirred for 3 hours. The reaction was terminated by adding 50 mL of 10% HCl (aq) to the reaction solution, and an organic layer was extracted therefrom by using 50 mL of diethylether. The extracted organic layer was dried by using anhydrous magnesium sulfate, and a distillation process was performed thereon under reduced pressure. Then, the residue obtained therefrom was separated and purified by silica gel column chromatography to obtain 5.03 g (yield: 81%) of Intermediate I-17. The obtained compound was identified by LC-MS: (C$_{21}$H$_{24}$BBrO$_2$S M+ cal.: 430.1 found: 431.1).

Synthesis of Intermediate I-18

5.0 g (11.6 mmol) of Intermediate I-17, 3.7 g (13.9 mmol) of 2-chloro-4,6-diphenyl-1,3,5-triazine, 0.67 g (0.58 mmol) of $Pd(PPh_3)_4$, and 4.8 g (34.8 mmol) of $K_2CO_3$ were dissolved in 50 mL of a mixed solution of $THF/H_2O$ (1:1) and stirred at a temperature of 80° C. for 5 hours. The reaction mixture was cooled to room temperature, and an organic layer was extracted therefrom by using 50 mL of diethylether. The extracted organic layer was dried by using anhydrous magnesium sulfate, and a distillation process was performed thereon under reduced pressure. Then, the residue obtained therefrom was separated and purified by silica gel column chromatography to obtain 15.6 g (yield: 72%) of Intermediate I-18. The obtained compound was identified by LC-MS: ($C_{30}H_{22}BrN_3S$ M+ cal.: 535.1 found: 536.1).

Synthesis of Compound 22

2.56 g (yield: 77%) of Compound 22 was obtained in the same (or substantially the same) manner as in Synthesis of Compound 1 except that Intermediate I-18 and 9,9-dimethyl-9,10-dihydroacridine were used instead of Intermediate I-5 and 9,9-dimethyl-9,10-dihydroacridine. The obtained compound was identified by LC-MS and NMR: ($C_{45}H_{36}N_4S$ M+ cal.: 664.3 found: 665.3).

Synthesis Example 20: Synthesis of Compound 43

Synthesis of Intermediate I-19

4.67 g (yield: 80%) of Intermediate I-19 was obtained in the same (or substantially the same) manner as in Synthesis of Intermediate I-17 except that 5.13 g (15.0 mmol) of 2,8-dibromodibenzo[b,e][1,4]dioxine were used instead of Intermediate I-16. The obtained compound was identified by LC-MS: ($C_{18}H_{18}BBrO_4$ M+ cal.: 388.0 found: 389.0).

Synthesis of Intermediate I-20

3.46 g (yield: 70%) of Intermediate I-20 was obtained in the same (or substantially the same) manner as in Synthesis of Intermediate I-18 except that Intermediate I-19 was used instead of Intermediate I-17. The obtained compound was identified by LC-MS: ($C_{27}H_{16}BrN_3O_2$ M+ cal.: 493.0 found: 494.0).

Synthesis of Compound 43

2.33 g (yield: 75%) of Compound 43 was obtained in the same (or substantially the same) manner as in Synthesis of Compound 1 except that Intermediate I-20 and 9,9-dimethyl-9,10-dihydroacridine were used instead of Intermediate I-5 and 9,9-dimethyl-9,10-dihydroacridine. The obtained compound was identified by LC-MS and NMR: ($C_{42}H_{30}N_4O_2$ M+ cal.: 622.2 found: 623.2).

Synthesis Example 21: Synthesis of Compound 64

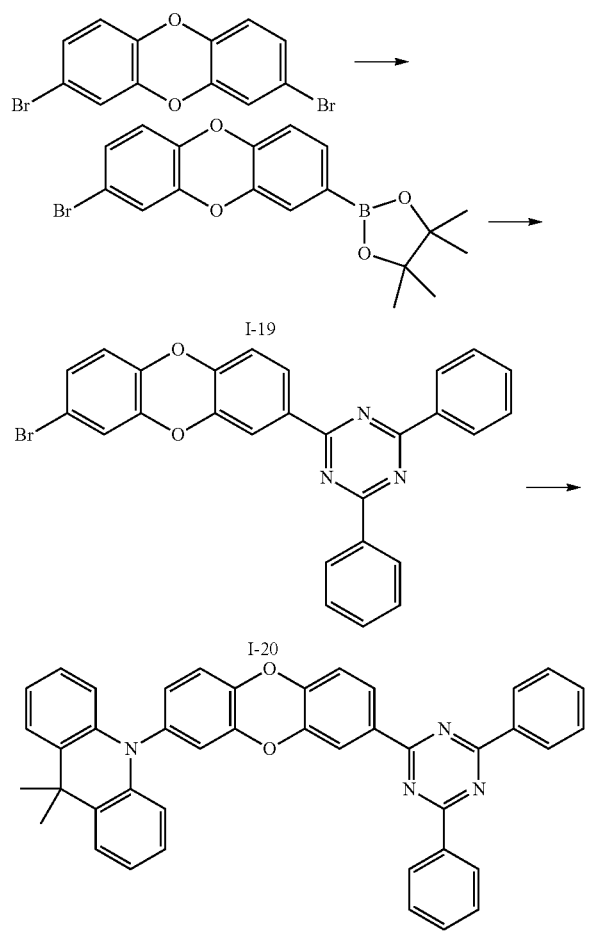

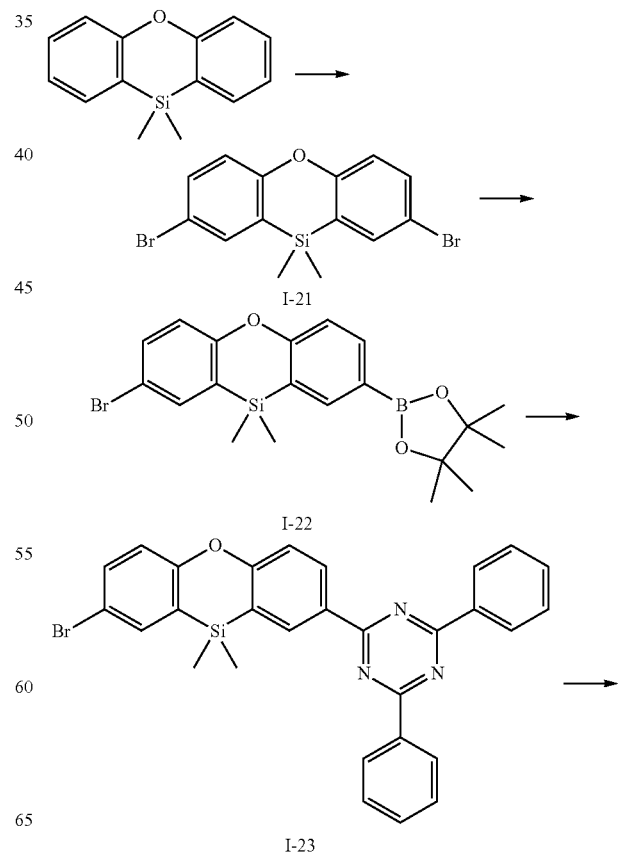

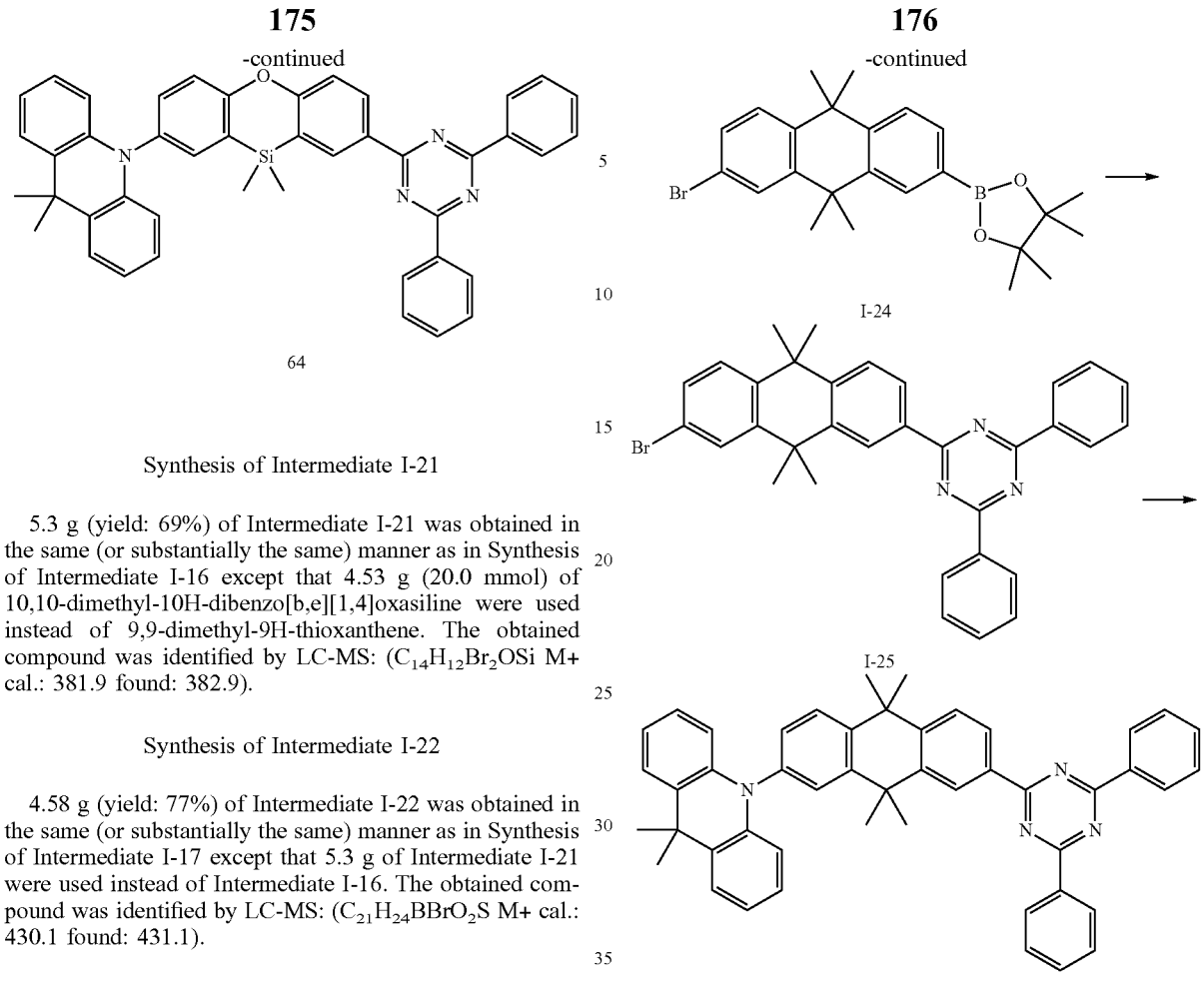

Synthesis of Intermediate I-21

5.3 g (yield: 69%) of Intermediate I-21 was obtained in the same (or substantially the same) manner as in Synthesis of Intermediate I-16 except that 4.53 g (20.0 mmol) of 10,10-dimethyl-10H-dibenzo[b,e][1,4]oxasiline were used instead of 9,9-dimethyl-9H-thioxanthene. The obtained compound was identified by LC-MS: ($C_{14}H_{12}Br_2OSi$ M+ cal.: 381.9 found: 382.9).

Synthesis of Intermediate I-22

4.58 g (yield: 77%) of Intermediate I-22 was obtained in the same (or substantially the same) manner as in Synthesis of Intermediate I-17 except that 5.3 g of Intermediate I-21 were used instead of Intermediate I-16. The obtained compound was identified by LC-MS: ($C_{21}H_{24}BBrO_2S$ M+ cal.: 430.1 found: 431.1).

Synthesis of Intermediate I-23

4.09 g (yield: 73%) of Intermediate I-23 was obtained in the same (or substantially the same) manner as in Synthesis of Intermediate I-18 except that 4.5 g of Intermediate I-22 were used instead of Intermediate I-17. The obtained compound was identified by LC-MS: ($C_{29}H_{22}BrN_3OSi$ M+ cal.: 535.1 found: 536.1).

Synthesis of Compound 64

2.63 g (yield: 79%) of Compound 64 was obtained in the same (or substantially the same) manner as in Synthesis of Compound 1 except that Intermediate I-23 and 9,9-dimethyl-9,10-dihydroacridine were used instead of Intermediate I-5 and 9,9-dimethyl-9,10-dihydroacridine. The obtained compound was identified by LC-MS and NMR: ($C_{44}H_{36}N_4OSi$ M+ cal.: 664.3 found: 665.3).

Synthesis Example 22: Synthesis of Compound 85

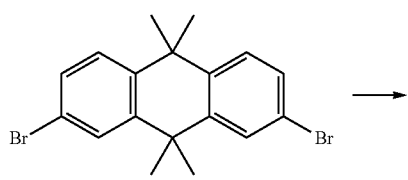

Synthesis of Intermediate I-24

4.89 g (yield: 74%) of Intermediate I-24 was obtained in the same (or substantially the same) manner as in Synthesis of Intermediate I-17 except that 5.9 g (15.0 mmol) of 2,7-dibromo-9,9,10,10-tetramethyl-9,10-dihydroanthracene were used instead of Intermediate I-16. The obtained compound was identified by LC-MS: ($C_{24}H_{30}BBrO_2$ M+ cal.: 440.2 found: 441.2).

Synthesis of Intermediate I-25

4.22 g (yield: 71%) of Intermediate I-25 was obtained in the same (or substantially the same) manner as in Synthesis of Intermediate I-18 except that 4.8 g of Intermediate I-24 were used instead of Intermediate I-17. The obtained compound was identified by LC-MS: ($C_{33}H_{28}BrN_3$ M+ cal.: 545.1 found: 546.1).

Synthesis of Compound 85

2.73 g (yield: 81%) of Compound 85 was obtained in the same (or substantially the same) manner as in Synthesis of Compound 1 except that Intermediate I-25 and 9,9-dimethyl-9,10-dihydroacridine were used instead of Intermediate I-5 and 9,9-dimethyl-9,10-dihydroacridine. The obtained compound was identified by LC-MS and NMR: ($C_{48}H_{42}N_4$ M+ cal.: 674.3 found: 675.3).

Synthesis Example 23: Synthesis of Compound 106

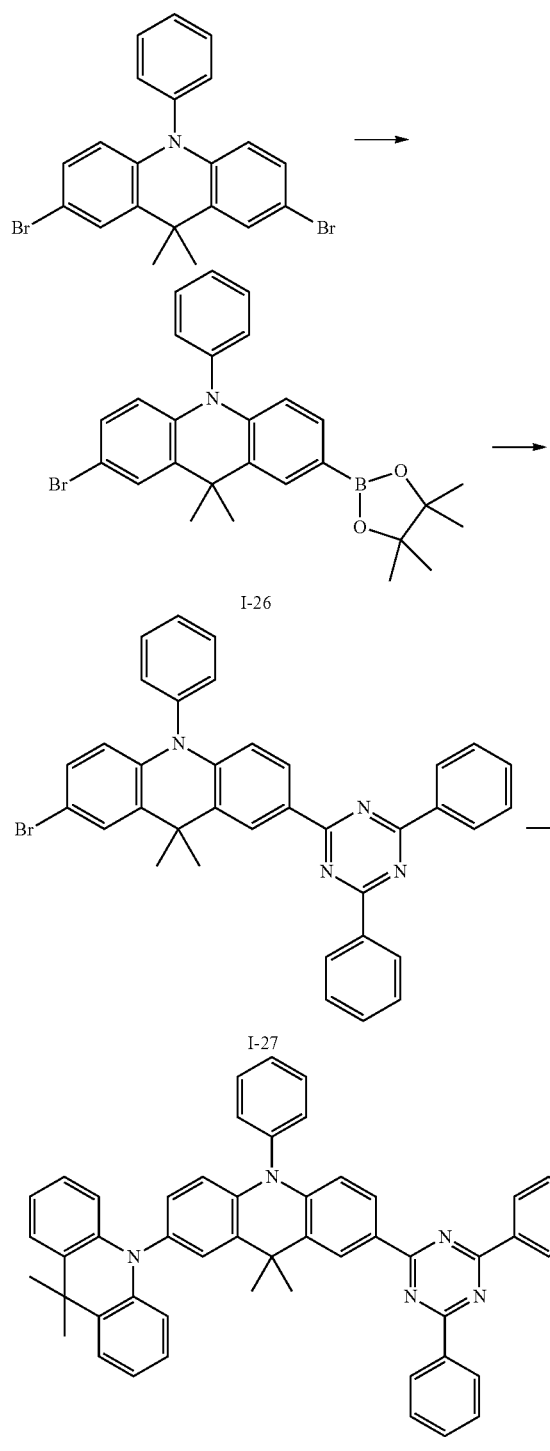

Synthesis of Intermediate I-26

5.58 g (yield: 76%) of Intermediate I-26 was obtained in the same (or substantially the same) manner as in Synthesis of Intermediate I-17 except that 6.6 g (15.0 mmol) of 2,7-dibromo-9,9-dimethyl-10-phenyl-9,10-dihydroacridine were used instead of Intermediate I-16. The obtained compound was identified by LC-MS: ($C_{27}H_{29}BBrNO_2$ M+ cal.: 489.1 found: 490.1).

Synthesis of Intermediate I-27

4.72 g (yield: 67%) of Intermediate I-27 was obtained in the same (or substantially the same) manner as in Synthesis of Intermediate I-18 except that 5.8 g of Intermediate I-26 were used instead of Intermediate I-17. The obtained compound was identified by LC-MS: ($C_{36}H_{27}BrN_4$ M+ cal.: 594.1 found: 595.1).

Synthesis of Compound 106

3.0 g (yield: 83%) of Compound 106 was obtained in the same (or substantially the same) manner as in Synthesis of Compound 1 except that Intermediate I-27 and 9,9-dimethyl-9,10-dihydroacridine were used instead of Intermediate I-5 and 9,9-dimethyl-9,10-dihydroacridine. The obtained compound was identified by LC-MS and NMR: ($C_{51}H_{41}N_5$ M+ cal.: 723.3 found: 724.3).

Synthesis Example 24: Synthesis of Compound 133

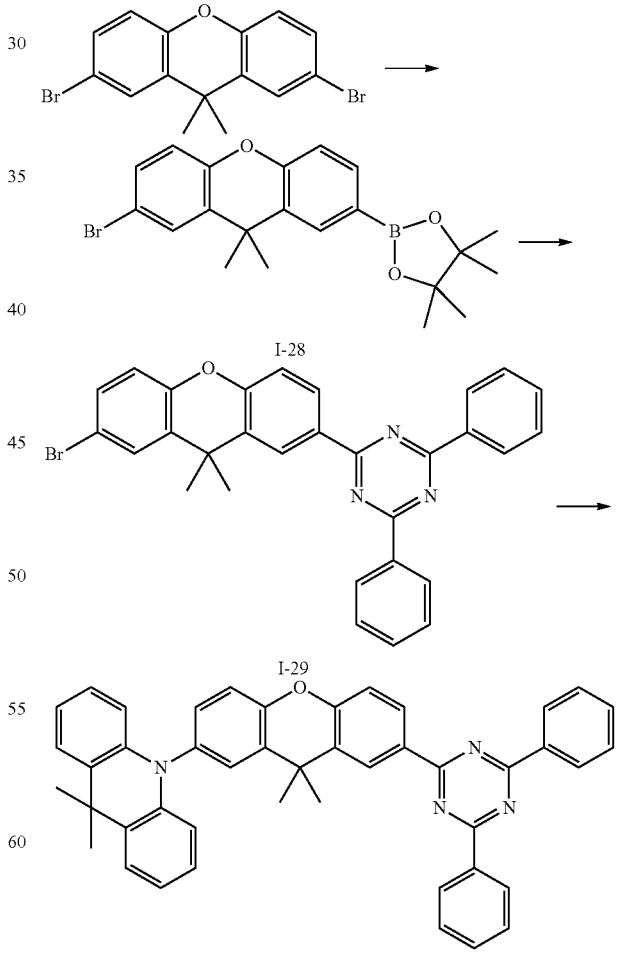

Synthesis of Intermediate I-28

9.21 g (yield: 74%) of Intermediate I-28 was obtained in the same (or substantially the same) manner as in Synthesis of Intermediate I-17 except that 11.0 g (30.0 mmol) of 2,7-dibromo-9,9-dimethyl-9H-xanthene were used instead of Intermediate I-16. The obtained compound was identified by LC-MS: ($C_{21}H_{24}BBrO_3$ M+ cal.: 414.1 found: 415.1).

Synthesis of Intermediate I-29

3.92 g (yield: 68%) of Intermediate I-29 was obtained in the same (or substantially the same) manner as in Synthesis of Intermediate I-18 except that 4.6 g of Intermediate I-28 were used instead of Intermediate I-17. The obtained compound was identified by LC-MS: ($C_{30}H_{22}BrN_3O$ M+ cal.: 519.1 found: 520.1).

Synthesis of Compound 133

2.56 g (yield: 79%) of Compound 133 was obtained in the same (or substantially the same) manner as in Synthesis of Compound 1 except that Intermediate I-29 and 9,9-dimethyl-9,10-dihydroacridine were used instead of Intermediate I-5 and 9,9-dimethyl-9,10-dihydroacridine. The obtained compound was identified by LC-MS and NMR: ($C_{45}H_{36}N_4O$ M+ cal.: 648.3 found: 649.3).

Synthesis Example 25: Synthesis of Compound 137

Synthesis of Intermediate I-30

3.52 g (yield: 61%) of Intermediate I-30 was obtained in the same (or substantially the same) manner as in Synthesis of Intermediate I-18 except that 4.6 g of Intermediate I-28 and 4.2 g of 4'-bromo-3,2':6',3"-terpyridine were used instead of Intermediate I-17 and 2-chloro-4,6-diphenyl-1,3,5-triazine. The obtained compound was identified by LC-MS: ($C_{30}H_{22}BrN_3O$ M+ cal.: 519.1 found: 520.1).

Synthesis of Compound 137

2.34 g (yield: 72%) of Compound 137 was obtained in the same (or substantially the same) manner as in Synthesis of Compound 1 except that Intermediate I-30 and 9,9-dimethyl-9,10-dihydroacridine were used instead of Intermediate I-5 and 9,9-dimethyl-9,10-dihydroacridine. The obtained compound was identified by LC-MS and NMR: ($C_{45}H_{36}N_4O$ M+ cal.: 648.3 found: 649.3).

Synthesis Example 26: Synthesis of Compound 143

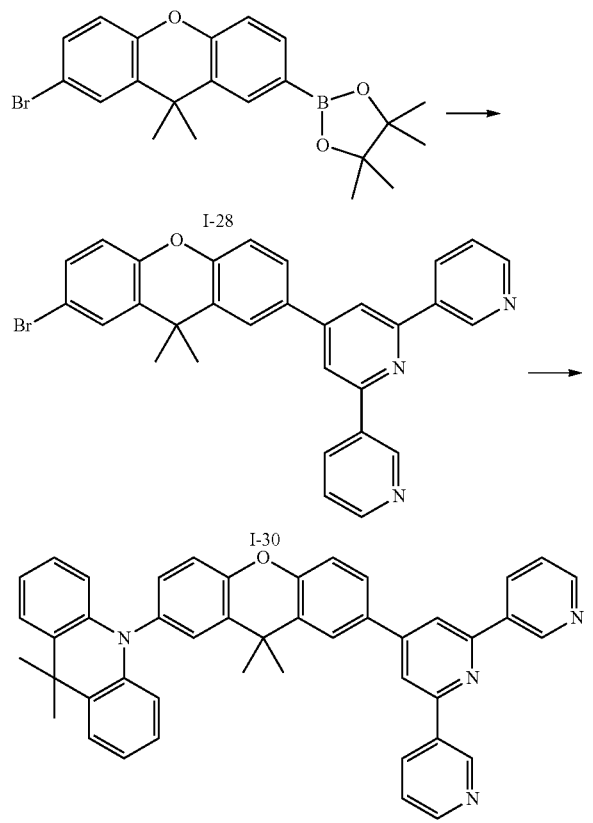

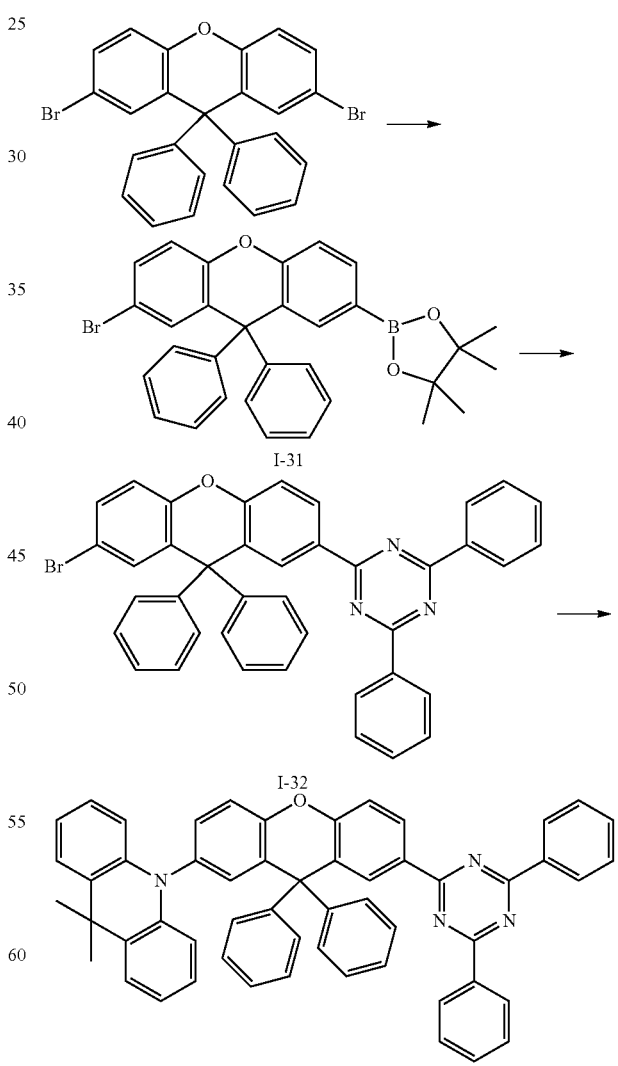

Synthesis of Intermediate I-31

6.07 g (yield: 75%) of Intermediate I-31 was obtained in the same (or substantially the same) manner as in Synthesis of Intermediate I-17 except that 7.4 g (15.0 mmol) of 2,7-dibromo-9,9-diphenyl-9H-xanthene were used instead of Intermediate I-16. The obtained compound was identified by LC-MS: ($C_{31}H_{28}BBrO_3$ M+ cal.: 538.1 found: 539.1).

Synthesis of Intermediate I-32

4.45 g (yield: 62%) of Intermediate I-32 was obtained in the same (or substantially the same) manner as in Synthesis of Intermediate I-18 except that 6.0 g of Intermediate I-31 were used instead of Intermediate I-17. The obtained compound was identified by LC-MS: ($C_{40}H_{26}BrN_3O$ M+ cal.: 643.1 found: 644.1).

Synthesis of Compound 137

2.63 g (yield: 68%) of Compound 143 was obtained in the same (or substantially the same) manner as in Synthesis of Compound 1 except that Intermediate I-33 and 9,9-dimethyl-9,10-dihydroacridine were used instead of Intermediate I-5 and 9,9-dimethyl-9,10-dihydroacridine. The obtained compound was identified by LC-MS and NMR: ($C_{55}H_{40}N_4O$ M+ cal.: 772.3 found: 773.3).

$^1$H NMR and Mass Spectrometry/Fast Atom Bombardment (MS/FAB) of Compounds synthesized according to Synthesis Examples 1 to 26 are shown in Table 1.

Synthesis methods of compounds other than Compounds shown in Table 1 should be apparent those of ordinary skill in the art by referring to the synthesis mechanisms and source materials described above.

TABLE 1

| Compound | $^1$H NMR (CDCl$_3$, 400 MHz) | LC-MS found | LC-MS calc. |
|---|---|---|---|
| 1 | 8.60 (d, 4H), 7.92 (d, 1H), 7.77 (s, 1H), 7.62-7.58 (m, 4H), 7.46-7.37 (m, 4H), 7.25-7.03 (m, 8H), 6.92 (s, 1H), 6.86 (d, 1H), 1.76 (s, 6H), 1.49 (s, 6H) | 648.3 | 649.3 |
| 3 | 8.62-8.56 (m, 4H), 7.91 (dd, 1H), 7.81 (d, 1H), 7.64-7.59 (m, 4H), 7.45-7.38 (m, 2H), 7.19-6.97 (m, 8H), 6.89-6.83 (m, 3H), 6.78 (dd, 1H), 1.50 (s, 6H) | 622.2 | 623.2 |
| 4 | 8.61-8.57 (m, 4H), 7.93 (dd, 1H), 7.83 (d, 1H), 7.66-7.59 (m, 4H), 7.48-7.40 (m, 2H), 7.31-7.17 (m, 5H), 7.03-6.92 (m, 5H), 6.93 (d, 1H), 6.88 (d, 1H), 11.51 (s, 6H) | 638.2 | 639.2 |
| 5 | 8.60-8.54 (m, 4H), 7.92 (d, 1H), 7.83 (d, 1H), 7.70 (d, 2H), 7.65-7.40 (m, 6H), 7.28-7.15 (m, 7H), 7.05 (d, 1H), 6.93 (d, 1H), 6.84 (d, 1H), 1.49 (s, 6H), 0.35 (s, 6H) | 664.3 | 665.3 |
| 6 | 8.64-8.59 (m, 4H), 7.90 (d, 1H), 7.80 (s, 1H), 7.67-7.27 (m, 10H), 7.18-6.99 (m, 9H), 6.89 (dt, 1H), 6.82-6.76 (m, 2H), 1.76 (s, 6H), 1.49 (s, 6H) | 724.3 | 725.3 |
| 10 | 8.61-8.57 (m, 4H), 7.92 (d, 1H), 7.81 (d, 1H), 7.59-7.39 (m, 8H), 7.32-7.03 (m, 11H), 6.93 (dt, 1H), 6.83-6.78 (m, 2H), 1.74 (s, 6H), 1.50 (s, 6H) | 724.3 | 725.3 |
| 12 | 6.62-8.58 (m, 4H), 7.92 (d, 1H), 7.81 (d, 1H), 7.63-7.38 (m, 9H), 7.28-7.03 (m, 12H), 6.84-6.81 (m, 1H), 1.75 (s, 6H), 1.51 (s, 6H) | 724.3 | 725.3 |
| 13 | 8.28-8.24 (m, 5H), 7.99 (s, 1H), 7.83 (d, 1H), 7.54-7.31 (m, 8H), 7.23-7.01 (m, 8H), 6.93 (d, 1H), 6.82 (dd, 1H), 1.76 (s, 6H), 1.49 (s, 6H) | 647.3 | 648.3 |
| 14 | 8.41-8.36 (m, 2H), 8.27 (d, 1H), 8.19-8.14 (m, 2H), 7.68 (s, 1H), 7.55-7.28 (m, 9H), 7.21-7.01 (m, 8H), 6.94 (d, 1H), 6.84 (d, 1H), 1.75 (s, 6H), 1.50 (s, 6H) | 647.3 | 648.3 |
| 15 | 8.28 (d, 1H), 8.02 (dd, 1H), 7.90-7.55 (m, 9H), 7.44-7.39 (m, 2H), 7.28-7.02 (m, 8H), 6.97 (d, 1H), 6.82 (dd, 1H), 1.75 (s, 6H), 1.49 (s, 6H) | 621.3 | 622.3 |
| 16 | 7.70-7.66 (m, 2H), 7.58-7.53 (m, 2H), 7.45-7.27 (m, 5H), 7.19-7.02 (m, 7H), 6.94 (d, 1H), 6.82 (dd, 1H), 1.74 (s, 6H), 1.50 (s, 6H) | 518.2 | 519.2 |
| 17 | 8.05 (s, 1H), 7.78 (d, 1H), 7.64-7.54 (m, 3H), 7.43-7.36 (m, 3H), 7.22-7.01 (m, 7H), 6.93 (d, 1H), 6.82 (dd, 1H), 1.74 (s, 6H), 1.49 (s, 6H) | 543.2 | 544.2 |
| 18 | 8.82 (s, 1H), 8.66 (d, 1H), 8.21-8.13 (m, 2H), 7.84-7.72 (m, 2H), 7.49-7.26 (m, 6H), 7.19-7.01 (m, 7H), 6.94 (d, 1H), 6.85 (dd, 1H), 1.73 (s, 6H), 1.50 (s, 6H) | 571.3 | 572.3 |
| 19 | 8.04 (s, 1H), 7.96 (d, 1H), 7.86-7.79 (m, 2H), 7.64-7.41 (m, 6H), 7.36 (d, 1H), 7.28-7.02 (m, 8H), 6.96 (d, 1H), 6.89 (dd, 1H), 1.74 (s, 6H), 1.51 (s, 6H) | 631.2 | 632.2 |
| 20 | 7.97-7.93 (m, 2H), 7.83-7.78 (m, 2H), 7.72-7.67 (m, 2H), 7.59-7.39 (m, 7H), 7.34 (d, 1H), 7.24-7.03 (m, 7H), 6.94 (d, 1H), 6.84 (dd, 1H), 1.75 (s, 6H), 1.50 (s, 6H) | 633.2 | 634.2 |
| 21 | 7.98-7.92 (m, 2H), 7.58-7.41 (m, 7H), 7.29-7.04 (m, 8H), 6.97 (d, 1H), 6.89 (dd, 1H), 1.76 (s, 6H), 1.52 (s, 6H) | 557.2 | 558.2 |

TABLE 1-continued

| Compound | $^1$H NMR (CDCl$_3$, 400 MHz) | LC-MS found | calc. |
|---|---|---|---|
| 22 | 8.63 (d, 4H), 8.48 (d, 1), 7.95 (s, 1H), 7.67-7.38 (m, 8H), 7.28 (d, 1H), 7.23-7.03 (m, 7H), 6.95 (s, 1H), 6.83 (d, 1H), 1.76 (s, 6H), 1.62 (s, 6H) | 664.3 | 665.3 |
| 43 | 8.60 (d, 4H), 8.44 (d, 1H), 8.02 (s, 1H), 7.59-7.38 (m, 8H), 7.29-7.06 (m, 8H), 6.97 (d, 2H), 1.68 (s, 6H) | 622.2 | 623.2 |
| 64 | 8.63 (d, 4H), 8.33-8.28 (m, 2H), 7.67-7.43 (m, 8H), 7.30-7.08 (m, 10, 1.76 (s, 6H), 0.27 (s, 6H) | 664.3 | 665.3 |
| 85 | 8.61-8.56 (m, 4H), 8.42 (d, 1H), 8.03 (s, 1H), 7.69-7.42 (m, 9H), 7.31-7.05 (m, 7), 6.97 (d, 1H), 6.81 (dd, 1H), 1.76 (s, 6H), 1.68 (s, 6H), 1.65 (s, 6H) | 674.3 | 675.3 |
| 106 | 8.67 (d, 4H), 8.51 (s, 1H), 8.39 (d, 1H), 7.67-7.41 (m, 8H), 7.28-7.05 (m, 10H), 6.95-6.90 (m, 2H), 6.83-6.79 (m, 3), 1.76 (s, 6H), 1.67 (s, 6H) | 723.3 | 724.3 |
| 129 | 8.63-8.59 (m, 4H), 8.51 (s, 1H), 8.49 (d, 1H), 7.82 (d, 1H), 7.69-7.38 (m, 12H), 7.19-6.98 (m, 7H), 6.93 (d, 1H), 6.82 (d, 1H), 1.75 (s, 6H), 1.45 (s, 6H) | 724.3 | 724.3 |
| 133 | 8.62 (d, 4H), 8.46 (d, 1H), 8.06 (s, 1H), 7.64-7.38 (m, 8H), 7.29-7.69 (m, 9H), 6.85 (d, 1H), 1.75 (s, 6H), 1.59 (s, 6H) | 648.3 | 649.3 |
| 137 | 8.82 (s, 2H), 8.53 (d, 2H), 8.23 (d, 2H), 7.91-7.87 (m, 3H), 7.44-7.39 (m, 5H), 7.27-6.89 (m, 10H), 1.76 (s, 6H), 1.59 (s, 6H) | 648.3 | 649.3 |
| 143 | 8.65-8.61 (m, 5H), 8.19 (s, 1H), 7.65-7.31 (m, 19H), 7.13-6.93 (m, 8H), 6.79 (d, 1H), 1.75 (s, 6H) | 772.3 | 773.3 |

Example 1

As an ITO anode, a Corning 15 Ω/cm$^2$ (1,200 Å) ITO glass substrate was cut to a size 50 mm×50 mm×0.7 mm, sonicated with isopropyl alcohol and pure water each for 5 minutes, and then cleaned by exposure to ultraviolet rays and ozone for 30 minutes. Then, the glass substrate was provided to a vacuum deposition apparatus.

α-NPD was vacuum-deposited on the ITO anode of the glass substrate to form a hole injection layer having a thickness of 300 Å, and TCTA (acting as a hole transport compound) was vacuum-deposited on the hole injection layer to form a hole transport layer having a thickness of 200 Å. CzSi (acting as a hole transport layer compound) was vacuum-deposited on the hole transport layer to form a hole transport region having a thickness of 100 Å.

DPEPO (host) and Compound 1 (dopant) were co-deposited on the hole transport region at a weight ratio of 90:10 to form an emission layer having a thickness of 200 Å. Then, DPEPO was deposited on the emission layer to form an electron transport layer having a thickness of 200 Å, and TPBI was deposited on the electron transport layer to a thickness of 300 Å. Then, LiF was deposited thereon to form an electron injection layer having a thickness of 10 Å, and Al was vacuum-deposited on the electron injection layer to form a LiF/Al cathode having a thickness of 1,000 Å, thereby completing the manufacture of an organic light-emitting device.

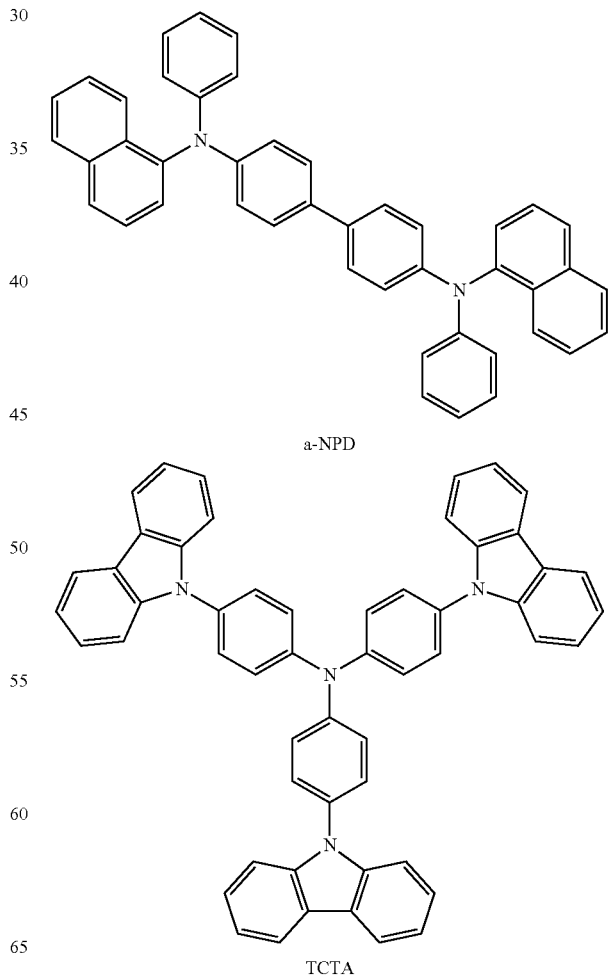

a-NPD

TCTA

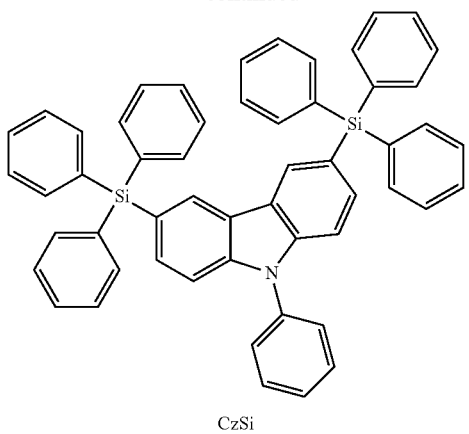

CzSi

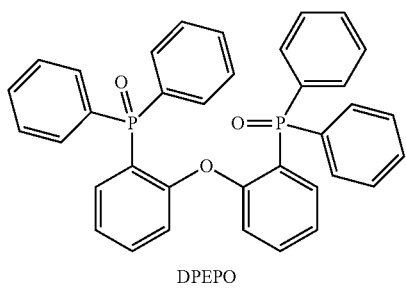

DPEPO

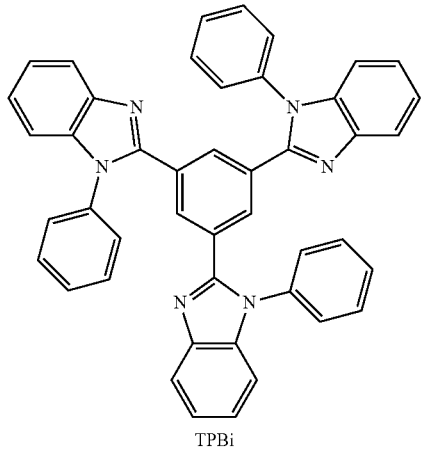

TPBi

Examples 2 to 24

Organic light-emitting devices were manufactured in the same (or substantially the same) manner as in Example 1, except that Compounds shown in Table 2 were respectively used in forming an emission layer.

Comparative Example 1

An organic light-emitting device was manufactured in the same (or substantially the same) manner as in Example 1, except that DMAC-DPS, which is a known compound, was used instead of Compound 1 as a TADF compound in forming an emission layer.

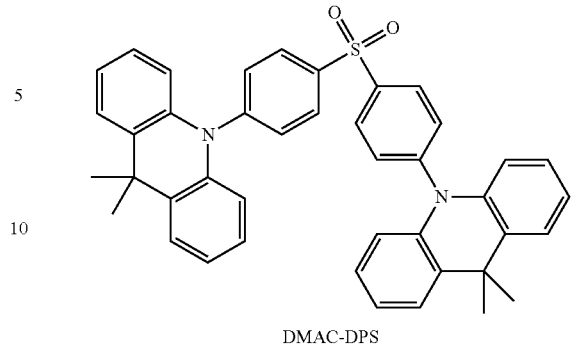

DMAC-DPS

Comparative Example 2

An organic light-emitting device was manufactured in the same (or substantially the same) manner as in Example 1, except that Compound A was used instead of Compound 1 in forming an emission layer.

Compound A

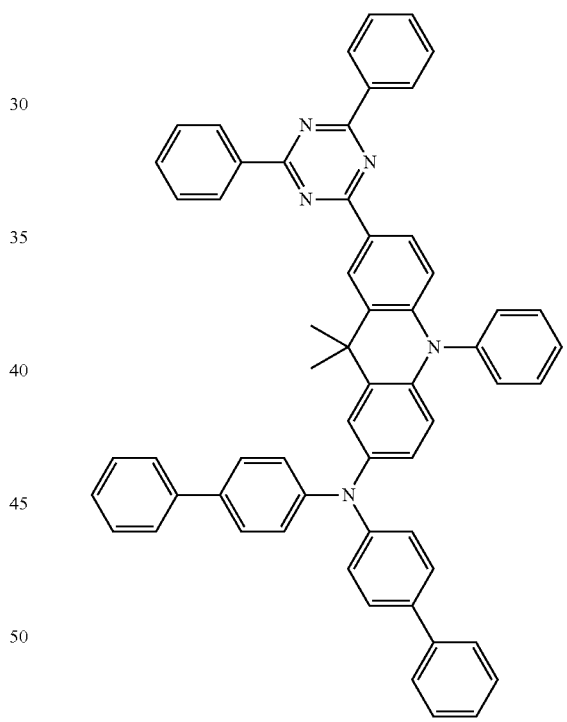

Comparative Example 3

An organic light-emitting device was manufactured in the same (or substantially the same) manner as in Example 1, except that 2% of TPD, which is a known fluorescent dopant, was used instead of Compound 1 in forming an emission layer.

Examples 25 to 29

Organic light-emitting devices were manufactured in the same (or substantially the same) manner as in Example 1, except that, in forming an emission layer, 15% of Compounds 6, 14, 18, 20, and 21 were respectively used, instead of Compound 1, as a first dopant, and 2% of TPD, which is a known fluorescent dopant, was used as a second dopant.

The driving voltage, current efficiency (cd/A), and maximum quantum efficiency (EQE) of the organic light-emitting devices manufactured according to Examples 1 to Example 24 and Comparative Examples 1 and 2 were measured at a luminance of 100 cd/m². Results thereof are shown in Table 2.

efficiency are exhibited, as compared with a case where a known delayed fluorescence material DMAC-DPS exhibiting a blue color is used as a dopant. Accordingly, it is confirmed that the compounds according to one or more embodiments may have low ΔEst and may be used as an effective delayed fluorescence material.

As can be seen from Table 3 (below), when the compounds according to one or more embodiments are used as a first dopant, as in Examples 25 to Example 29, maximum luminescence efficiency increases, as compared with Com-

TABLE 2

| TADF | Luminescent material | Driving voltage (V) | Luminance (cd/m²) | Efficiency (cd/A) | Maximum quantum efficiency (%) | Emission color |
|---|---|---|---|---|---|---|
| Example 1 | Compound 1 | 6.3 | 100 | 19.1 | 23 | Blue |
| Example 2 | Compound 3 | 6.3 | 100 | 19.2 | 22.8 | Bluish green |
| Example 3 | Compound 4 | 6.4 | 100 | 18.1 | 22 | Bluish green |
| Example 4 | Compound 5 | 6.3 | 100 | 16.3 | 19.2 | Blue |
| Example 5 | Compound 6 | 6.4 | 100 | 15.8 | 18.3 | Blue |
| Example 6 | Compound 10 | 6.4 | 100 | 18.6 | 22 | Blue |
| Example 7 | Compound 12 | 6.3 | 100 | 17.8 | 22.4 | Blue |
| Example 8 | Compound 13 | 6.2 | 100 | 16.2 | 18.9 | Blue |
| Example 9 | Compound 14 | 6.2 | 100 | 21.3 | 23.2 | Bluish green |
| Example 10 | Compound 15 | 6.3 | 100 | 15.2 | 19.4 | Blue |
| Example 11 | Compound 16 | 6.1 | 100 | 16.4 | 18.4 | Bluish green |
| Example 12 | Compound 17 | 6.1 | 100 | 15.3 | 17.9 | Blue |
| Example 13 | Compound 18 | 6.4 | 100 | 14.8 | 16.3 | Blue |
| Example 14 | Compound 19 | 6.5 | 100 | 13.2 | 14.3 | Blue |
| Example 15 | Compound 20 | 6.5 | 100 | 14.3 | 14.9 | Blue |
| Example 16 | Compound 21 | 6.3 | 100 | 19.6 | 23.6 | Blue |
| Example 17 | Compound 43 | 6.5 | 100 | 20.9 | 22.4 | Bluish green |
| Example 18 | Compound 64 | 6.4 | 100 | 18.9 | 22.3 | Bluish green |
| Example 19 | Compound 85 | 6.3 | 100 | 18.8 | 22.4 | Blue |
| Example 20 | Compound 106 | 6.4 | 100 | 17.6 | 19.8 | Blue |
| Example 21 | Compound 129 | 6.4 | 100 | 23.7 | 24.6 | Bluish green |
| Example 22 | Compound 133 | 6.3 | 100 | 19.3 | 23.1 | Blue |
| Example 23 | Compound 137 | 6.3 | 100 | 18.3 | 21.9 | Bluish green |
| Example 24 | Compound 143 | 6.4 | 100 | 21.6 | 23.2 | Bluish green |
| Comparative Example 1 | DMAC-DPS | 6.5 | 100 | 12.3 | 17.3 | Blue |
| Comparative Example 2 | Compound A | 6.3 | 100 | 3.3 | 2.4 | Blue |

Referring to Table 2, it is confirmed that, when the compounds according to one or more embodiments are used as a material for forming a dopant of an emission layer, a blue color and a bluish green color are exhibited, and improved luminescence efficiency and maximum quantum parative Example 3 using only an existing fluorescent dopant TPD. That is, due to the delayed fluorescence effect of the compound, luminescence efficiency may be improved when the compound according to one or more embodiments is used as an auxiliary dopant in an emission layer of a device.

TABLE 3
| TADF | Luminescent material | Driving voltage (V) | Luminance (cd/m2) | Efficiency (cd/A) | Maximum quantum efficiency (%) | Emission color |
|---|---|---|---|---|---|---|
| Example 25 | Compound 6 | 6.3 | 500 | 8.6 | 16.4 | Blue |
| Example 26 | Compound 14 | 6.2 | 500 | 7.7 | 15.2 | Blue |
| Example 27 | Compound 18 | 6.3 | 500 | 7.2 | 15.8 | Blue |
| Example 28 | Compound 20 | 6.3 | 500 | 6.8 | 14.7 | Blue |
| Example 29 | Compound 21 | 6.3 | 500 | 6.6 | 13.3 | Blue |
| Comparative Example 3 | TPD | 6.3 | 500 | 5.3 | 4.7 | Blue |
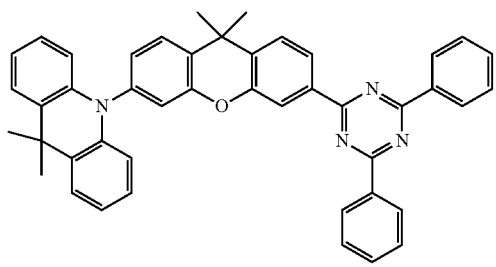
1
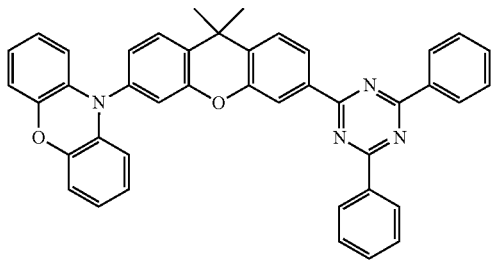
3
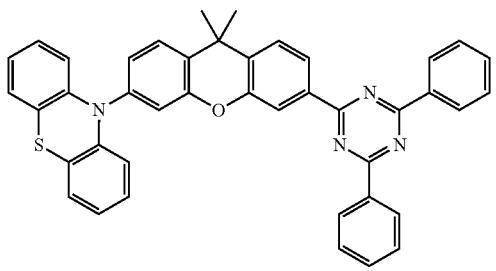
4
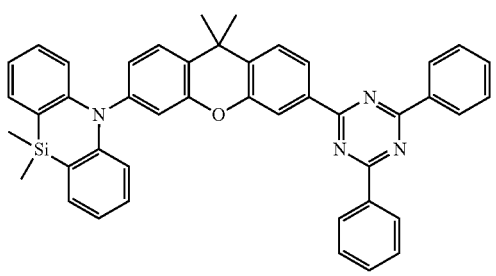
5

6
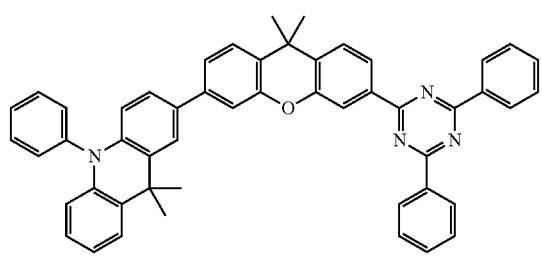
10
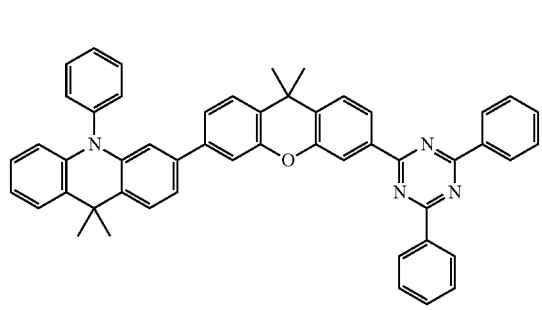
12
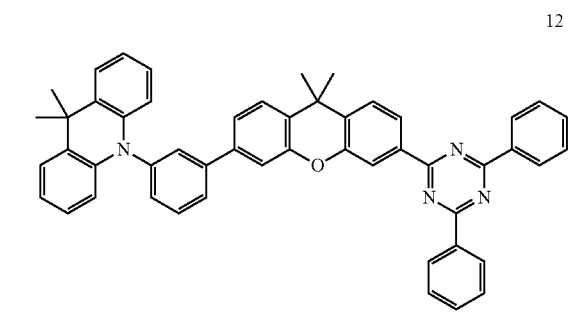
13
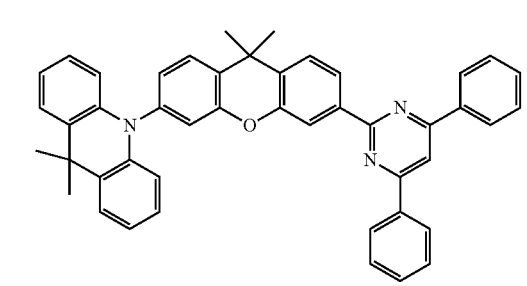
14
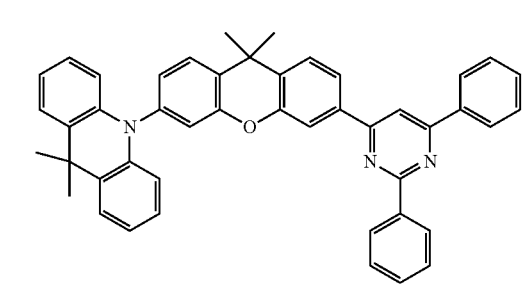

15
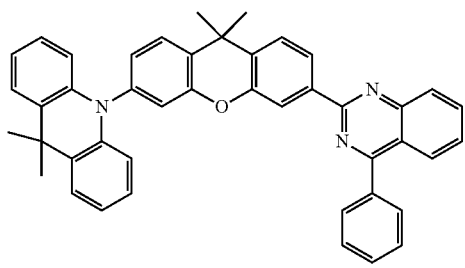
16
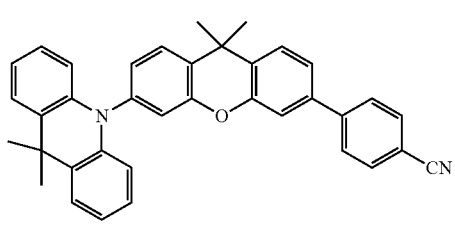
17
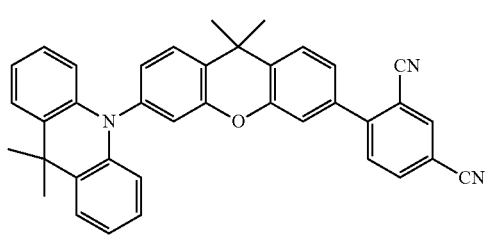
18
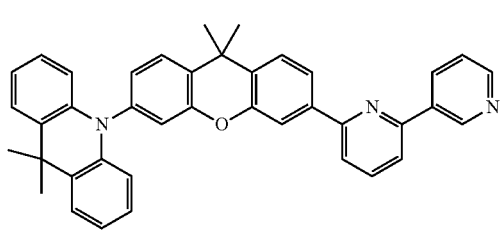
19
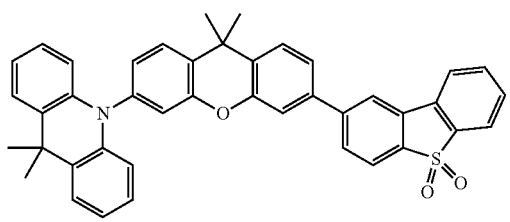
20
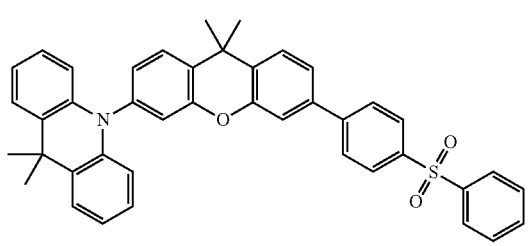

-continued
21
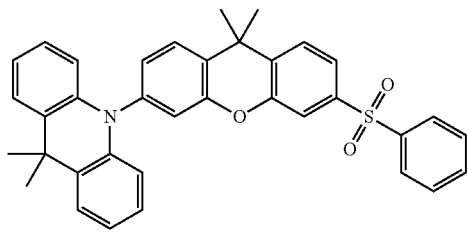
22
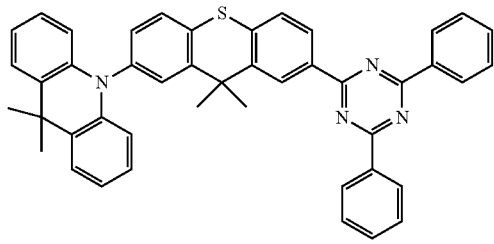
43
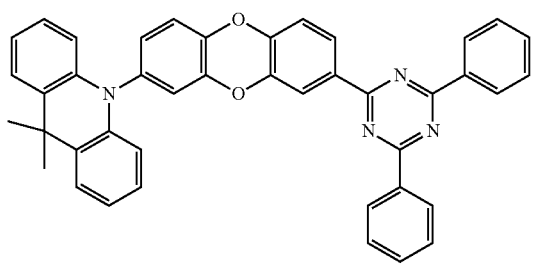
64
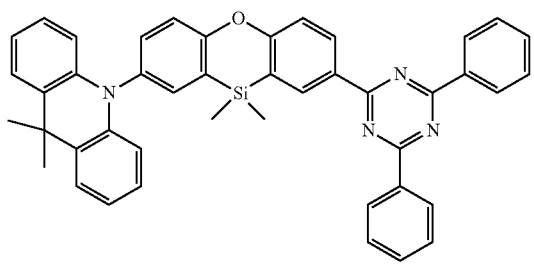
85
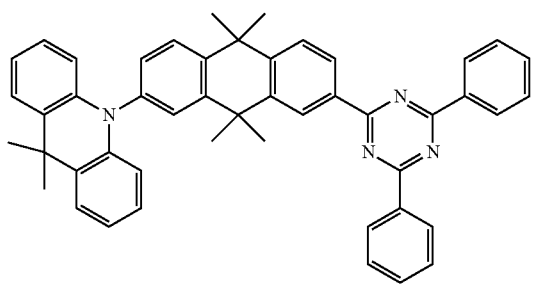

106
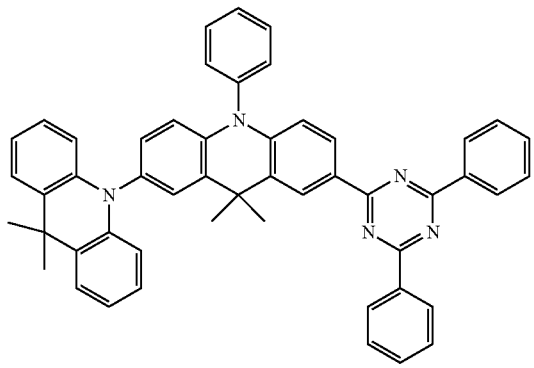
129
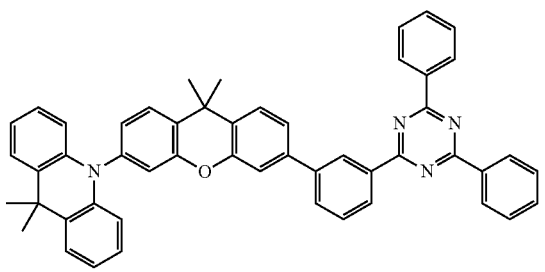
133
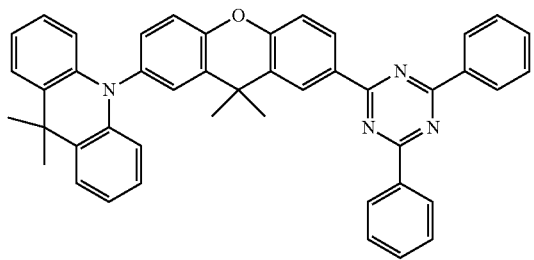
137
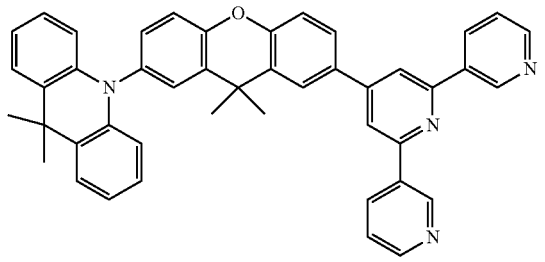
143
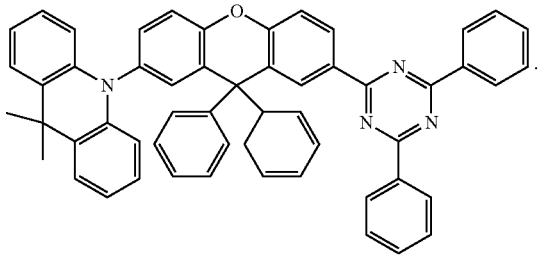
An organic light-emitting device according to an embodiment may have a low driving voltage, high efficiency, a long lifespan, and high maximum quantum efficiency.
As used herein, the terms "use," "using," and "used" may be considered synonymous with the terms "utilize," "utilizing," and "utilized," respectively.

In addition, the terms "substantially," "about," and similar terms are used as terms of approximation and not as terms of degree, and are intended to account for the inherent deviations in measured or calculated values that would be recognized by those of ordinary skill in the art.

Also, any numerical range recited herein is intended to include all subranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope of the present disclosure as defined by the following claims and equivalents thereof.

What is claimed is:

1. A condensed cyclic compound represented by Formula 1:

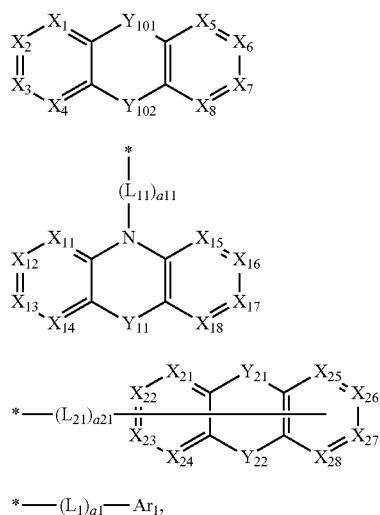

wherein, in Formulae 1 to 4, $X_1$ to $X_4$ are each independently $C(R_1)$, N, or carbon linked to a group represented by Formula 2 or 3, $X_5$ to $X_8$ are each independently $C(R_2)$, N, or carbon linked to a group represented by Formula 4, $X_{11}$ to $X_{18}$ are each independently $C(R_3)$ or N, $X_{21}$ to $X_{28}$ are each independently $C(R_4)$, N, or carbon linked to $(L_{21})_{a21}$, and at least one of $X_1$ to $X_4$ is carbon linked to a group represented by Formula 2 or 3, at least one of $X_5$ to $X_8$ is carbon linked to a group represented by Formula 4, and at least one of $X_{21}$ to $X_{28}$ is carbon linked to $(L_{21})_{a21}$, $Y_{101}$ and $Y_{102}$ are each independently selected from $C(R_{11})(R_{12})$, $Si(R_{11})(R_{12})$, O, S, and $N(R_{11})$, $Y_{11}$, $Y_{21}$, and $Y_{22}$ are each independently selected from $C(R_{21})(R_{22})$, $Si(R_{21})(R_{22})$, O, S, and $N(R_{21})$, provided that:

when $Y_{101}$ is O, $Y_{102}$ is $C(R_{11})(R_{12})$, $Si(R_{11})(R_{12})$, O or $N(R_{11})$, when $Y_{11}$ is $C(R_{21})(R_{22})$, $Si(R_{21})(R_{22})$, O or $N(R_{21})$ and $Y_{101}$ is S, $Y_{102}$ is $C(R_{11})(R_{12})$, $Si(R_{11})(R_{12})$, S or $N(R_{11})$, when $Y_{11}$ and $Y_{101}$ are each S, $Y_{102}$ is $C(R_{11})(R_{12})$, $Si(R_{11})(R_{12})$, or S, and when $Y_{11}$ is S and $Y_{101}$ is $N(R_{11})$, $Y_{102}$ is $C(R_{11})(R_{12})$, $Si(R_{11})(R_{12})$, O or $N(R_{11})$;

$L_1$, $L_{11}$, and $L_{21}$ are each independently a substituted or unsubstituted $C_3$-$C_{60}$ carbocyclic group or a substituted or unsubstituted $C_1$-$C_{60}$ heterocyclic group, a1, a11, and a21 are each independently an integer from 0 to 3, wherein, when a1 is two or more, two or more $L_1(s)$ are identical to or different from each other, when a11 is two or more, two or more $L_{11}(s)$ are identical to or different from each other, and when a21 is two or more, two or more $L_{21}(s)$ are identical to or different from each other, $Ar_1$ is a substituted or unsubstituted $C_3$-$C_{60}$ carbocyclic group, a substituted or unsubstituted $C_1$-$C_{60}$ heterocyclic group, or *—$S(=O)_2(Q_{101})$, $R_1$ to $R_4$, $R_{11}$ to $R_{12}$, and $R_{21}$ to $R_{22}$ are each independently selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —$Si(Q_1)(Q_2)(Q_3)$, —$N(Q_1)(Q_2)$, —$B(Q_1)(Q_2)$, —$C(=O)(Q_1)$, —$S(=O)_2(Q_1)$, and —$P(=O)(Q_1)(Q_2)$, at least one substituent of the substituted $C_3$-$C_{60}$ carbocyclic group, the substituted $C_1$-$C_{60}$ heterocyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group is selected from:

deuterium, —F, —Cl, —Br, —I, a hydroxyl group, a cyano group, a nitro group, an amino group, an amidino group, a hydrazino group, a hydrazono group, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —N($Q_{11}$)($Q_{12}$), —B($Q_{11}$)($Q_{12}$), —C(=O)($Q_{11}$), —S(=O)$_2$($Q_{11}$), and —P(=O)($Q_{11}$)($Q_{12}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, and a terphenyl group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, and a terphenyl group, each substituted with at least one selected from deuterium, —F, —Cl, —Br, —I, a hydroxyl group, a cyano group, a nitro group, an amino group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, a terphenyl group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), and —P(=O)($Q_{21}$)($Q_{22}$); and —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), $Q_{101}$, $Q_1$ to $Q_3$, $Q_{11}$ to $Q_{13}$, $Q_{21}$ to $Q_{23}$, and $Q_{31}$ to $Q_{33}$ are each independently selected from hydrogen, deuterium, —F, —Cl, —Br, —I, a hydroxyl group, a cyano group, a nitro group, an amino group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, and a terphenyl group, and \* indicates a binding site to a neighboring atom.

2. The condensed cyclic compound of claim 1, wherein $X_1$ to $X_4$ are each independently $C(R_1)$ or carbon linked to a group represented by Formula 2 or 3, $X_5$ to $X_8$ are each independently $C(R_2)$ or carbon linked to a group represented by Formula 4, $X_{11}$ to $X_{18}$ are each $C(R_3)$, and $X_{21}$ to $X_{28}$ are each independently $C(R_4)$ or carbon linked to $(L_{21})_{a21}$.

3. The condensed cyclic compound of claim 1, wherein, in Formulae 2 and 3, $L_1$, $L_{11}$, and $L_{21}$ are each independently selected from:

a phenylene group, a pentalenylene group, an indenylene group, a naphthylene group, an azulenylene group, a heptalenylene group, an indacenylene group, an acenaphthylene group, a fluorenylene group, a spiro-bifluorenylene group, a spiro-fluorene-benzofluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a dibenzosilolylene group, a benzocarbazolylene group, a dibenzocarbazolylene group, a thiadiazolylene group, an imidazopyridinylene group, and an imidazopyrimidinylene group; and a phenylene group, a pentalenylene group, an indenylene group, a naphthylene group, an azulenylene group, a heptalenylene group, an indacenylene group, an acenaphthylene group, a fluorenylene group, a spiro-bifluorenylene group, a spiro-fluorene-benzofluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a dibenzosilolylene group, a benzocarbazolylene group, a dibenzocarbazolylene group, a thiadiazolylene group, an imidazopyridinylene group, and an imidazopyrimidinylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolylene group, a benzocarbazolyl group, a dibenzocarbazolyl group, a thiadiazolyl group, an imidazopyridinyl group, an imidazopyrimidinyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), and $Q_{31}$ to $Q_{33}$ are each independently selected from a $C_1$-$C_{10}$ alkyl group, a $C_1$-$C_{10}$ alkoxy group, a phenyl group, a phenyl group substituted with a $C_1$-$C_{10}$ alkyl group, a biphenyl group, a terphenyl group, a naphthyl group, and a dibenzofuranyl group.

4. The condensed cyclic compound of claim 1, wherein, in Formulae 2 and 3, $L_1$, $L_{11}$, and $L_{21}$ are each independently selected from groups represented by Formulae 3-1 to 3-49:

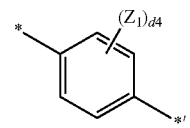

Formula 3-1

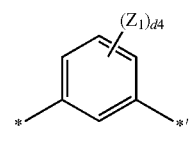

Formula 3-2

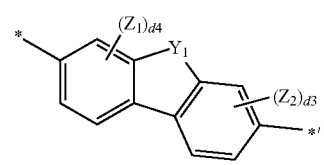

Formula 3-3

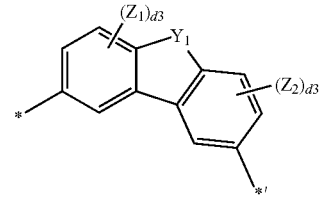

Formula 3-4

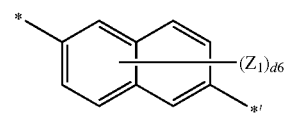

Formula 3-5

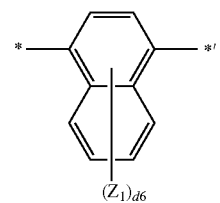

Formula 3-6

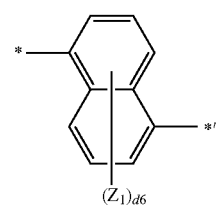

Formula 3-7

-continued
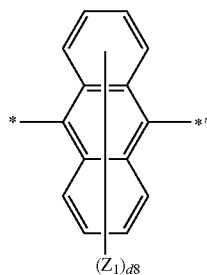
(Z₁)d8
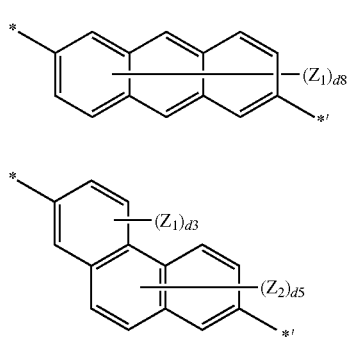
Formula 3-9
Formula 3-10
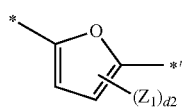
Formula 3-11
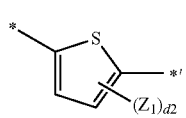
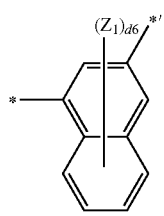
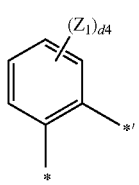
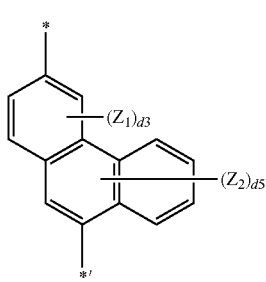
-continued
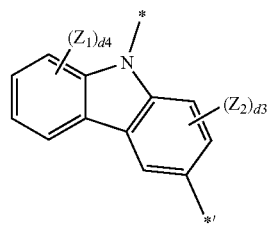
Formula 3-8
Formula 3-9
Formula 3-12
Formula 3-13
Formula 3-14
Formula 3-15
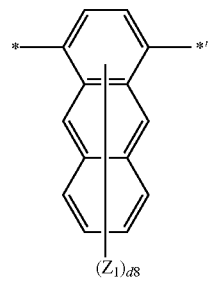
Formula 3-16
Formula 3-17
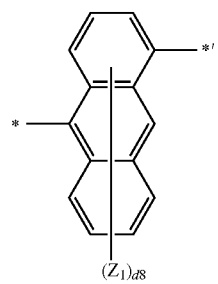
Formula 3-18
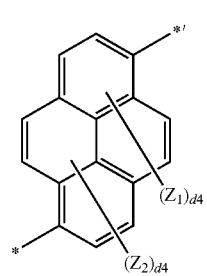
Formula 3-19
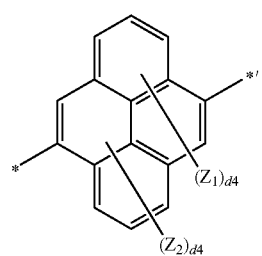
Formula 3-20

-continued
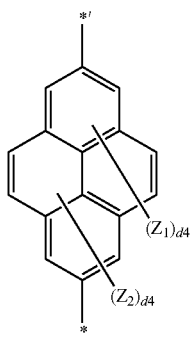
Formula 3-21
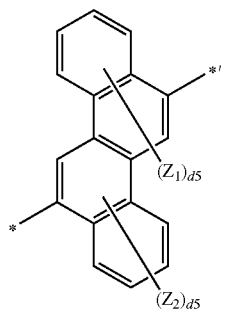
Formula 3-22
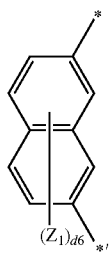
Formula 3-23
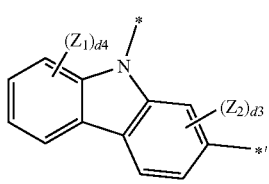
Formula 3-24
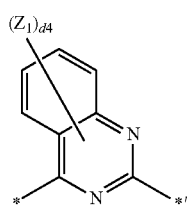
Formula 3-25
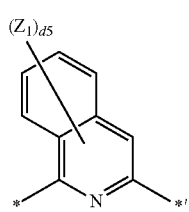
Formula 3-26
-continued
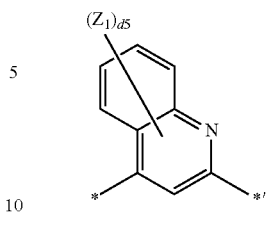
Formula 3-27
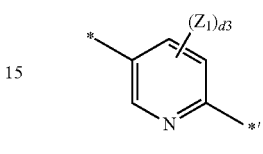
Formula 3-28
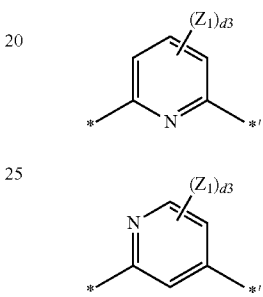
Formula 3-29
Formula 3-30
Formula 3-31
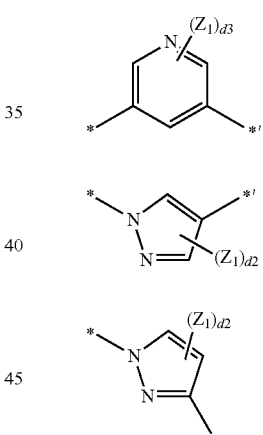
Formula 3-32
Formula 3-33
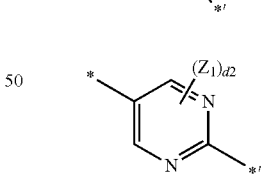
Formula 3-34
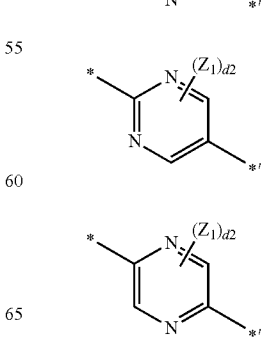
Formula 3-35
Formula 3-36

-continued

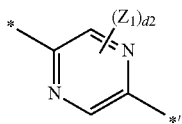
Formula 3-37

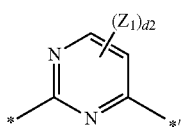
Formula 3-38

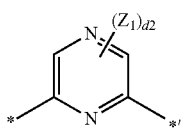
Formula 3-39

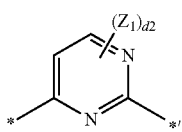
Formula 3-40

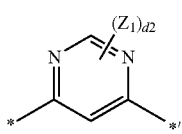
Formula 3-41

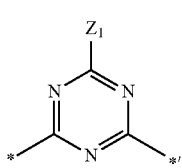
Formula 3-42

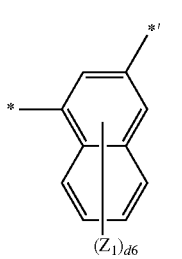
Formula 3-43

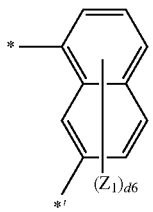
Formula 3-44

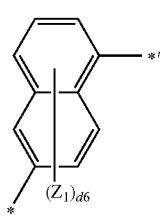
Formula 3-45

-continued

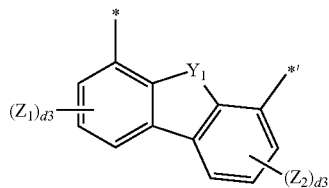
Formula 3-46

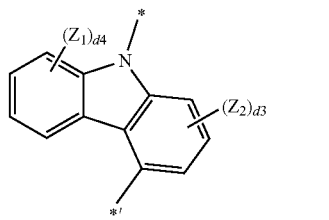
Formula 3-47

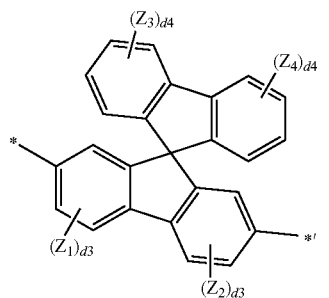
Formula 3-48

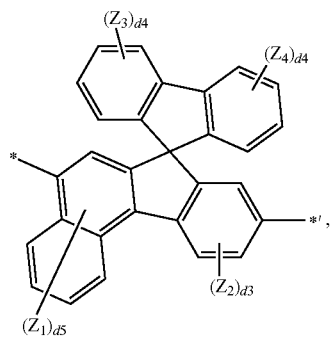
Formula 3-49 wherein, in Formulae 3-1 to 3-49, $Y_1$ is O, S, $C(Z_5)(Z_6)$, $N(Z_5)$, or $Si(Z_5)(Z_6)$, $Z_1$ to $Z_6$ are each independently selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkenyl group, a $C_1$-$C_{20}$ alkynyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), $Q_{31}$ to $Q_{33}$ are each independently selected from a $C_1$-$C_{10}$ alkyl group, a $C_1$-$C_{10}$ alkoxy group, a phenyl group, a biphenyl group, a terphenyl group, and a naphthyl group, d2 is 1 or 2,
d3 is an integer from 1 to 3,
d4 is an integer from 1 to 4,
d5 is an integer from 1 to 5,
d6 is an integer from 1 to 6,
d8 is an integer from 1 to 8, and
* and *' each indicate a binding site to a neighboring atom.

5. The condensed cyclic compound of claim 1, wherein a11 is 0 or 1, and a21 is O.

6. The condensed cyclic compound of claim 1, wherein $Ar_1$ in Formula 4 is selected from groups represented by Formulae 4A to 4N:

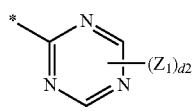
4A

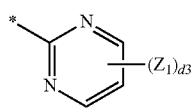
4B

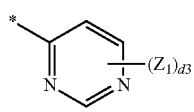
4C

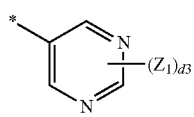
4D

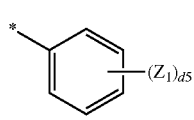
4E

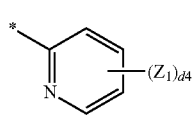
4F

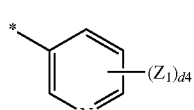
4G

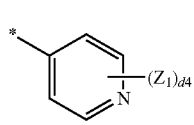
4H

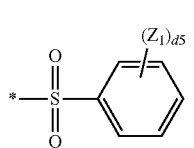
4I

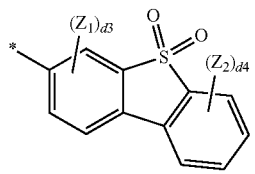
4J

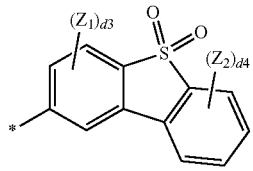
4K

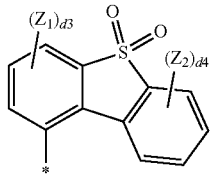
4L

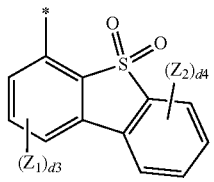
4M

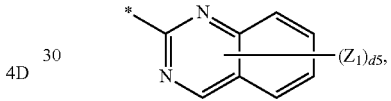
4N wherein in Formulae 4A to 4N, $Z_1$ and $Z_2$ are each independently selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkenyl group, a $C_1$-$C_{20}$ alkynyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), $Q_{31}$ to $Q_{33}$ are each independently selected from a $C_1$-$C_{10}$ alkyl group, a $C_1$-$C_{10}$ alkoxy group, a phenyl group, a biphenyl group, a terphenyl group, and a naphthyl group, d2 is 1 or 2,
d3 is an integer from 1 to 3,
d4 is an integer from 1 to 4,
d5 is an integer from 1 to 5, and
* indicates a binding site to a neighboring atom.

7. The condensed cyclic compound of claim 1, wherein $Ar_1$ in Formula 4 is selected from groups represented by Formulae 4-1 to 4-20:

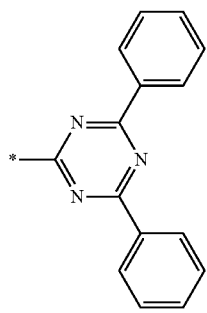 4-1
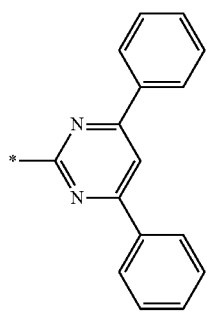 4-2
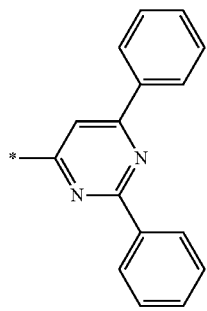 4-3
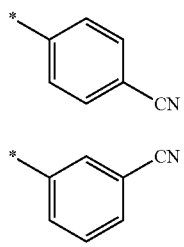 4-4
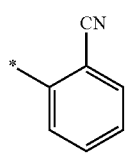 4-5
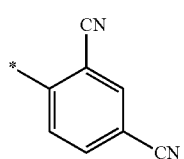 4-6
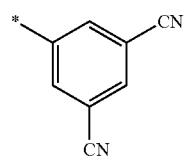 4-7
-continued
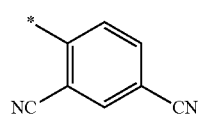 4-8
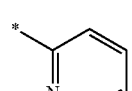 4-9
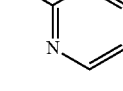 4-10
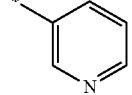 4-11
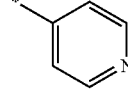 4-12
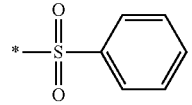 4-13
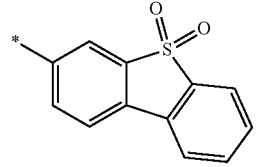 4-14
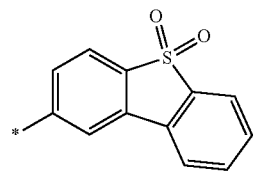 4-15
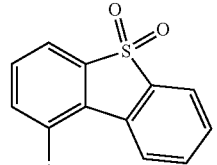 4-16
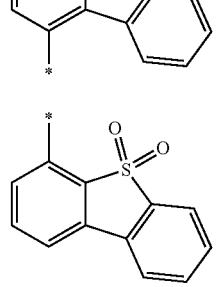 4-17

-continued 4-18

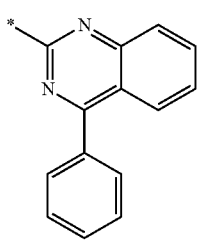

4-19

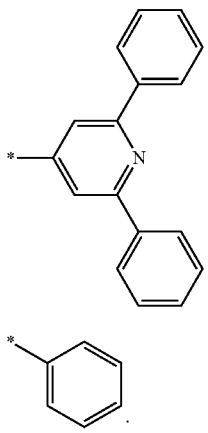

4-20

8. The condensed cyclic compound of claim 1, wherein $R_1$ to $R_4$ are each independently selected from hydrogen, deuterium, —F, —Cl, —Br, —I, a hydroxyl group, a cyano group, a nitro group, a $C_1$-$C_{20}$ alkyl group, and a $C_1$-$C_{20}$ alkoxy group.

9. The condensed cyclic compound of claim 1, wherein $R_{11}$ to $R_{12}$ and $R_{21}$ to $R_{22}$ are each independently selected from:

hydrogen, deuterium, —F, —Cl, —Br, —I, a hydroxyl group, a cyano group, a nitro group, a $C_1$-$C_{20}$ alkyl group, and a $C_1$-$C_{20}$ alkoxy group;

a phenyl group, a biphenyl group, a terphenyl group, a naphthyl group, a pyridinyl group, and a pyrimidinyl group; and a $C_1$-$C_{20}$ alkyl group, a $C_1$-$C_{20}$ alkoxy group, a phenyl group, a biphenyl group, a terphenyl group, a naphthyl group, a pyridinyl group, and a pyrimidinyl group, each substituted with at least one selected from deuterium, —F, —Cl, —Br, —I, a hydroxyl group, a cyano group, and a nitro group.

10. The condensed cyclic compound of claim 1, wherein the condensed cyclic compound represented by Formula 1 is represented by one of Formulae 1A to 1P:

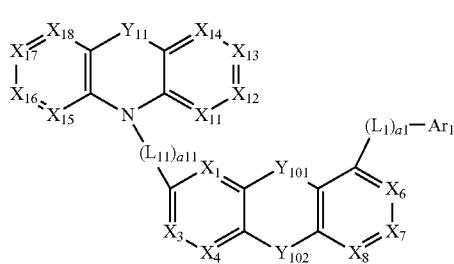

1A

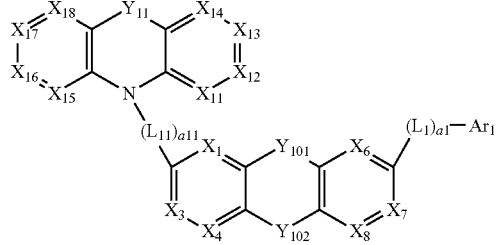

1B

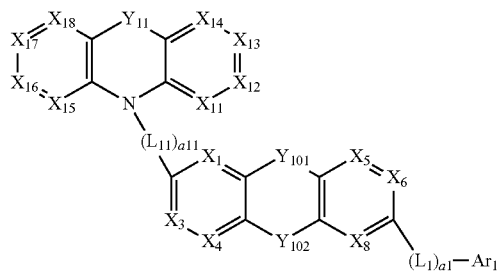

1C

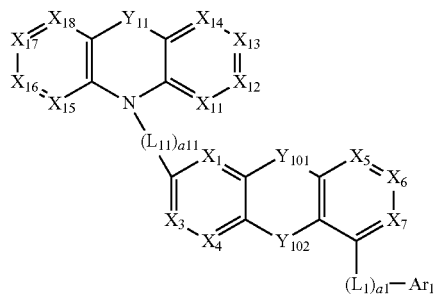

1D

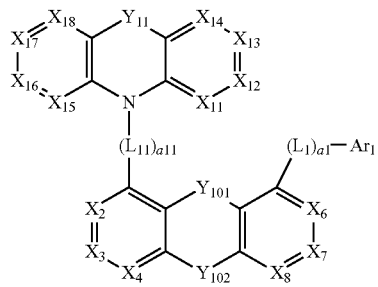

1E

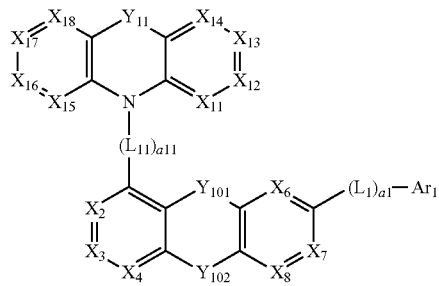

1F

1G 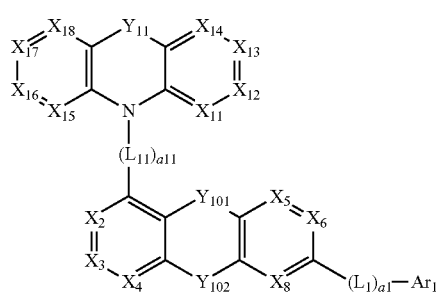
1H 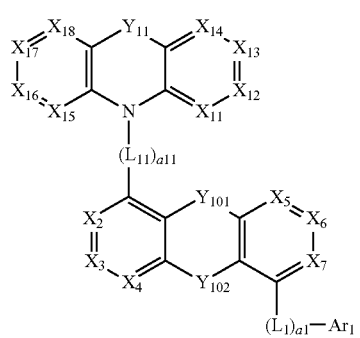
1I 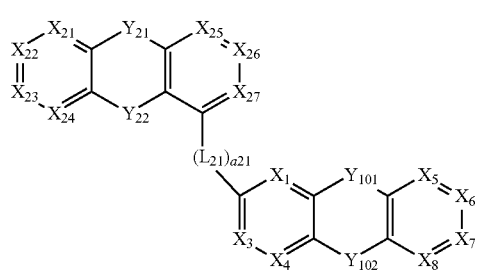
1J 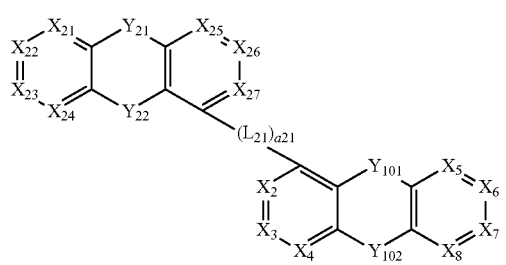
1K 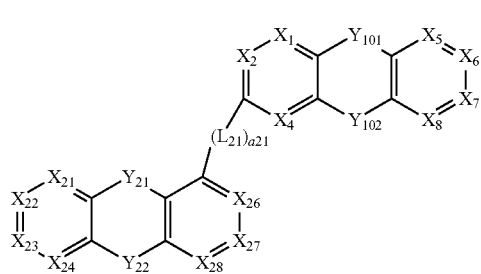
1L 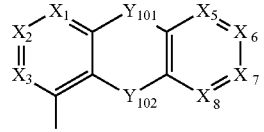
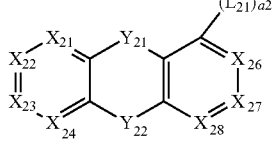
1M 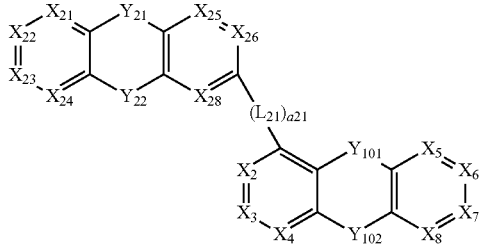
1N 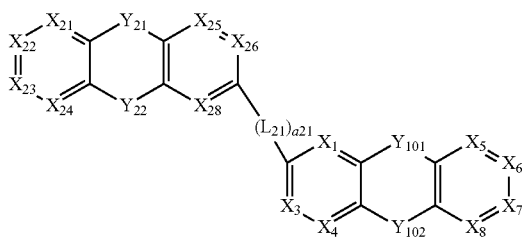
1O 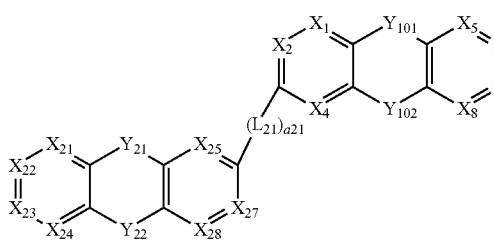
1P 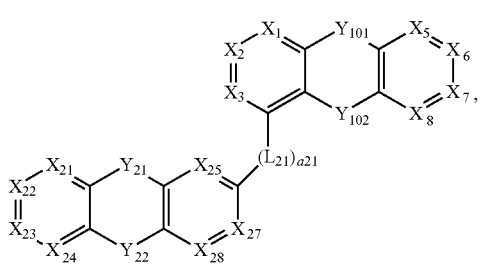
wherein $X_1$ to $X_8$, $X_{11}$ to $X_{18}$, $X_{21}$ to $X_{28}$, $Y_{101}$ to $Y_{102}$, $Y_{11}$, $Y_{21}$ to $Y_{22}$, $L_1$, $L_{11}$, $L_{21}$,
a1, a11, and a21 in Formulae 1A to 1P are the same as described in claim 1.
11. The condensed cyclic compound of claim 1, wherein the condensed cyclic compound represented by Formula 1 is selected from Compounds 1 to 144:

219
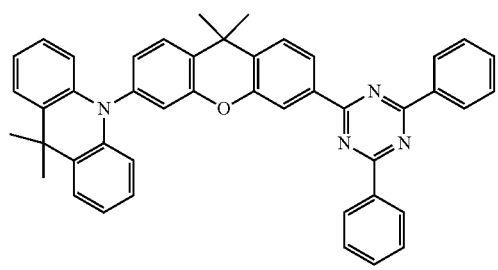
1
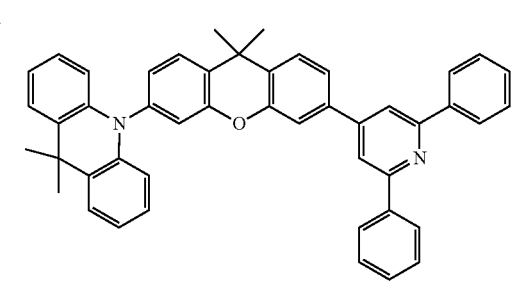
2
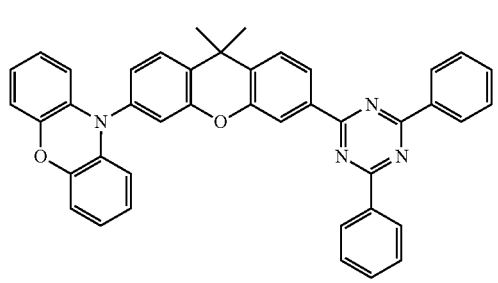
3
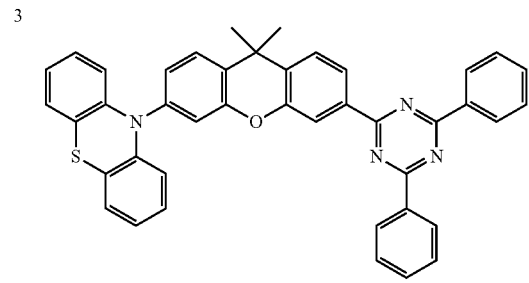
4
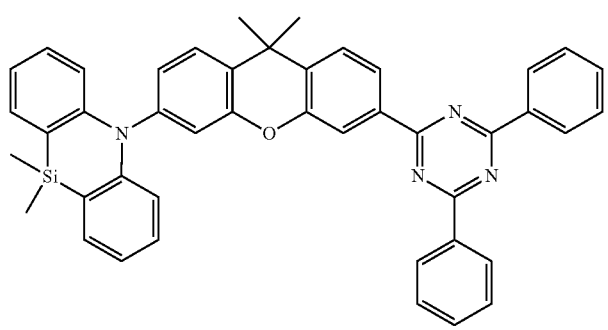
5
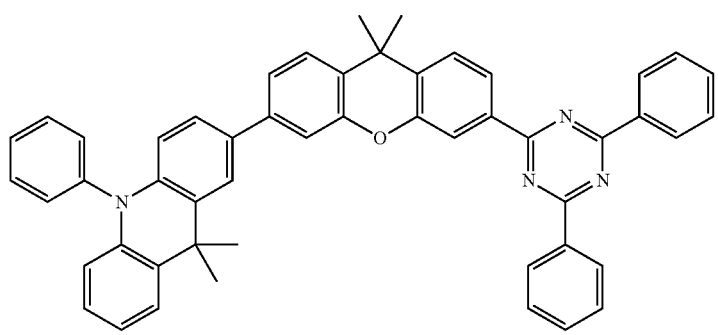
6
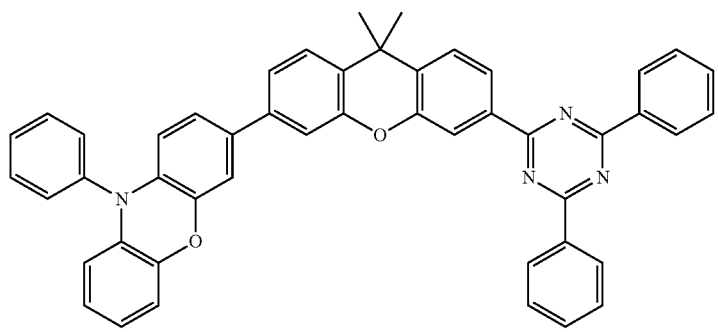
7

8
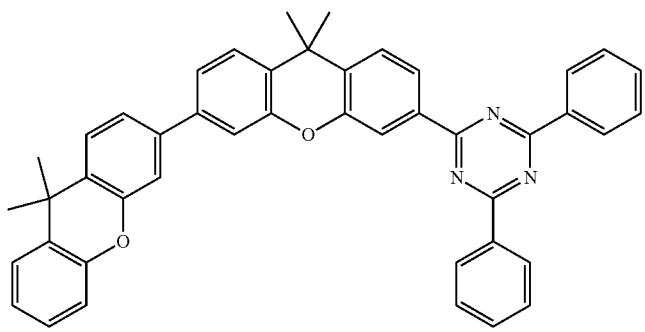
9
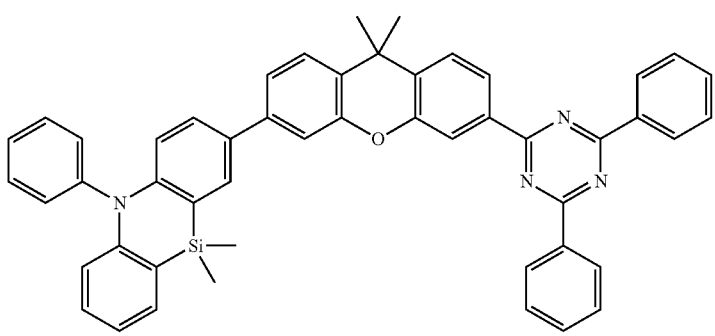
10
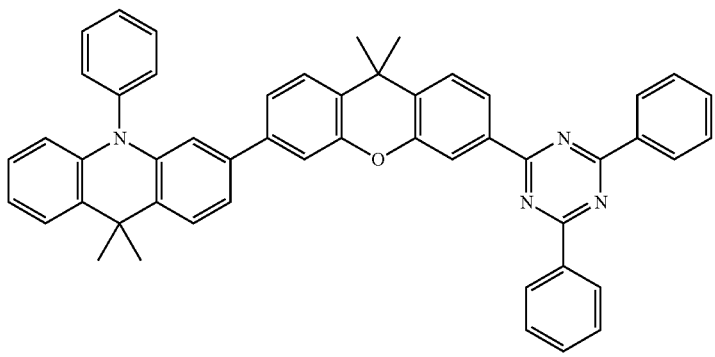
11
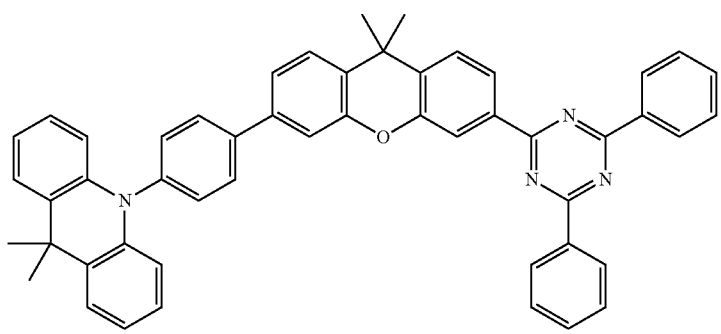

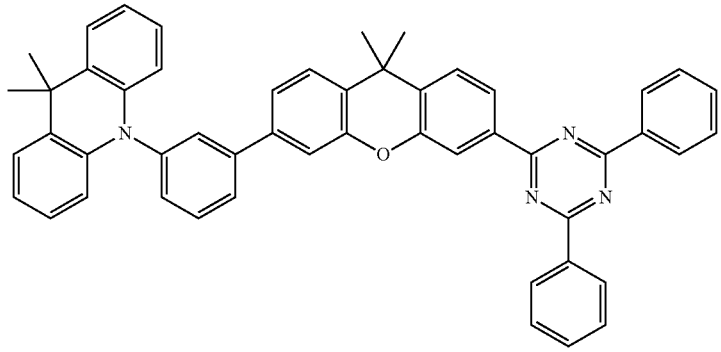
12
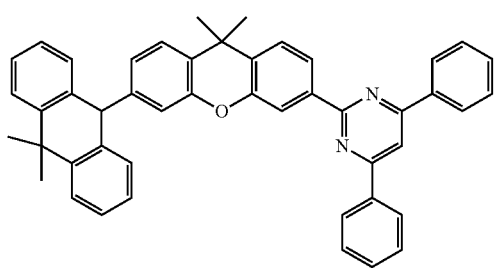
13
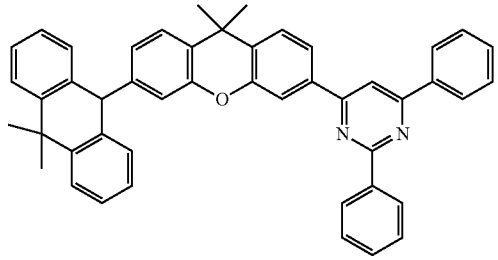
14
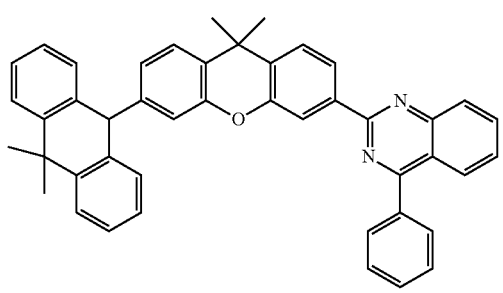
15
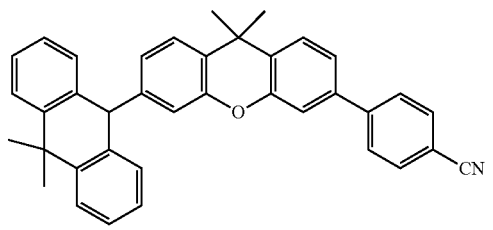
16
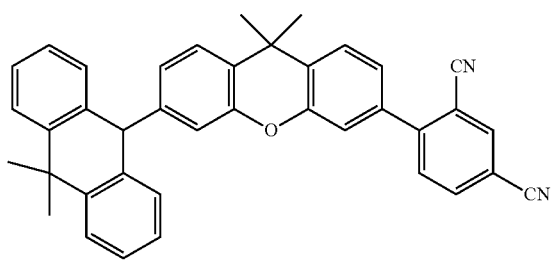
17
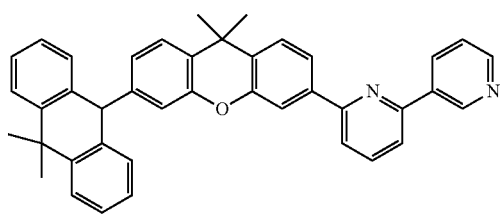
18
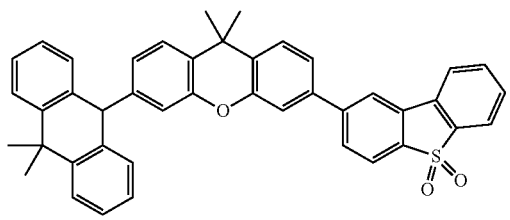
19
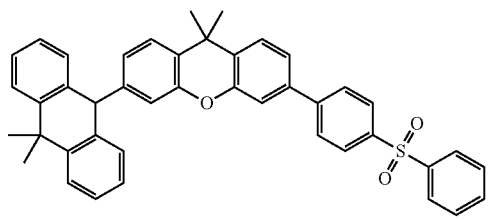
20

-continued
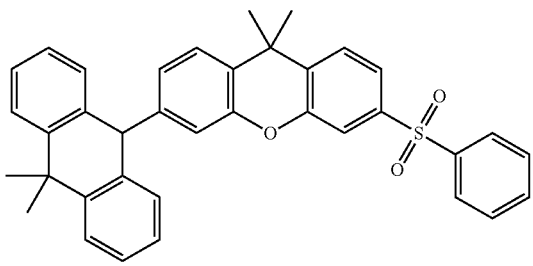
21
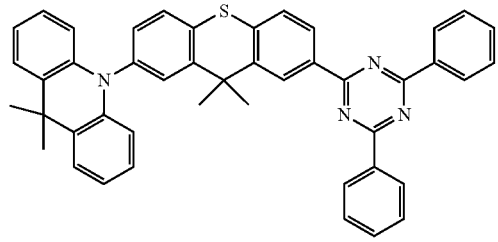
22
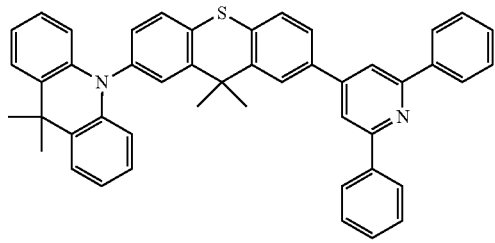
23
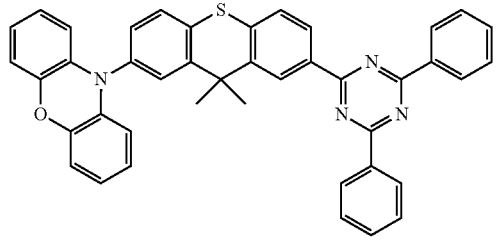
24
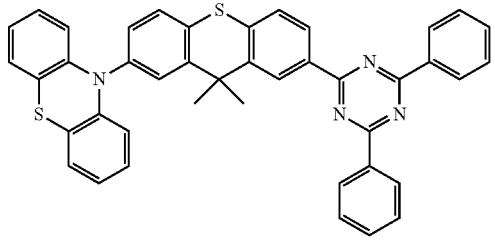
25
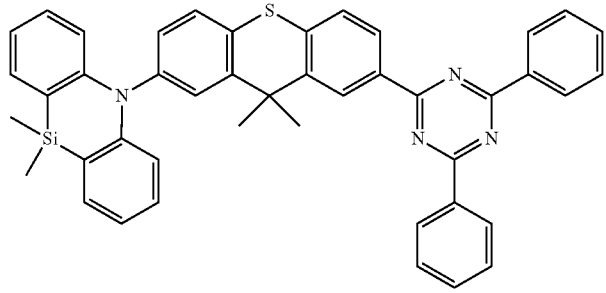
26
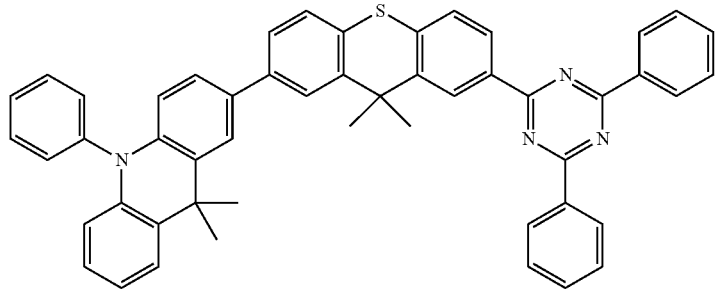
27

-continued
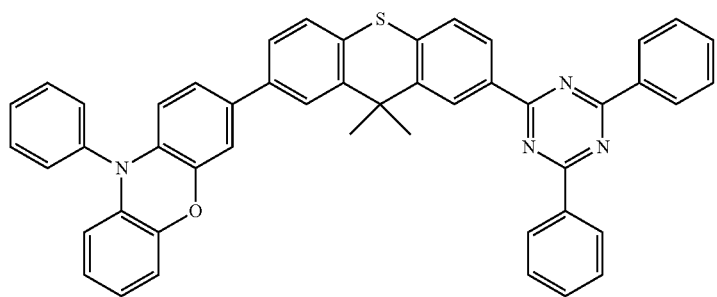
28
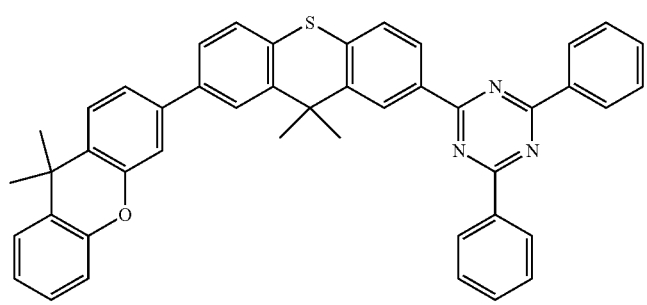
29
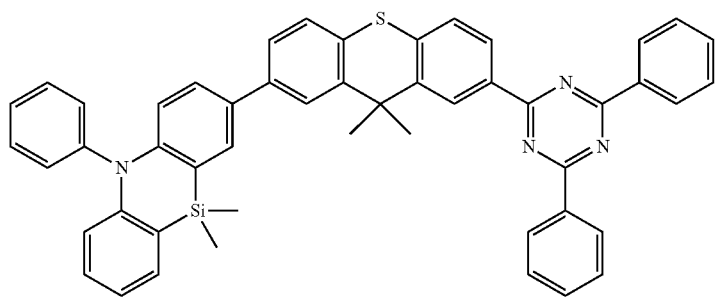
30
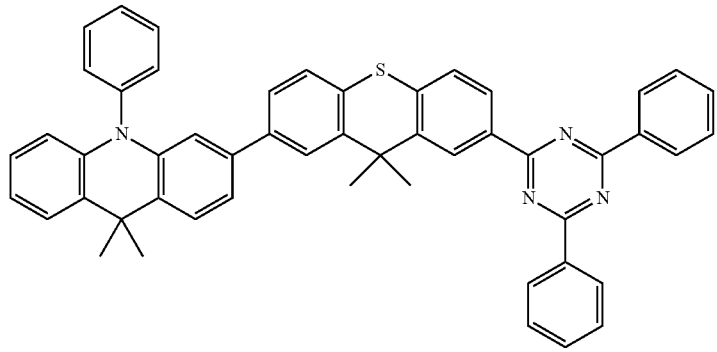
31
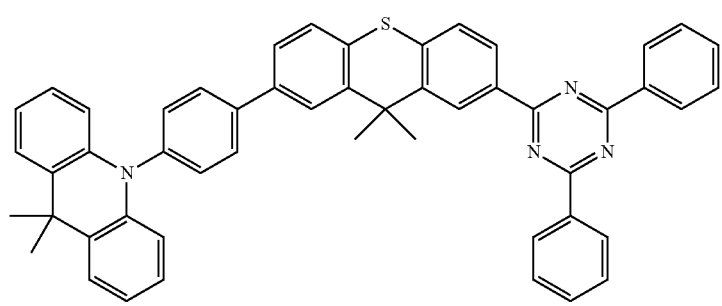
32

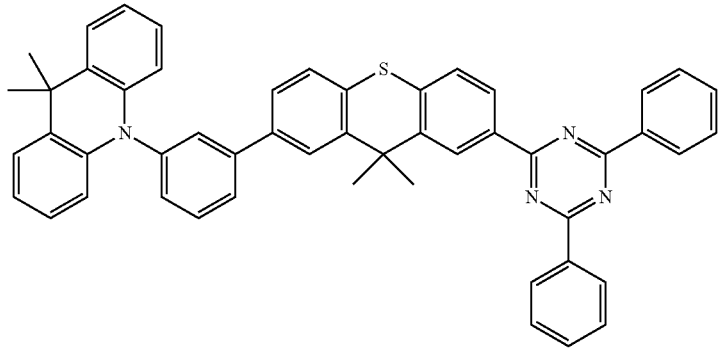
33
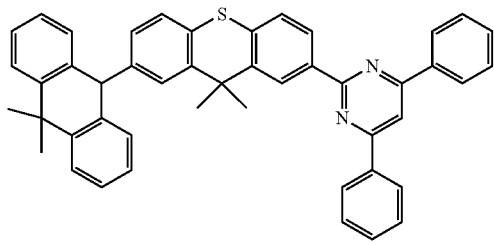
34
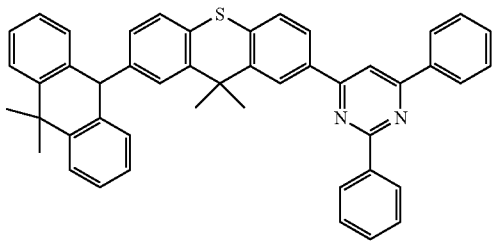
35
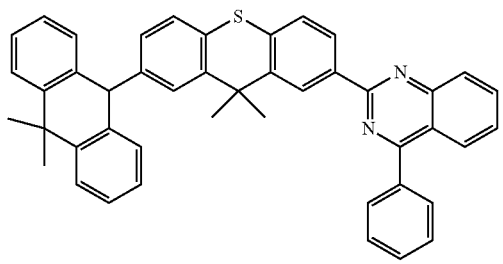
36
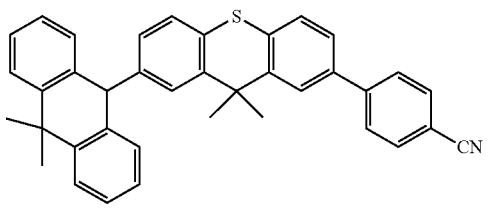
37
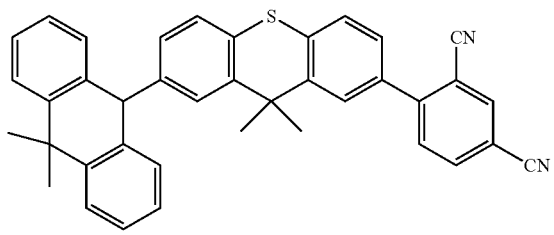
38
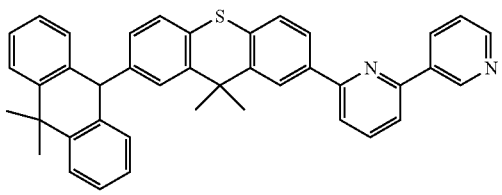
39
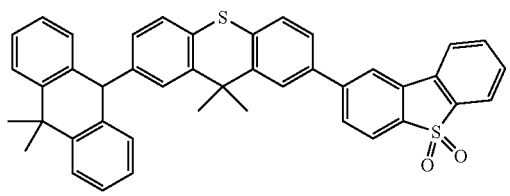
40
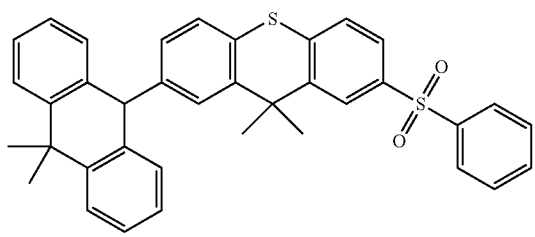
42
41

-continued
| 43 | 44 |
|---|---|
| 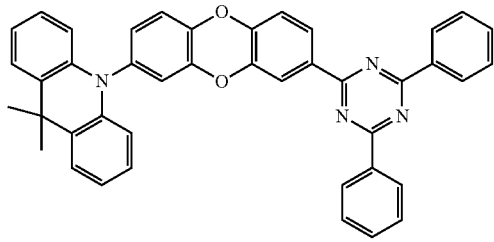 | 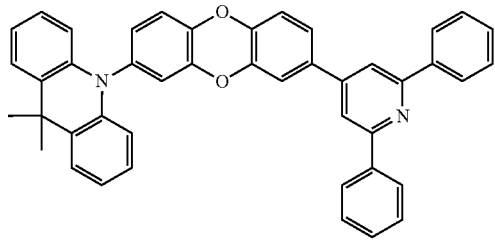 |
| 45 | 46 |
| 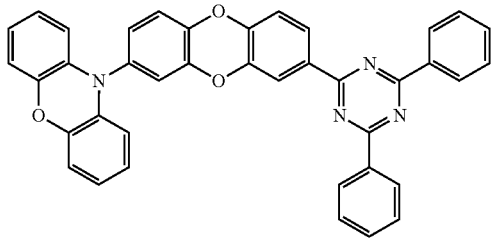 | 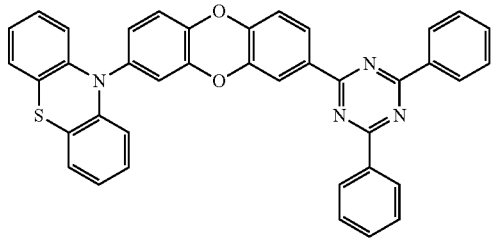 |
47
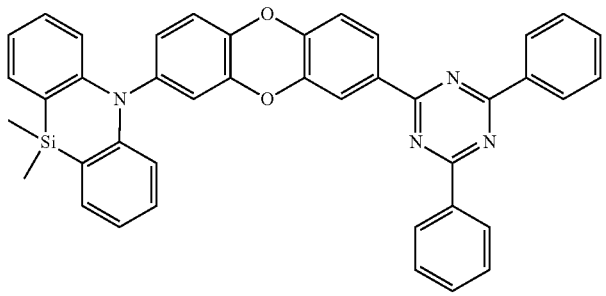
48
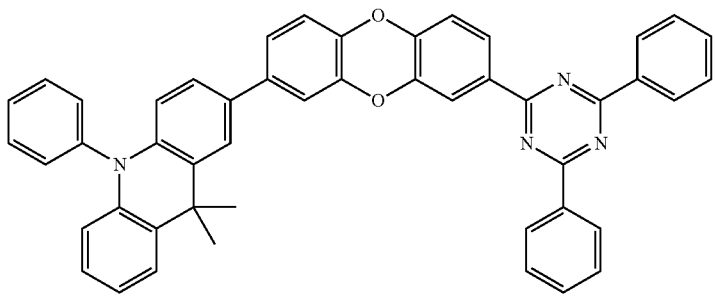
49
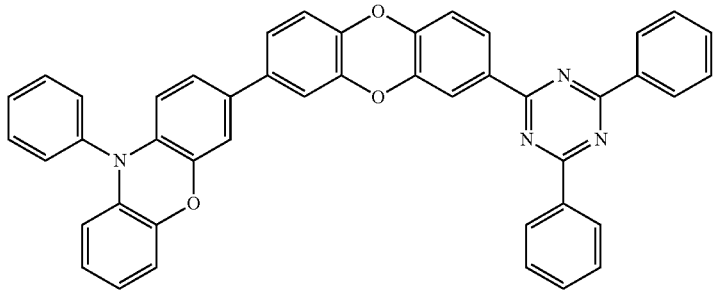

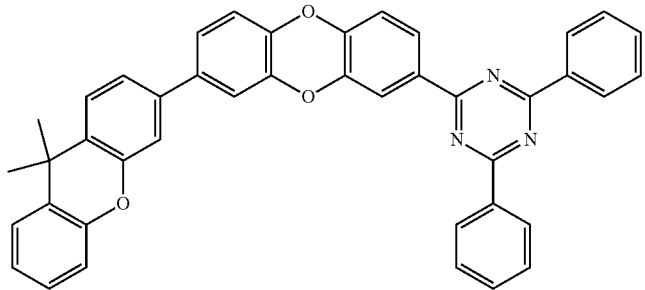
50
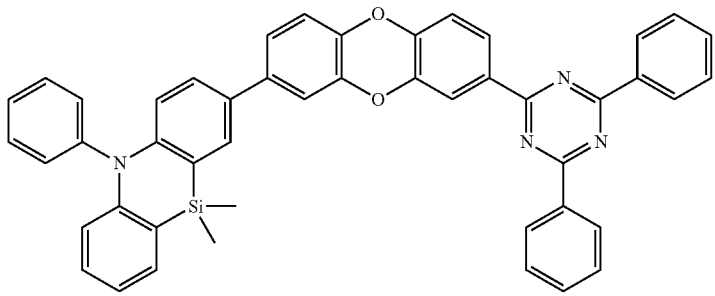
51
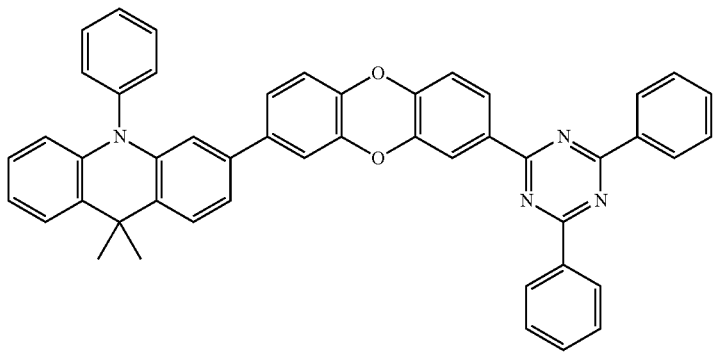
52
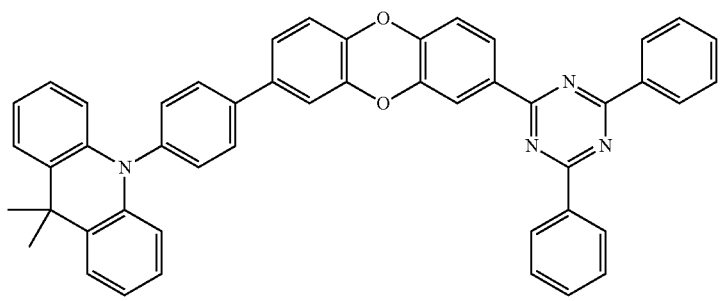
53
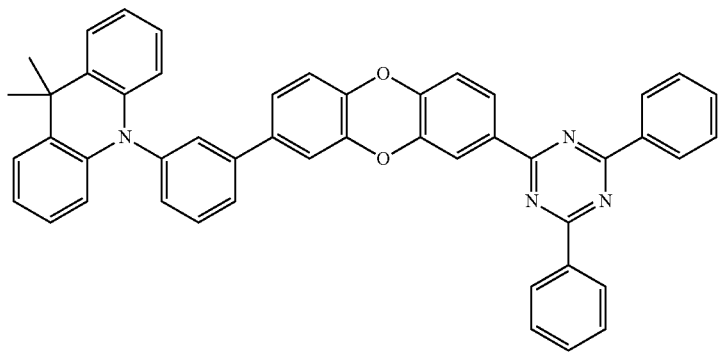
54

-continued
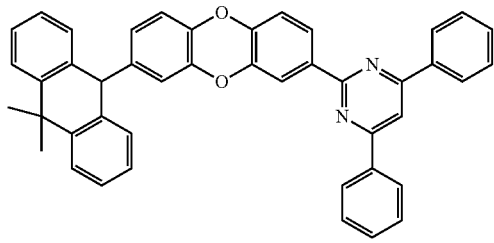
55
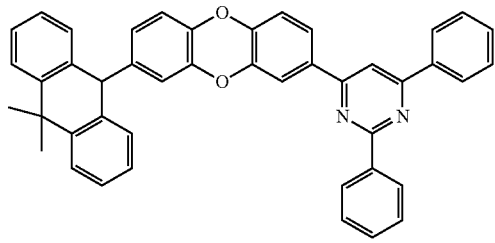
56
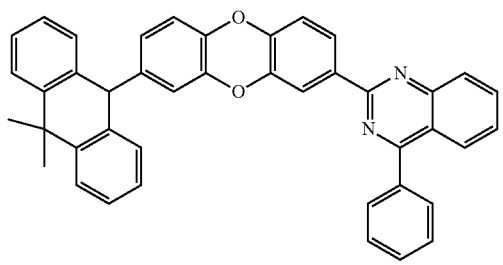
57
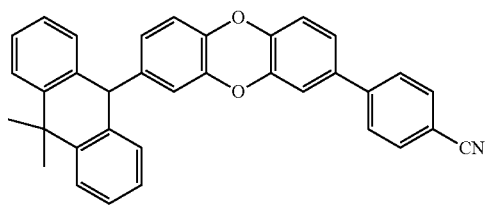
58
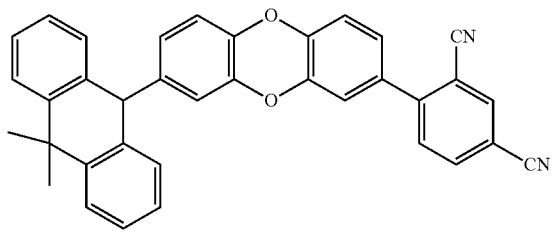
59
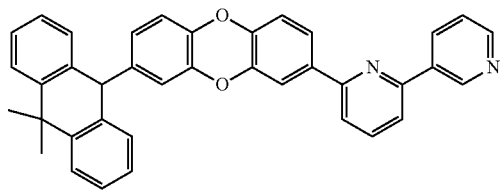
60
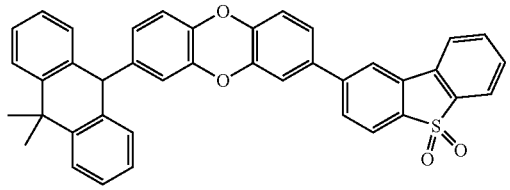
61
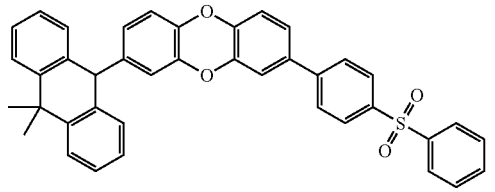
62
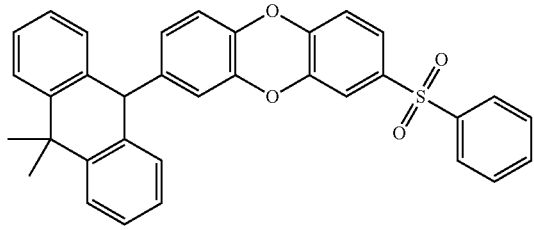
63
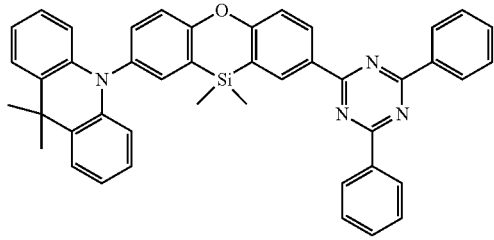
64
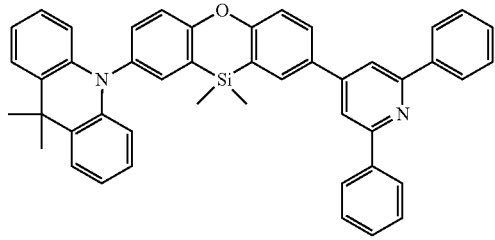
65

-continued
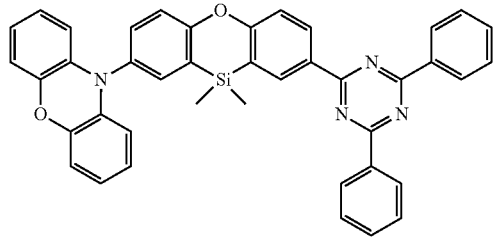
66
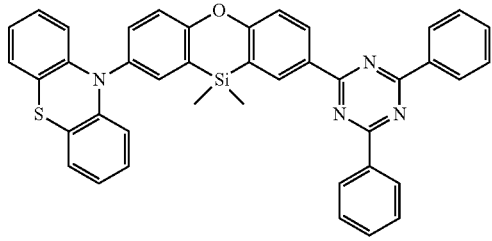
67
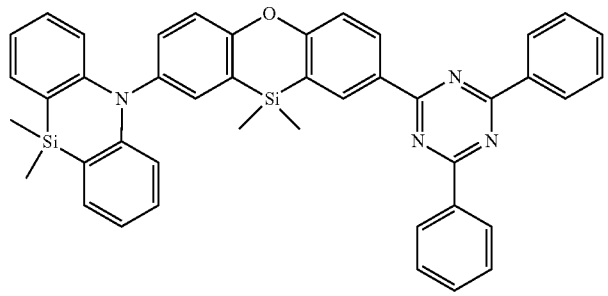
68
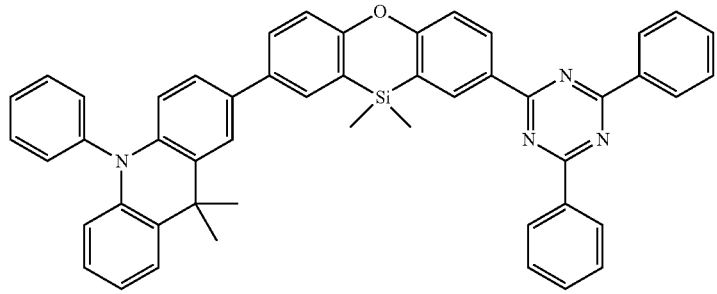
69
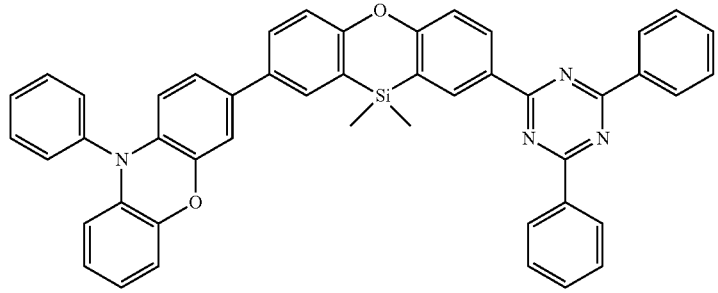
70
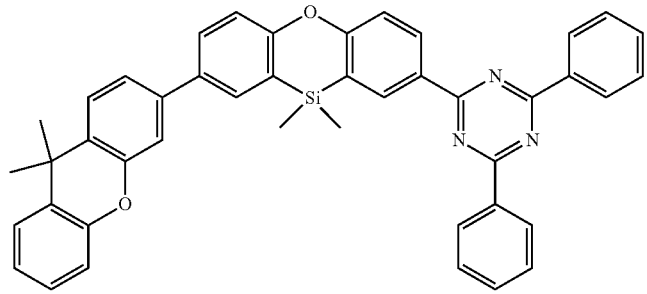
71

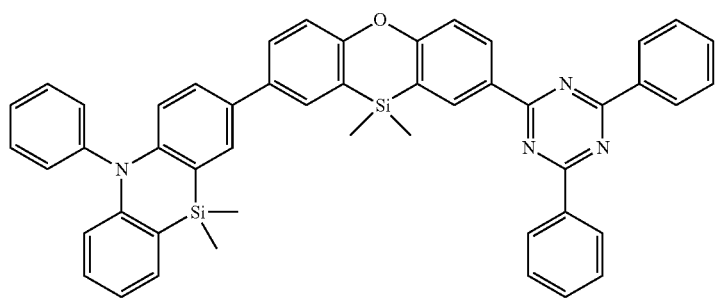
72
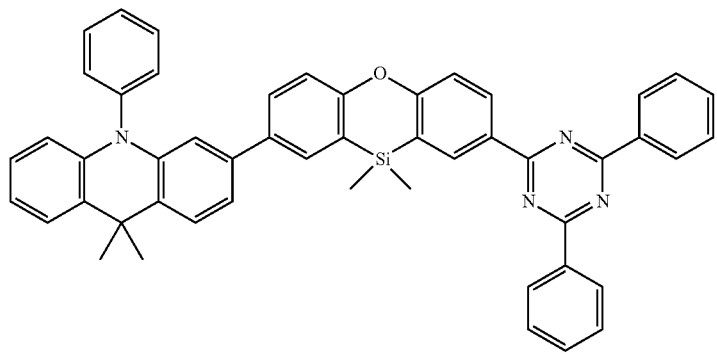
73
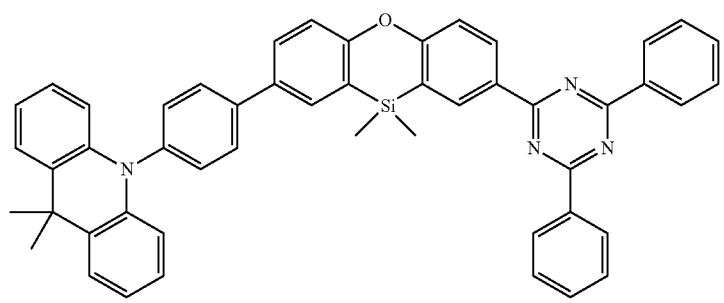
74
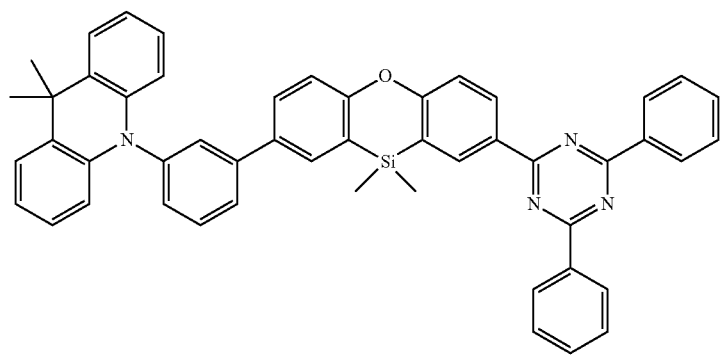
75
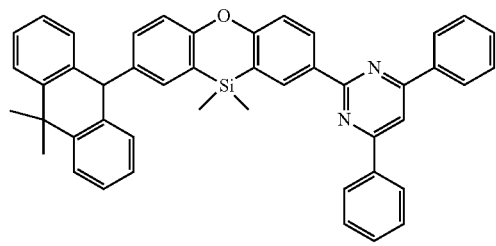
76
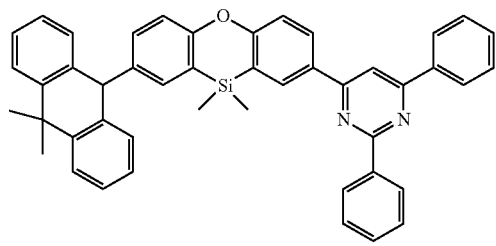
77

-continued
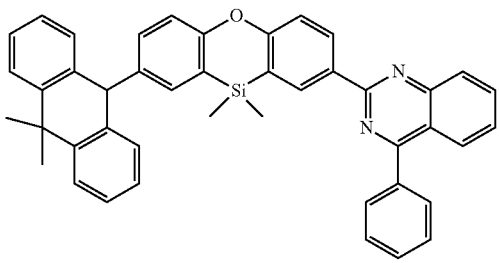
78
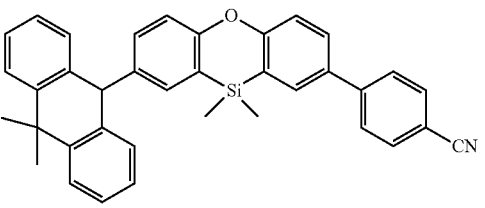
79
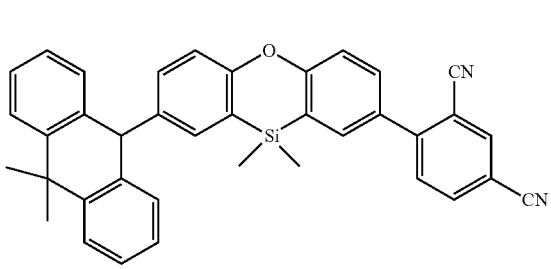
80
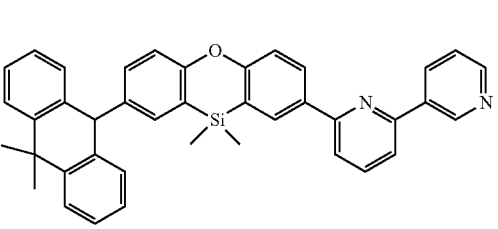
81
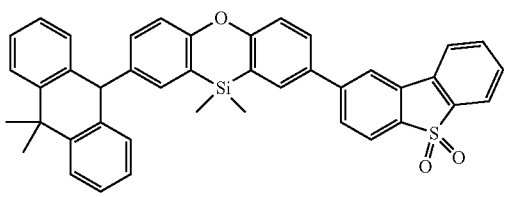
82
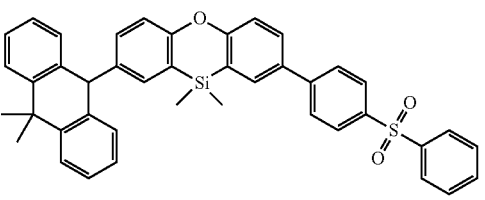
83
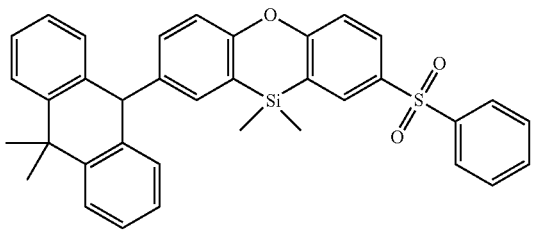
84
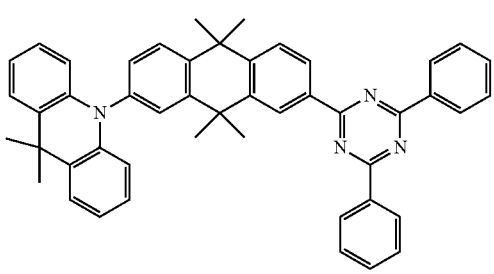
85
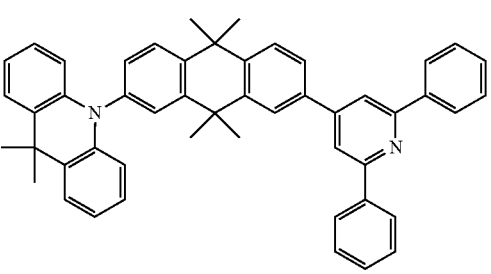
86
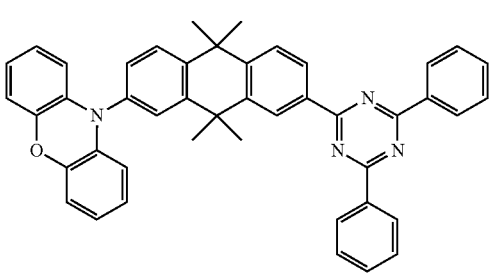
87
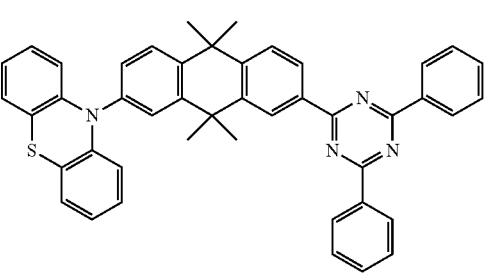
88

89
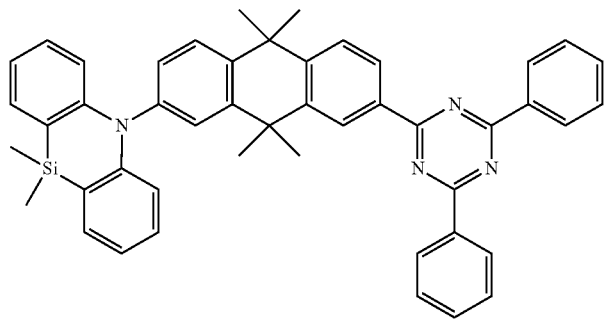
90
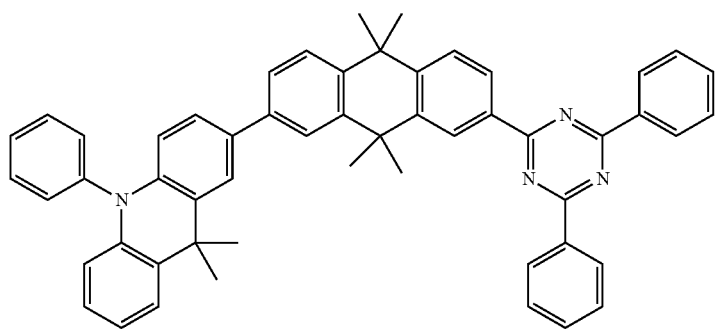
91
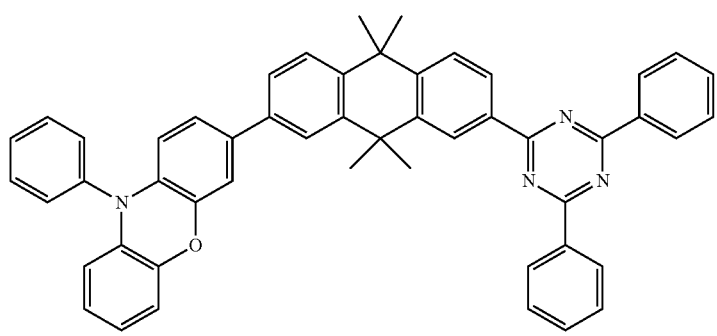
92
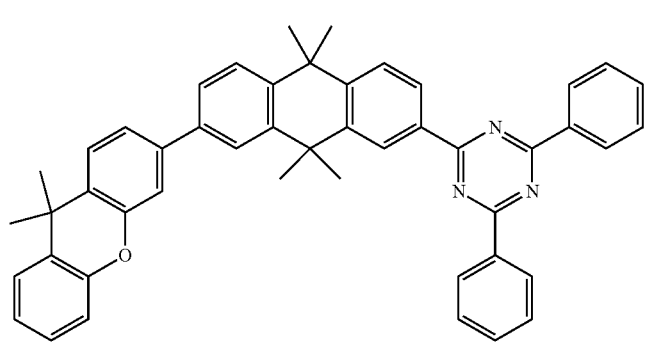
93
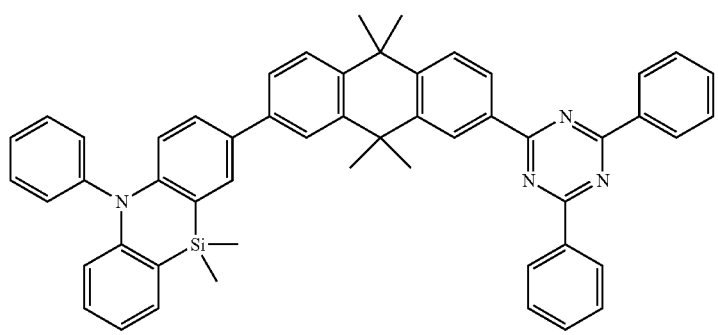

94
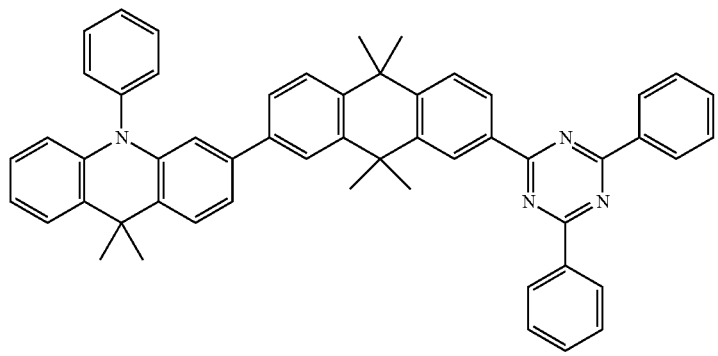
95
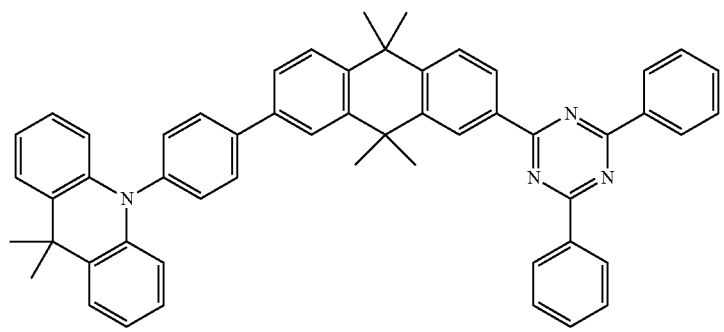
96
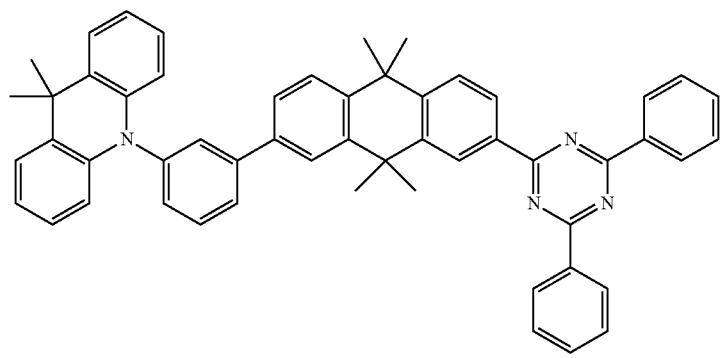
97
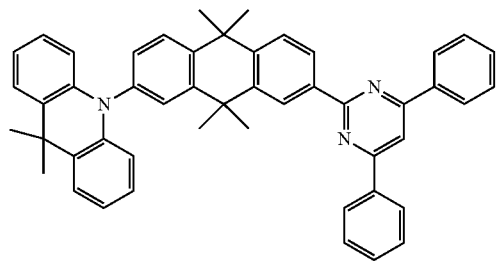
98
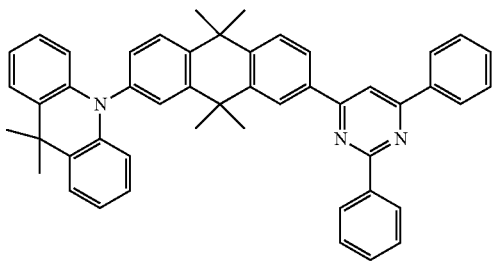
99
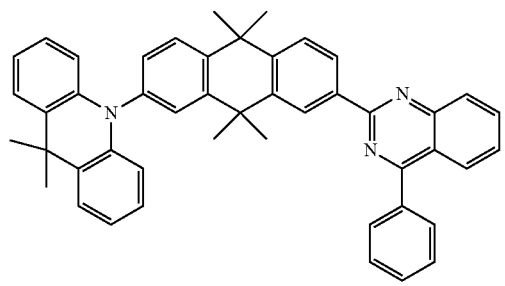
100
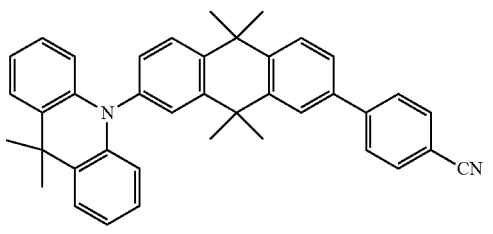

-continued
101 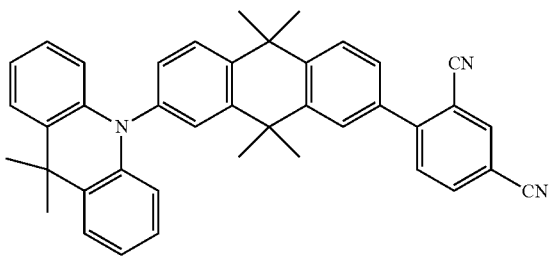
102 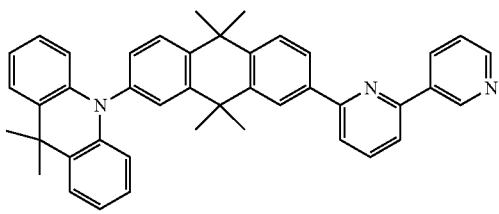
103 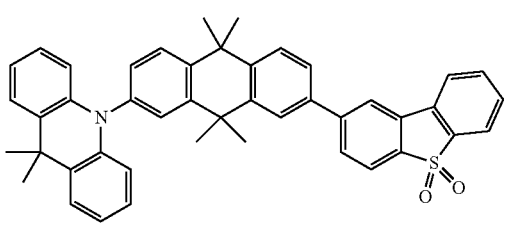
104 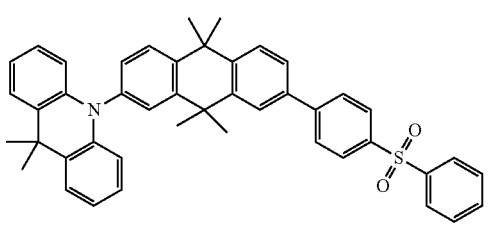
105 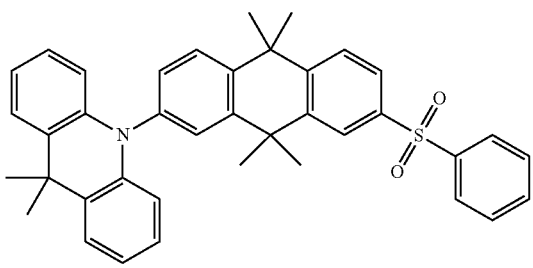
106 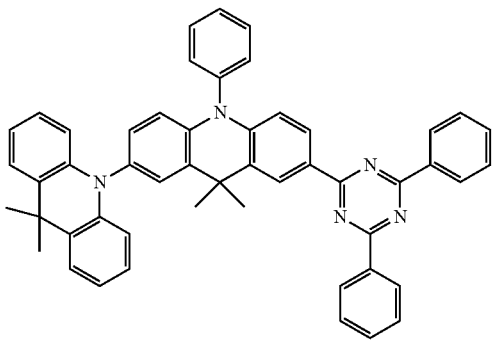
107 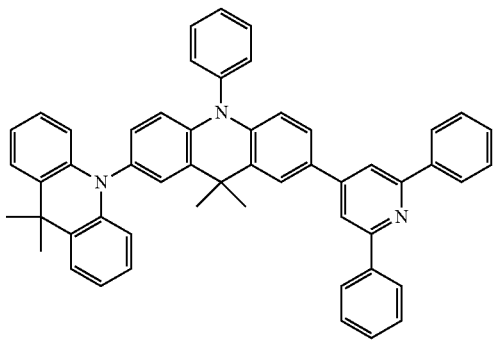
108 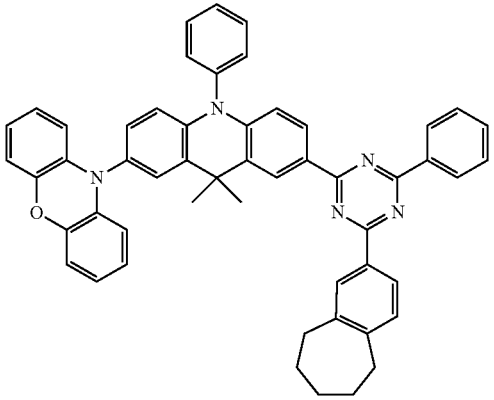
109 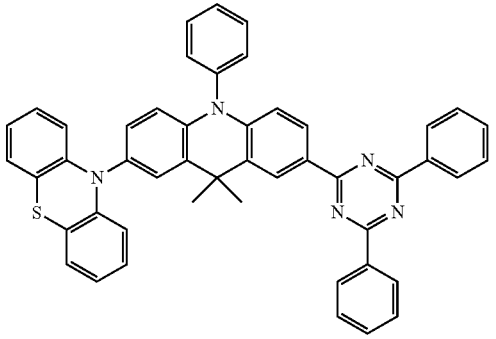

-continued
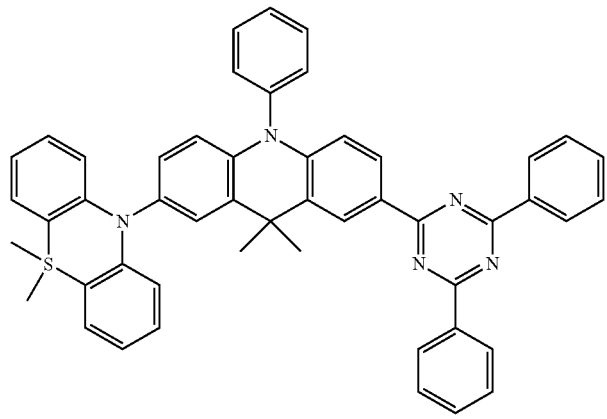
110
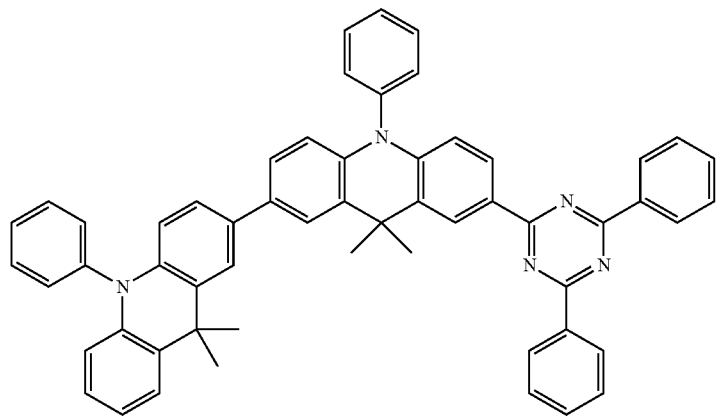
111
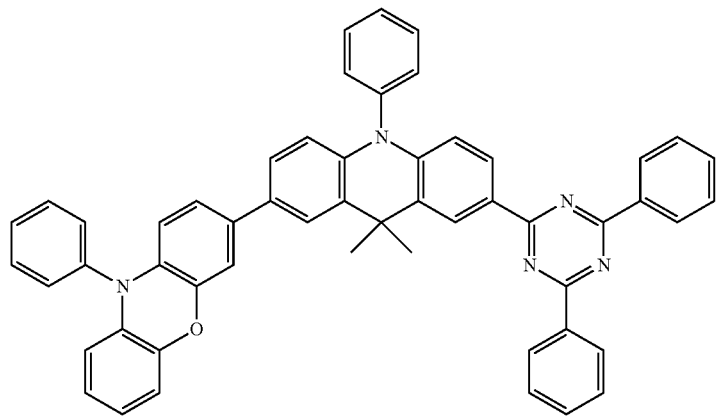
112

113
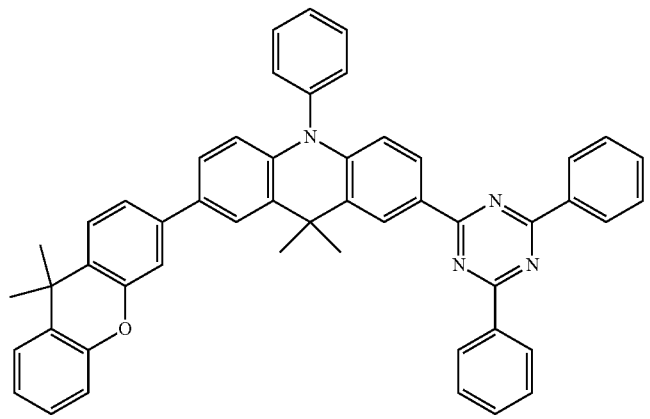
114
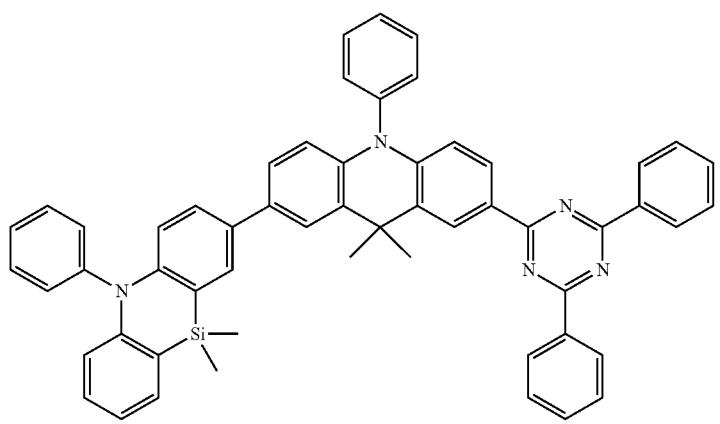
115
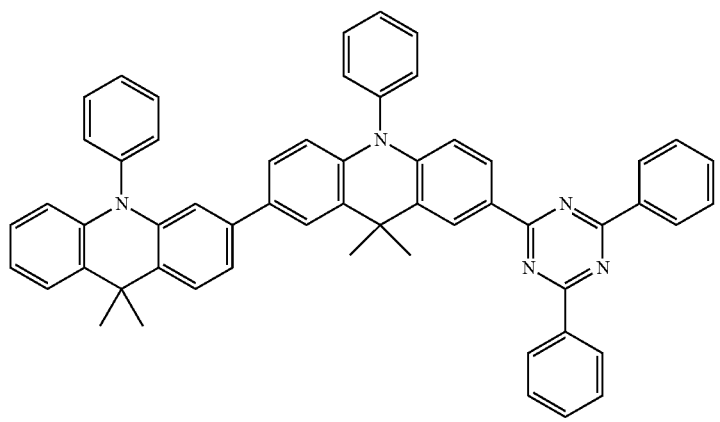

116
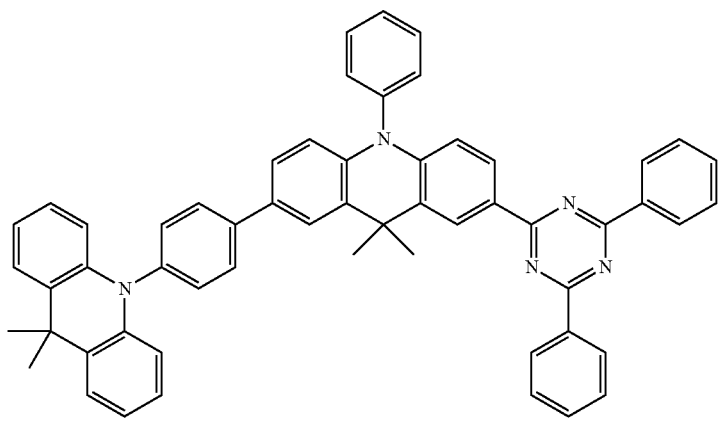
117
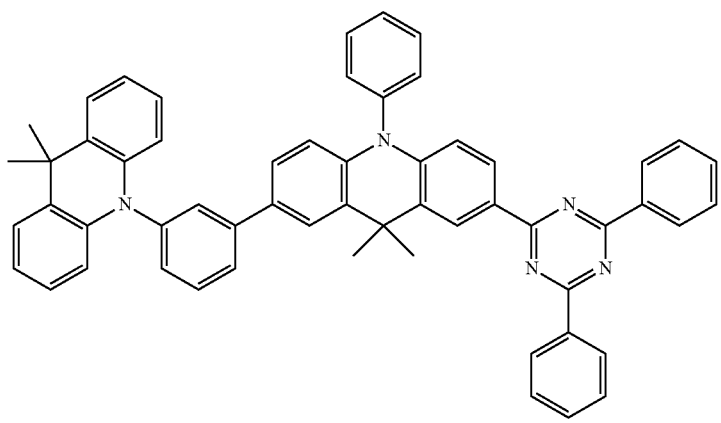
118
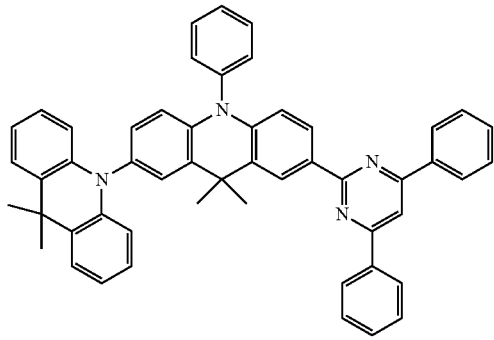
119
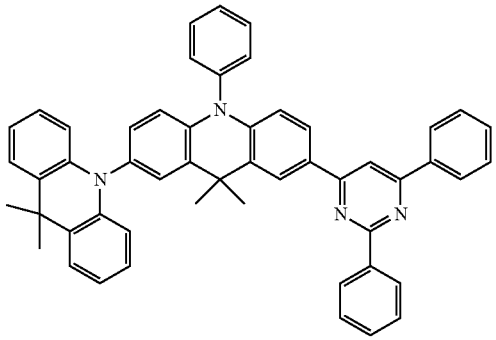
120
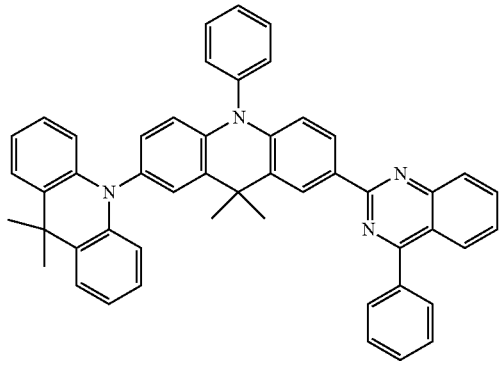
121
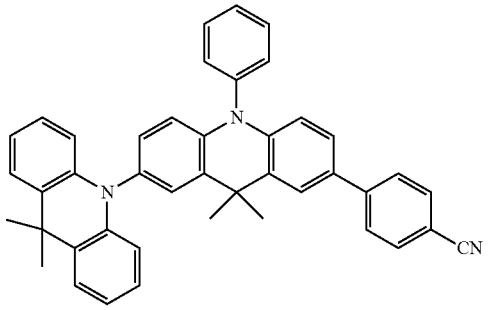

-continued
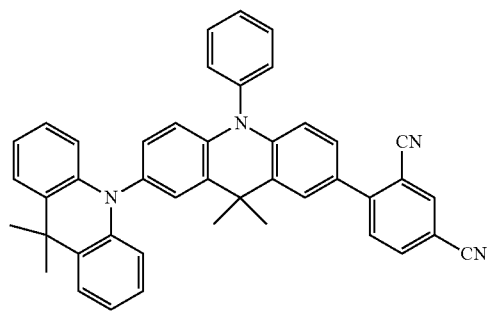
122
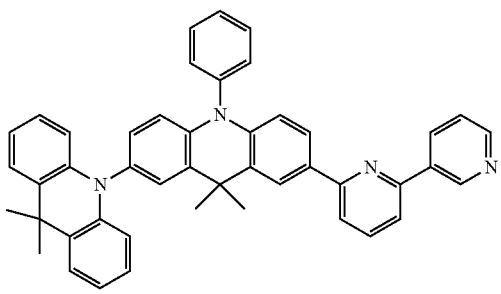
123
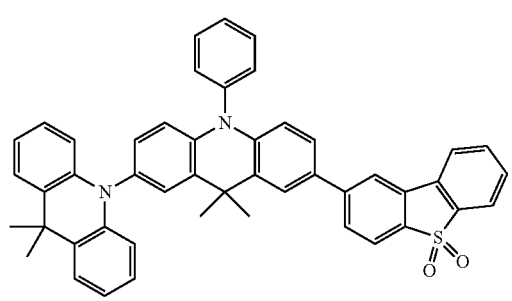
124
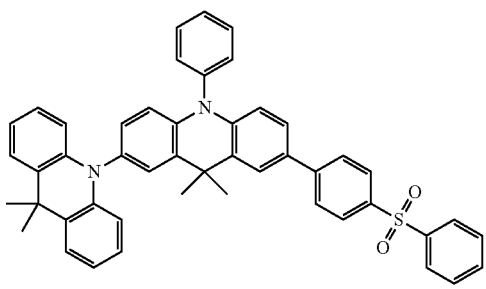
125
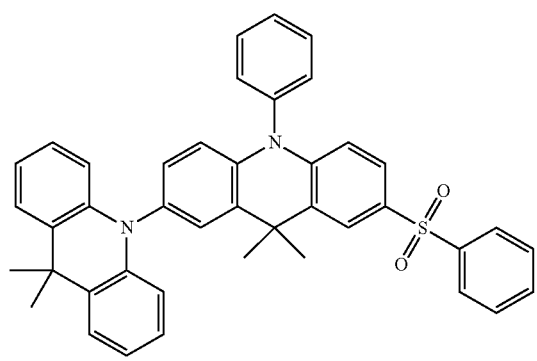
126
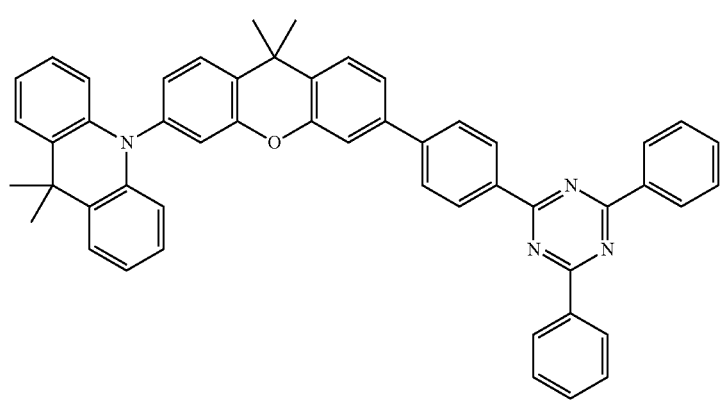
127

-continued
128
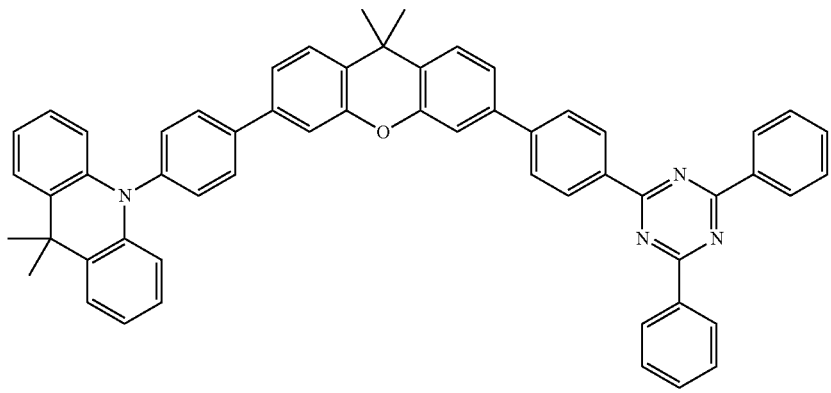
129
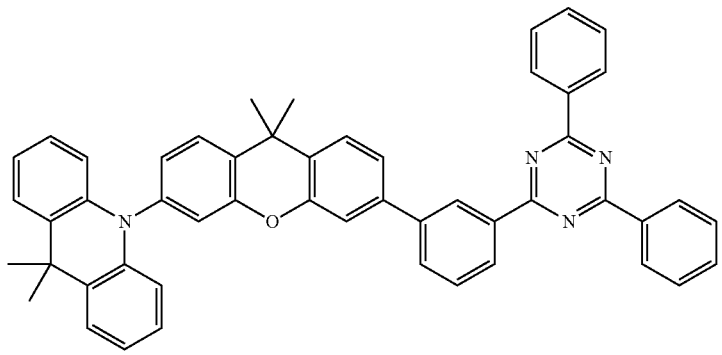
130
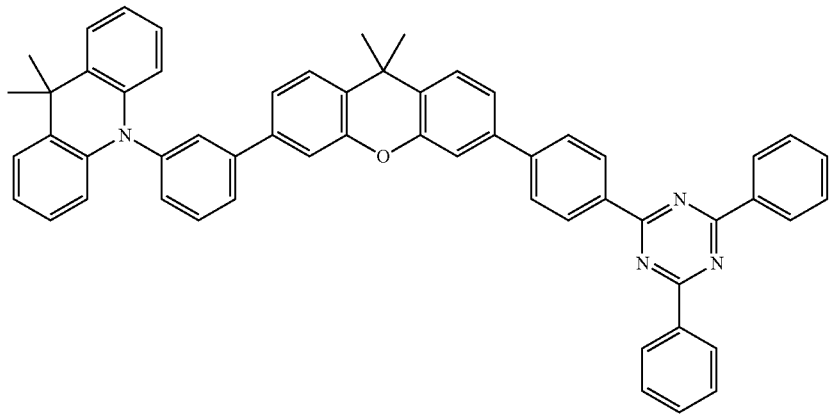
131
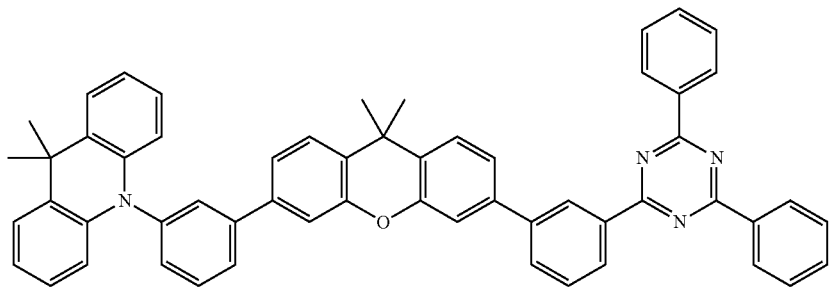

-continued
132
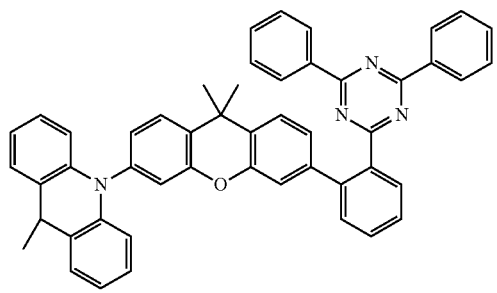
133
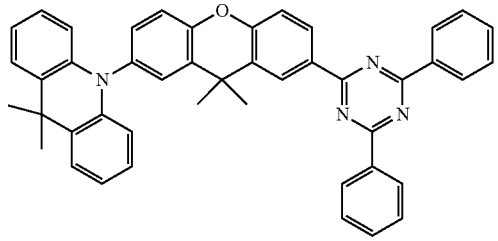
134
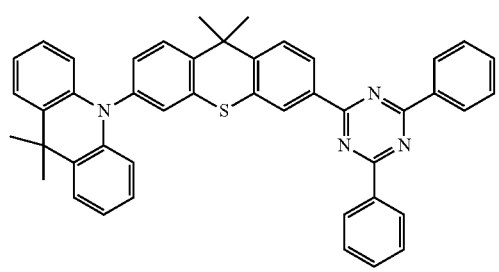
135
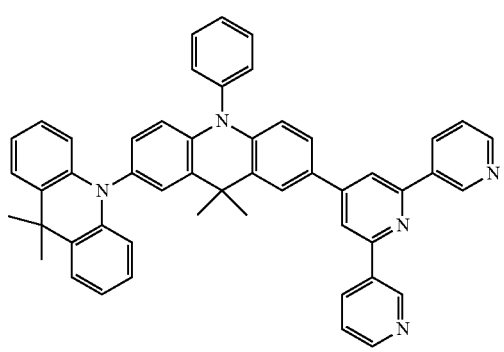
136
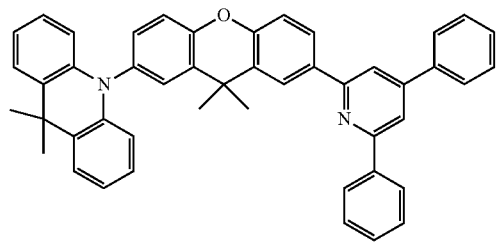
137
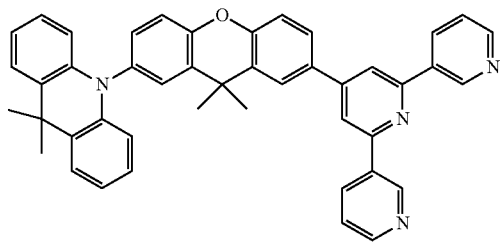
138
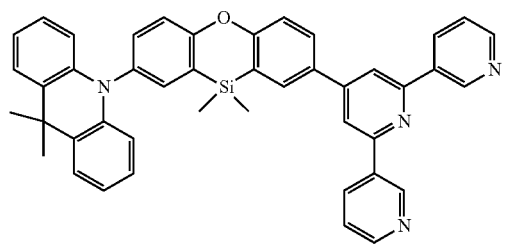
139
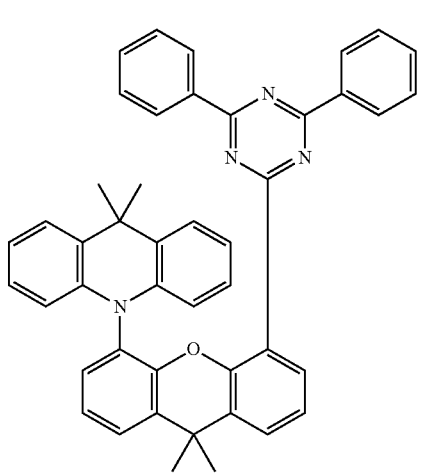

-continued

140
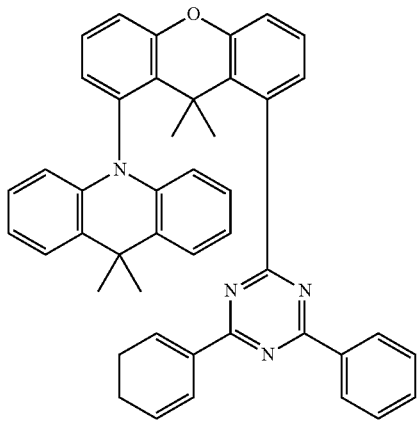

141
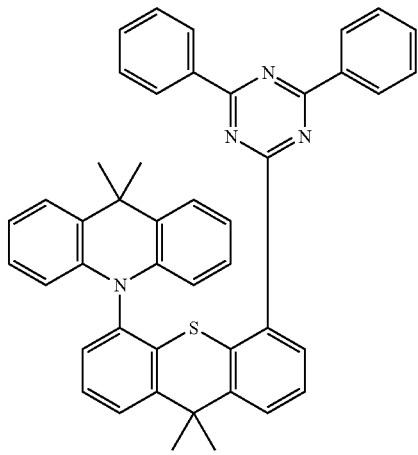

142
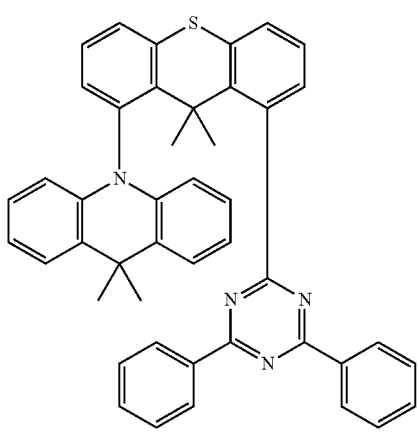

143
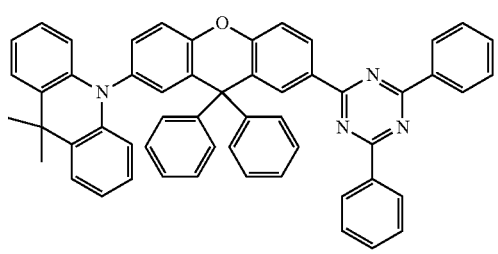

144
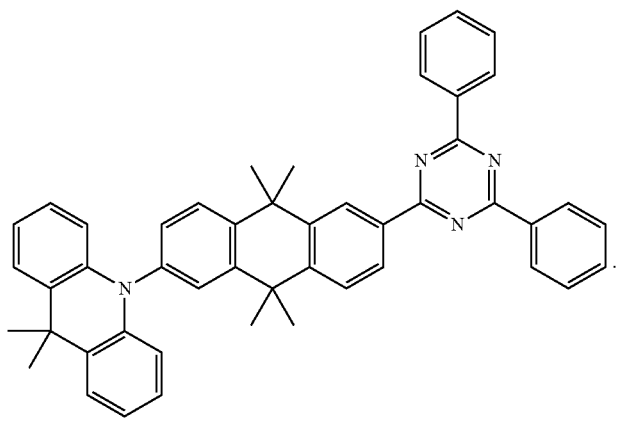

12. An organic light-emitting device comprising:
a first electrode;
a second electrode facing the first electrode; and
an organic layer between the first electrode and the second electrode, the organic layer comprising an emission layer and the condensed cyclic compound of claim 1.

13. The organic light-emitting device of claim 12, wherein
the first electrode is an anode,
the second electrode is a cathode,
the organic layer further comprises a hole transport region between the first electrode and the emission layer, and an electron transport region between the emission layer and the second electrode,
the hole transport region comprises a hole injection layer, a hole transport layer, an emission auxiliary layer, an electron blocking layer, or any combination thereof, and
the electron transport region comprises a buffer layer, a hole blocking layer, an electron control layer, an electron transport layer, an electron injection layer, or any combination thereof.

14. The organic light-emitting device of claim 12, wherein the emission layer comprises a dopant and a host, and the dopant comprises the condensed cyclic compound.

15. An organic light-emitting device comprising:
a first electrode;
a second electrode facing the first electrode; and
an organic layer between the first electrode and the second electrode, the organic layer comprising an emission layer,
wherein the emission layer comprises a dopant and a host,
the dopant comprises a condensed cyclic compound represented by Formula 1, and
the host in the emission layer comprises at least one selected from an anthracene-based compound, a pyrene-based compound, and a spiro-bifluorene-based compound:

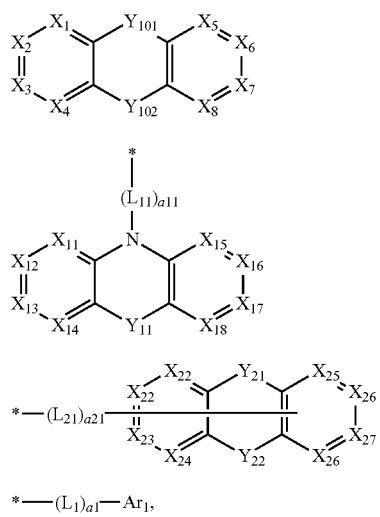

Formula 1

Formula 2

Formula 3

Formula 4 wherein, in Formulae 1 to 4,
$X_1$ to $X_4$ are each independently $C(R_1)$, N, or carbon linked to a group represented by Formula 2 or 3,
$X_5$ to $X_8$ are each independently $C(R_2)$, N, or carbon linked to a group represented by Formula 4,
$X_{11}$ to $X_{18}$ are each independently $C(R_3)$ or N,
$X_{21}$ to $X_{28}$ are each independently $C(R_4)$, N, or carbon linked to $(L_{21})_{a21}$, and
at least one of $X_1$ to $X_4$ is carbon linked to a group represented by Formula 2 or 3, at least one of $X_5$ to $X_8$ is carbon linked to a group represented by Formula 4, and at least one of $X_{21}$ to $X_{28}$ is carbon linked to $(L_{21})_{a21}$,
$Y_{101}$ and $Y_{102}$ are each independently selected from $C(R_{11})(R_{12})$, $Si(R_{11})(R_{12})$, O, S, and $N(R_{11})$,
$Y_{11}$, $Y_{21}$, and $Y_{22}$ are each independently selected from $C(R_{21})(R_{22})$, $Si(R_{21})(R_{22})$, O, S, and $N(R_{21})$,
$L_1$, $L_{11}$, and $L_{21}$ are each independently a substituted or unsubstituted $C_3$-$C_{60}$ carbocyclic group or a substituted or unsubstituted $C_1$-$C_{60}$ heterocyclic group,
a1, a11, and a21 are each independently an integer from 0 to 3, wherein, when a1 is two or more, two or more $L_1$(s) are identical to or different from each other, when a11 is two or more, two or more $L_{11}$(s) are identical to or different from each other, and when a21 is two or more, two or more $L_{21}$(s) are identical to or different from each other,
$Ar_1$ is a substituted or unsubstituted $C_3$-$C_{60}$ carbocyclic group or a substituted or unsubstituted $C_1$-$C_{60}$ heterocyclic group, or *—$S(=O)_2(Q_{101})$, $R_1$ to $R_4$, $R_{11}$ to $R_{12}$, and $R_{21}$ to $R_{22}$ are each independently selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —$Si(Q_1)(Q_2)(Q_3)$, —$N(Q_1)(Q_2)$, —$B(Q_1)(Q_2)$, —$C(=O)(Q_1)$, —$S(=O)_2(Q_1)$, and —$P(=O)(Q_1)(Q_2)$,
at least one substituent of the substituted $C_3$-$C_{60}$ carbocyclic group, the substituted $C_1$-$C_{60}$ heterocyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group is selected from:
deuterium, —F, —Cl, —Br, —I, a hydroxyl group, a cyano group, a nitro group, an amino group, an amidino group, a hydrazino group, a hydrazono group, a $C_1$-$C_{60}$ alkyl group, a $C_2$-$C_{60}$ alkenyl group, a $C_2$-$C_{60}$ alkynyl group, and a $C_1$-$C_{60}$ alkoxy group;
a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$Si(Q_{11})(Q_{12})(Q_{13})$, —$N(Q_{11})(Q_{12})$, —$B(Q_{11})(Q_{12})$, —$C(=O)(Q_{11})$, —$S(=O)_2(Q_{11})$, and —$P(=O)(Q_{11})(Q_{12})$;
a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, and a terphenyl group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, and a terphenyl group, each substituted with at least one selected from deuterium, —F, —Cl, —Br, —I, a hydroxyl group, a cyano group, a nitro group, an amino group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, a terphenyl group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), and —P(=O)($Q_{21}$)($Q_{22}$); and —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), $Q_{101}$, $Q_1$ to $Q_3$, $Q_{11}$ to $Q_{13}$, $Q_{21}$ to $Q_{23}$, and $Q_{31}$ to $Q_{33}$ are each independently selected from hydrogen, deuterium, —F, —Cl, —Br, —I, a hydroxyl group, a cyano group, a nitro group, an amino group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, and a terphenyl group, and

* indicates a binding site to a neighboring atom.

16. The organic light-emitting device of claim 12, wherein the emission layer comprises a dopant and a host, and the host comprises the condensed cyclic compound.

17. An organic light-emitting device comprising:
a first electrode;
a second electrode facing the first electrode; and
an organic layer between the first electrode and the second electrode, the organic layer comprising an emission layer,
wherein the emission layer comprises a dopant and a host,
the host comprises a condensed cyclic compound represented by Formula 1, and
the dopant in the emission layer comprises at least one selected from a styryl-based compound and an amine-based compound:

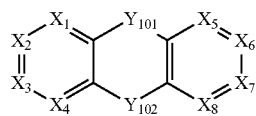

Formula 1

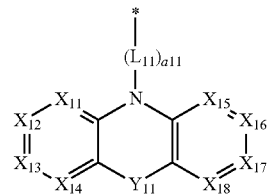

Formula 2

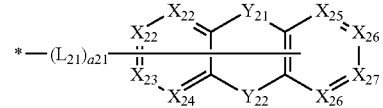

Formula 3

*—($L_1$)$_{a1}$—Ar$_1$,

Formula 4 wherein, in Formulae 1 to 4, $X_1$ to $X_4$ are each independently C($R_1$), N, or carbon linked to a group represented by Formula 2 or 3, $X_5$ to $X_8$ are each independently C($R_2$), N, or carbon linked to a group represented by Formula 4, $X_{11}$ to $X_{18}$ are each independently C($R_3$) or N, $X_{21}$ to $X_{28}$ are each independently C($R_4$), N, or carbon linked to ($L_{21}$)$_{a21}$, and at least one of $X_1$ to $X_4$ is carbon linked to a group represented by Formula 2 or 3, at least one of $X_5$ to $X_8$ is carbon linked to a group represented by Formula 4, and at least one of $X_{21}$ to $X_{28}$ is carbon linked to ($L_{21}$)$_{a21}$, $Y_{101}$ and $Y_{102}$ are each independently selected from C($R_{11}$)($R_{12}$), Si($R_{11}$)($R_{12}$), O, S, and N($R_{11}$), $Y_{11}$, $Y_{21}$, and $Y_{22}$ are each independently selected from C($R_{21}$)($R_{22}$), Si($R_{21}$)($R_{22}$), O, S, and N($R_{21}$), $L_1$, $L_{11}$, and $L_{21}$ are each independently a substituted or unsubstituted $C_3$-$C_{60}$ carbocyclic group or a substituted or unsubstituted $C_1$-$C_{60}$ heterocyclic group, a1, a11, and a21 are each independently an integer from 0 to 3, wherein, when a1 is two or more, two or more $L_1$(s) are identical to or different from each other, when a11 is two or more, two or more $L_{11}$(s) are identical to or different from each other, and when a21 is two or more, two or more $L_{21}$(s) are identical to or different from each other, Ar$_1$ is a substituted or unsubstituted $C_3$-$C_{60}$ carbocyclic group, a substituted or unsubstituted $C_1$-$C_{60}$ heterocyclic group, or *—S(=O)$_2$($Q_{101}$), $R_1$ to $R_4$, $R_{11}$ to $R_{12}$, and $R_{21}$ to $R_{22}$ are each independently selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si(Q$_1$)(Q$_2$)(Q$_3$), —N(Q$_1$)(Q$_2$), —B(Q$_1$)(Q$_2$), —C(=O)(Q$_1$), —S(=O)$_2$(Q$_1$), and —P(=O)(Q$_1$)(Q$_2$), at least one substituent of the substituted C$_3$-C$_{60}$ carbocyclic group, the substituted C$_1$-C$_{60}$ heterocyclic group, the substituted C$_1$-C$_{60}$ alkyl group, the substituted C$_2$-C$_{60}$ alkenyl group, the substituted C$_2$-C$_{60}$ alkynyl group, the substituted C$_1$-C$_{60}$ alkoxy group, the substituted C$_3$-C$_{10}$ cycloalkyl group, the substituted C$_1$-C$_{10}$ heterocycloalkyl group, the substituted C$_3$-C$_{10}$ cycloalkenyl group, the substituted C$_1$-C$_{10}$ heterocycloalkenyl group, the substituted C$_6$-C$_{60}$ aryl group, the substituted C$_6$-C$_{60}$ aryloxy group, the substituted C$_6$-C$_{60}$ arylthio group, the substituted C$_1$-C$_{60}$ heteroaryl group, the substituted monovalent non-aromatic condensed polycyclic group, and the substituted monovalent non-aromatic condensed heteropolycyclic group is selected from:

deuterium, —F, —Cl, —Br, —I, a hydroxyl group, a cyano group, a nitro group, an amino group, an amidino group, a hydrazino group, a hydrazono group, a C$_1$-C$_{60}$ alkyl group, a C$_2$-C$_{60}$ alkenyl group, a C$_2$-C$_{60}$ alkynyl group, and a C$_1$-C$_{60}$ alkoxy group;

a C$_1$-C$_{60}$ alkyl group, a C$_2$-C$_{60}$ alkenyl group, a C$_2$-C$_{60}$ alkynyl group, and a C$_1$-C$_{60}$ alkoxy group, each substituted with at least one selected from deuterium, —F, —Cl, —Br, —I, a hydroxyl group, a cyano group, a nitro group, an amino group, an amidino group, a hydrazino group, a hydrazono group, a C$_3$-C$_{10}$ cycloalkyl group, a C$_1$-C$_{10}$ heterocycloalkyl group, a C$_3$-C$_{10}$ cycloalkenyl group, a C$_1$-C$_{10}$ heterocycloalkenyl group, a C$_6$-C$_{60}$ aryl group, a C$_6$-C$_{60}$ aryloxy group, a C$_6$-C$_{60}$ arylthio group, a C$_1$-C$_{60}$ heteroaryl group, a monovalent non-aromatic condensed polycyclic group, a monovalent non-aromatic condensed heteropolycyclic group, —Si(Q$_{11}$)(Q$_{12}$)(Q$_{13}$), —N(Q$_{11}$)(Q$_{12}$), —B(Q$_{11}$)(Q$_{12}$), —C(=O)(Q$_{11}$), —S(=O)$_2$(Q$_{11}$), and —P(=O)(Q$_{11}$)(Q$_{12}$);

a C$_3$-C$_{10}$ cycloalkyl group, a C$_1$-C$_{10}$ heterocycloalkyl group, a C$_3$-C$_{10}$ cycloalkenyl group, a C$_1$-C$_{10}$ heterocycloalkenyl group, a C$_6$-C$_{60}$ aryl group, a C$_6$-C$_{60}$ aryloxy group, a C$_6$-C$_{60}$ arylthio group, a C$_1$-C$_{60}$ heteroaryl group, a monovalent non-aromatic condensed polycyclic group, a monovalent non-aromatic condensed heteropolycyclic group, a biphenyl group, and a terphenyl group;

a C$_3$-C$_{10}$ cycloalkyl group, a C$_1$-C$_{10}$ heterocycloalkyl group, a C$_3$-C$_{10}$ cycloalkenyl group, a C$_1$-C$_{10}$ heterocycloalkenyl group, a C$_6$-C$_{60}$ aryl group, a C$_6$-C$_{60}$ aryloxy group, a C$_6$-C$_{60}$ arylthio group, a C$_1$-C$_{60}$ heteroaryl group, a monovalent non-aromatic condensed polycyclic group, a monovalent non-aromatic condensed heteropolycyclic group, a biphenyl group, and a terphenyl group, each substituted with at least one selected from deuterium, —F, —Cl, —Br, —I, a hydroxyl group, a cyano group, a nitro group, an amino group, an amidino group, a hydrazino group, a hydrazono group, a C$_1$-C$_{60}$ alkyl group, a C$_2$-C$_{60}$ alkenyl group, a C$_2$-C$_{60}$ alkynyl group, a C$_1$-C$_{60}$ alkoxy group, a C$_3$-C$_{10}$ cycloalkyl group, a C$_1$-C$_{10}$ heterocycloalkyl group, a C$_3$-C$_{10}$ cycloalkenyl group, a C$_1$-C$_{10}$ heterocycloalkenyl group, a C$_6$-C$_{60}$ aryl group, a C$_6$-C$_{60}$ aryloxy group, a C$_6$-C$_{60}$ arylthio group, a C$_1$-C$_{60}$ heteroaryl group, a monovalent non-aromatic condensed polycyclic group, a monovalent non-aromatic condensed heteropolycyclic group, a biphenyl group, a terphenyl group, —Si(Q$_{21}$)(Q$_{22}$)(Q$_{23}$), —N(Q$_{21}$)(Q$_{22}$), —B(Q$_{21}$)(Q$_{22}$), —C(=O)(Q$_{21}$), —S(=O)$_2$(Q$_{21}$), and —P(=O)(Q$_{21}$)(Q$_{22}$); and —Si(Q$_{31}$)(Q$_{32}$)(Q$_{33}$), —N(Q$_{31}$)(Q$_{32}$), —B(Q$_{31}$)(Q$_{32}$), —C(=O)(Q$_{31}$), —S(=O)$_2$(Q$_{31}$), and —P(=O)(Q$_{31}$)(Q$_{32}$), Q$_{101}$, Q$_1$ to Q$_3$, Q$_{11}$ to Q$_{13}$, Q$_{21}$ to Q$_{23}$, and Q$_{31}$ to Q$_{33}$ are each independently selected from hydrogen, deuterium, —F, —Cl, —Br, —I, a hydroxyl group, a cyano group, a nitro group, an amino group, an amidino group, a hydrazino group, a hydrazono group, a C$_1$-C$_{60}$ alkyl group, a C$_2$-C$_{60}$ alkenyl group, a C$_2$-C$_{60}$ alkynyl group, a C$_1$-C$_{60}$ alkoxy group, a C$_3$-C$_{10}$ cycloalkyl group, a C$_1$-C$_{10}$ heterocycloalkyl group, a C$_3$-C$_{10}$ cycloalkenyl group, a C$_1$-C$_{10}$ heterocycloalkenyl group, a C$_6$-C$_{60}$ aryl group, a C$_1$-C$_{60}$ heteroaryl group, a monovalent non-aromatic condensed polycyclic group, a monovalent non-aromatic condensed heteropolycyclic group, a biphenyl group, and a terphenyl group, and

* indicates a binding site to a neighboring atom.

18. The organic light-emitting device of claim 13, wherein the hole transport region comprises a p-dopant, and
the p-dopant has a lowest unoccupied molecular orbital (LUMO) energy level of −3.5 eV or less.

19. The organic light-emitting device of claim 13, wherein the electron transport region comprises an alkali metal, an alkaline earth metal, a rare earth metal, an alkali metal compound, an alkaline earth-metal compound, a rare earth metal compound, an alkali metal complex, an alkaline earth-metal complex, a rare earth metal complex, or any combination thereof.

20. The organic light-emitting device of claim 12, wherein the emission layer is a first emission layer for emitting first color light,
the organic light-emitting device further comprises i) at least one second emission layer for emitting second color light, or ii) at least one second emission layer for emitting second color light and at least one third emission layer for emitting third color light, between the first electrode and the second electrode,
a maximum emission wavelength of the first color light, a maximum emission wavelength of the second color light, and a maximum emission wavelength of the third color light are identical to or different from each other, and
the first color light and the second color light are emitted in the form of mixed light, or the first color light, the second color light, and the third color light are emitted in the form of mixed light.

* * * * *